(12) United States Patent  (10) Patent No.: US 9,216,249 B2
Smith et al.  (45) Date of Patent: Dec. 22, 2015

(54) INFUSION PUMPS

(75) Inventors: Roger E. Smith, Ivins, UT (US); James Causey, Simi Valley, CA (US); Scott R. Gibson, Granada Hills, CA (US)

(73) Assignee: perQflo, LLC, Valencia, CA (US)

( * ) Notice: Subject to any disclaimer, the term of this patent is extended or adjusted under 35 U.S.C. 154(b) by 831 days.

(21) Appl. No.: 12/890,339

(22) Filed: Sep. 24, 2010

(65) Prior Publication Data

US 2012/0078217 A1  Mar. 29, 2012

(51) Int. Cl.
*A61K 9/22* (2006.01)
*A61M 5/145* (2006.01)

(52) U.S. Cl.
CPC .............. *A61M 5/145* (2013.01); *A61M 5/1452* (2013.01); *A61M 2205/12* (2013.01)

(58) Field of Classification Search
CPC .......... A61M 2205/12; A61M 5/1452; A61M 5/14216; A61M 5/14546; A61M 5/172; A61M 5/142; A61M 2205/073; A61M 2205/50; A61M 1/288; A61M 2005/1402
USPC ................................................. 604/151, 500
See application file for complete search history.

(56) References Cited

U.S. PATENT DOCUMENTS

| 2,627,270 | A |   | 2/1953  | Glass           |        |
|-----------|---|---|---------|-----------------|--------|
| 3,701,345 | A |   | 10/1972 | Jones et al.    |        |
| 4,116,240 | A |   | 9/1978  | Guiney          |        |
| 4,206,764 | A |   | 6/1980  | Williams        |        |
| 4,529,401 | A |   | 7/1985  | Leslie et al.   |        |
| 4,731,058 | A |   | 3/1988  | Doan            |        |
| 4,985,015 | A |   | 1/1991  | Obermann et al. |        |
| 5,244,461 | A | * | 9/1993  | Derlien ........................ | 604/65 |
| 5,281,111 | A |   | 1/1994  | Plambeck et al. |        |
| 5,378,126 | A |   | 1/1995  | Abrahamson et al. |      |
| 5,380,314 | A |   | 1/1995  | Herweck et al.  |        |
| 5,505,709 | A |   | 4/1996  | Funderburk et al. |      |
| 5,531,697 | A | * | 7/1996  | Olsen et al. .................... | 604/131 |
| 5,586,868 | A |   | 12/1996 | Lawless et al.  |        |
| 5,665,065 | A |   | 9/1997  | Colman          |        |
| 5,695,473 | A |   | 12/1997 | Olsen           |        |
| 5,816,779 | A |   | 10/1998 | Lawless et al.  |        |
| 5,858,001 | A |   | 1/1999  | Tsals et al.    |        |
| 5,935,106 | A |   | 8/1999  | Olsen           |        |
| 5,954,696 | A |   | 9/1999  | Ryan            |        |
| 5,984,894 | A |   | 11/1999 | Poulsen et al.  |        |
| 6,033,377 | A |   | 3/2000  | Rasmussen et al. |       |
| 6,248,093 | B1|   | 6/2001  | Moberg          |        |

(Continued)

FOREIGN PATENT DOCUMENTS

WO   WO 0170307 A1   9/2001
WO   WO 0220073 A2   3/2002

(Continued)

OTHER PUBLICATIONS

PCT Int. Search Report and Written Opinion dated Feb. 7, 2012, in related PCT App. Ser. No. PCT/US2001/052867.
U.S. Appl. No. 12/890,135, filed Sep. 24, 2010, entitled "Infusion Pumps."
U.S. Appl. No. 12/890,166, filed Sep. 24, 2010, entitled "Infusion Pumps."
U.S. Appl. No. 12/890,207, filed Sep. 24, 2010, entitled "Infusion Pumps."

(Continued)

*Primary Examiner* — Kami A Bosworth
*Assistant Examiner* — Brandy S Lee
(74) *Attorney, Agent, or Firm* — Henricks, Slavin & Holmes LLP

(57) ABSTRACT

Ambulatory infusion pumps, pump assemblies, cartridges, baseplates, cannulas, insertion tools, and related components as well as combinations thereof and related methods.

22 Claims, 61 Drawing Sheets

(56) References Cited

U.S. PATENT DOCUMENTS

| | | |
|---|---|---|
| 6,296,907 B1 | 10/2001 | Viksne |
| 6,458,102 B1 | 10/2002 | Mann et al. |
| 6,461,331 B1 | 10/2002 | Van Antwerp |
| 6,482,186 B1 | 11/2002 | Douglas et al. |
| 6,520,930 B2 | 2/2003 | Critchlow et al. |
| 6,537,251 B2 | 3/2003 | Klitmose |
| 6,585,695 B1 | 7/2003 | Adair et al. |
| 6,585,698 B1 | 7/2003 | Packman et al. |
| 6,629,949 B1 | 10/2003 | Douglas |
| 6,641,566 B2 | 11/2003 | Douglas et al. |
| 6,656,158 B2 | 12/2003 | Mahoney et al. |
| 6,656,159 B2 | 12/2003 | Flaherty |
| 6,659,980 B2 | 12/2003 | Moberg et al. |
| 6,692,457 B2 | 2/2004 | Flaherty |
| 6,699,218 B2 | 3/2004 | Flaherty et al. |
| 6,723,072 B2 | 4/2004 | Flaherty et al. |
| 6,736,796 B2 | 5/2004 | Shekalim |
| 6,752,787 B1 | 6/2004 | Causey, III et al. |
| 6,768,425 B2 | 7/2004 | Flaherty et al. |
| 6,800,071 B1 | 10/2004 | McConnell et al. |
| 6,817,990 B2 | 11/2004 | Yap et al. |
| 6,830,558 B2 | 12/2004 | Flaherty et al. |
| 6,852,104 B2 | 2/2005 | Blomquist |
| 6,902,207 B2 | 6/2005 | Lickliter |
| 6,937,955 B2 | 8/2005 | Barnes |
| 6,939,324 B2 | 9/2005 | Gonnelli et al. |
| 7,029,455 B2 | 4/2006 | Flaherty |
| 7,033,338 B2 | 4/2006 | Vilks et al. |
| 7,063,684 B2 | 6/2006 | Moberg |
| 7,137,964 B2 | 11/2006 | Flaherty |
| 7,179,226 B2 | 2/2007 | Crothall et al. |
| 7,193,521 B2 | 3/2007 | Moberg et al. |
| 7,214,207 B2 | 5/2007 | Lynch et al. |
| 7,250,037 B2 | 7/2007 | Shermer et al. |
| 7,303,543 B1 | 12/2007 | Maule et al. |
| 7,306,578 B2 | 12/2007 | Gray et al. |
| 7,311,693 B2 | 12/2007 | Shekalim |
| 7,390,314 B2 | 6/2008 | Stutz, Jr. et al. |
| 7,455,663 B2 | 11/2008 | Bikovsky |
| 7,481,792 B2 | 1/2009 | Gonnelli et al. |
| 7,510,544 B2 | 3/2009 | Vilks et al. |
| 7,534,226 B2 | 5/2009 | Mernoe et al. |
| 7,569,050 B2 | 8/2009 | Moberg et al. |
| 7,621,893 B2 | 11/2009 | Moberg et al. |
| 7,632,247 B2 | 12/2009 | Adams |
| 7,641,628 B2 | 1/2010 | Daoud et al. |
| 7,641,649 B2 | 1/2010 | Moberg et al. |
| 7,713,258 B2 | 5/2010 | Adams et al. |
| 7,713,262 B2 | 5/2010 | Adams et al. |
| 7,794,434 B2 | 9/2010 | Mounce et al. |
| 7,806,868 B2 | 10/2010 | De Polo et al. |
| 8,430,849 B2 | 4/2013 | Smith et al. |
| 8,568,361 B2 | 10/2013 | Yodfat et al. |
| 8,777,901 B2 | 7/2014 | Smith et al. |
| 8,905,972 B2 | 12/2014 | Smith et al. |
| 8,915,879 B2 | 12/2014 | Smith et al. |
| 2001/0034502 A1 | 10/2001 | Moberg et al. |
| 2001/0041869 A1 | 11/2001 | Causey et al. |
| 2001/0053887 A1 | 12/2001 | Douglas et al. |
| 2002/0040208 A1 | 4/2002 | Flaherty |
| 2002/0077598 A1 | 6/2002 | Yap et al. |
| 2002/0091358 A1 | 7/2002 | Klitmose |
| 2002/0123740 A1 | 9/2002 | Flaherty et al. |
| 2002/0151855 A1 | 10/2002 | Douglas et al. |
| 2002/0173748 A1 | 11/2002 | McConnell et al. |
| 2002/0173769 A1 | 11/2002 | Gray et al. |
| 2002/0183616 A1 | 12/2002 | Toews et al. |
| 2003/0040700 A1 | 2/2003 | Hickle et al. |
| 2003/0055380 A1 | 3/2003 | Flaherty |
| 2003/0073952 A1 | 4/2003 | Flaherty et al. |
| 2003/0100863 A1 | 5/2003 | Shekalim |
| 2003/0125672 A1 | 7/2003 | Adair et al. |
| 2003/0135159 A1 | 7/2003 | Daily et al. |
| 2003/0161744 A1 | 8/2003 | Vilks et al. |
| 2003/0163088 A1 | 8/2003 | Blomquist |
| 2003/0163090 A1 | 8/2003 | Blomquist et al. |
| 2003/0163223 A1 | 8/2003 | Blomquist |
| 2003/0167036 A1 | 9/2003 | Flaherty |
| 2003/0167039 A1 | 9/2003 | Moberg |
| 2003/0199085 A1 | 10/2003 | Berger et al. |
| 2003/0199824 A1 | 10/2003 | Mahoney et al. |
| 2003/0199825 A1 | 10/2003 | Flaherty |
| 2003/0216683 A1 | 11/2003 | Shekalim |
| 2003/0233069 A1 | 12/2003 | Gillespie et al. |
| 2004/0003493 A1 | 1/2004 | Adair et al. |
| 2004/0078028 A1 | 4/2004 | Flaherty et al. |
| 2004/0085215 A1* | 5/2004 | Moberg et al. ................ 340/679 |
| 2004/0092865 A1 | 5/2004 | Flaherty |
| 2004/0092873 A1 | 5/2004 | Moberg |
| 2004/0092878 A1 | 5/2004 | Flaherty |
| 2004/0127844 A1 | 7/2004 | Flaherty |
| 2004/0133166 A1 | 7/2004 | Moberg et al. |
| 2004/0138612 A1 | 7/2004 | Shermer et al. |
| 2004/0153032 A1 | 8/2004 | Garribotto et al. |
| 2004/0176727 A1 | 9/2004 | Shekalim |
| 2004/0220551 A1 | 11/2004 | Flaherty et al. |
| 2004/0235446 A1 | 11/2004 | Flaherty et al. |
| 2004/0243065 A1 | 12/2004 | McConnell et al. |
| 2004/0254533 A1 | 12/2004 | Schriver et al. |
| 2005/0021000 A1 | 1/2005 | Adair et al. |
| 2005/0021005 A1 | 1/2005 | Flaherty et al. |
| 2005/0022274 A1 | 1/2005 | Campbell et al. |
| 2005/0065472 A1 | 3/2005 | Cindrich et al. |
| 2005/0090808 A1 | 4/2005 | Malave et al. |
| 2005/0148938 A1 | 7/2005 | Blomquist |
| 2005/0182366 A1 | 8/2005 | Vogt |
| 2005/0197626 A1 | 9/2005 | Moberg et al. |
| 2005/0215982 A1 | 9/2005 | Malave et al. |
| 2005/0222645 A1 | 10/2005 | Malave et al. |
| 2005/0234404 A1 | 10/2005 | Vilks et al. |
| 2005/0238507 A1 | 10/2005 | DiIanni et al. |
| 2006/0074381 A1 | 4/2006 | Malave et al. |
| 2006/0178633 A1 | 8/2006 | Garibotto et al. |
| 2006/0184154 A1 | 8/2006 | Moberg et al. |
| 2006/0189939 A1 | 8/2006 | Gonnelli et al. |
| 2006/0200112 A1 | 9/2006 | Paul |
| 2006/0206054 A1 | 9/2006 | Shekalim |
| 2006/0282290 A1 | 12/2006 | Flaherty et al. |
| 2007/0021733 A1 | 1/2007 | Hansen et al. |
| 2007/0049870 A1 | 3/2007 | Gray et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0100283 A1 | 5/2007 | Causey et al. |
| 2007/0118405 A1 | 5/2007 | Campbell et al. |
| 2007/0123819 A1 | 5/2007 | Mernoe et al. |
| 2007/0149861 A1 | 6/2007 | Crothall et al. |
| 2007/0149926 A1 | 6/2007 | Moberg |
| 2007/0156092 A1 | 7/2007 | Estes et al. |
| 2007/0167905 A1 | 7/2007 | Estes et al. |
| 2007/0167912 A1* | 7/2007 | Causey et al. ................ 604/131 |
| 2007/0173762 A1 | 7/2007 | Estes et al. |
| 2007/0179444 A1 | 8/2007 | Causey et al. |
| 2007/0219480 A1 | 9/2007 | Kamen |
| 2007/0228071 A1 | 10/2007 | Kamen et al. |
| 2007/0276329 A1 | 11/2007 | Mernoe |
| 2007/0282269 A1 | 12/2007 | Carter et al. |
| 2007/0287960 A1 | 12/2007 | Adams et al. |
| 2007/0293826 A1* | 12/2007 | Wall et al. ..................... 604/200 |
| 2007/0299397 A1 | 12/2007 | Alferness et al. |
| 2007/0299398 A1 | 12/2007 | Alferness et al. |
| 2007/0299399 A1 | 12/2007 | Alferness et al. |
| 2007/0299400 A1 | 12/2007 | Alferness et al. |
| 2007/0299401 A1 | 12/2007 | Alferness et al. |
| 2007/0299405 A1 | 12/2007 | Kaufmann et al. |
| 2007/0299408 A1 | 12/2007 | Alferness et al. |
| 2008/0021395 A1 | 1/2008 | Yodfat et al. |
| 2008/0027296 A1 | 1/2008 | Hadvary et al. |
| 2008/0045902 A1 | 2/2008 | Estes et al. |
| 2008/0045903 A1 | 2/2008 | Estes et al. |
| 2008/0045904 A1 | 2/2008 | Estes et al. |
| 2008/0045931 A1 | 2/2008 | Estes et al. |
| 2008/0058718 A1 | 3/2008 | Adams et al. |
| 2008/0097318 A1 | 4/2008 | Adams |

(56) References Cited

U.S. PATENT DOCUMENTS

| | | |
|---|---|---|
| 2008/0097324 A1 | 4/2008 | Adams et al. |
| 2008/0097381 A1 | 4/2008 | Moberg et al. |
| 2008/0119790 A1 | 5/2008 | Hawkins et al. |
| 2008/0132842 A1 | 6/2008 | Flaherty |
| 2008/0167620 A1 | 7/2008 | Adams |
| 2008/0215006 A1 | 9/2008 | Thorkild |
| 2008/0215015 A1 | 9/2008 | Cindrich et al. |
| 2008/0215035 A1 | 9/2008 | Yodfat et al. |
| 2008/0234630 A1 | 9/2008 | Iddan et al. |
| 2008/0255516 A1 | 10/2008 | Yodfat et al. |
| 2008/0281270 A1 | 11/2008 | Cross et al. |
| 2008/0312512 A1 | 12/2008 | Brukalo et al. |
| 2008/0312584 A1 | 12/2008 | Montgomery et al. |
| 2008/0312585 A1 | 12/2008 | Brukalo et al. |
| 2008/0319416 A1 | 12/2008 | Yodfat et al. |
| 2009/0006129 A1 | 1/2009 | Thukal et al. |
| 2009/0048563 A1 | 2/2009 | Ethelfeld et al. |
| 2009/0048578 A1 | 2/2009 | Adams et al. |
| 2009/0054866 A1 | 2/2009 | Teisen-Simony et al. |
| 2009/0062747 A1 | 3/2009 | Saul |
| 2009/0062768 A1 | 3/2009 | Saul |
| 2009/0067989 A1 | 3/2009 | Estes et al. |
| 2009/0069784 A1 | 3/2009 | Estes et al. |
| 2009/0069787 A1 | 3/2009 | Estes et al. |
| 2009/0076451 A1 | 3/2009 | Teisen-Simony |
| 2009/0076453 A1 | 3/2009 | Mejlhede et al. |
| 2009/0088682 A1 | 4/2009 | Cross et al. |
| 2009/0088689 A1 | 4/2009 | Carter |
| 2009/0088690 A1 | 4/2009 | Carter et al. |
| 2009/0088691 A1 | 4/2009 | Carter et al. |
| 2009/0088692 A1 | 4/2009 | Adams et al. |
| 2009/0088693 A1 | 4/2009 | Carter |
| 2009/0088694 A1 | 4/2009 | Carter et al. |
| 2009/0099523 A1 | 4/2009 | Grant et al. |
| 2009/0131860 A1 | 5/2009 | Nielsen |
| 2009/0143735 A1 | 6/2009 | De Polo et al. |
| 2009/0156989 A1 | 6/2009 | Carter et al. |
| 2009/0163865 A1 | 6/2009 | Hines et al. |
| 2009/0163866 A1 | 6/2009 | Hines et al. |
| 2009/0182277 A1 | 7/2009 | Carter |
| 2009/0192471 A1 | 7/2009 | Carter et al. |
| 2009/0198186 A1 | 8/2009 | Mernoe et al. |
| 2009/0198215 A1 | 8/2009 | Chong et al. |
| 2009/0221971 A1 | 9/2009 | Mejlhede et al. |
| 2009/0240240 A1 | 9/2009 | Hines et al. |
| 2009/0254037 A1 | 10/2009 | Bryant, Jr. et al. |
| 2009/0254041 A1 | 10/2009 | Krag et al. |
| 2009/0259176 A1 | 10/2009 | Yairi |
| 2009/0326453 A1 | 12/2009 | Adams et al. |
| 2009/0326454 A1 | 12/2009 | Cross et al. |
| 2009/0326455 A1 | 12/2009 | Carter |
| 2009/0326456 A1 | 12/2009 | Cross et al. |
| 2009/0326472 A1 | 12/2009 | Carter et al. |
| 2010/0049128 A1 | 2/2010 | McKenzie et al. |
| 2010/0069848 A1 | 3/2010 | Alferness et al. |
| 2010/0137695 A1 | 6/2010 | Yodfat et al. |
| 2010/0198060 A1* | 8/2010 | Fago et al. .................. 600/432 |
| 2012/0022452 A1 | 1/2012 | Welsch et al. |
| 2012/0078170 A1 | 3/2012 | Smith et al. |
| 2012/0078181 A1 | 3/2012 | Smith et al. |
| 2012/0078182 A1 | 3/2012 | Smith et al. |
| 2012/0078183 A1 | 3/2012 | Smith et al. |
| 2012/0078184 A1 | 3/2012 | Smith et al. |
| 2012/0078216 A1 | 3/2012 | Smith et al. |
| 2012/0078222 A1 | 3/2012 | Smith et al. |
| 2012/0078285 A1 | 3/2012 | Smith et al. |
| 2012/0184907 A1 | 7/2012 | Smith et al. |
| 2015/0073386 A1 | 3/2015 | Smith et al. |

FOREIGN PATENT DOCUMENTS

| | | |
|---|---|---|
| WO | WO 0228455 A1 | 4/2002 |
| WO | WO 0249509 A2 | 6/2002 |
| WO | WO 02094352 A2 | 11/2002 |
| WO | WO 03045302 A2 | 6/2003 |
| WO | WO 03074121 A1 | 9/2003 |
| WO | WO 2004098390 A2 | 11/2004 |
| WO | WO 2005018703 A2 | 3/2005 |
| WO | WO 2005018705 A2 | 3/2005 |
| WO | WO 2005037350 A2 | 4/2005 |
| WO | WO 2005046756 A2 | 5/2005 |
| WO | WO 2005072794 A2 | 8/2005 |
| WO | WO 2005072795 A2 | 8/2005 |
| WO | WO 2006032689 A1 | 3/2006 |
| WO | WO 2006032692 A1 | 3/2006 |
| WO | WO 2006061354 A1 | 6/2006 |
| WO | WO 2006104806 A2 | 10/2006 |
| WO | WO 2006108809 A1 | 10/2006 |
| WO | WO 2007038059 A2 | 4/2007 |
| WO | WO 2007038060 A2 | 4/2007 |
| WO | WO 2007038091 A2 | 4/2007 |
| WO | WO 2007142867 A2 | 12/2007 |
| WO | WO 2007142890 A2 | 12/2007 |
| WO | WO 2008040762 A1 | 4/2008 |
| WO | WO 2008078318 A2 | 7/2008 |
| WO | WO 2008103175 A1 | 8/2008 |
| WO | WO 2008122983 A1 | 10/2008 |
| WO | WO 2008139458 A2 | 11/2008 |
| WO | WO 2008139459 A1 | 11/2008 |
| WO | WO 2008139460 A2 | 11/2008 |
| WO | WO 2009016635 A2 | 2/2009 |
| WO | WO 2009016636 A2 | 2/2009 |
| WO | WO 2009016637 A2 | 2/2009 |
| WO | WO 2009045776 A2 | 4/2009 |
| WO | WO 2009045779 A2 | 4/2009 |
| WO | WO 2009045781 A2 | 4/2009 |
| WO | WO 2009045784 A2 | 4/2009 |
| WO | WO 2009045785 A2 | 4/2009 |
| WO | WO 2009066288 A1 | 5/2009 |
| WO | WO 2009081399 A1 | 7/2009 |
| WO | WO 2009088956 A2 | 7/2009 |
| WO | WO 2009097292 A2 | 8/2009 |
| WO | WO 2009113075 A1 | 9/2009 |
| WO | WO 2009116045 A1 | 9/2009 |
| WO | WO 2009125398 A2 | 10/2009 |
| WO | WO 2009133557 A2 | 11/2009 |
| WO | WO 2009146080 A2 | 12/2009 |
| WO | WO 2009158651 A2 | 12/2009 |
| WO | WO 2010022069 A2 | 2/2010 |
| WO | WO 2010026580 A2 | 3/2010 |
| WO | WO 2010029551 A2 | 3/2010 |

OTHER PUBLICATIONS

U.S. Appl. No. 12/890,229, filed Sep. 24, 2010, entitled "Infusion Pumps."

U.S. Appl. No. 12/890,258, filed Sep. 24, 2010, entitled "Infusion Pumps."

U.S. Appl. No. 12/890,277, filed Sep. 24, 2010, entitled "Infusion Pumps."

U.S. Appl. No. 12/890,300, filed Sep. 24, 2010, entitled "Infusion Pumps."

U.S. Appl. No. 12/890,320, filed Sep. 24, 2010, entitled "Infusion Pumps."

U.S. Appl. No. 13/300,574, filed Nov. 19, 2011, entitled "Infusion Pumps."

Gnanalingham et al., "Accuracy and reproducibility of low dose insulin administration using pen-injectors and syringes," Arch Dis Child 1998; 79: 59-62.

Nono Nordisk Canada, Inc., "NovoPen4 User Manual English," 2009.

Kristensen et al., "Dose accuracy and durability of a durable insulin pen before and after simulated lifetime use," Current Medical Research and Opinion, Oct. 2011; 27, No. 10: 1877-1883.

Animas Corp., "OneTouch Ping Owner's Booklet," Jul. 2008.

Garget al., "U-500 insulin: why, when and how to use in clinical practice," Diabetes/Metabolism Research and Reviews, Abstract, Nov. 2006, vol. 23, Is. 4, 265-268.

(56) References Cited

OTHER PUBLICATIONS

Knee et al., "A novel use of U-500 insulin for continuous subcutaneous insulin infusion in patients with insulin resistance," Endocrine Practice, vol. 9, No. 3, (May 2003).

Medtronic, "The MiniMed, Paradigm Real-Time, Insulin Pump and Continuous Glucose Monitor System, Insulin Pump UserGuide," (2008).

CareFusion, Alaris SE Pump Directions for Use (2011).

* cited by examiner

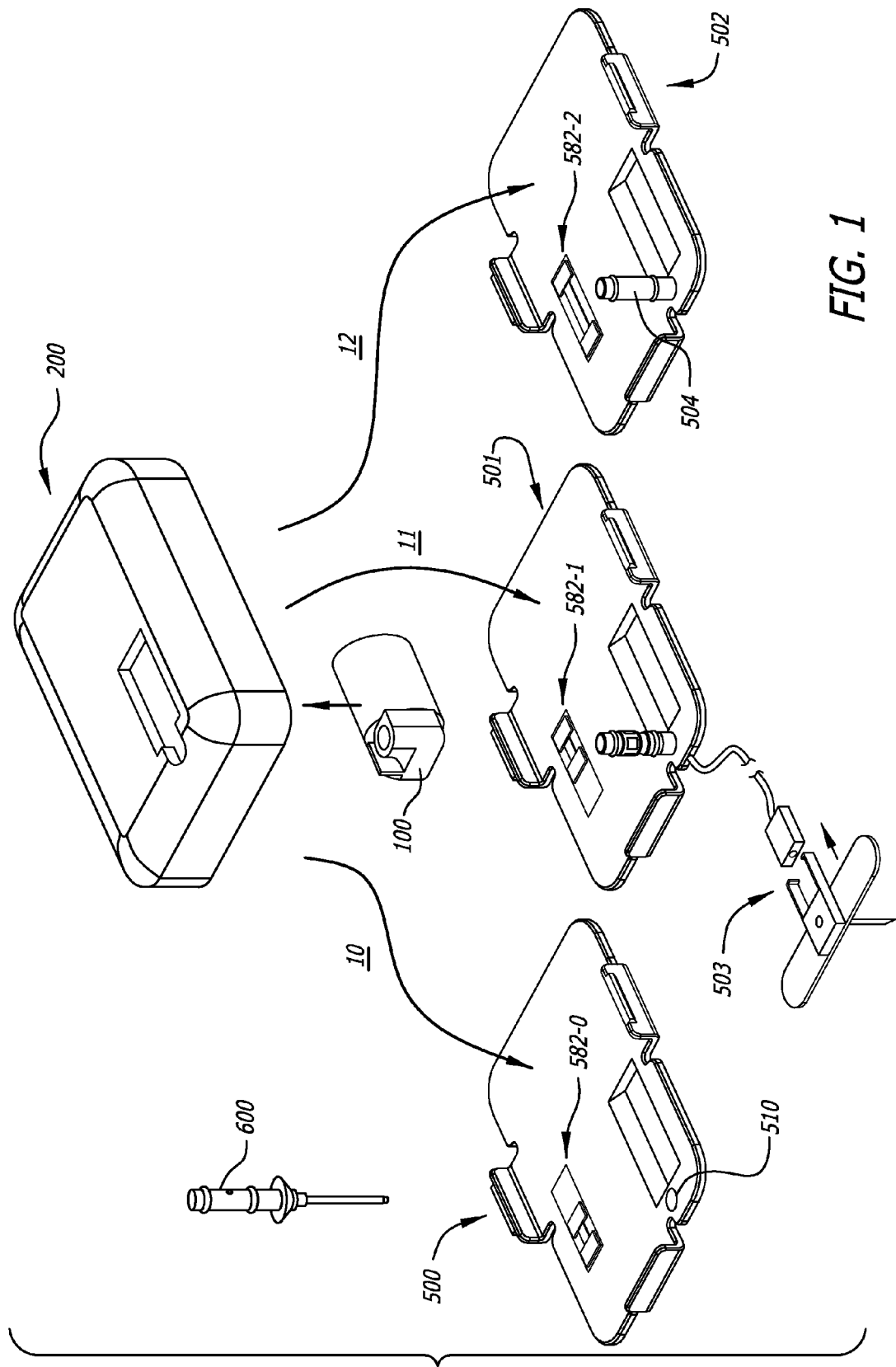

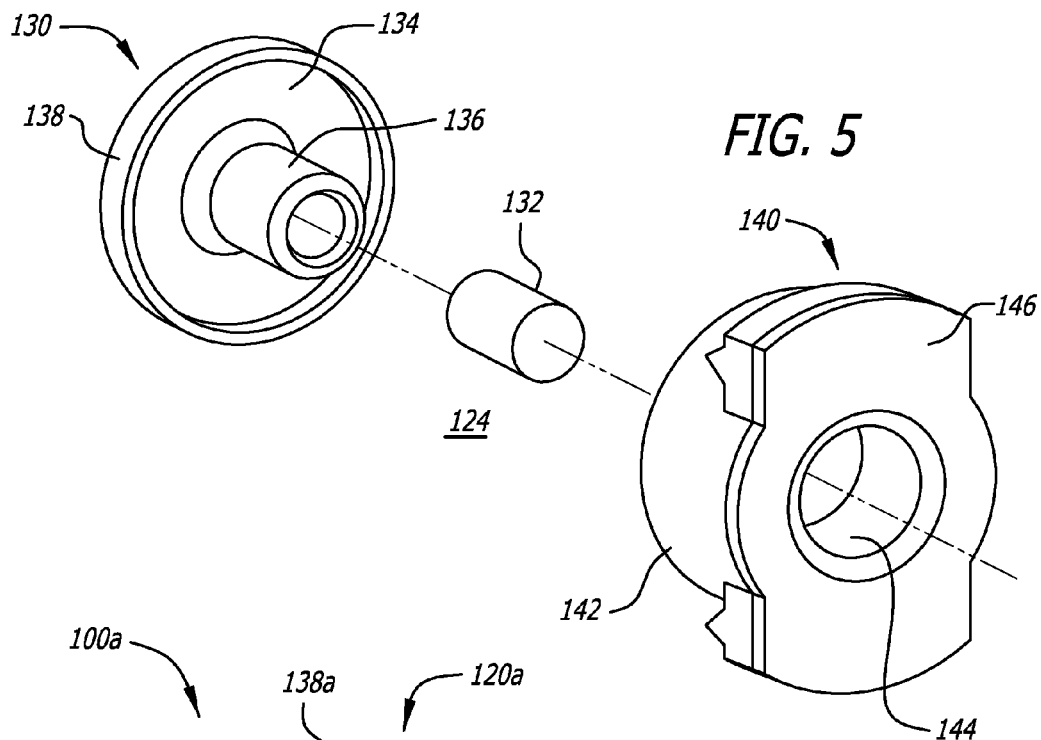
FIG. 5
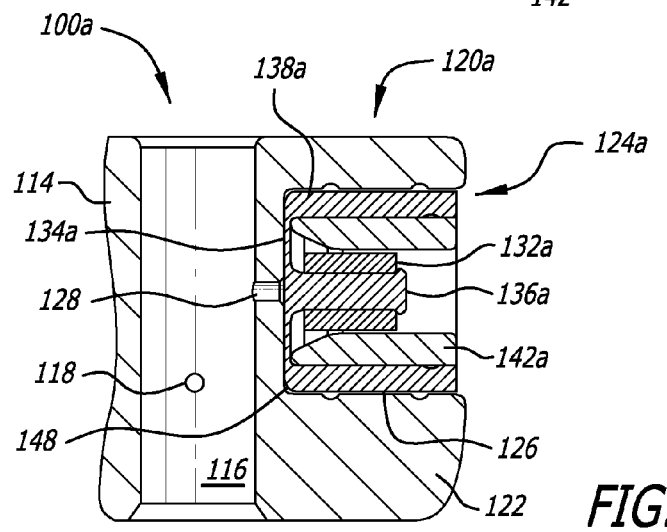
FIG. 6
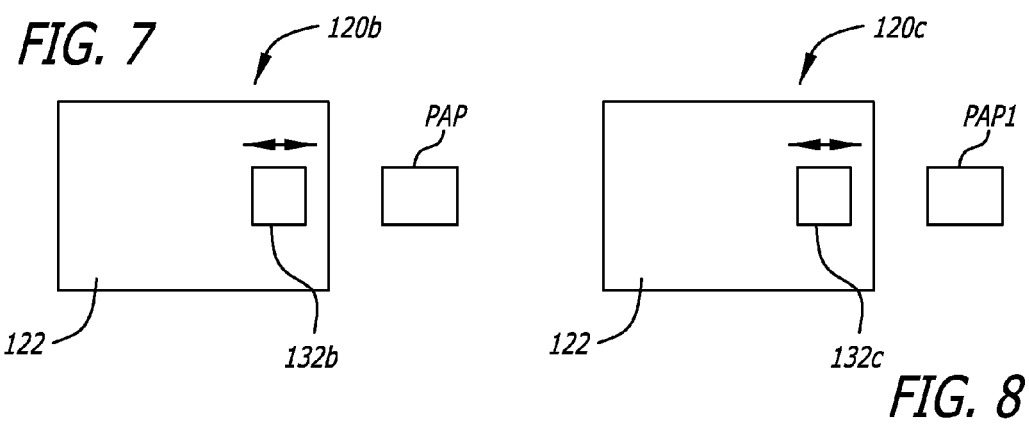
FIG. 7
FIG. 8

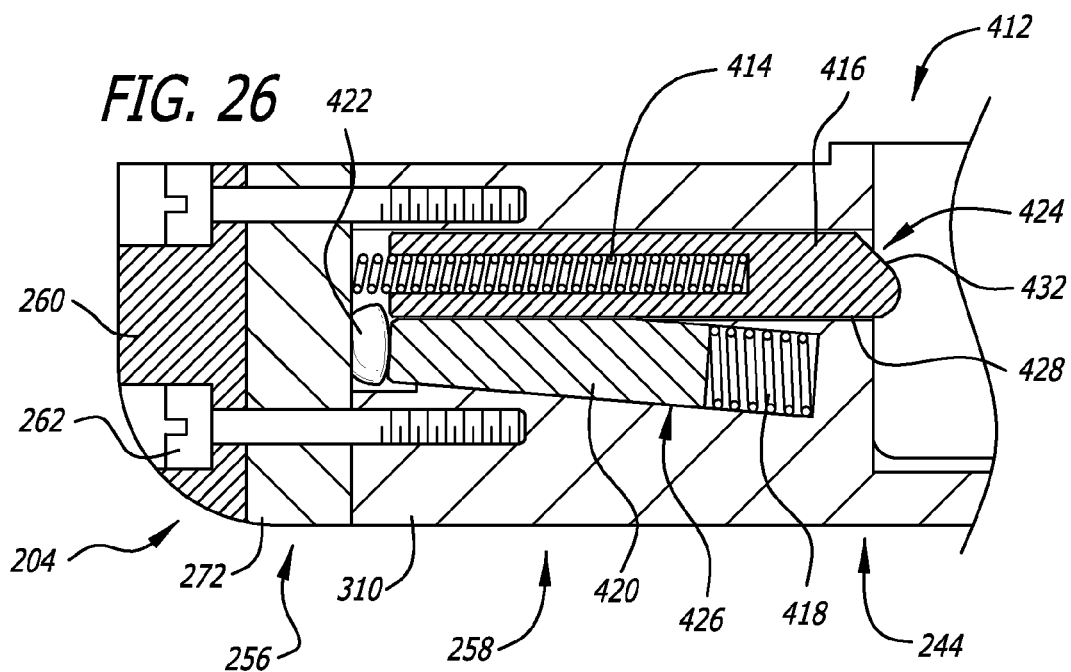
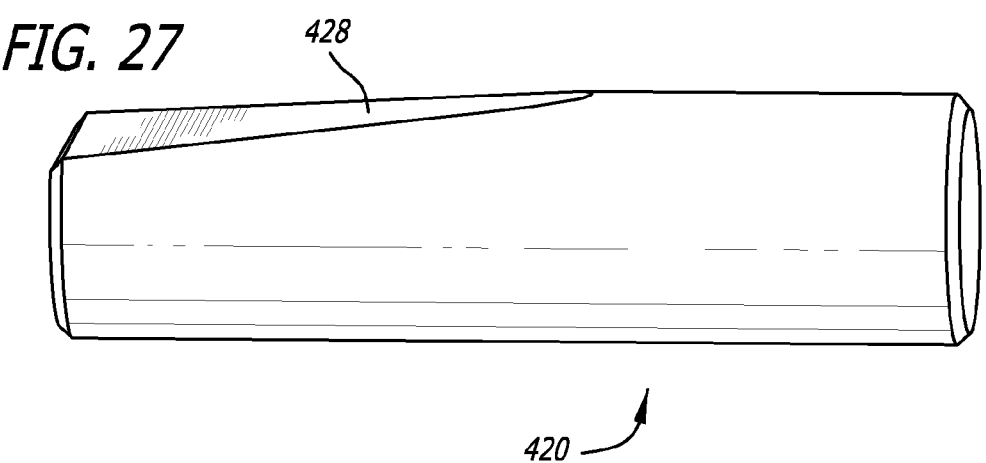

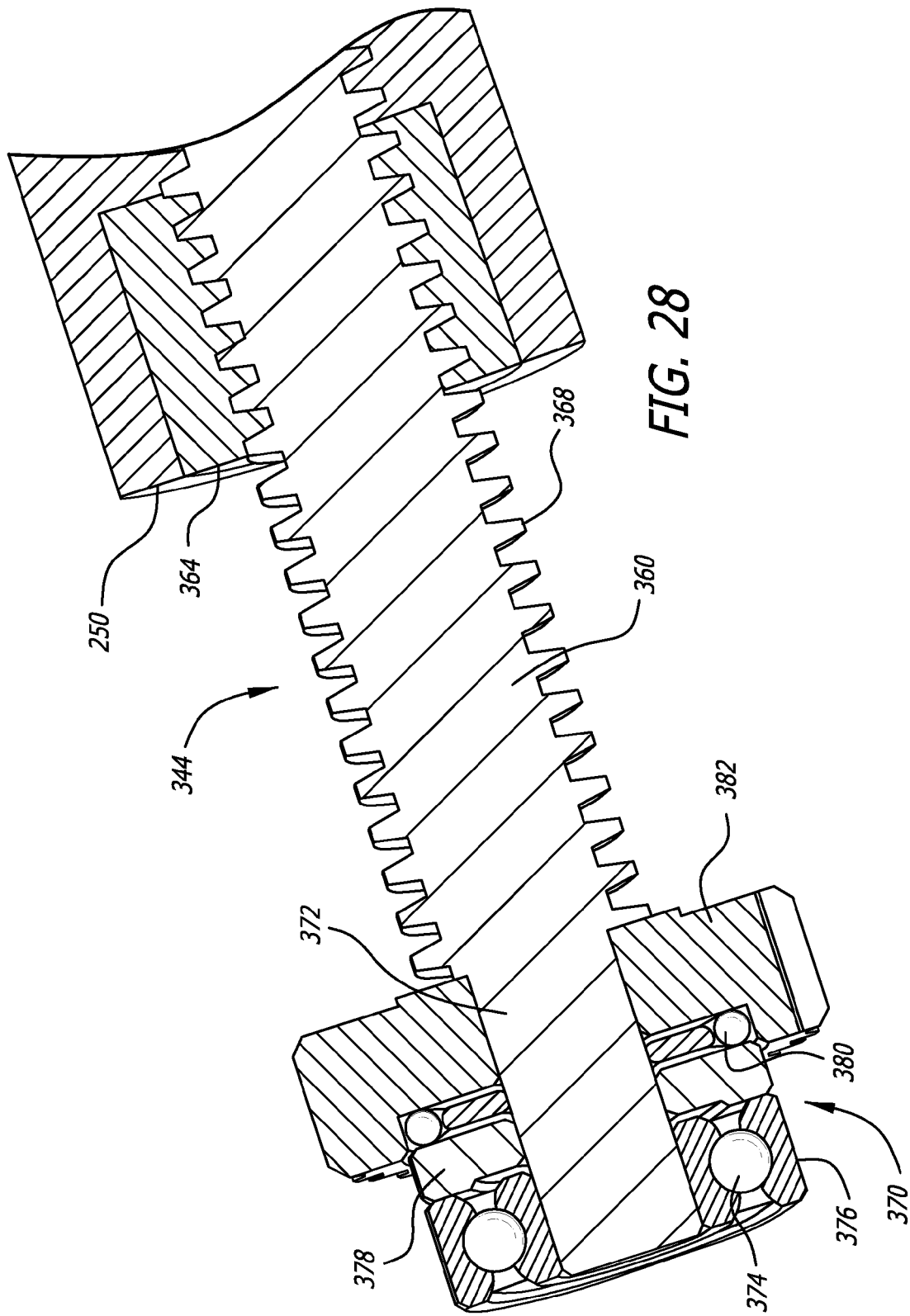

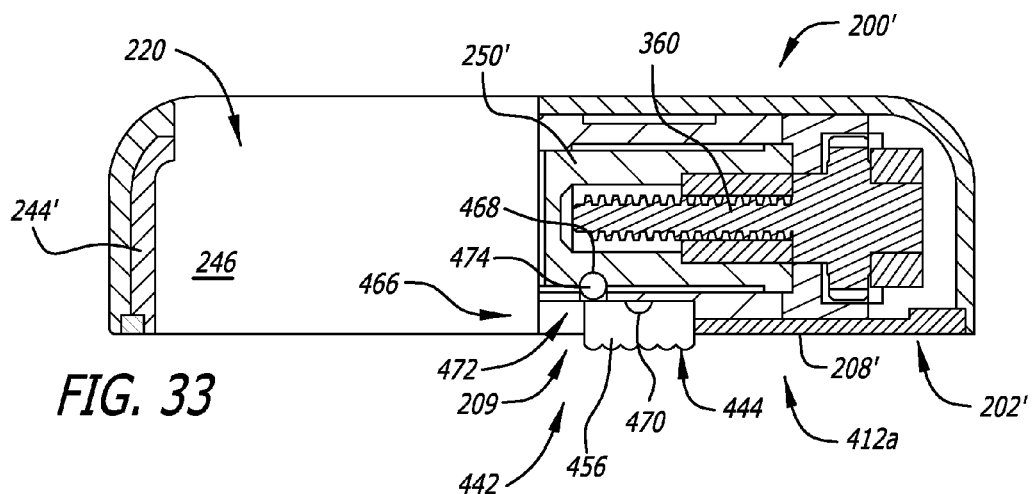
FIG. 33
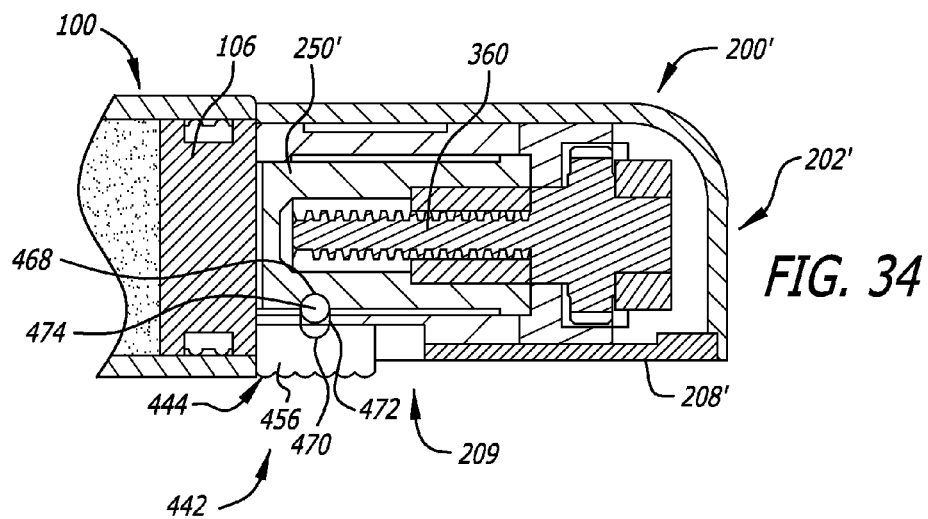
FIG. 34
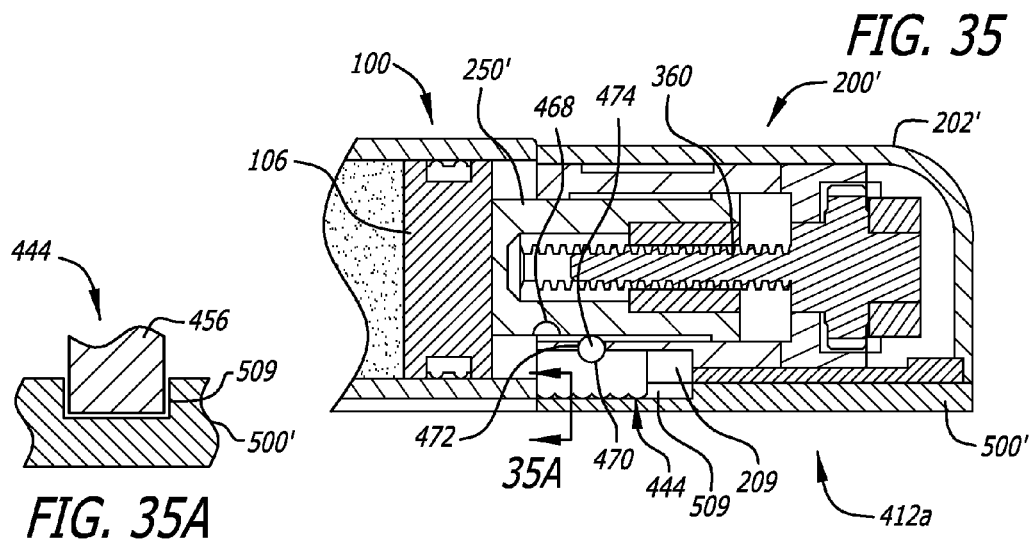
FIG. 35
FIG. 35A

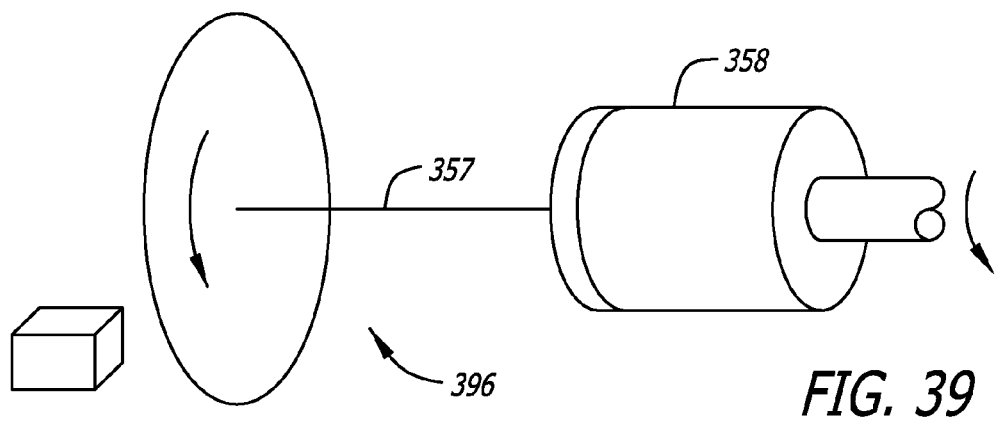
FIG. 39
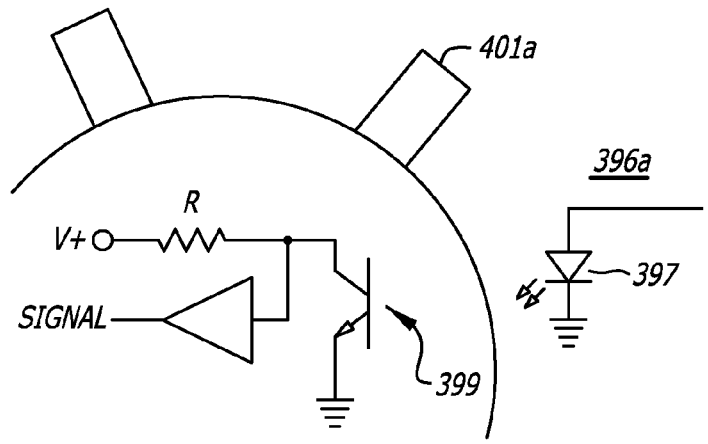
FIG. 40A
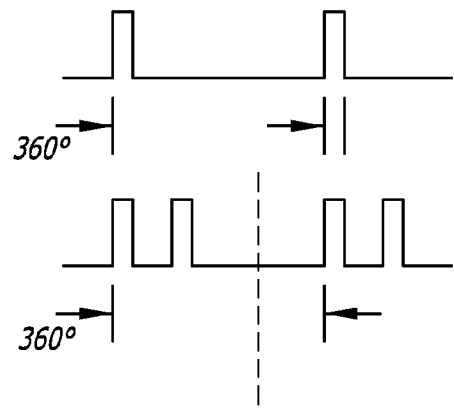

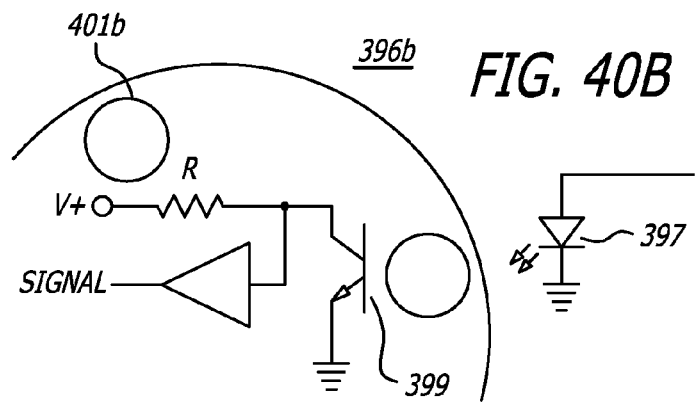
FIG. 40B
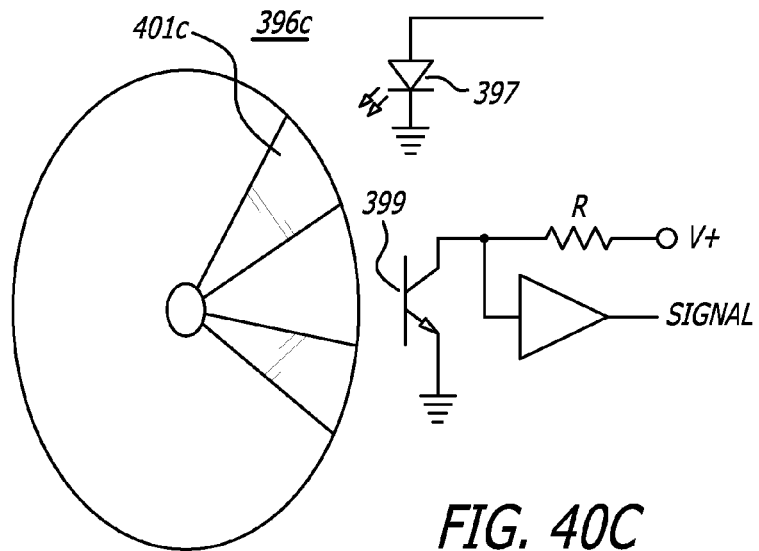
FIG. 40C
FIG. 40D
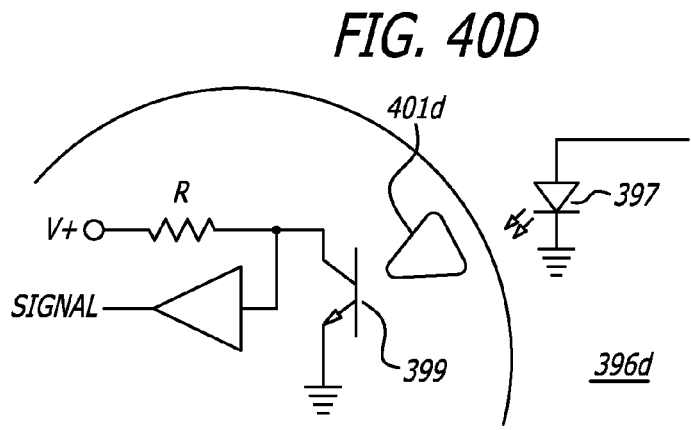

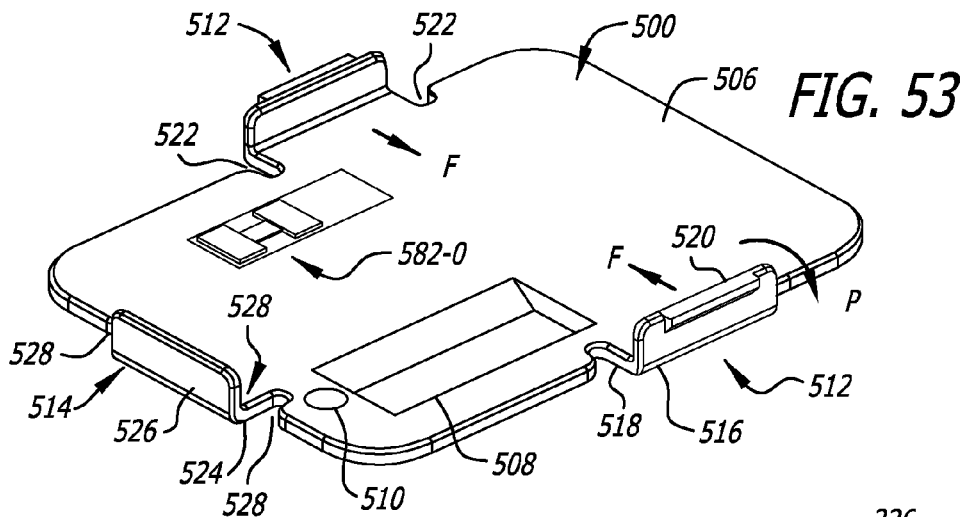
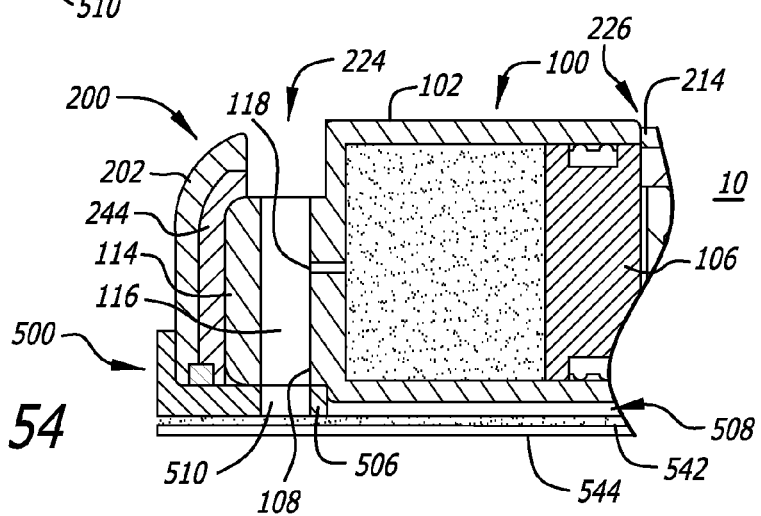
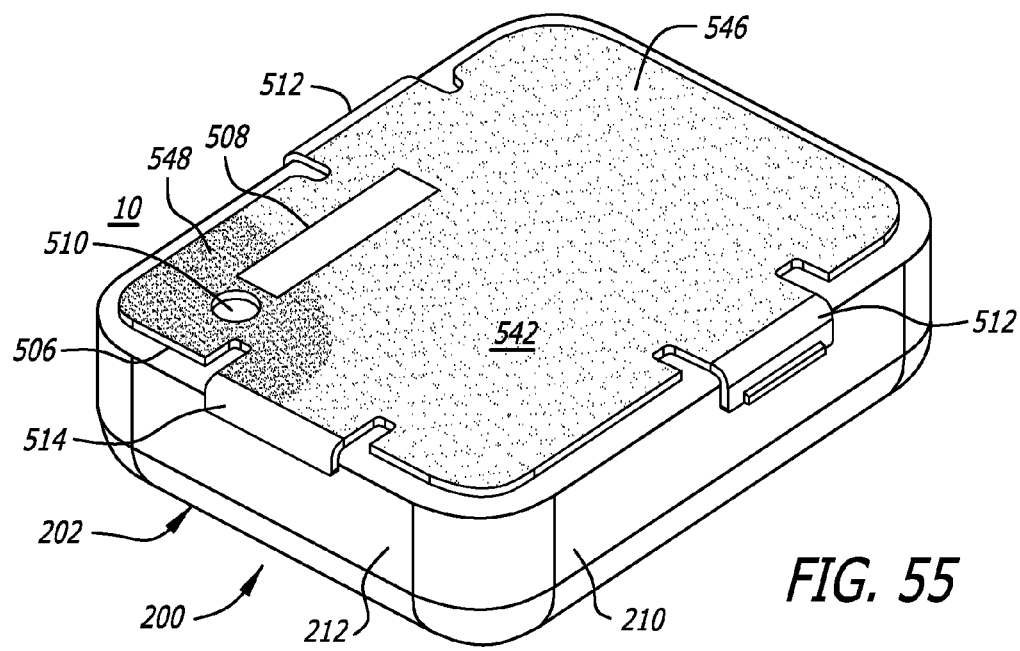

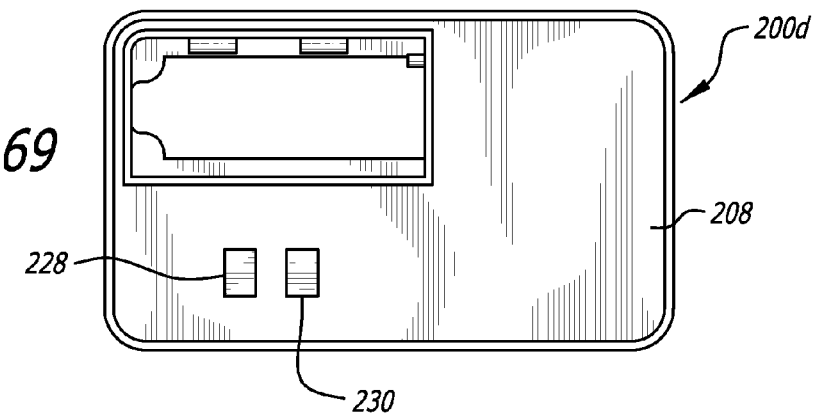
FIG. 69
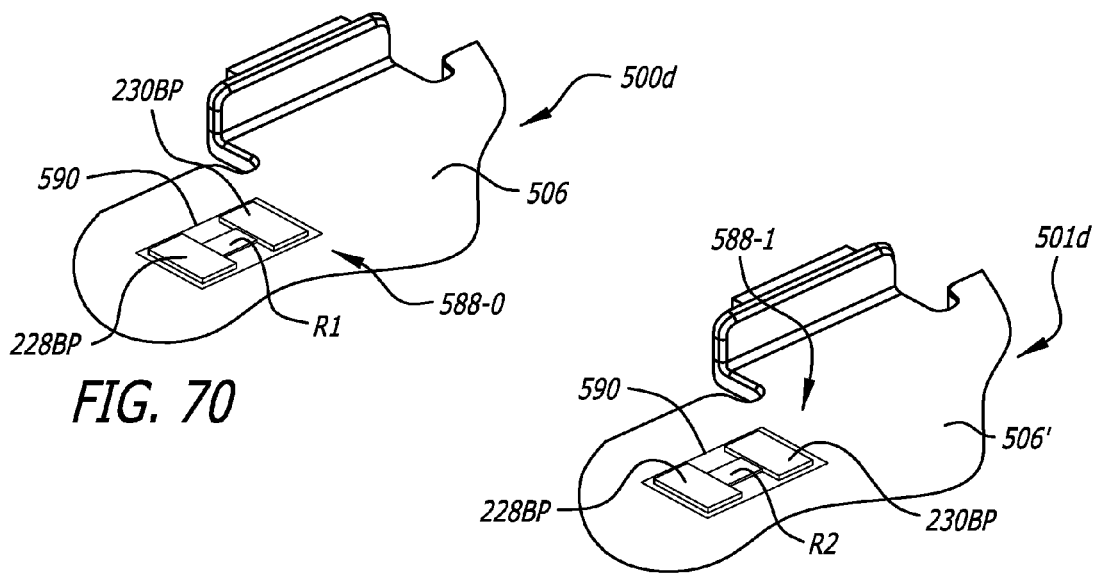
FIG. 70
FIG. 71
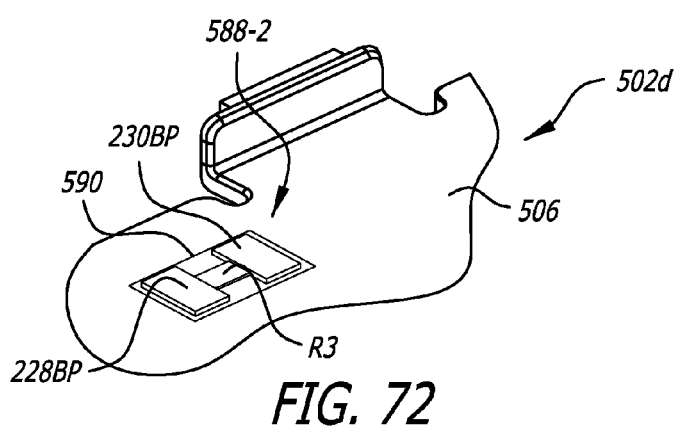
FIG. 72

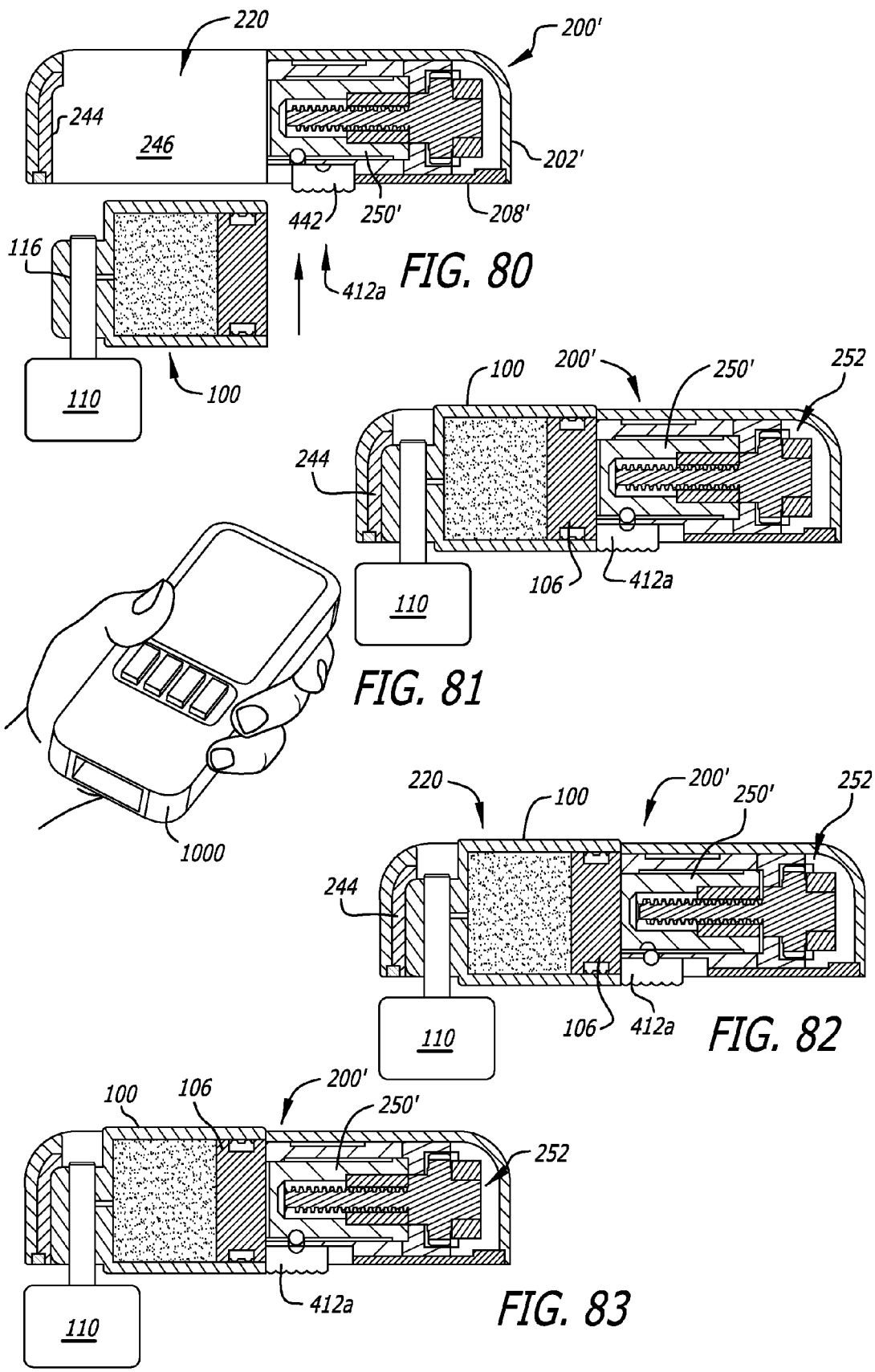

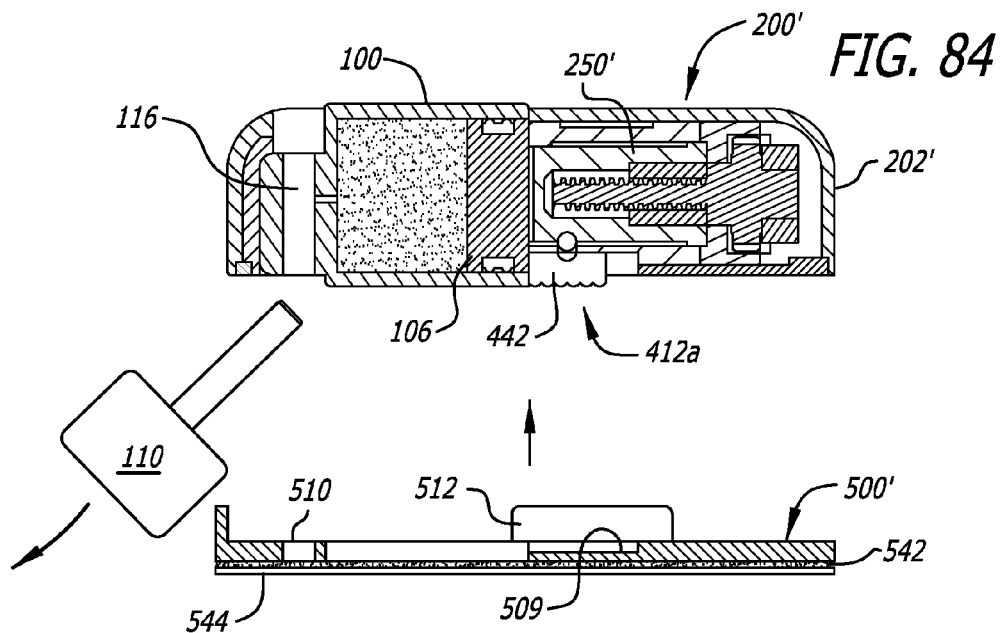
FIG. 84
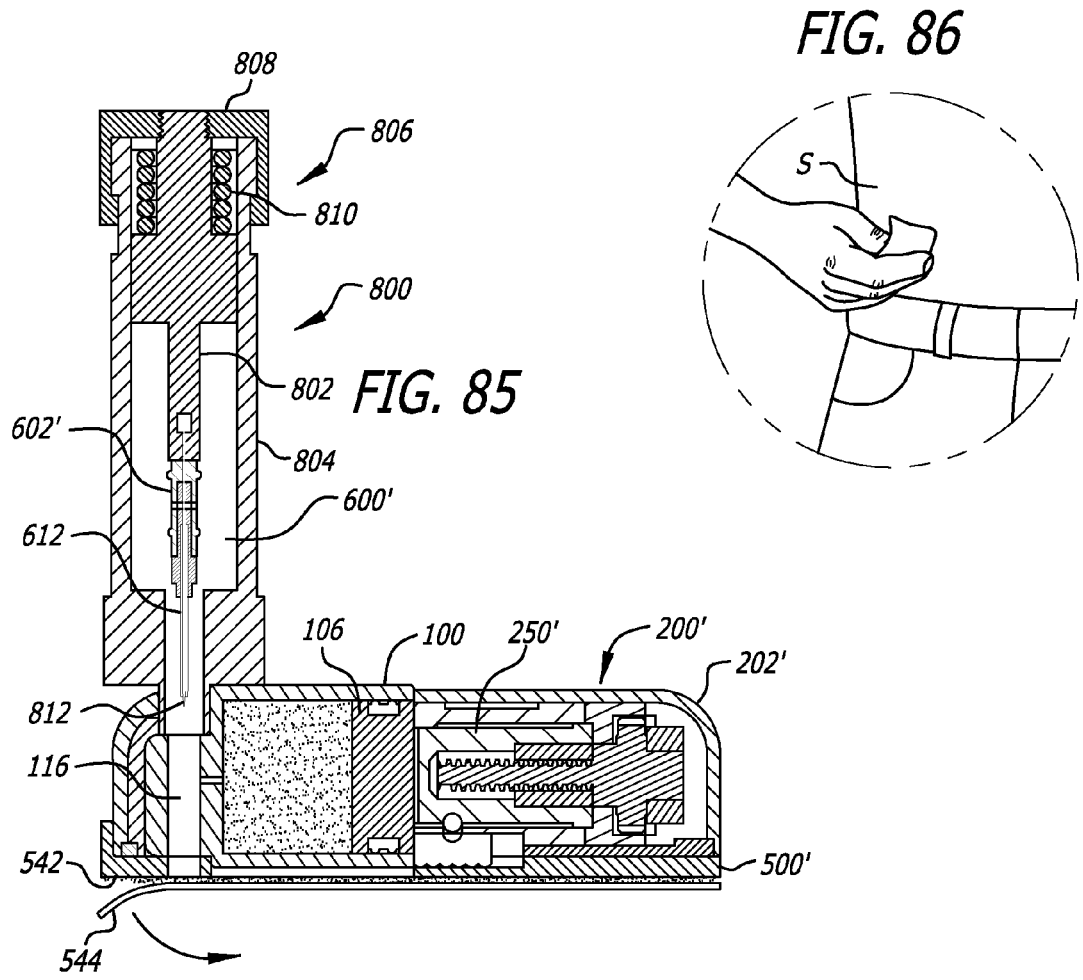
FIG. 85
FIG. 86

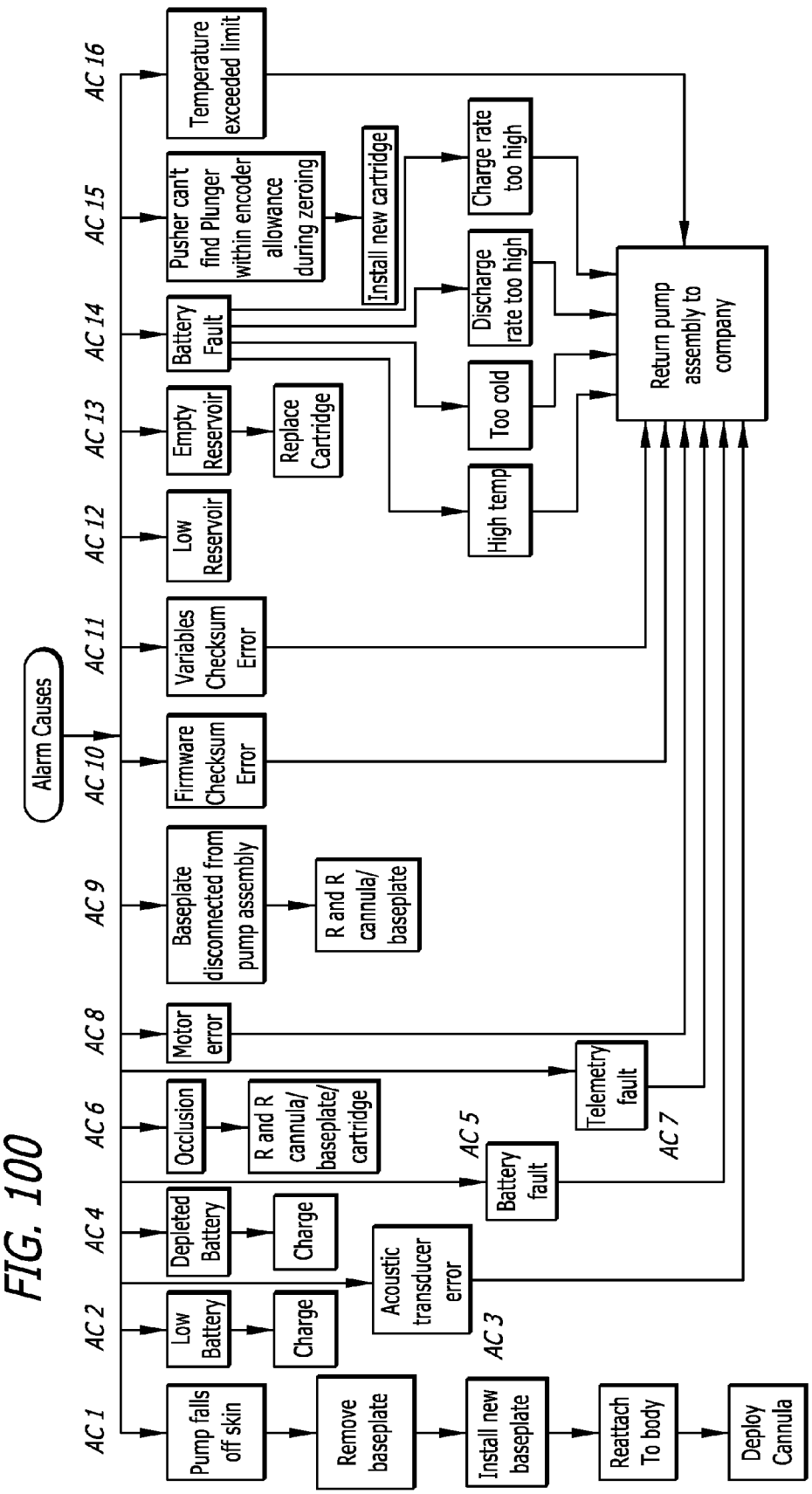

INFUSION PUMPS

BACKGROUND

1. Field

The present devices and methods relate generally to ambulatory infusion pumps.

2. Description of the Related Art

Ambulatory infusion pumps (also referred to herein simply as "infusion pumps") are relatively small, at least substantially self-contained devices that are used to introduce drugs and other infusible substances (collectively "medicament") into patients' bodies. Some infusion pumps are configured to be worn on a belt or carried in a clothing pocket. Other infusion pumps are configured to be adhered to skin in patch-like fashion. Infusion pumps are advantageous in that they may be used to, for example, subcutaneously introduce (or "infuse") medicament on an ongoing or even continuous basis outside of a clinical environment. Infusion pumps are also advantageous in that they greatly reduce the frequency of subcutaneous access events such as needle-based shots. One example of a medicament that may be introduced by an infusion pump is a liquid formulation of insulin, which is a relatively large protein molecule used to treat diabetes mellitus. Other exemplary medicaments that may be introduced by an infusion pump include, but are not limited to, drugs that treat cancers and drugs that suppress the perception of pain.

Many conventional infusion pumps have improved patient health and quality of life. Nevertheless, the present inventors have determined that conventional infusion pumps are susceptible to a wide range of improvements. By way of example, but not limitation, the present inventors have determined that it would be desirable to provide an infusion pump that is smaller, more accurate and/or provides more operational flexibility than conventional infusion pumps.

SUMMARY

A medicament cartridge in accordance with at least one of the present inventions includes a medicament reservoir, that has a total filled volume, and a plunger movable to controllably dispense out of the reservoir an amount of medicament of 0.1% or less of the total filled volume and with a single-dose precision of better than plus or minus 20%. The reservoir may be defined by a cartridge barrel, and/or the precision may be obtained within a dispensing period of less than eight hours. The present inventions also include apparatus that comprise such a cartridge in combination with a pump assembly configured to drive fluid from the cartridge, such a cartridge in combination with a baseplate that can be attached to a pump assembly, and such a cartridge in combination with a cannula that may be in fluid communication with the reservoir, as such pump assemblies, baseplates and cannulas are described in the context of the examples herein, defined by the claims herein or known to those of skill in the art, as well as systems that comprise such a cartridge in combination with two or more of a pump assembly, a baseplate and a cannula.

A method in accordance with at least one of the present inventions includes pushing a plunger so as to controllably dispense out of a medicament reservoir an amount of medicament of 0.1% or less of the total filled volume of the reservoir and with a single-dose precision of better than plus or minus 20%. The precision may be obtained within a dispensing period of less than eight hours.

A medicament cartridge in accordance with at least one of the present inventions includes a barrel and a plunger. The barrel defines at least a substantial portion of a medicament reservoir having an inner surface and an outlet port. The plunger may be located within the barrel, include a plunger body having an outer surface with a pair of outer plunger-body rings that have tight tolerances with the inner surface of the barrel, a circumferential recessed area between plunger-body rings, and an o-ring structure, in the circumferential recessed area and compressed by an inner surface of the barrel, having a pair of spaced circumferential compressible rings. The present inventions also include apparatus that comprise such a cartridge in combination with a pump assembly configured to drive fluid from the cartridge, such a cartridge in combination with a baseplate that can be attached to a pump assembly, and such a cartridge in combination with a cannula that may be in fluid communication with the reservoir, as such pump assemblies, baseplates and cannulas are described in the context of the examples herein, defined by the claims herein or known to those of skill in the art, as well as systems that comprise such a cartridge in combination with two or more of a pump assembly, a baseplate and a cannula.

A medicament cartridge in accordance with at least one of the present inventions includes a barrel defining an inner diameter and a plunger movable over a stroke length. The stroke length to inner diameter ratio may be about 1.0 or less. The present inventions also include apparatus that comprise such a cartridge in combination with a pump assembly configured to drive fluid from the cartridge, such a cartridge in combination with a baseplate that can be attached to a pump assembly, and such a cartridge in combination with a cannula that may be in fluid communication with the reservoir, as such pump assemblies, baseplates and cannulas are described in the context of the examples herein, defined by the claims herein or known to those of skill in the art, as well as systems that comprise such a cartridge in combination with two or more of a pump assembly, a baseplate and a cannula.

A medicament cartridge in accordance with at least one of the present inventions includes a cartridge body defining a medicament reservoir and having an outlet port, a manifold, connected to the cartridge body, having a through-bore in fluid communication with the outlet port. The present inventions also include apparatus that comprise such a cartridge in combination with a pump assembly configured to drive fluid from the cartridge, such a cartridge in combination with a baseplate that can be attached to a pump assembly, and such a cartridge in combination with a cannula that may be in fluid communication with the reservoir, as such pump assemblies, baseplates and cannulas are described in the context of the examples herein, defined by the claims herein or known to those of skill in the art, as well as systems that comprise such a cartridge in combination with two or more of a pump assembly, a baseplate and a cannula.

A system in accordance with at least one of the present inventions includes an infusion pump assembly, a medicament cartridge and a baseplate. The infusion pump assembly may include a housing, a cartridge receiving area in the housing, and a plunger pusher. The medicament cartridge may include a plunger, a through-bore and a medicament reservoir having an outlet port. The baseplate may be configured to be attached to the housing. The infusion pump assembly and the medicament cartridge may be respectively configured such that plunger will be operably aligned with the plunger pusher when the medicament cartridge is positioned in the cartridge receiving area and the baseplate is attached to the housing. The present inventions also include the pump assembly, medicament cartridge and baseplate in the system on an individual basis, as well as any and all pairings thereof.

An infusion pump system in accordance with at least one of the present inventions includes a disposable first portion and a reusable second portion. The disposable first portion includes a medicament reservoir, medicament in the reservoir, and the entire medicament fluid path of the infusion pump system. The reusable second portion includes a motor and is free of any portion of the medicament fluid path. The disposable first portion and the reusable second portion may be respectively configured such that the reusable second portion is positionable in an operative position where operation of the motor causes the medicament to be dispensed out of the medicament reservoir. The present inventions also include the disposable and reusable portions of the system on an individual basis.

An apparatus in accordance with at least one of the present inventions includes a medicament cartridge with a barrel having a reservoir and a plunger, and an infusion pump assembly including a housing with a cartridge receiving area, a plunger pusher and a drive mechanism to drive the plunger pusher. The pusher may be unconnectable to the plunger and incapable of applying a pulling force to the plunger. The present inventions also include the pump assembly and medicament cartridge in the apparatus on an individual basis. The present inventions also include systems that comprise such an apparatus in combination with a baseplate and/or a cannula, as such baseplates and cannulas are described in the context of the examples herein, defined by the claims herein or known to those of skill in the art.

A medicament cartridge in accordance with at least one of the present inventions includes a barrel defining a reservoir and a plunger, located in the barrel, that does not include structure which would allow a pump assembly plunger pusher to pull the plunger. The present inventions also include apparatus that comprise such a cartridge in combination with a pump assembly configured to drive fluid from the cartridge, such a cartridge in combination with a baseplate that can be attached to a pump assembly, and such a cartridge in combination with a cannula that may be in fluid communication with the reservoir, as such pump assemblies, baseplates and cannulas are described in the context of the examples herein, defined by the claims herein or known to those of skill in the art, as well as systems that comprise such a cartridge in combination with two or more of a pump assembly, a baseplate and a cannula.

An infusion pump assembly in accordance with at least one of the present inventions includes a housing including a medicament cartridge storage area, a first face having a medicament cartridge insertion opening, a second face opposite the first face and having a cartridge observation opening, a fluid displacement device associated with the cartridge storage area, and a drive mechanism that drives the fluid displacement device. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

An infusion pump assembly in accordance with at least one of the present inventions includes a pump housing having opposing first and second faces, a plunger pusher and a drive mechanism that moves the plunger pusher bi-directionally along an axis. The first face may have an insertion opening generally normal to the axis through which the medicament cartridge can be inserted into an inserted position. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

An apparatus in accordance with at least one of the present inventions includes an infusion pump assembly and a baseplate. The infusion pump assembly may include a housing having opposing first and second faces, a plunger pusher, and a drive mechanism that moves the plunger pusher along an axis. The first face may have a medicament cartridge insertion opening through which the medicament cartridge can be inserted to an inserted position in the housing and operatively aligned with the plunger pusher. The baseplate may be attachable to the housing so as to at least partially cover the insertion opening with a cartridge in the inserted position. The present inventions also include the pump assembly and baseplate in the apparatus on an individual basis. The present inventions also include systems that comprise such an apparatus in combination with a medicament cartridge and/or a cannula, as such cartridges and cannulas are described in the context of the examples herein, defined by the claims herein or known to those of skill in the art.

A method in accordance with at least one of the present inventions includes the step of inserting a medicament cartridge, which has a medicament reservoir and a plunger, through a pump assembly housing insertion opening in a direction generally perpendicular to the drive axis of the pump assembly plunger pusher to an inserted position where the plunger is operatively aligned with the plunger pusher.

An infusion pump assembly in accordance with at least one of the present inventions includes a housing having a medicament cartridge insertion opening, a chassis defining a medicament cartridge compartment communicating with the insertion opening, and a plunger pusher movable in and out of the medicament cartridge compartment. The insertion opening may be generally normal to a longitudinal axis of the plunger pusher. The present inventions also include apparatus that comprise such a pump assembly in combination with a medicament cartridge having a plunger, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

An infusion pump apparatus in accordance with at least one of the present inventions includes an infusion pump assembly, with a housing and a plunger pusher, and a medicament cartridge. The medicament cartridge may be positionable in the housing in an inserted position and have a cartridge front wall with an outer surface, a medicament reservoir, and a plunger having a dry side. The infusion pump assembly may also have a clamp that clamps the reservoir between the dry side of the plunger and the outer surface of the cartridge front wall. The present inventions also include the pump assembly and medicament cartridge in the apparatus on an individual basis. The present inventions also include systems that comprise such an apparatus in combination with a baseplate and/or a cannula, as such baseplates and cannulas are described in the context of the examples herein, defined by the claims herein or known to those of skill in the art.

An infusion pump apparatus in accordance with at least one of the present inventions includes an infusion pump assembly, with a housing, and a medicament cartridge. The pump assembly housing may have a cartridge receiving area defining a forward corner. The medicament cartridge may have a reservoir and an unpowered part of an occlusion sensor. A powered part of the occlusion sensor may be positioned in the pump assembly housing, outside of the medicament cartridge and proximate to the forward corner of the cartridge receiving area. The infusion pump assembly may also include at least one resilient member positioned to bias the medicament cartridge when in the inserted position into the forward corner of the receiving area. The present inventions also include the pump assembly and medicament cartridge in the apparatus on an individual basis. The present inventions also include systems that comprise such an apparatus in combination with a baseplate and/or a cannula, as such baseplates and cannulas are described in the context of the examples herein, defined by the claims herein or known to those of skill in the art.

An infusion pump assembly in accordance with at least one of the present inventions includes a housing having therein a plunger pusher and a chassis. The chassis defines a forward area and a rear end, and may include first and second side frame members, attached together and forming a cartridge receiving compartment at the forward area of the chassis, and a gear cap attached with at least one fastener to at least one of the first and second side frame members at the rear end of the chassis. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

An infusion pump assembly in accordance with at least one of the present inventions includes a housing with a cartridge insertion opening and a cartridge receiving area communicating with the insertion opening, a rigid wall securely mounted in the cartridge receiving area, a device that engages an aft end of a medicament cartridge and pushes the medicament cartridge against the rigid wall to a held position. A plunger pusher and a plunger pusher drive mechanism may be provided in the housing. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

An infusion pump assembly in accordance with at least one of the present inventions includes a housing having a cartridge receiving area, a plunger pusher and a pusher drive mechanism, and a contact member biased forward so that an end thereof extends into the cartridge receiving area. The contact member, with a cartridge in the cartridge receiving area and the plunger pusher in a non-retracted position, may be blocked from rearward movement relative to the cartridge receiving area and thereby locking the cartridge in the cartridge receiving area. The contact member, with the plunger pusher in a retracted position, may be able to retract relative to the receiving area thereby allowing the cartridge to be inserted into or removed from the inserted position. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

An infusion pump assembly in accordance with at least one of the present inventions includes a housing and an interlock. The housing may have a cartridge receiving area, a plunger pusher and a plunger drive mechanism. The interlock prevents removal of a medicament cartridge from the cartridge receiving area when the cartridge is in the inserted position and the plunger pusher is in a non-retracted position, and allows removal of the medicament cartridge from the cartridge receiving area when the cartridge is in the inserted position and the plunger pusher is a retracted position. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

A method of operating a pump module in accordance with at least one of the present inventions includes the step of causing a cartridge biasing member to change from a blocking condition where the member blocks removal of a medicament cartridge from the pump module, to a release condition where the cartridge biasing member allows the medicament cartridge to be removed from the pump module, in response to a receipt of an instruction from a remote control.

An infusion pump assembly in accordance with at least one of the present inventions includes a housing with a medicament cartridge receiving area, a plunger pusher located in the housing and movable in and out of the cartridge receiving area, and a slidable latch movable between a first position that does not prevent a medicament cartridge from being inserted into and removed from the cartridge receiving area and a second position, when at least a portion of the pusher is in the cartridge receiving area, that prevents removal of the medicament cartridge from the cartridge receiving area. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

An infusion pump assembly in accordance with at least one of the present inventions includes a housing with a medicament cartridge receiving area, a plunger pusher located in the housing and movable between a home position outside the cartridge receiving area and a position within the cartridge receiving area, a drive mechanism, including a motor, operatively connected to the plunger pusher, and a switch. The switch may be located relative to the plunger pusher such that the switch is actuated when the plunger pusher is retracted, from a position where at least a portion of the plunger pusher is within the cartridge receiving area, to a home position. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

An infusion pump assembly in accordance with at least one of the present inventions includes a housing having a cartridge receiving area, a plunger pusher movable in and out of the cartridge receiving area, a pusher drive mechanism including a motor and a controller. The controller may be configured to automatically cause the motor to withdraw the plunger pusher out of the cartridge receiving area (a) after receiving a signal from the encoder indicating that a predetermined number of rotation counts of the motor, which indicate that the reservoir is empty, have occurred or (b) when there is a lack of encoder signals. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

An apparatus in accordance with at least one of the present inventions includes a medicament cartridge and an infusion pump assembly. The medicament cartridge may have a reservoir and a plunger. The infusion pump assembly may include a housing having a cartridge receiving compartment and a plunger pusher defining a longitudinal axis. The plunger pusher may be movable from a home position allowing the medicament cartridge to be inserted into and removed from the cartridge receiving compartment in a direction generally perpendicular to the longitudinal axis of the plunger pusher and another position wherein at least a portion of the plunger pusher is in the medicament cartridge. The present inventions also include the pump assembly and medicament cartridge in the apparatus on an individual basis. The present inventions also include systems that comprise such an apparatus in combination with a baseplate and/or a cannula, as such baseplates and cannulas are described in the context of the examples herein, defined by the claims herein or known to those of skill in the art.

An apparatus in accordance with at least one of the present inventions includes an infusion pump assembly, a medicament cartridge and a latch assembly. The infusion pump assembly may include a housing and a plunger pusher that moves the plunger pusher along a pusher axis. The medicament cartridge may include a barrel, defining a medicament reservoir, and a plunger in the barrel, and be positioned in the housing such that the plunger pusher is positioned to push the plunger. The latch assembly may be configured to block removal of the medicament cartridge from the housing in a direction orthogonal to the pusher axis when at least a portion of the pusher is within the cartridge. The present inventions also include the pump assembly, medicament cartridge and latch assembly in the apparatus on an individual basis. The present inventions also include systems that comprise such an apparatus in combination with a baseplate and/or a cannula, as such baseplates and cannulas are described in the context of the examples herein, defined by the claims herein or known to those of skill in the art.

An apparatus in accordance with at least one of the present inventions includes an infusion pump assembly with a housing having a cartridge receiving area, a baseplate that is attachable to the housing and has an opening and bottom surface adhesive, a movable member, and an alarm. The movable member may be pushed to a first position by the user's skin when the baseplate is adhered to the user's skin by the adhesive and may be biased to a second position extended out the opening in the baseplate when the baseplate is separated from the user's skin after attachment thereto. The alarm may be activated in response to the movable member moving to the second position. The present inventions also include the various components in the apparatus on an individual basis, as well as any and all combinations thereof. The present inventions also include systems that comprise such an apparatus in combination with a medicament cartridge and/or a cannula, as such cartridges and cannulas are described in the context of the examples herein, defined by the claims herein or known to those of skill in the art.

An apparatus in accordance with at least one of the present inventions includes an infusion pump assembly with a housing having a cartridge receiving area, a controller, an alarm, a baseplate that is attachable to the housing and has bottom surface adhesive, and an RF circuit. The RF circuit may include a transmitting antenna and a receiving antenna, and be configured to send a signal to the controller, indicating that the baseplate has become separated from the user's skin. The controller may activate the alarm in response. The present inventions also include the various components in the apparatus on an individual basis, as well as any and all combinations thereof. The present inventions also include systems that comprise such an apparatus in combination with a medicament cartridge and/or a cannula, as such cartridges and cannulas are described in the context of the examples herein, defined by the claims herein or known to those of skill in the art.

An apparatus in accordance with at least one of the present inventions includes an infusion pump assembly with a housing having a cartridge receiving area, a controller, an alarm, a baseplate that is attachable to the housing and has bottom surface adhesive, and an electrical circuit. The electrical circuit may include a first terminal and a second terminal spaced from the first terminal, be configured to be completed between the first and second terminals by the user's skin when the baseplate is adhered to the skin by the adhesive, to be broken when the baseplate becomes separated from the user's skin, and to send a signal to the controller when the baseplate has become separated from the user's skin. The controller may activate the alarm in response. The present inventions also include the various components in the apparatus on an individual basis, as well as any and all combinations thereof. The present inventions also include systems that comprise such an apparatus in combination with a medicament cartridge and/or a cannula, as such cartridges and cannulas are described in the context of the examples herein, defined by the claims herein or known to those of skill in the art.

An infusion pump assembly in accordance with at least one of the present inventions includes a housing having a cartridge compartment, a fluid displacement device, and a rechargeable battery, adapted to drive the fluid displacement device, mounted in the housing outside of the cartridge compartment. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

A method in accordance with at least one of the present inventions may include the steps of removing, from an assembled device that includes an infusion pump assembly with a medicament cartridge therein and a baseplate secured to the pump assembly housing, the pump assembly housing from the baseplate, connecting the recharging terminals on the pump assembly to a recharging device, and recharging the rechargeable battery in the housing.

A system in accordance with at least one of the present inventions includes a baseplate, a cannula, a pump assembly, a battery recharging unit, and a controller. The pump assembly may include a housing, a medicament reservoir, a fluid displacement device, and a rechargeable battery for the fluid displacement device in the housing. The housing may be separable from the baseplate and cannula with the cannula remaining secured to and extending out from the baseplate such that the housing is in a separate condition. The housing, in the separate condition, may be operatively connected to the battery recharging unit such that the recharging of the battery by the recharging unit is controlled by the controller. The present inventions also include the various components in the system on an individual basis, as well as any and all combinations thereof.

An infusion pump assembly in accordance with at least one of the present inventions includes a housing with a cartridge receiving area, a plunger pusher, a stepper motor, having a shaft and coils, operatively connected to the plunger pusher, an encoder, operably connected to the motor shaft, that generates encoder output representative of shaft position, a battery operatively connected to the motor, an analog-to-digital (A/D) converter that generates A/D converter output that is a digital representation of battery voltage, and a controller. The controller may (a) operate through a driver circuit to control the operation of the motor and to pulse-width modulate energy from the battery applied to the motor coils, (b) read the encoder output and (c) read the A/D converter output. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

An infusion pump assembly in accordance with at least one of the present inventions includes a housing, having a medicament cartridge receiving area, a fluid displacement device, a drive mechanism that drives the fluid displacement device, a receiving area sensor that senses when the cartridge sensor element is in a predetermined location within the cartridge receiving area, and a controller operably connected to the sensor and drive mechanism. The controller may be configured to prevent the drive mechanism from driving the fluid displacement device unless the receiving area sensor senses that the cartridge sensor element is in the predetermined location. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

An infusion pump assembly in accordance with at least one of the present inventions includes a housing, a plunger pusher, a medicament reservoir, a plunger, a drive mechanism that drives the plunger pusher and has a stepper motor and an encoder, and a controller. The controller may be configured to cause the motor to propel the pusher against the plunger according to a medicament dispensing program having a plurality of dispensing operations and to, for at least one of the dispensing operations, cause the motor to stop from a pusher propelling velocity by slowly decreasing the frequency of the waveform delivered to the motor to maintain constant positive control of the motor and thereby to precisely control how many turns the motor makes and thus the precise distance the pusher advances before stopping. Such precise distance control results in accurate controlled medicament dispensing from the reservoir. The present inventions also include systems that comprise such an apparatus in combination with a baseplate and/or a cannula, as such baseplates and cannulas are described in the context of the examples herein, defined by the claims herein or known to those of skill in the art.

A method in accordance with at least one of the present inventions includes the steps of propelling a plunger pusher relative to the plunger of a medicament cartridge with a motor, and controlling motor torque such that the torque is continuously within a range having a lower limit that is sufficient to overcome stiction of the cartridge plunger and move the plunger and an upper limit that is low enough so as to not cause leakage past plunger seals due to excessive pressure in the cartridge reservoir.

A system in accordance with at least one of the present inventions includes a medicament cartridge, an infusion pump assembly, a baseplate, and a cannula. The medicament cartridge may have a medicament reservoir and a manifold connected to the medicament reservoir and having a through-bore. The infusion pump assembly may be configured to receive the medicament cartridge. The baseplate may have a baseplate opening and bottom surface adhesive, and be configured to be secured to the infusion pump assembly. The cannula may be dimensioned to be inserted through the through-bore and the baseplate opening, when the medicament cartridge in place in the infusion pump assembly and the baseplate attached to the infusion pump assembly, to an inserted position. The baseplate and the cannula may be respectively configured such that the baseplate and the cannula will be secured to one another when the cannula reaches the inserted position and will remain secured to one another when the infusion pump assembly is subsequently removed from the baseplate. The present inventions also include the pump assembly, medicament cartridge, baseplate and cannula in the system on an individual basis, as well as any and all pairings thereof.

A system in accordance with at least one of the present inventions includes a medicament cartridge having a reservoir and a manifold through-bore, a pump assembly including a medicament cartridge receiving area, a bottom surface, and a bottom surface opening, and a baseplate, having a baseplate opening, configured to be secured to the pump assembly. The medicament cartridge, pump assembly and baseplate may be respectively configured such that when the baseplate is secured to the pump assembly with the medicament cartridge in the cartridge receiving area, the baseplate will be over the bottom surface opening and the baseplate opening will be aligned with the manifold through-bore. The cannula may be dimensioned to be inserted into the manifold through-bore and the baseplate opening. The present inventions also include the pump assembly, medicament cartridge, baseplate and cannula in the system on an individual basis, as well as any and all pairings thereof.

An infusion pump cannula in accordance with at least one of the present inventions includes a cannula head having a bottom opening, a side opening, a medicament fluid path between the side and bottom openings, an upper sealing device above the side opening and a lower sealing device below the side opening, and a cannula tube connected to the cannula head and in fluid communication with the medicament fluid path. The cannula head and/or the cannula may be configured to secure the infusion pump cannula to the opening in an infusion pump baseplate. The present inventions also include apparatus that comprise such a cannula in combination with a pump assembly configured to drive fluid from a cartridge, such a cannula in combination with a baseplate that can be attached to a pump assembly, and such a cannula in combination with a cartridge, as such pump assemblies, baseplates and cartridges are described in the context of the examples herein, defined by the claims herein or known to those of skill in the art, as well as systems that comprise such a cannula in combination with two or more of a pump assembly, a baseplate and a cartridge.

An apparatus in accordance with at least one of the present inventions includes an infusion pump assembly and a baseplate. The infusion pump assembly may include a housing having a cartridge receiving area, a bottom opening, and housing electrical contacts. The infusion pump assembly may also include a fluid displacement device, a drive mechanism that drives the fluid displacement device, and a slidable latch associated with the housing. The slidable latch may be movable between a unlatched position that does not prevent the medicament cartridge from being inserted into and removed from the cartridge receiving area and a latched position that prevents removal of the medicament cartridge from the cartridge receiving area, and have a protruding portion. The baseplate may be configured to at least partially cover the housing bottom opening, and may have an upper surface, a recessed area on the upper surface, and baseplate electrical contacts. The infusion pump assembly and baseplate may be respectively configured such that (1) the baseplate and housing may be attachable to one another with the baseplate electrical contacts in electrical contact with the housing electrical contacts and (2) the baseplate and housing can only be attached to one another when the slidable latch is in the latched position and the protruding portion mates with the recessed area. The present inventions also include the pump assembly and baseplate in the apparatus on an individual basis. The present inventions also include systems that comprise such an apparatus in combination with a medicament cartridge and/or a cannula, as such cartridges and cannulas are described in the context of the examples herein, defined by the claims herein or known to those of skill in the art.

An apparatus in accordance with at least one of the present inventions includes an infusion pump assembly and a baseplate. The infusion pump assembly may include a housing having a medicament cartridge receiving area, a fluid displacement device in the housing, and a drive mechanism operably connected to the fluid displacement device. The baseplate may be attachable to the housing, define a bottom surface and a cannula opening, and include a first adhesive on the bottom surface adjacent to an opening for a cannula and a second adhesive on the bottom surface and spaced a distance away from the opening, the first adhesive being an adhesive that adheres more aggressively to human skin than the second adhesive. The present inventions also include the pump assembly and baseplate in the apparatus on an individual basis. The present inventions also include systems that comprise such an apparatus in combination with a medicament cartridge and/or a cannula, as such cartridges and cannulas are described in the context of the examples herein, defined by the claims herein or known to those of skill in the art.

An apparatus in accordance with at least one of the present inventions includes an infusion pump assembly and a baseplate. The infusion pump assembly may include a housing, having a cartridge receiving area, a fluid displacement device, and a fluid displacement device drive mechanism. The baseplate may include a plate member having a top opening, an edge opening and a baseplate fluid path between the top opening and the edge opening, a tubing at the edge opening and communicating with an end of the fluid path, and a connector having an opening in the cartridge receiving area that defines at least a portion of a fluid path between the cartridge receiving area and the baseplate fluid path. The present inventions also include the pump assembly and baseplate in the apparatus on an individual basis. The present inventions also include systems that comprise such an apparatus in combination with a medicament cartridge and/or a cannula, as such cartridges and cannulas are described in the context of the examples herein, defined by the claims herein or known to those of skill in the art.

A method in accordance with at least one of the present inventions includes making a baseplate type determination with the controller based on the baseplate identification device and controlling the fluid displacement device with the controller based at least in part on the determined baseplate type.

A system in accordance with at least one of the present inventions includes a housing, a fluid displacement device and drive mechanism in the housing, a rechargeable battery in the housing and adapted to power the drive mechanism, a pair of contacts operatively connected to the rechargeable battery and supported by the housing, and a controller. The controller may determine from a detected resistor value whether the pair of contacts is operatively connected to terminals of a first baseplate having a first resistor value or to terminals of a second baseplate having a second resistor value. The controller may also operate the drive mechanism in a first mode associated with the first baseplate in response to a first baseplate determination and operate the drive mechanism is a second mode associated with the second baseplate in response to a second baseplate determination. The present inventions also include systems that also include a medicament cartridge and/or a cannula, as such cartridges and cannulas are described in the context of the examples herein, defined by the claims herein or known to those of skill in the art.

A kit in accordance with at least one of the present inventions includes a first baseplate, a second baseplate, and an infusion pump assembly. The first baseplate may have a first baseplate pattern of targets, and the second baseplate may have a second baseplate pattern of targets that is different than the first pattern. The infusion pump assembly may include an emitter/detector configured to detect the first and second baseplate patterns and a controller configured to determine, based on a detected baseplate pattern, which of the first and second baseplates is attached to the housing. The controller may also be configured to operate in a first mode when the first baseplate is attached to the housing, and to operate in a second mode, which is different than the first mode, when the second baseplate is attached to the housing. The targets may be, in some implementations, reflective and/or occluded targets. The present inventions also include the pump assembly and baseplate sets of the kit on an individual basis. The present inventions also include a kit that comprises a baseplate set and a medicament cartridge. The present inventions also include systems that comprise such a kit in combination with a medicament cartridge and/or a cannula, as such cartridges and cannulas are described in the context of the examples herein, defined by the claims herein or known to those of skill in the art.

A kit in accordance with at least one of the present inventions includes a first baseplate, a second baseplate, and an infusion pump assembly. The first baseplate may have a first baseplate identification device, and the second baseplate may have a second baseplate identification device. The infusion pump assembly may include a connector assembly that operatively connects to an identification device on a baseplate that is secured to the housing. The controller may be configured to determine, based on a detected baseplate identification device, which one of the first and second baseplates is attached to the housing. The present inventions also include the pump assembly and baseplate sets of the kit on an individual basis. The present inventions also include a kit that comprises a baseplate set and a medicament cartridge. The present inventions also include systems that comprise such a kit in combination with a medicament cartridge and/or a cannula, as such cartridges and cannulas are described in the context of the examples herein, defined by the claims herein or known to those of skill in the art.

A system in accordance with at least one of the present inventions includes a medicament cartridge, an infusion pump assembly, a baseplate, and a cannula. The medicament cartridge, infusion pump assembly, baseplate and cannula may be respectively configured such that, when the medicament cartridge is in the pump assembly cartridge receiving area and the baseplate is attached to the pump assembly housing, the cannula can be inserted through a cartridge through-bore and a baseplate opening and connected to the baseplate, thereby defining a baseplate-cartridge-cannula unit. The medicament cartridge, infusion pump assembly, baseplate and cannula may also be configured such that, when the pump assembly pusher is in the home position and a latch is in the non-blocking position, the infusion pump assembly is separable from the baseplate-cartridge-cannula unit. The present inventions also include the pump assembly, medicament cartridge and baseplate in the system on an individual basis, as well as any and all pairings thereof.

A method in accordance with at least one of the present inventions includes the step of arranging a medicament cartridge, infusion pump assembly, baseplate and cannula into an assembled system where at least the medicament cartridge and the cannula define a medicament dispensing flow path unit, and removing the infusion pump assembly from the medicament dispensing flow path unit.

An apparatus in accordance with at least one of the present inventions includes a medicament cartridge and an infusion pump assembly. The medicament cartridge may include a medicament reservoir, a plunger and an outlet port. The infusion pump assembly may include a housing having a cartridge receiving area, a plunger pusher, a drive mechanism, that drives the plunger pusher and has a motor, a lead screw, a gear assembly operatively positioned between the motor and the lead screw, and an encoder, and a controller. The medicament cartridge may be insertable through an opening in the housing and into the cartridge receiving area to an inserted position where the plunger is proximate to but spaced from the plunger pusher. The controller may be configured to execute, with the medicament cartridge in the inserted position, a plunger pusher zeroing procedure including causing the motor to advance the plunger pusher to contact the plunger and then to back the plunger pusher off a predetermined distance from the plunger. The present inventions also include the pump assembly and medicament cartridge in the apparatus on an individual basis. The present inventions also include systems that comprise such an apparatus in combination with a baseplate and/or a cannula, as such baseplates and cannulas are described in the context of the examples herein, defined by the claims herein or known to those of skill in the art.

An apparatus in accordance with at least one of the present inventions includes a medicament cartridge and an infusion pump assembly. The medicament cartridge may include a medicament reservoir, a plunger, an outlet port, a removable seal positioned at the outlet port, The infusion pump assembly may include a housing with a cartridge receiving area, a plunger pusher, and a drive mechanism. The medicament cartridge may be inserted through an opening in the housing with the seal in a sealed position and into the cartridge receiving area to an inserted position where the plunger proximate to but spaced a small distance from the plunger pusher. The present inventions also include the pump assembly and medicament cartridge in the apparatus on an individual basis. The present inventions also include systems that comprise such an apparatus in combination with a baseplate and/or a cannula, as such baseplates and cannulas are described in the context of the examples herein, defined by the claims herein or known to those of skill in the art.

An infusion pump method in accordance with at least one of the present inventions, which may be associated with an infusion pump assembly including a plunger pusher and a medicament cartridge including a reservoir and a plunger that has a dry side and an outlet port, includes the steps of propelling the plunger pusher such that the plunger pusher contacts the dry side of a plunger while the plunger outlet port is sealed and, in response to sensing that the plunger pusher has contacted the plunger, reversing the drive direction of the motor to withdraw the plunger pusher a predetermined distance from the dry side of the plunger as part of a plunger pusher zeroing procedure.

An infusion pump assembly in accordance with at least one of the present inventions includes a housing, having a cartridge receiving area, a plunger pusher, a motor to drive the plunger pusher, an encoder associated with the motor, and a controller. The controller may be configured to control the operation of the motor and to adjust a medicament dispensing program to compensate for the amount of reverse rotation of the motor that occurs when electrical power is not being delivered to the motor and the controller receives a signal from the encoder that the controller interprets as a reverse motor rotation signal. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

An infusion pump assembly in accordance with at least one of the present inventions includes a housing, a plunger pusher, a drive mechanism, with a motor and an encoder, to drive the plunger pusher, and a controller. The controller may store a medicament dispensing program and be configured to determine from signals from the encoder, when the motor is not being electrically driven, whether the motor is rotating in reverse and to adjust the medicament dispensing program to take into account the amount of reverse rotation. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

An infusion pump assembly in accordance with at least one of the present inventions includes a housing having a cartridge receiving area, a plunger pusher, a drive mechanism, with a motor and a gear assembly, that drives the plunger pusher, and a controller. The controller may be configured to detect operation errors of the motor and/or gear assembly and/or to detect reverse turning of the motor when not receiving electrical power. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

A method in accordance with at least one of the present inventions includes the steps of dispensing medicament from an infusion pump assembly reservoir in accordance with a medicament dispensing program and adjusting the medicament dispensing program to compensate for an amount of reverse rotation of the infusion pump assembly motor that occurs when electrical power is not being delivered to the motor.

An infusion pump assembly in accordance with at least one of the present inventions includes a housing, having cartridge receiving area, a plunger pusher, a pusher drive mechanism with a motor, a lead screw, a gear assembly operatively between the lead screw and the motor, and an encoder, and a controller operably connected to the motor. The controller may be configured to (1) cause the motor to be powered at a predetermined dispensing torque level and (2) determine that the gear assembly is not operating properly, when the cartridge is not in the receiving area, in response to receipt of at least one signal from the encoder indicating that the motor is turning when the motor is being powered to run at a low torque level that is below the predetermined dispensing torque level. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

An infusion pump assembly in accordance with at least one of the present inventions includes a housing, having a cartridge receiving area, a plunger pusher, a drive mechanism, including a motor, that drives the plunger pusher, and a controller that controls the operation of the motor. The controller may be configured to automatically withdraw the pusher to a home position in response to a receipt of a signal indicating that the medicament reservoir is empty. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

A method in accordance with at least one of the present inventions includes the steps of pushing the plunger of a medicament cartridge located in an infusion pump assembly with a plunger pusher such that a portion of the plunger pusher is within the medicament cartridge, and withdrawing the plunger pusher from within the medicament cartridge, without instruction from the user to do so, in response to a determination by the infusion pump assembly that the medicament cartridge is empty.

An infusion pump assembly in accordance with at least one of the present inventions includes a housing configured to receive a medicament cartridge, a plunger pusher, a pusher drive mechanism with a motor, a lead screw, a gear assembly, and an encoder, and a controller. The controller may be configured to execute a gear assembly verification procedure including the following procedure parts: (a) delivering motor driving sequence of pulses to the motor instructing torque to be applied in a rewind direction to the motor at less than 70% of a torque applied for normal delivery in a forward direction and thereby rotating the motor, (b) determining that the gear assembly is not operating properly if signals from the encoder indicate that the motor is approximately synchronized with the motor driving sequence of pulses, and (c) determining that the gear assembly is operating properly if signals from the encoder indicate that the motor is not synchronized with the motor driving sequence of pulses. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

An infusion pump assembly in accordance with at least one of the present inventions includes a housing, a plunger pusher, a drive mechanism and alarm. The pump assembly may be configured such that the alarm will be activated when one, all, or any combination of less than all of the following conditions is met: (1) no baseplate is attached to the housing, (2) a baseplate attached to the housing becomes separated from the skin of a user, (3) the plunger pusher does not contact the dry side of a reservoir plunger after advancing a predetermined distance or a range of predetermined distances corresponding to an expected location of the dry side of the plunger in a pusher zeroing procedure, (4) a temperature in the housing exceeds a predetermined temperature, (5) motor current is too low, and (6) the battery has a charging fault. The present inventions also include apparatus that comprise such a pump assembly in combination with a medicament cartridge, such a pump assembly in combination with a baseplate that can be attached thereto, and such a pump assembly in combination with a cannula, as such cartridges, baseplates and cannulas are described in the context of the examples herein, defined by the claims herein or known to those of skill in the art, as well as systems that comprise such a pump assembly in combination with two or more of a medicament cartridge, a baseplate and a cannula.

An apparatus in accordance with at least one of the present inventions includes an infusion pump assembly and a remote control. The infusion pump assembly may include a controller that stores medicament dispensing program information, determines time remaining in the dispensing program based at least in part on the medicament dispensing program information and encoder signals, and generates a time remaining signal. Alternatively, or in addition, the controller may be configured to determine the amount of time remaining until the pump assembly battery will require recharging and generate a time remaining signal. The remote control may include a user interface, be operably connected to the pump assembly controller, and be configured to generate an indicator detectable by a user which indicates the time remaining in the medicament dispensing program and/or the time remaining until the pump assembly battery will require recharging. The present inventions also include the pump assembly and remote control in the apparatus on an individual basis. The present inventions also include systems that comprise such an apparatus in combination with a medicament cartridge and/or a cannula and/or a baseplate, as such cartridges, cannulas and baseplates are described in the context of the examples herein, defined by the claims herein or known to those of skill in the art.

A method in accordance with at least one of the present inventions includes the steps of learning from a remote control the amount of time remaining in a subcutaneous dispensing program and/or time remaining until a pump assembly battery will require recharging, determining whether or not removing a medicament cartridge from the associated infusion pump and replacing the removed medicament cartridge with a new medicament cartridge at the end of the time remaining would be convenient or inconvenient and/or determining whether or not recharging the pump assembly battery at the end of the time remaining would be convenient or inconvenient, and replacing the medicament cartridge before the medicament cartridge is empty and/or recharging the pump assembly battery before it requires recharging in response to a determination that replacement at the end of the time remaining would be inconvenient.

The features and attendant advantages of the present inventions will become apparent as the inventions become better understood by reference to the following detailed description when considered in conjunction with the accompanying drawings.

BRIEF DESCRIPTION OF THE DRAWINGS

Detailed description of exemplary embodiments will be made with reference to the accompanying drawings.

FIG. 1 is an exploded perspective view of an exemplary infusion pump kit including an infusion pump system, with an infusion pump assembly, a medicament cartridge, and a baseplate, a cannula and two additional baseplates.

FIG. 5 is an exploded perspective view of the cartridge portion of a pressure sensor.

FIG. 6 is a section view of the cartridge portion of another exemplary pressure sensor.

FIG. 7 is a schematic block diagram of another exemplary pressure sensor.

FIG. 8 is a schematic block diagram of another exemplary pressure sensor.

FIG. 26 is a section view taken on line 26-26 in FIG. 25.

FIG. 27 is an elevation view of a portion of the latch mechanism illustrated in FIGS. 23-26.

FIG. 28 is a section view of the lead screw, gear, thrust bearing and pusher portions of the pump module illustrated in FIG. 19.

FIG. 33 is a section view of an exemplary pump assembly including the latch illustrated in FIG. 32 in an unlatched state.

FIG. 34 is another section view of a pump assembly including the latch illustrated in FIG. 32 in an unlatched state.

FIG. 35 is another section view of a pump assembly including the latch illustrated in FIG. 32 in a latched state.

FIG. 35A is a section view taken along line 35A-35A in FIG. 35.

FIG. 39 is a schematic view of a motor and an encoder.

FIG. 40A is a schematic view of an optical encoder system.

FIG. 40B is a schematic view of another optical encoder system.

FIG. 40C is a schematic view of yet another optical encoder system.

FIG. 40D is a schematic view of still another optical encoder system.

FIG. 53 is a perspective view of an exemplary baseplate.

FIG. 54 is a section view of a portion of a system including the baseplate illustrated in FIG. 53.

FIG. 55 is a bottom perspective view of the system illustrated in FIG. 54 with the adhesive liner removed.

FIG. 69 is a bottom view of a portion of an exemplary pump assembly.

FIG. 70 is a perspective view of a portion of an exemplary baseplate.

FIG. 71 is a perspective view of a portion of an exemplary baseplate.

FIG. 72 is a perspective view of a portion of an exemplary baseplate.

FIG. 80 is a section view showing a medicament cartridge being inserted into the exemplary pump assembly illustrated in FIG. 33.

FIGS. 81-83 are section views showing the pump assembly and cartridge illustrated in FIG. 80 during an exemplary pusher zeroing procedure.

FIG. 84 is a section view showing the removal of a plug from the cartridge illustrated in FIG. 83 and the attachment of a body adherable baseplate to the pump assembly.

FIG. 85 is a section view showing a cannula inserter, with a cannula, attached to the exemplary system including the pump assembly, baseplate and cartridge illustrated in FIG. 84.

FIG. 86 is a front view showing a patient's skin being cleaned.

FIG. 100 is a flow chart showing exemplary alarm conditions.

DETAILED DESCRIPTION

Figure 1A:
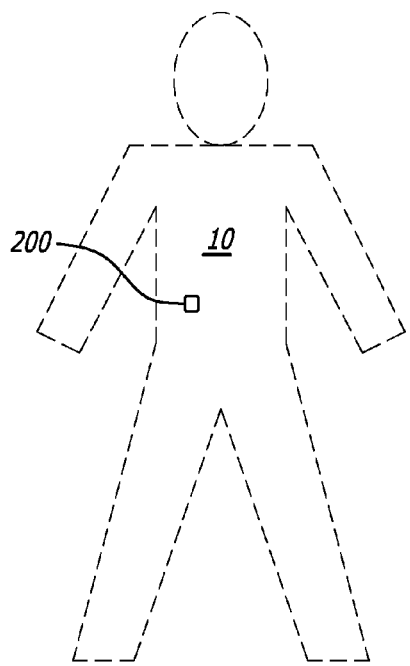
FIG. 1A is a schematic view showing use of an exemplary infusion pump system.

The following is a detailed description of the best presently known modes of carrying out the inventions. This description is not to be taken in a limiting sense, but is made merely for the purpose of illustrating the general principles of the inventions.

The detailed description of the exemplary embodiments is organized as follows:
I. Introduction
II. Exemplary System Overview
III. Exemplary Medicament Cartridges
IV. Exemplary Pump Assemblies
   A. Exemplary Housings
   B. Exemplary Pump Modules Overview
   C. Exemplary Chassis
   D. Exemplary Plunger Pushers and Drive Mechanisms
   E. Exemplary Reservoir Clamping
   F. Exemplary Cartridge Lock and Bias Apparatus
   G. Exemplary Encoders
   H. Exemplary Pressure/Occlusion Sensors
   I. Exemplary Fall-Off Detectors
   J. Exemplary Batteries and Battery Rechargers
   K. Exemplary Alarms
   L. Exemplary System Controllers
   M. Exemplary Motor Control
V. Exemplary Baseplates and Cannulas
VI. Exemplary Baseplate Identification
VII. Exemplary Basic Operation
VIII. Exemplary Operational Methodologies
   A. Exemplary Cartridge Position Check
   B. Exemplary Pusher "Zeroing" Procedure
   C. Exemplary Occlusion Detection
   D. Exemplary Accounting For Unpowered Motor Reverse
   E. Exemplary Motor Stopping
   F. Exemplary Automatic Plunger Pusher Retraction Procedures
   G. Exemplary Gear Assembly Verification Procedure
IX. Exemplary Remote Controls and Associated Methodologies The section titles and overall organization of the present detailed description are for the purpose of convenience only and are not intended to limit the present inventions.

It should also be noted here that the specification describes a wide variety of structures and methods, mainly in the context of cartridge-based infusion pumps that are especially well-suited for the subcutaneous delivery of very high concentration insulin (e.g., the U-500 insulin discussed below). Nevertheless, it should be appreciated that the present inventions are applicable to a wide variety of infusion pumps and medicaments. By way of example, but not limitation, many of the present inventions are also applicable to infusion pumps that are not cartridge-based (e.g., pumps with refillable reservoirs and single use pumps). Also, although the illustrated embodiments may employ a cartridge with a plunger, a fluid displacement device in the form of a plunger pusher, and a drive mechanism that includes a motor, other fluid displacement devices may include, regardless of the type of cartridge or reservoir employed, piston pumps (e.g., electromagnet pumps), MEMS pumps, peristaltic pumps and any other suitable pumps as well as corresponding drive mechanisms. The present inventions are also applicable to medicaments such as, for example, drugs to mask pain, chemotherapy and other cancer related drugs, antibiotics, hormones, GLP-1, Glucagon, various other drugs that include large molecules and proteins that may require a high level of delivery accuracy, as well as to relatively high concentration insulin (i.e., U-200 and above) such as U-400 insulin.

I. INTRODUCTION

From the perspective of most patients, two important aspects of ambulatory infusion pumps are size and convenience. As noted above, some ambulatory infusion pumps are frequently intended to be worn on a belt, carried in a pocket, or otherwise supported within a holder of some kind (referred to collectively as "pocket pumps"). Such infusion pumps transfer fluid from a reservoir to an infusion set by way of an elongate tube. Subcutaneous access may be obtained by way of a cannula in the infusion set. Other ambulatory infusion pumps are intended to be adhered to the skin at the delivery site (sometimes referred to as "patch pumps"). Here, the cannula or other subcutaneous access device may extend directly from the infusion device. Given these modes of use, patients typically prefer the pump to be as small as possible so that the pump will be more comfortable, less obtrusive, and less visible.

One commercially available ambulatory infusion pump is the OmniPod® insulin pump from Insulet Corporation in Bedford, Mass. The OmniPod® insulin pump has overall dimensions of about 62.5 mm×42.9 mm×17.7 mm, i.e., has an overall volume of about 47.5 cc, and has a reservoir volume of about 2.0 cc. Although this pump is relatively small, many patients would prefer an even smaller pump. Reducing reservoir volume is a simple method of reducing the overall size of an infusion pump. Unfortunately, when the volume of the reservoir is reduced, all other things being equal, there is a corresponding reduction in convenience because the smaller reservoir requires more frequent refilling or replacement.

The present inventors have determined that smaller reservoirs can be employed, without a corresponding reduction in convenience, by increasing the concentration of the medicament dispensed therefrom. In the exemplary context of insulin therapy, some conventional infusion pumps have reservoirs which hold 2 milliliters (ml) of U-100 insulin. U-100 insulin is an insulin containing 100 international units (IU) of insulin activity per 1 ml and, accordingly, the 2 ml reservoir stores 200 IUs. One common insulin dose is 0.5 IU, which equates to a dispensed volume of 5 microliters (μl) of U-100 per dose, 400 doses per 2 ml reservoir, and about 4.5 days of therapy at the common dosage. At least some conventional infusion pumps are capable of delivering 5 μl/dose with a delivery accuracy level that is acceptable for relatively low concentration U-100 insulin.

Higher concentration insulins are, however, commercially available. Humulin® R U-500 insulin, which is available from Eli Lilly and Company in Indianapolis, Ind., contains 500 IU/ml. Although the use of high concentration insulin would facilitate the use of a much smaller reservoir (e.g., 300 IU in a 0.600 ml reservoir), and could result in much smaller pumps for a given number of dosages, the five-fold increase in insulin concentration (as compared to U-100 insulin) necessitates a five-fold increase in fluid delivery accuracy. U-500 insulin is currently administered by injection and with certain conventional insulin pumps for patients who require more than about 200 IU/day. The accuracy of certain conventional pumps is adequate for patients who require about 200 IU/day or more. For example, conventional insulin pumps generally alert the patient (e.g., with an alarm) when approximately 3 IUs of U-100 insulin are missed on delivery, which corresponds to 30 μl of missed delivery. Using U-500 insulin, the missed volume for a 3 IUs alert is reduced to six μl due to the higher insulin concentration, and conventional infusion pumps are not capable of this level of accuracy.

The present inventors have determined that there are a plethora of factors that must be addressed if the goal is to deliver 1 μl/dose at an acceptable level of delivery accuracy. For example, the six μl alert requirement means that the present infusion pump assembly must be very stiff (or "low compliance") to ensure delivery accuracy over all conditions of operating pressures, frictions, temperatures and so forth. In the context of the exemplary cartridges described below, the displacement may be about 1 IU of U-500 insulin per 0.001 inch of stroke, i.e., 2.0 μl/0.001 inch of stroke. The present inventors have determined that factors which can contribute to accuracy/precision during drug delivery may include: rotational accuracy of gearform (wobble and gearform consistency); encoder resolution; motor backdrive; encoder consistency (rotational spacing); motor phase balance; and motor control circuit excitation consistency (excitation pulse width accuracy and switch accuracy). The present inventors have determined that factors which can contribute to axial (error) movement under load may include: thrust bearing (internal movement); thrust bearing (slip in mount); lead screw (axial deformation); nut-to-lead screw gearform deflection; plunger body compression; plunger body-to-seal axial slip; plunger seal-to-low friction layer axial slip; thrust bearing-to-lead screw axial slip; cartridge body deformation/axial slip; lead screw-to-transverse gear axial slip; lead screw-to-transverse gear axial slip; push rod-to-nut axial deformation; cartridge body hydraulic expansion; sense diaphragm hydraulic deflection; infusion set hydraulic expansion; cannula movement in cartridge extending or shortening fluid path; and fluid path bubble compression. The relevance of many of these factors is discussed below in the appropriate contexts.

Another convenience related issue identified by the present inventors relates to the fact that a patient may desire to use a pocket pump in some instances and a patch pump in others. In addition to the added expense, switching between two different infusion pumps may adversely effect the patient's medicament delivery regimen. Notwithstanding the desire of some patients to switch back and forth, the mere fact that some patients prefer a pocket pump while others prefer a patch pump forces manufacturers to choose between designing, testing and obtaining approval for two different pumps or simply staying out of one of the markets.

II. SYSTEM OVERVIEW

Figure 1B:
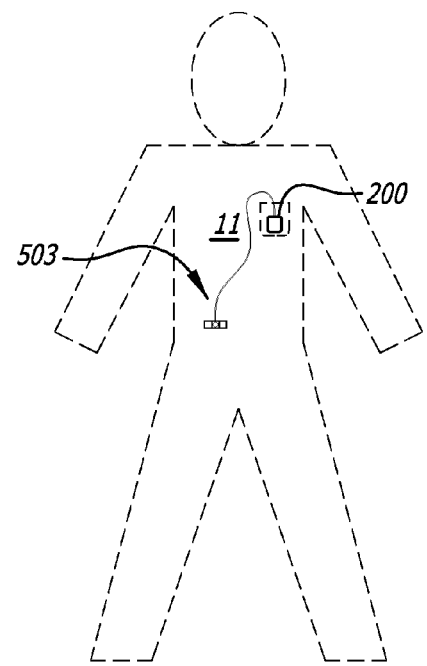
FIG. 1B is a schematic view showing use of an exemplary infusion pump system.

Exemplary ambulatory infusion systems, which are generally represented by reference numerals 10, 11 and 12 in FIG. 1, include a medicament cartridge (or "cartridge") 100, an ambulatory infusion pump assembly (or "pump assembly") 200, and one of the baseplates 500, 501 and 502. Generally speaking, the cartridge 100 may be inserted into the pump assembly 200 and the appropriate baseplate 500-502 may be secured to the pump assembly. To that end, and as discussed in greater detail in Section V below, the baseplates 500-502 in the illustrated implementations are configured for different modes of system operation. Baseplate 500 is a body adherable baseplate that may be used in conjunction with a cannula (e.g., cannula 600 in FIGS. 56-57) that is directly connected to the cartridge 100 so that the system 10 may be deployed as a "patch-pump" (FIG. 1A). Baseplate 501 is configured to connect the cartridge 100 to an infusion set 503 so that the system 11 may be deployed as a "pocket pump," a "belt-worn pump" or some other wearable pump (FIG. 1B). Baseplate 502 is a medicament non-delivery baseplate that may be used to seal the cartridge 100 during periods of non-use (e.g., by way of plug 504), thereby defining a non-use system 12.

In other words, using the same medicament cartridge (e.g., cartridge 100) and pump assembly (e.g., pump assembly 200), the user may configure the system for use as "pocket pump" or a "patch pump" by simply selecting the appropriate baseplate 500 or 501 and attaching the baseplate to the pump assembly. The user may also switch from one configuration to another, in many instances without removing the cartridge from the pump assembly, by simply removing one baseplate and replacing it with another baseplate.

Whether configured as a "pocket pump" or a "patch pump," the system may be configured to provide basal delivery of medicament in accordance with a delivery profile provided by a physician by way of a clinician's programming unit. For example, the system may include a program that stores a number of delivery profiles (e.g. delivery profiles associated a 24-hour delivery cycle and delivery profiles for particular situations such as sleep or illness). Each delivery profile specifies multiple doses (or pump "operations") over time, e.g. a particular number of doses at particular times or a particular number of doses per unit time. In some implementations, a dose may be the volume associated with the minimum controllable displacement of a cartridge plunger. The system may also be configured to provide bolus delivery in response to an instruction from a patient remote control. A bolus instruction may come in response to a high glucose level measurement in the case of a diabetic patient, an increase in pain level in the case of a pain management patient, or some other symptom. The system may also be configured to perform other functions, such as ending medicament delivery, in response to instructions from a patient remote control.

The parts of the present systems that do not come into contact with medicament during normal operation (e.g., operation not associated with a cartridge that is damaged and leaking) may be considered the reusable parts, while the parts that do come into contact with medicament during normal operation, and may define portions of the medicament delivery (or "flow") path, may be considered the disposable parts. In the illustrated embodiments, the pump assembly 200, which includes structures such as the motor and various mechanical structures, the controller and the battery (and may be more expensive), is reusable, while the cartridge 100, baseplates 500-502 and cannula 600 (if any) are disposable.

The pump assembly 200 in the exemplary system 10 (and 11) does not come into contact with medicament because the cartridge 100, which is accessible from outside the pump assembly 200, includes its own manifold. Medicament can, therefore, flow directly from the cartridge reservoir to the associated cannula or other device without contacting the pump assembly. Such an arrangement is advantageous for a variety of reasons. For example, portions of the medicament delivery path from the reservoir to the cannula (or infusion set tube) can become clogged or otherwise in need of repair. Such repair may be inconvenient and costly in the context of many conventional infusion pumps because the pump mechanism (e.g., a piston or peristaltic pump) is part of the medicament delivery path. The present systems obviate this unpleasant aspect of some conventional infusion pumps by removing the medicament flow path from the reusable portion of the system. The present systems also provide less expensive long term therapy, as compared to many conventional systems, because the more expensive portions are reusable.

The infusion pumps described herein address the accuracy/precision factors and the axial movement factors noted above by providing a more accurate, less compliant infusion pump. For example, the constructions of the cartridge (e.g., the inside diameter is constant, and the plunger is configured to be urged precisely in response to movement of the drive mechanism), the rigidity of the chassis and the precision of the drive mechanism, as well as the operation procedures of the drive mechanism, allow for an amount of medicament of 0.1% or less of the total filled volume of the reservoir to be controllably dispensed with single-dose precisions that range from plus or minus (+/−) 20% to +/−5%. This precision can be obtained after a dispensing period of six to eight hours or less resulting in a dose accuracy of from +/−20% to +/−5%. The dispensed amount can be as low as 0.23-0.27 µl/dose. The dose can be dispensed in as little as two seconds or less for small volumes, or longer times for larger volumes such as those associated with basal delivery.

Figure 2:
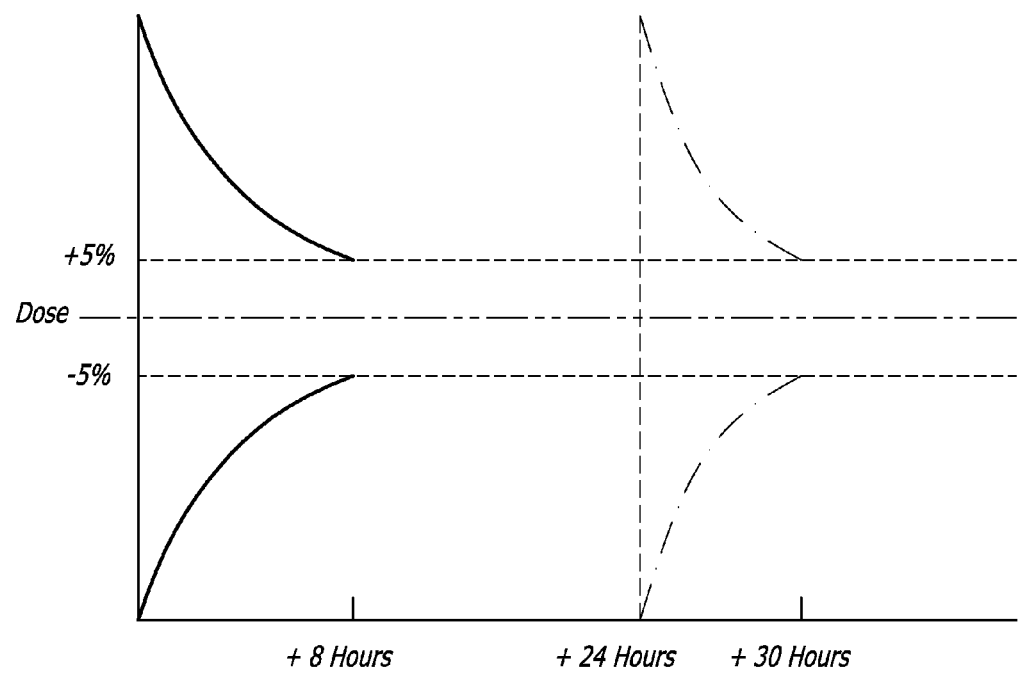
FIG. 2 is a precision graph showing dispensing performance.

For example, 300 units of U-500 insulin (0.6 mL or 600 µl) can be provided in the reservoir of one of the cartridges described below, and within a two hour or less stabilization period, medicament can be controllably dispensed from the cartridge with a precision of +/−5% and with 0.5 unit per dose (1.0 µl/dose). As graphically illustrated in FIG. 2, the ability to obtain a single-dose precision of better than +/−5% in as little as six to eight hours or less is vastly superior to the standard set forth in the International Electrotechnical Standard (IEC) for the safety of infusion pumps and controllers (IEC 60601-2-24), which provides for a 24-hour stabilization period before precision measurements are even taken. In other words, although the IEC 60601-2 delivery test provides a twenty-four hour stabilization period during which pump operation is allowed to be untested, the present pumps, from a clinical perspective, may be tested without such a stabilization period. This "time-to-precision" superiority is especially important in the context of high concentration medicaments because the adverse effects of prolonged over-delivery or under-delivery are magnified. For example, a "time-to-precision" of six hours may be appropriate in the context of U-500 insulin and Type-1 diabetics who use basal rates of less than one IU/hour.

The precision capabilities associated with the present system, and the corresponding ability to use a very highly concentrated medicament (e.g., U-500 insulin) and relatively highly concentrated medicaments (e.g., U-200 to U-400 insulin) also facilitate, if so desired, a marked decrease in ambulatory infusion pump size as compared to conventional pumps. For example, one exemplary pump assembly 100 described below has dimensions of about 40 mm×32 mm×11 mm, for an overall volume of about 14 cc. This is considerably less than the approximately 47 cc overall volume of the aforementioned OmniPod® insulin pump.

III. EXEMPLARY MEDICAMENT CARTRIDGES

The exemplary system is, as noted above, a cartridge-based system in that medicament cartridges 100 are inserted into the pump assembly 200 and later removed from the pump assembly. The cartridges 100 may also be, but are not required to be, prefilled and disposable. Prefilled cartridges are advantageous for a variety of reasons. By way of example, but not limitation, some users prefer to avoid cartridge filling procedures because they are inconvenient and tend to involve needles. User-based refilling also increases the likelihood that air bubbles will be introduced into the cartridge, while prefilling by the manufacturer of the cartridge and/or the medicament can be accomplished without any substantial introduction of air bubbles using, for example, a vacuum filling procedure. A lack of bubbles is very important in the context of dosage accuracy in that air is compressible and liquid medicament is not. For example, 20 µl of air will have a compressibility of about 6 µl at a 5 psi operating pressure, which can adversely effect pressure sensing in the system. If the system is configured to alert the user of missed dosing equal to approximately 6 µl (3 IUs for U-500 insulin), 6 µl (3 IUs for U-500 insulin) will be delayed before there is a user alert. In addition, the presence of 20 µl of air in the cartridge results in the patient not receiving 10 IUs of U-500 insulin during the life of the cartridge. Prefilled cartridges with less than 5 µl of air bubbles are preferred when U-500 is the stored medicament.

Figure 3A:
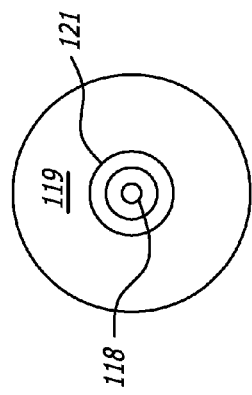
FIG. 3A is an end view of the interior of an exemplary medicament cartridge.
Figure 4:
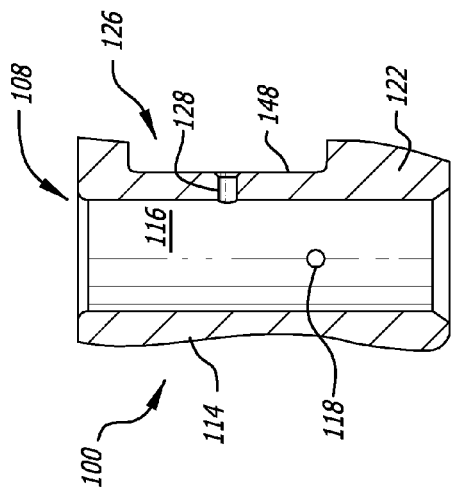
FIG. 4 is a section view taken along line 4-4 in FIG. 3.
Figure 3:
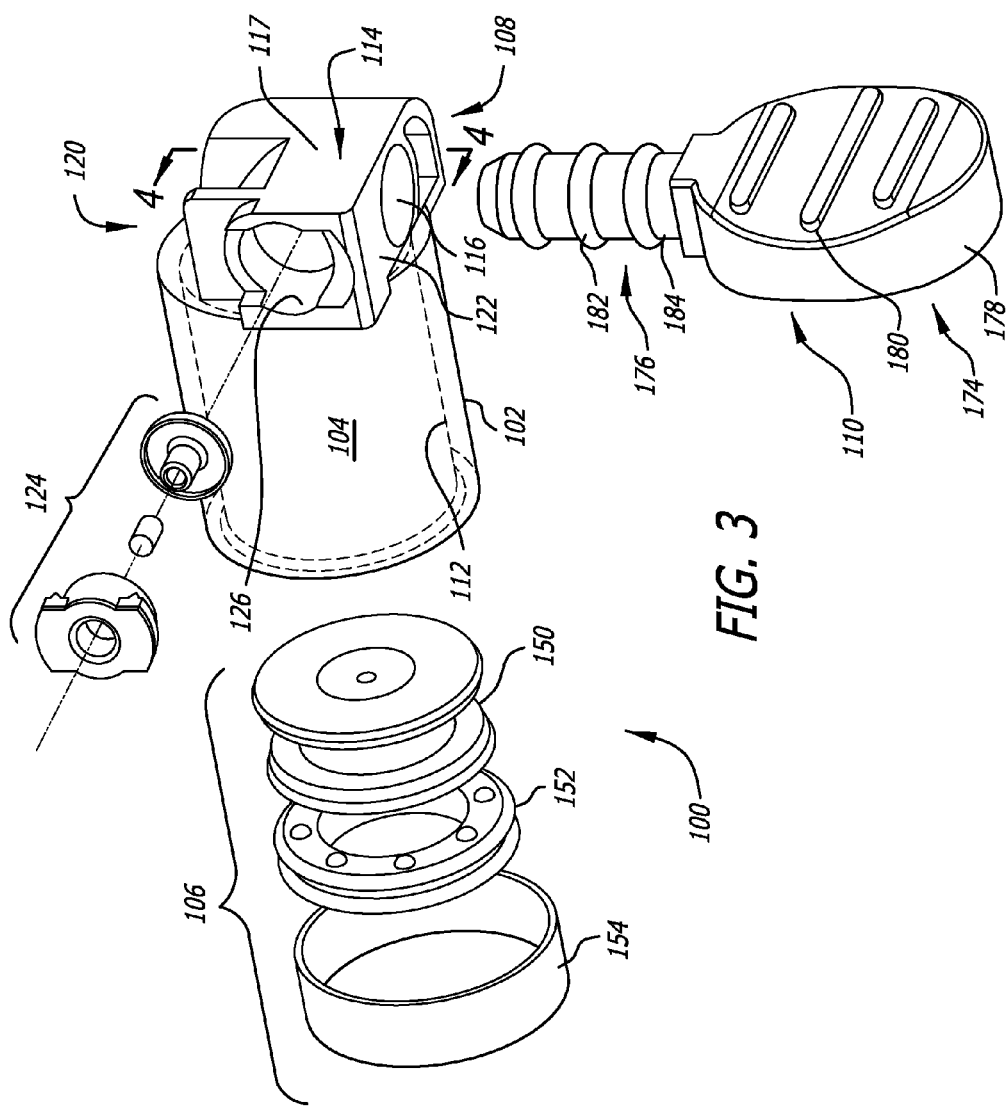
FIG. 3 is an exploded perspective view of an exemplary medicament cartridge.
Figure 9:
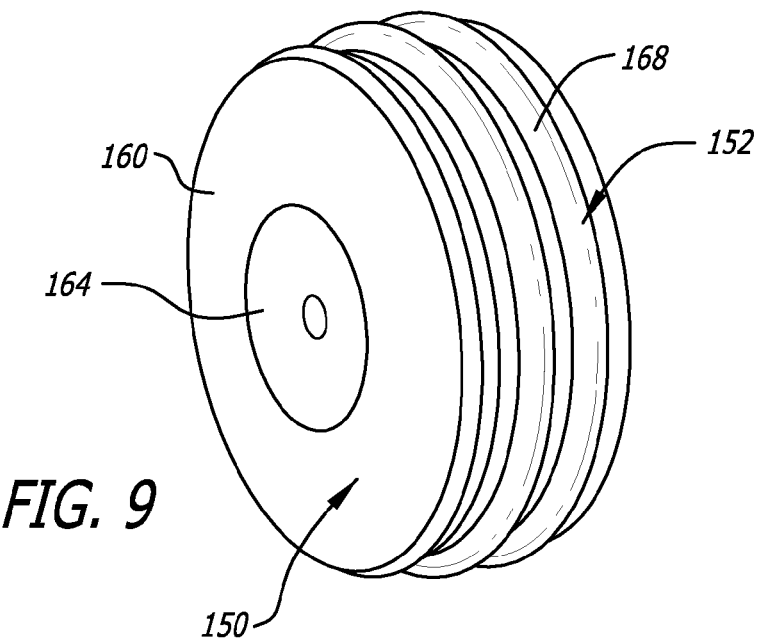
FIG. 9 is a perspective view of a portion of the plunger in the exemplary medicament cartridge illustrated in FIG. 3.

As illustrated in FIGS. 3 and 4, the exemplary medicament cartridge 100 may include a body portion (or "barrel") 102, which defines a medicament reservoir 104, a plunger 106 that is held by friction within the body portion, and a manifold 108 that may be used to connect the reservoir to, for example, cannulas and baseplate structures in the manner described below with reference to, for example, FIGS. 57 and 63. Medicament is identified by reference numeral 101 in FIG. 23. The plunger 106 is moved within the body portion 102 to vary the volume of the reservoir 104. In particular, the plunger 106 moves in a dispensing direction where reservoir volume is decreased, but does not substantially move to increase volume during use of the cartridge 100. The cartridge 100 may also be provided with a plug 110 that prevents leakage from a prefilled reservoir 104 (e.g., prefilled in a vacuum with U-500 insulin) during packaging, shipping, storage and handling, and can be used in a pusher zeroing procedure as described in Section VIII-B below.

Referring first to the body portion 102, and although the present inventions are not limited to any particular shape, the exemplary body portion 102 is cylindrical in overall shape and has a cylindrical inner surface 112 that defines the cylindrical reservoir 104 (FIG. 3). The body portion 102 and inner surface 112 may be other shapes in other implementations. By way of example, but not limitation, the overall shape of the body portion 102 and the shape of the inner surface 112 may both be oval in cross-section, or the overall shape of the body portion may be rectangular and the shape of the inner surface may be oval or circular in cross-section. The inner surface 112 may also be a non-curved, such as rectangular or square in cross-section.

The exemplary manifold 108 illustrated in FIGS. 3 and 4 has a body portion 114 that defines a through-bore 116 and the front wall 117 of the cartridge. The through-bore 116 is directly connected to a relatively short reservoir outlet port 118 (i.e., is connected without additional tubing). The through-bore 116 and outlet port 118 facilitate a direct fluidic connection between the cartridge 100 and the aforementioned cannulas and baseplates that have a portion thereof inserted into the through-bore. The reservoir outlet port 118 may also be parallel to the direction of plunger movement (note FIG. 54). Such an orientation results in a short, direct and efficient medicament dispensing path as the plunger 106 reduces the volume of medicament in the reservoir 104.

Additionally, as illustrated in FIG. 4A, the inner surface of the body portion end wall 119, i.e., the wall that the plunger 106 abuts when the reservoir is empty, may include an annular recess 121 which traps bubbles that may be present in the reservoir and prevents them from exiting the cartridge 100. In one exemplary implementation, the annular recess 121 is a 0.25 mm deep semi-circle in cross-section, is 0.5 mm from the circumferential edge of the outlet port 118, and is 0.5 mm wide (i.e., 0.5 mm from the ID to the OD). Such bubble entrapment reduces the likelihood that bubbles will be dispensed and, accordingly, reduces the likelihood that medicament dispensing and occlusion sensing will suffer bubble-related decreases in accuracy. Other ways to trap bubbles at the end wall 119 include, but are not limited to, concentric recesses, hydrophilic filters and elevated outlet ports.

At least some of the exemplary implementations may employ pressure data in various contexts. For example, a pressure sensor may be used to detect occlusions downstream from the reservoir outlet port 118 that are impeding, or completely preventing, medicament flow. To that end, a medicament cartridge may include some or all of the pressure sensor itself. In the illustrated implementation, the cartridge 100 includes the cartridge portion 120 of the pressure sensor 234 that is described in Section IV-H below with reference to FIGS. 41 and 42. The pressure sensor may also be used to detect the presence of a cartridge in the pump assembly, as is also described below.

The exemplary pressure sensor cartridge portion 120 illustrated in FIGS. 3 and 4 includes a pressure sensor housing 122, which may be integral with (as shown) or otherwise connected to or carried by the manifold 108, and a detectable structure 124. The detectable structure 124, whose movement can be detected as described below, is mounted in a pressure sensor housing recess 126 and communicates with the through-bore 116 by way of an aperture 128 so as to expose the detectable structure to the fluid pressure in the through-bore. As shown in FIG. 5, the exemplary detectable structure 124 has a deflectable part 130 with a magnet 132 (e.g., a neodymium magnet), a resilient diaphragm 134 (e.g., a silicone diaphragm) that carries the magnet by way of a sleeve 136, and a diaphragm retention ring 138 (e.g., an olefin polymer retention ring). The exemplary detectable structure 124 also has a cap 140 with a cylindrical abutment 142, a bore 144 in which the magnet 132 and sleeve 136 are located, and a flange 146. During assembly, the detectable structure 124 is inserted into the housing recess 126 until the retention ring 138 abuts the recess wall 148 (FIG. 4). The cap 140 is thereafter inserted into the recess 126 until the cylindrical abutment 142 engages the retention ring 138 and the flange 146 is flush with the pressure sensor housing 122 (FIG. 1). The diaphragm 134, which is exposed to reservoir pressure by way of the aperture 128, flexes in response to pressure increases, such as during an occlusion event, thereby moving the magnet 132. The movement is sensed by the pump assembly portion 236 (e.g., Hall-effect sensor or magnetoresistive sensor) of the pressure sensor 234 as described in Section IV-H below with reference to FIGS. 41 and 42. Thus, in this implementation, the cartridge portion 120 may be thought of as the "unpowered" portion of the pressure sensor 234 and the pump assembly portion 236 may be thought of as the "powered portion." Moreover, the more expensive portion, e.g., a sensor such as a Hall-effect or magnetoresistive sensor, is part of the reusable pump assembly 200.

Generally speaking, air (not medicament) acts on the diaphragm 134 because of the air cushion formed between the plug 110 and diaphragm during manufacture. That said, the sensor 234, which includes the cartridge portion 120, can detect a pressure change corresponding to six µl of medicament (i.e., the three IU of U-500 insulin) or less of plunged medicament that is being held up by a blockage. The six µl of medicament generally corresponds to the volume created by deflection of the detectable structure 124 (note FIG. 42).

Another exemplary cartridge portion of a pressure sensor is generally represented by reference numeral 120a in FIG. 6. The cartridge portion 120a may be part of a medicament cartridge 100a that is otherwise identical to cartridge 100. Cartridge portion 120a is substantially similar to cartridge portion 120 and similar elements are represented by similar reference numerals. For example, the cartridge portion 120a includes a detectable structure 124a. Here, however, the diaphragm 134a includes a post 136a on which a cylindrical magnet 132a is mounted. In other words, instead of the magnet 132a being in a sleeve, this magnet 132a defines a sleeve. The diaphragm 134a also includes an integral mounting member 138a that is press-fit into the recess 126 with a cylindrical wedge 142a.

It should also be noted that the present pressure sensors are not limited to the type of devices described with reference to FIGS. 5 and 6. By way of example, but not limitation, a cartridge portion 120b (FIG. 7) may include a diaphragm that carries a magnetically permeable structure 132b which changes the inductance of a coil in the pump assembly portion PAP of the sensor when moved relative thereto. A similar arrangement may employ an optical element and a corresponding optical sensor, and FIG. 7 may also be considered a representation thereof (with the optical element represented by reference number 132b). Another exemplary pressure sensor may be in the form of an electrical switch that includes a pump assembly portion PAP1 with a pair of switch contacts and a cartridge portion 120c with a diaphragm which carries an electrical conductor 132c that connects the contacts when the diaphragm moves a predetermined distance (FIG. 8).

With respect to dimensions, the exemplary cartridge 100 may be configured to have a reservoir 104 whose volume is less than or equal to about 1000 µl and, some implementations, between about 500-700 µl. For perspective, and as noted above, a 600 µl (0.600 ml) reservoir would store 300 units of U-500 insulin, which corresponds to about one week's worth of insulin for a patient using approximately 40 IU of insulin per day. Such volumes may achieved by way of a body portion 102 with an inner diameter of 9.8 mm, with a tolerance+/−1.0 mm in some instances and a tolerance of +/−0.1 mm in others, an outer diameter of 11.8 mm, with a tolerance +/−1.0 mm in some instances and a tolerance of +/−0.10 mm in others, a stroke length (i.e., the distance that the plunger 106 travels from the full position to the empty position) of 8.5 mm+/−2.0 mm, and a length of 17.5 mm, with a tolerance of +/−1.0 mm in some instances and a tolerance of +/−0.10 mm in others.

It should be noted here that the stroke length to inner diameter ratio of the present reservoir 104 may be about 1.0 or less. For example, in some implementations, the ratio may be 0.86, or may range from about 0.75 (or less) to about 1.0.

The plunger may play a substantial role in the dosage accuracy associated with the present system. The exemplary plunger 106 illustrated in FIGS. 3 and 9-12 includes a plunger body 150, a seal 152, and a friction reduction layer 154 that provides a low coefficient of friction between the friction bearing surface of the plunger 106 and barrel inner surface 112.

Figure 10:
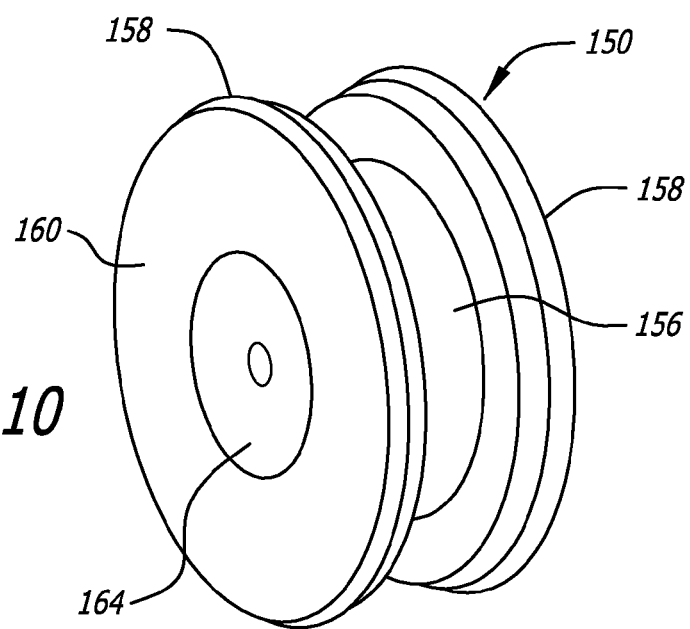
FIG. 10 is a perspective view of the body portion of the plunger illustrated in FIG. 9.
Figure 12:
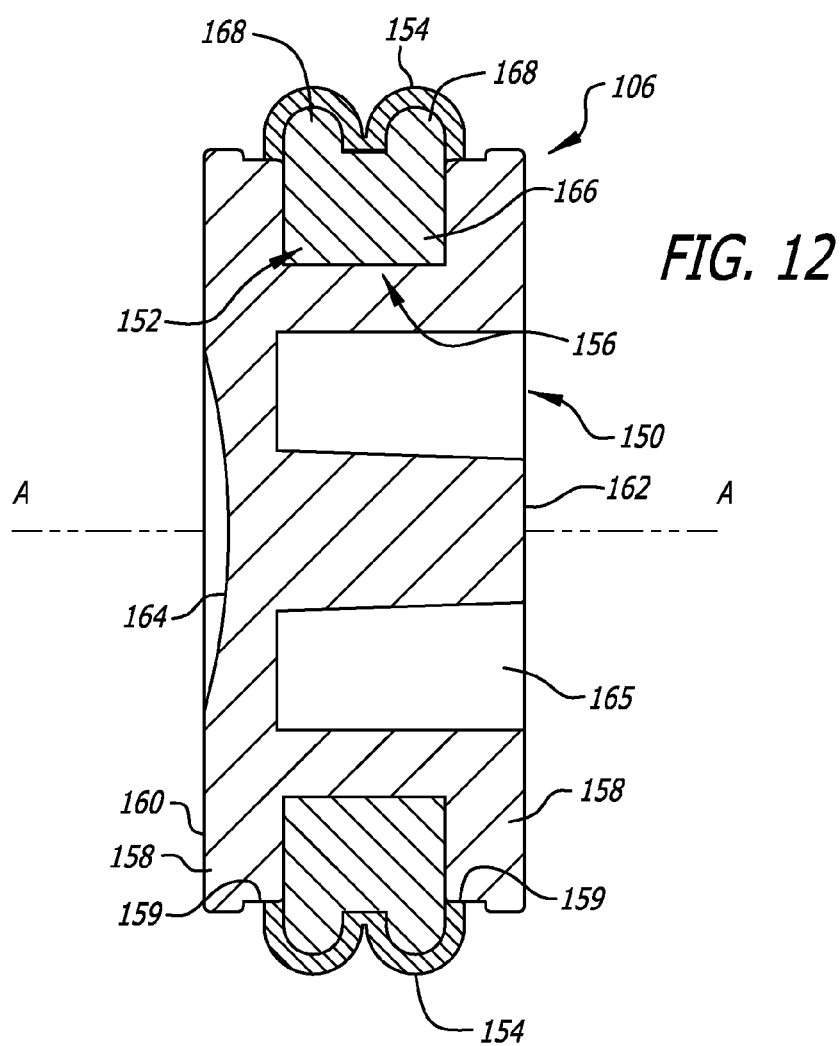
FIG. 12 is a section view of the plunger illustrated in FIG. 3.

Referring more specifically to FIGS. 10 and 12, the plunger body 150 may be spool-shaped, in that it is a solid structure with a recessed middle portion 156 and circumferential rings 158. The recessed middle portion 156 and circumferential rings 158 extend circumferentially around the axis A (FIG. 12). Indentations 159 may be provided for a portion of the friction reduction layer 154. The spacing between circumferential rings 158 and the barrel inner surface 112 may be relatively small, i.e., there is close tolerance, to minimize plunger wobble. For example, the diameter of the rings 158 may be about 9.7 mm with a tolerance of +/−0.06 mm and the spacing can be 0.10 mm with a tolerance of +/−0.073 mm in some instances and a tolerance of +/−0.12 mm in others. The plunger body 150 also has forward and rearward facing (relative to the direction of plunger travel during medicament dispensing) surfaces 160 and 162. Put another way, with reference to the medicament in the reservoir 104, the surface 160 is the "wet side" and surface 162 is the "dry side." The forward facing surface 160 may be provided with a concave recess 164 that is at least substantially aligned with the reservoir outlet port 118. A generally annular indentation 165 extends into the plunger body 150 from the rearward facing surface 162. In addition to reducing the weight of the plunger 106, the indentation facilitates removal of the plunger body from the mold during manufacture.

In other implementations, the plunger body may be planar on the wet and/or dry sides. Such a plunger body would resemble the simplified illustration of plunger body 150 in FIG. 34. The plunger body surfaces interfacing with the inner surface of the barrel may also be cylindrical, that is, planar in cross section as opposed to rounded.

Figure 11:
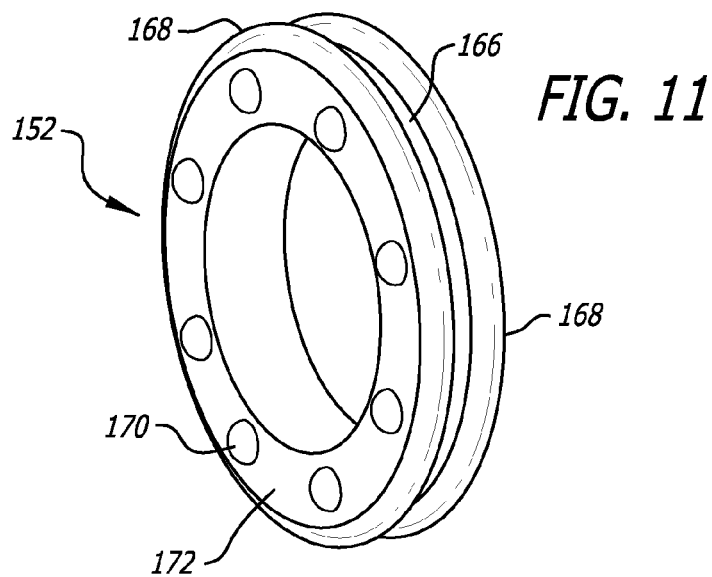
FIG. 11 is a perspective view of the seal portion of the plunger illustrated in FIG. 9.

Referring to FIGS. 10-12, the seal 152 may be located between the plunger body 150 and the friction reduction layer 154, and within the plunger body recessed middle portion 156 between the circumferential rings 158. As such, the seal 152 in the illustrated implementation acts on the plunger body 150, as well as the friction reduction layer 154, and is radially and axially constrained. The seal 152, which may include an annular base portion 166 and a pair of o-rings 168, also provides enough force to press the friction reduction layer 154 outwardly against the inner surface 112 of cartridge body 102 and establishes a seal that will hold under the pressures associated with the present systems and methods. Moreover, given the radial and axial constraints, the amount of seal compression (and the resulting sealing force) is more predictable than it would be otherwise.

The seal 152 is under radial and axial compression forces which provide a sealing load on both the friction reduction layer 154 and the plunger body 150. The radial and partial axial compression forces also force the friction reduction layer 154 outward against the cartridge barrel inner surface 112. Overcompression is undesirable as the resultant seal has a wide range of static/running forces, so compression is engineered to be within a predictable range.

The seal 152 may also be provided with a plurality of protrusions 170 (FIGS. 11 and 12), such as integrally molded protrusions, on the forward facing surface 172 (as shown) and/or on the rearward facing surface (not shown). The protrusions 170 ensure that the seal 152 is axially stable (or properly constrained) between the plunger body circumferential rings 158, and will typically be compressed into the annular base portion 166 as shown in FIG. 12. Constraining the seal 152 in this manner makes it more likely that the seal will accurately track movement of the plunger body 150 and, in turn, facilitates accurate reduction in reservoir volume. The protrusions 170 also prevent overcompression of the exemplary seal 152 in the plunger body 150, which could lead to unpredictable seating and unpredictable forces on the friction reduction layer 154 and, therefore, on the cartridge barrel 102.

It should also be noted here that the plunger 106 in the illustrated embodiment is not connectable (or "is unconnectable") to the plunger pusher 250 (note FIGS. 45-47) that pushes the plunger forwardly toward the outlet port 118. Put another way, and referring to FIG. 12, the plunger body 150 does not include any structural components that are (or could be) connected to the plunger pusher. For example, the plunger body 150 does not include an unthreaded opening, a threaded opening, a fastener, a magnetic catch, a ratchet, or other such instrumentality. The dry side of the plunger body could also be planar (and noted above). Given the lack of connectability, under no circumstances will reverse movement of the plunger pusher 250 pull the plunger 106 rearwardly and draw medicament back and air (if any) into the reservoir 104. The plunger 106 can only move forwardly when being contacted by, and/or due to operation of, the plunger pusher 250.

Although there are numerous possible configurations that would not be connectable to a plunger pusher, the exemplary plunger body 150 simply has a smooth rearward facing surface 162 that may be planar (as shown in the simplified illustrated presented in FIG. 34) or curved. Additionally, or alternatively, the plunger pusher 250 (note FIGS. 18, 23 and 25) may be unconnectable to the plunger, as is discussed in Section IV-D below, for the same reasons.

With respect to materials, the body portion 102, manifold 108 and plunger body 150 of the exemplary cartridge 100 may be formed from plastic, glass or a combination of glass and plastic, and the seal 152 may formed from rubber, such as bromobutyl rubber. The body portion 102 and manifold 108 may be integrally formed, or formed separately and joined to one another (e.g., by ultrasonically or laser welding). One suitable plastic is cyclic olefin polymer (COP). It should be noted, however, that the particular medicament that is to be stored in the cartridge 100 should be taken into account. For example, each milliliter of Humulin® R U-500 insulin contains 500 units of biosynthetic human insulin, 16 mg glycerin, 2.5 mg Metacresol as a preservative, and zinc-oxide calculated to supplement endogenous zinc to obtain a total zinc content of 0.017 mg/100 units. Sodium hydroxide and/or hydrochloric acid may be added during manufacture to adjust the pH. Other ingredients, such as phenol (preservative), surfactants, and buffering agents may be added as required. As such, Humulin® R U-500 insulin may be better suited for long term storage in glass than it is for long term storage in plastic. In those instances where storage in a plastic cartridge (e.g., a COP cartridge) is desired due to the inherent advantages of plastic as compared to glass (e.g., lighter, less expensive and more durable), a bioequivalent of Humulin® R U-500 may be employed. Here, the formulation of Humulin® R U-500 may be adjusted to increase the stability of the insulin by, for example, changing preservative, changing stabilizers, and changing buffering agents.

Figure 17:
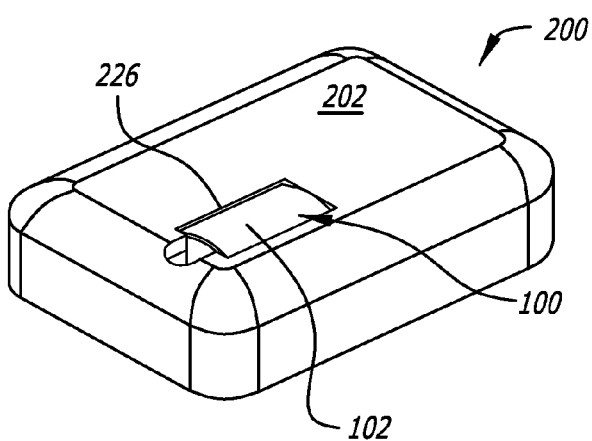
FIG. 17 is perspective view of the exemplary pump assembly illustrated in FIG. 15 with a cartridge inserted.

In at least some implementations, the cartridge body portion 102 may be formed from transparent glass, transparent COP or some other suitable transparent material. There are a variety of advantages associated with a transparent cartridge body portion 102. For example, as shown in FIG. 17 and discussed in Section IV below, the pump assembly 200 and cartridge 100 are respectively configured such the body portion 102 will protrude through an opening 226 in the housing top wall 214 when the cartridge is inserted into the pump assembly. In one implementation, the cartridge 100 will protrude less the one mm (which equates to five percent of the volume of reservoir 104). The patient will be able to see the medicament in reservoir 104 and readily determine, when for example the medicament is insulin, whether or not the medicament is cloudy (which indicates a loss of effectiveness), as well as roughly estimate what portion of the original medicament volume remains in the reservoir.

The friction reduction layer 154 in the exemplary embodiment may be formed in a variety of ways. The friction reduction layer 154 may be, for example, a polytetrafluoroethylene (PTFE) sleeve that is shrink wrapped over the plunger body 150 and seal 152 (as shown in FIG. 12). Ethylene tetrafluoroethylene (ETFE) and fluorinated ethylene propylene (FEP), which are in the same family as PTFE, may also be employed. Alternately, the friction reduction layer 154 can be implemented as a low friction coating or surface modification of the seal 152. Coatings could be formed from a fluorinated polymers such as FEP and PTFE. When combined with a COP cartridge body portion 102 and the other above-described aspects of the plunger 106, the present friction reduction layer 154 provides a break force (static friction) of less than five pounds and running forces (dynamic friction) of two to four or five pounds.

As to the exemplary plug 110 illustrated in FIG. 3, and as alluded to above, the plug is a removable sealing device that is inserted into the cartridge through-bore 116 during manufacture to prevent leakage from a prefilled reservoir 104, by way of the outlet port 118, during packaging, shipping, storage and handling. The plug 110 will typically remain in place in the through-bore 116 until the cartridge 100 is in place within the pump assembly 200 and is ready for medicament dispensing. At that point, the plug 110 will be manually removed by the user. Although the plug 110 is not limited to any particular configuration, the implementation illustrated in FIG. 3 includes a bulbous head 174 and a stem 176. The head 174 may have a disk portion 178 and a plurality of gripping protrusions 180, while the stem 176 may have a plurality of spaced sealing rings 182 carried on a cylindrical member 184. Suitable material for the plug 110 includes, but is not limited to, bromobutyl rubber. An internal core (not shown), such as a fiber core, may be provided in some instances in order to prevent the plug from ripping during manual removal subsequent to the pusher zeroing procedure described in Section VIII-B below.

In some instances, long term interaction between the medicament and the pressure sensor diaphragm (e.g., diaphragm 134) during shipping and storage may be problematic. Accordingly, in at least some implementations, the respective configurations of the cartridge 100 and plug 110 are such that the pressure sensor aperture 128 will be isolated from the reservoir outlet port 118 by a portion of a fully inserted plug. For example, at least one of the sealing rings 182 may be between the pressure sensor aperture 128 and reservoir outlet port 118 when the plug is fully inserted.

Figure 13:
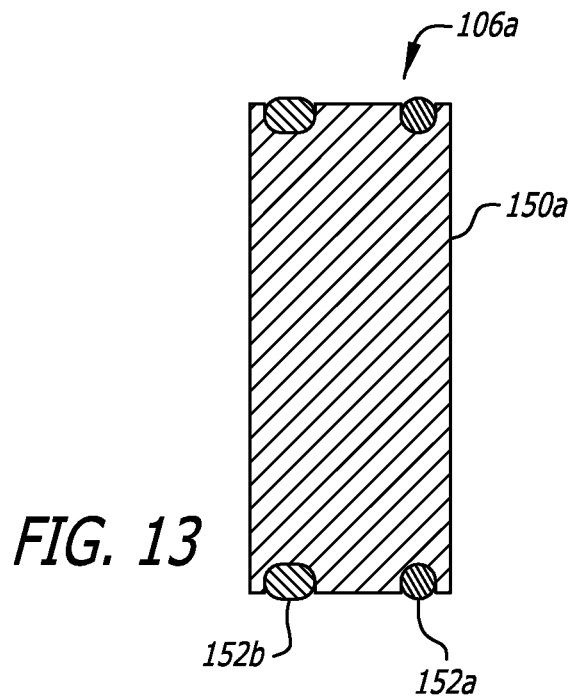
FIG. 13 is a section view of another exemplary plunger.

Another exemplary plunger, which is generally represented by reference numeral 106a in FIG. 13, includes a plunger body 150a, a forward (relative to the direction of travel) o-ring seal 152a, and a friction control device 152b that is spaced from the o-ring seal. The friction control device 152b may be in form of an o-ring (as shown) or in the form of an overmolded part in some embodiments. The friction control device 152b provides for a consistent, reliable resistance of the plunger 106a to pushing force (e.g., from the plunger pusher) and may be configured such that at least one pound of force is required to push and move the plunger. This functionality may be accomplished in a variety of ways. For example, the o-ring seal 152a and friction control device 152b may be formed from different materials, and/or may be differently shaped, and/or may be differently sized. For example the o-ring seal 152a may be made of chlorobutyl rubber or bromobutyl rubber, and the friction control device 152b of silicone or polytetrafluoroethylene.

Figure 14:
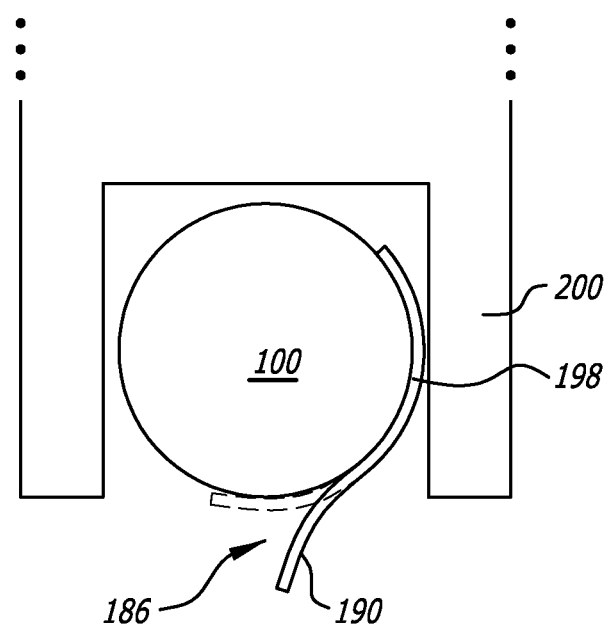
FIG. 14 is a simplified view of medicament cartridge with a removal tab.

At least some embodiments of the present pump assembly 200 include a latch or other mechanism that prevents the cartridge 100 from simply falling out of the pump assembly when the associated baseplate is removed. Here, a small amount of pushing force (via the top opening 226 in FIG. 15) and/or pulling force (via the insertion opening 218 in FIG. 16) is used to remove the cartridge. Turning to FIG. 14, a medicament cartridge (e.g., cartridge 100) may be provided with a pull tab 186 that allows the user to pull the cartridge from the pump assembly 200 and/or simply makes the cartridge easier to grasp in those instances where pulling force is not required. In the illustrated example, the pull tab 186 has a main portion 188 that is firmly secured to the cartridge 100 and a handle portion 190. The handle portion 190 may include a low tack adhesive to hold it to the cartridge body until the time of use. Alternatively, the handle portion 190 may simply hang free or may be pushed out of the way (shown by dotted lines). Instead of and/or in addition to the pull tab 186, an outward bias device (such as one or more springs) may be mounted to the cartridge or within in the cartridge compartment. Pull-out ribbons may also be provided.

IV. EXEMPLARY PUMP ASSEMBLIES

Figure 15:
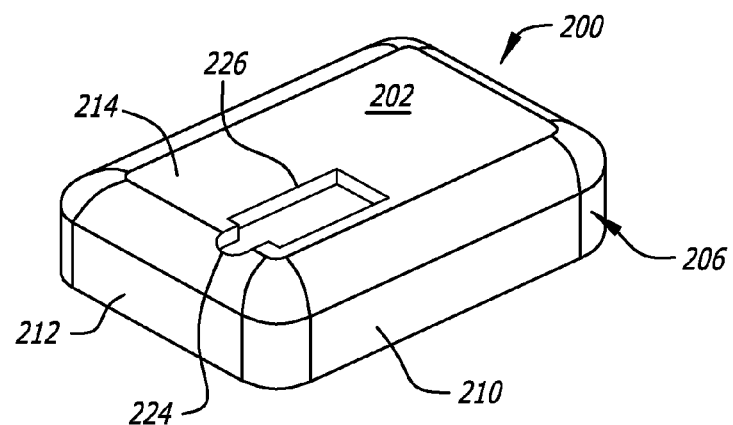
FIG. 15 is a perspective view of an exemplary pump assembly.
Figure 18:
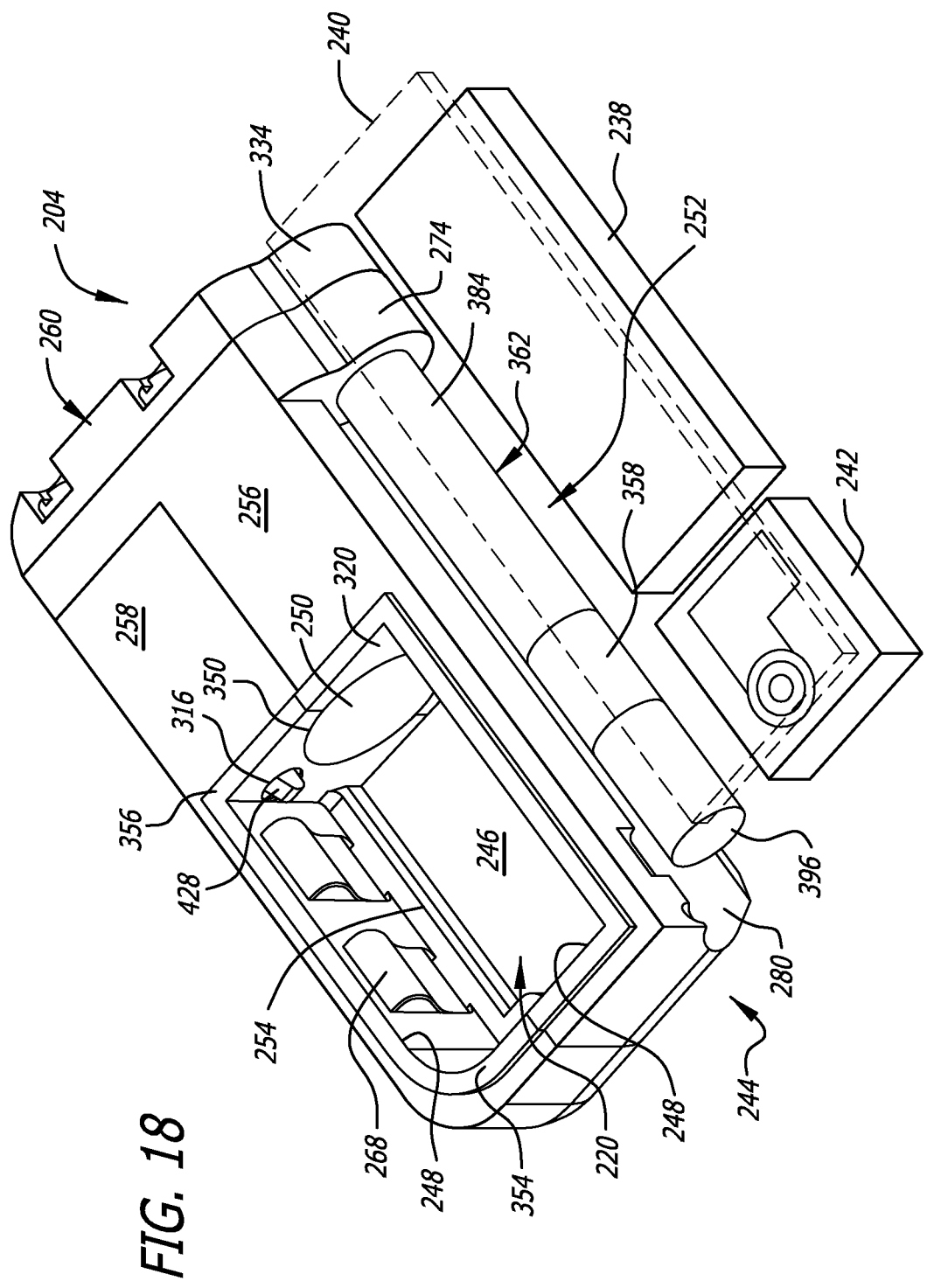
FIG. 18 is a perspective view of an exemplary pump module.
Figure 23:
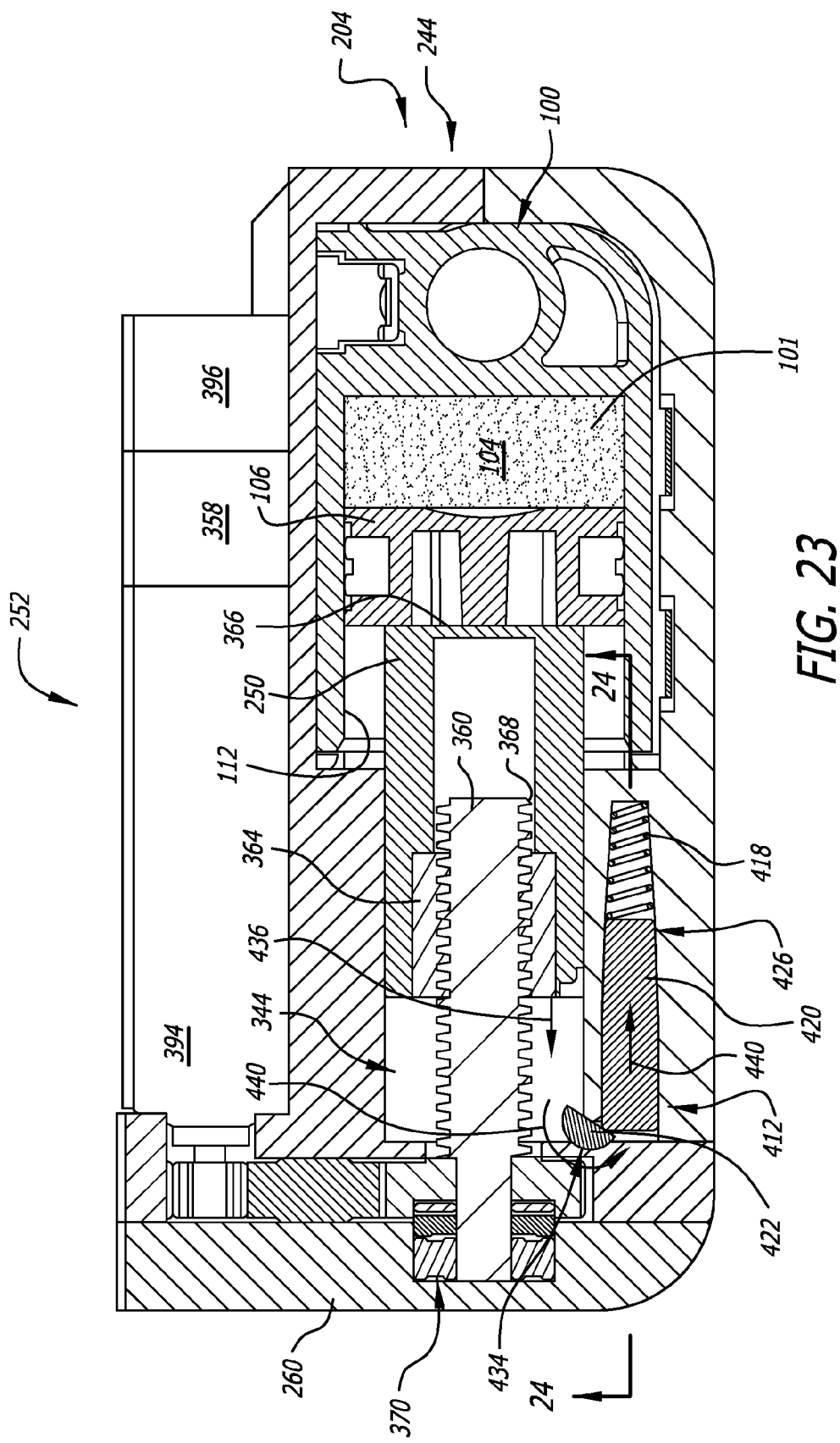
FIG. 23 is a section view of the pump module illustrated in FIG. 19 with a partially filled medicament cartridge positioned therein and a latch mechanism in a lock position.

Briefly, the exemplary pump assembly 200 may include an external housing ("housing"), which is generally represented by reference numeral 202 in FIG. 15, and a pump module, which is generally represented by reference numeral 204 in FIG. 18, that is located within the housing. Other structures that may be carried within the housing 202 include, but are not limited to a rechargeable battery 238, a circuit board controller 240 and an alarm 242, as are illustrated in FIG. 18. When the medicament cartridge 100 is inserted into the pump assembly 200, as illustrated in FIG. 23, the cartridge plunger 106 of the medicament cartridge 100 will be proximate to and facing the plunger pusher 250 of the pump module 204. The drive mechanism 252 of the pump module may then drive the pusher 250 relative to the cartridge plunger 106 to controllably and precisely dispense medicament from the cartridge reservoir 104.

A. Exemplary Housings

Figure 16:
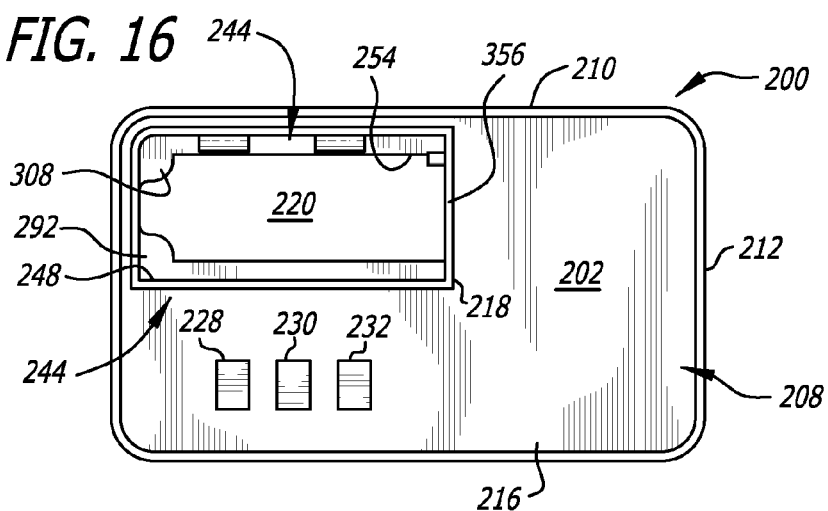
FIG. 16 is a bottom view of the exemplary pump assembly illustrated in FIG. 15.

Referring first to FIG. 15-17, the housing 202 has a top portion 206 and a bottom portion 208. The top portion 206, which includes two side walls 210, two end walls 212, a top wall 214 and rounded corners therebetween, generally defines the internal volume in which the pump module 204 and other pump assembly components are carried, as well as the overall volume of the pump assembly 200. The bottom portion 208 includes a bottom wall 216, which functions as a cover for most of the internal volume, and an insertion opening 218 in the bottom wall through which the cartridge 100 is inserted into the cartridge receiving (or "cartridge storage") area 220. The outer surface of the top wall 214 defines the "top face" or "top surface" of the housing 202, and the outer surface of the bottom wall 216 defines the "bottom face" or "bottom surface" of the housing. In the illustrated embodiment, the insertion opening 218 abuts a thin rim 356 that is flush with the exterior surface of the bottom wall. The rim 356 is part of the chassis 244 (FIG. 14) of the pump module 204.

The configuration of the pump assembly 200 generally, and the housing 202 and insertion opening 218 in particular, is such that the cartridge 100 is inserted through the insertion opening 218 and into the cartridge receiving area 220 in a direction that is normal to plunger pusher 250, as well as the axis along which the plunger pusher travels (note FIGS. 1 and 80).

The top wall 214 of the housing 202 may also be provided with one or more openings. For example, a through-bore opening 224 may be provided in the housing top wall 214 to provide access to the cartridge through-bore 116 (FIGS. 3-4). Such access may be required during a cannula insertion process, such as that described below with reference to FIGS. 45-48.

The top wall 214 of the housing 202 may also be provided with an opening 226 for the cartridge body 102 (or "cartridge body opening 226") in some implementations. The through-bore opening 224 and cartridge body opening 226 are merged into a single cartridge opening in the illustrated embodiment. Such openings may be separate in other embodiments. As alluded to in Section III in the context of the exemplary cartridge 100, an opening facilitates observation of the medicament and plunger in a cartridge formed from transparent material. Additionally, in the illustrated embodiment, the pump assembly 200 is configured (i.e., sized, shaped, etc.) such that a portion of the associated cartridge (e.g., cartridge 100) may protrude through the cartridge body opening 226 when the cartridge is in the cartridge receiving area 220. For example, the relative configurations of the cartridge 100 and pump assembly 200 may be such that the cartridge body 102 protrudes slightly (e.g., about 0.40-1.00 mm, or five percent of the reservoir volume) through the opening 226 in the housing top wall 214, as is illustrated in FIG. 17. The cartridge body inner surface 112 will, however, be located below the inner surface of the top wall 214. The length of the cartridge body opening 226 is substantially equal to the length of the cartridge body 102, with appropriate clearance, while the width is somewhat less than the diameter of the cartridge body. For example, the width of the opening 226 may be about 60 to 90% of the diameter and is about 83% in the illustrated implementation.

One important advantage of the cartridge/pump assembly relationship described in the preceding paragraph is size reduction. Allowing a portion of the cartridge 100 to protrude through the cartridge body opening 226 eliminates the need to accommodate that portion of cartridge below the inner surface of the housing top wall 214, which in turn allows for a reduction in the overall thickness (or "profile") of the pump assembly 200. The reduction is equal to the sum of the length of the protrusion, the thickness of the housing top wall 214, and any clearance that would have been necessary between the inner surface of the top wall and the cartridge in a "cartridge enclosed" implementation. In the context of ambulatory infusion pumps, where every reduction in size is important, this is a significant savings.

The pump assembly 200 may also be configured (i.e., sized, shaped, etc.) such that a portion of the associated cartridge (e.g., cartridge 100) protrudes through the insertion opening 218 on the bottom surface of the housing 202 when the cartridge is in the cartridge receiving area 220. In such an implementation, the associated baseplate (e.g., baseplate 500) may be provided with an aperture 508 (or a recess) to accommodate the protruding portion of the cartridge as is discussed in Section V below with reference to FIGS. 53-55. Typically, although not necessarily, the cartridge 100 will not protrude substantially beyond the bottom surface of the baseplate or will not protrude beyond the bottom surface of the baseplate at all. Protrusion of the cartridge through the insertion opening 218 affords the same size related advantages as the cartridge opening 226 in the housing top wall 214, which is to reduce the thickness of the housing 202.

A plurality of electrical contacts 228, 230 and 232 may extend through (or be carried on) the housing bottom portion 208, as is illustrated in FIG. 16. As discussed in greater detail in Sections IV-J and VI below, two of the contacts (e.g., contacts 228 and 230) may be used to electrically connect the pump assembly 200 to a battery recharger (e.g., charger 700 in FIG. 49) and all of the contacts, at least in some implementations, may be used by the pump assembly during a baseplate identification procedure described.

With respect to dimensions, some embodiments of the exemplary housing 202 may have the following dimensions: length dimensions of 42 mm+/−1.0, 42 mm+/−0.10, 40+/−1.0 mm, 40+/−0.10 mm or 40+/−5.0 mm; width dimensions of 34 mm+/−1.0, 34 mm+/−0.10 mm, 32 mm+/−1.0 mm, 32 mm+/−0.10 mm or 32 mm+/−5 mm; overall thickness or height dimensions of 11 mm+/−1.0 mm or 11 mm+/−0.10 mm; and wall thickness dimensions on the order of 1.0 mm+/−0.10 mm. Suitable housing materials include, but are not limited to, plastic or other materials having a modulus of elasticity of 0.2-1.0 million psi.

B. Exemplary Pump Module Overview

As noted above with reference to FIG. 15, internal components of the exemplary pump assembly 200 may include, among other things, the pump module 204, rechargeable battery 238, circuit board controller 240 and alarm 242. Exemplary pump modules are described below with reference to FIGS. 18-39. Other components may include the pump assembly portion 236 of a pressure sensor.

C. Exemplary Chassis

Figure 25:
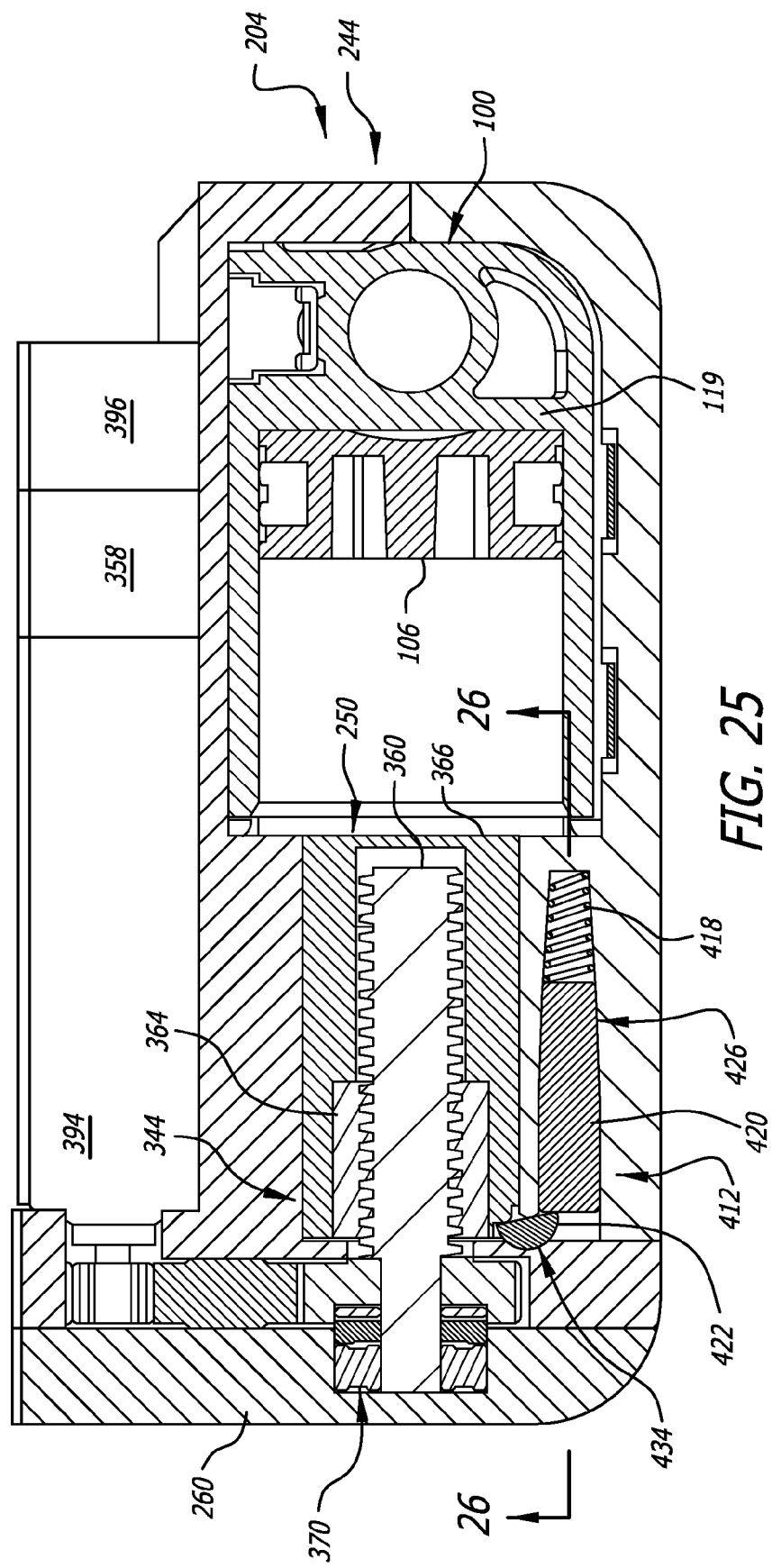
FIG. 25 is a section view of the pump module illustrated in FIG. 19 with an empty medicament cartridge positioned therein and the latch mechanism in an unlock position.

Briefly, and referring first to FIG. 18, the exemplary pump module 204 may have a rigid chassis 244, which is configured to form a cartridge compartment 246 that defines the cartridge receiving area 220, a plunger pusher (or "pusher") 250 that drives the cartridge plunger 106 (FIG. 25) in the dispensing direction, and a drive mechanism 252 that drives the plunger pusher in the dispensing (or "forward") direction and the retraction direction. The rigid chassis 244 may, among other things, provide a low compliance, very rigid mounting structure for receiving and securely holding the medicament cartridge 100 relative to the plunger pusher 250, and is shown in FIGS. 23 and 25.

The chassis 244, and thereby the pump module 204, may be molded snap in, hooked, bonded or attached with fasteners to the bottom portion 208 of the pump assembly housing 202. As can be seen in FIG. 16, when the chassis 244 is positioned in the housing 202, the large bottom opening 248 directly communicates with the medicament cartridge receiving area 220. The exemplary chassis 244 also includes an opposing, and smaller, top opening 254 that directly communicates with the top wall opening 226 in the housing 202, as shown in FIGS. 15 and 17.

Figure 20:
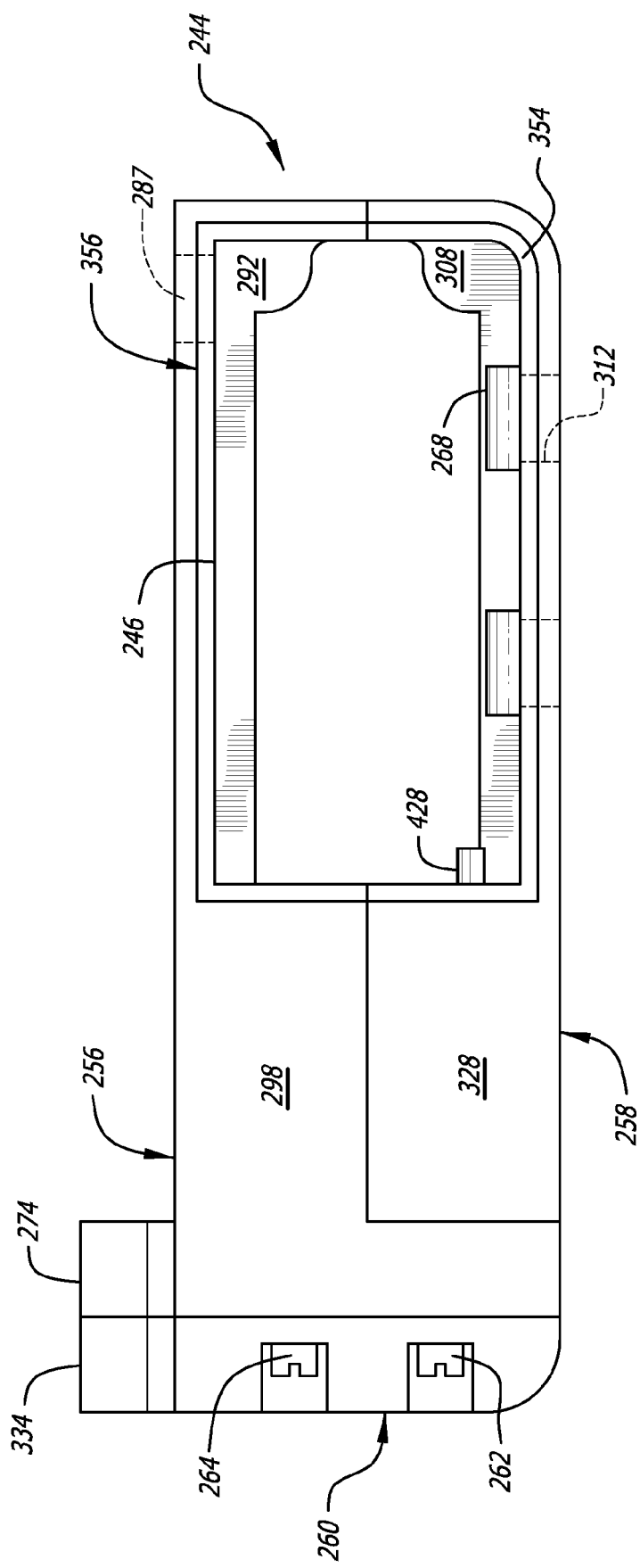
FIG. 20 is a plan view of an exemplary chassis.

Turning to FIG. 20, the components of the exemplary chassis 244, which is described in extensive detail below, may include a first side frame member 256, a second side frame member 258, an end gear cap 260, two long fasteners 262, two shorter fasteners 264, a connector bar 266 (FIG. 21), and two spring bias clips 268. The exemplary rigid chassis 244 is shown in exploded form in FIGS. 21 and 22 to illustrate the various chassis components and the assembly thereof.

Figure 21:
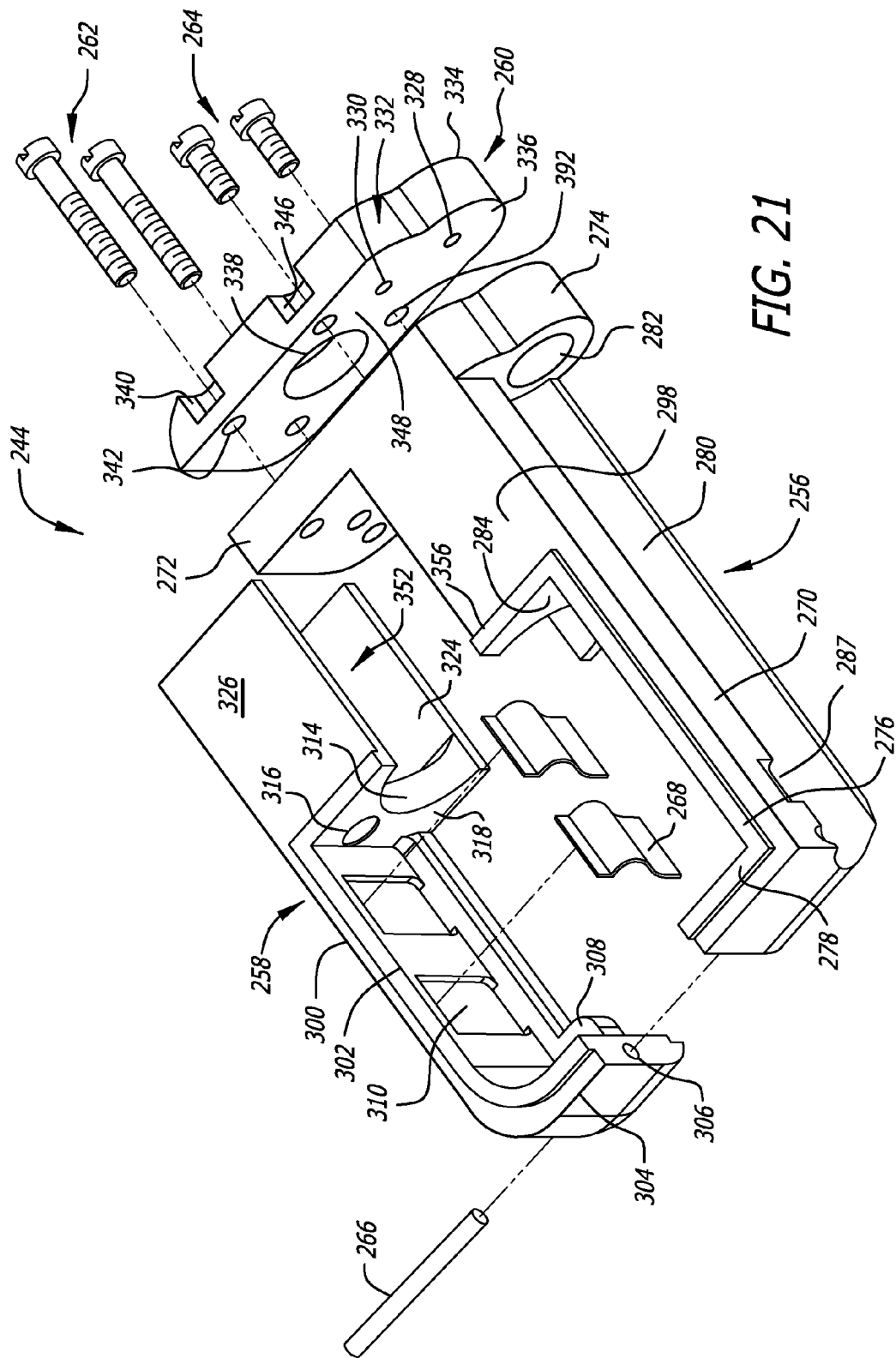
FIG. 21 is a front exploded perspective view of the chassis of FIG. 20.
Figure 22:
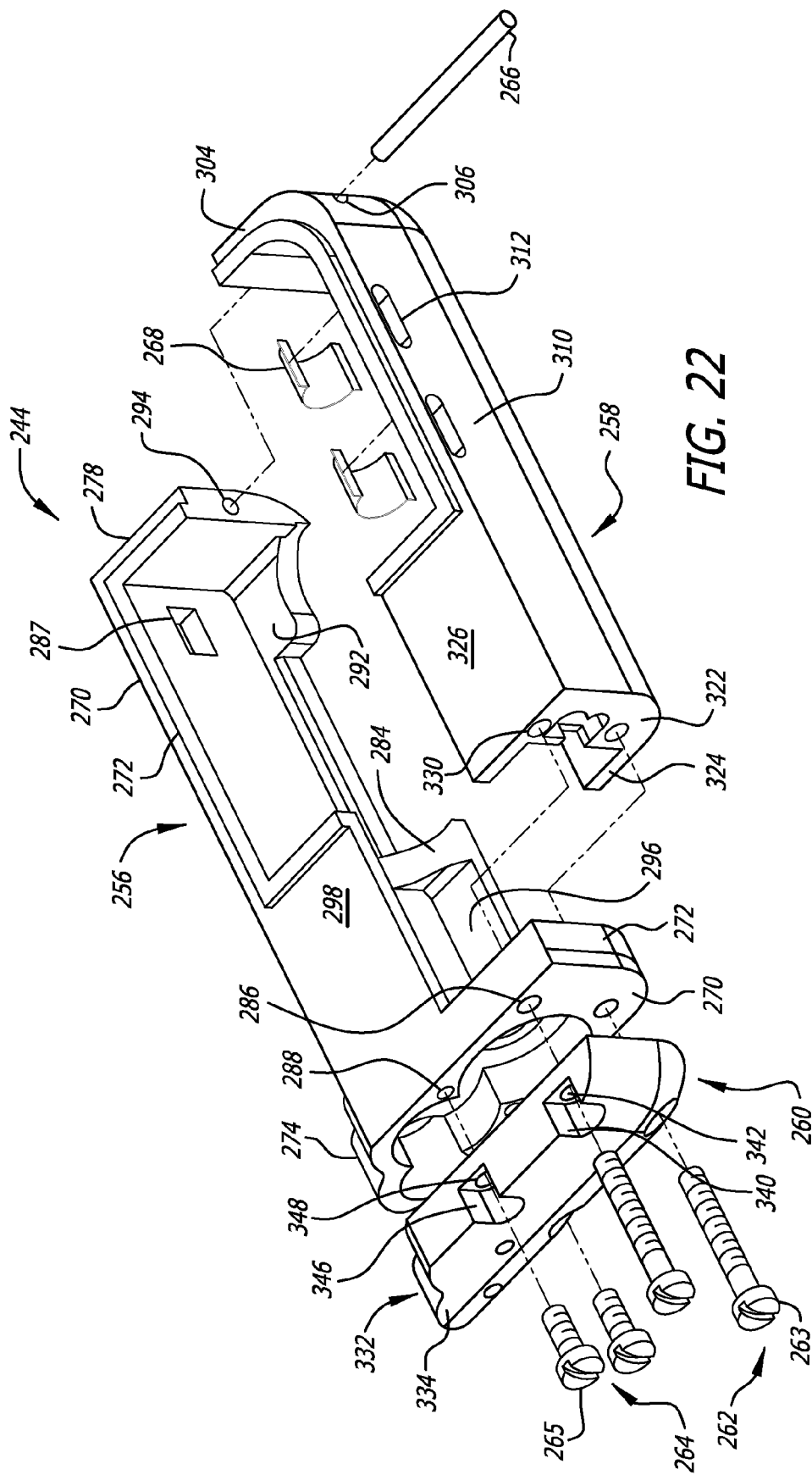
FIG. 22 is a rear exploded perspective view of the chassis of FIG. 20.

The first side frame member 256 illustrated in FIGS. 21 and 22 may include a first side longitudinal portion 270, a rear transverse dog leg 272, a bulging portion 274, a first forward recessed area 276 defining part of the cartridge compartment 246 and a first forward transverse portion 278 defining another part of the cartridge compartment 246. The longitudinal portion 270 has an outer elongate recessed area 280 ending at the bulging portion 274, which has a through-hole 282. A first half 284 of a circular longitudinal opening 350 (FIG. 18) may be formed at the rear of the cartridge compartment 246 by the first side frame member 256. The longitudinal portion 270 may have a side through-opening or window 287 at a forward location in the cartridge compartment 246. In some embodiments, the opening 287 may be sealed with a transparent cover such as a transparent film. The dog leg 272 may have two large fastener openings (or "holes") 286 and two small fastener openings 288 in a rearward face 290. Engagement portion 292 extends inwardly from the longitudinal portion 270 and the forward transverse portion 278 and into the cartridge compartment 246. The forward transverse portion 278 may have a side opening 294. Top and bottom body plate portions 296, 298 extend inwardly from the longitudinal portion 270, forwardly from the dog leg 272 and rearwardly from the cartridge compartment 246.

The second side frame member 258 illustrated in FIGS. 21 and 22 may include a second side longitudinal portion 300, a second forward recessed area 302 defining part of the cartridge compartment 246 and a second forward transverse portion 304 defining part of the cartridge compartment 246 and having a transverse through-hole 306. An engagement portion 308 extends into the cartridge compartment 246 from the second side longitudinal portion 300 and the second forward transverse portion 304. As shown in FIG. 21, two spaced recessed areas 310 may be formed on the inward surface of the second side longitudinal portion 300 and at the cartridge compartment 246, and lateral through-openings 312 may be formed at upper ends of these recessed areas, as can be seen in FIG. 22. A second half 314 of the large longitudinal opening 350 may be formed at the rear of the cartridge compartment 246, as shown in FIG. 21. A longitudinal through-opening 316 may be near the second half 314 of the opening, as can be seen in FIG. 21, and through a wall 318 of the second side frame member 258. The wall 318 forms a portion of the aft wall 320 (FIG. 18) of the cartridge compartment 246. The rear end of the second side frame member 258 may include a wall 322 extending between top and bottom body plate portions 324, 326 and inward from the second side longitudinal portion 300. As can be seen in FIG. 22, the wall 322 may include upper and lower openings 328, 330.

It may be noted here, with reference to FIGS. 16 and 17, that the chassis engagement portions 292, 308 at least in substantial part define the periphery of the top opening 254 of the chassis 244. The engagement portions 292, 308 may also form abutment surfaces for the medicament cartridge 100 to block a top surface of the medicament cartridge from impacting the housing 202 as a small portion of the cartridge extends through the housing opening 226 (FIG. 17).

The exemplary end gear cap 260 illustrated in FIGS. 21 and 22 may be formed by a body portion 332 having a bulging portion 334 and a flat inward back face 336. Referring to FIG. 21, the inward back face 336 may include two small recess openings 328, 330, a first one in the bulging portion 334 and a second one close to the first one, as well as a central circular large recess opening 338. The outward rear surface of the body portion 332 may have two recessed wells 340, each communicating with respective through-openings 342, and two recessed wells 346, each communicating with respective through-openings 348, as shown in FIG. 21.

The configuration of the exemplary chassis 244 allows the chassis to be subsequently disassembled and reassembled in order to, for example, retrieve, repair and/or replace components of the pump module 204.

The assembly of the chassis components can be understood from a comparison of FIGS. 21 and 22 to FIGS. 18 and 20, with an emphasis on the dotted lines in FIGS. 21 and 22. The order of the assembly steps may be varied from those set forth below as would be apparent to those skilled in the art. Operative positions of the components of the drive mechanism 252 (FIG. 18) and drive line 344 (FIG. 25) in and relative to the chassis 244 are described below with reference to FIGS. 23 and 25, for example.

Figure 19:
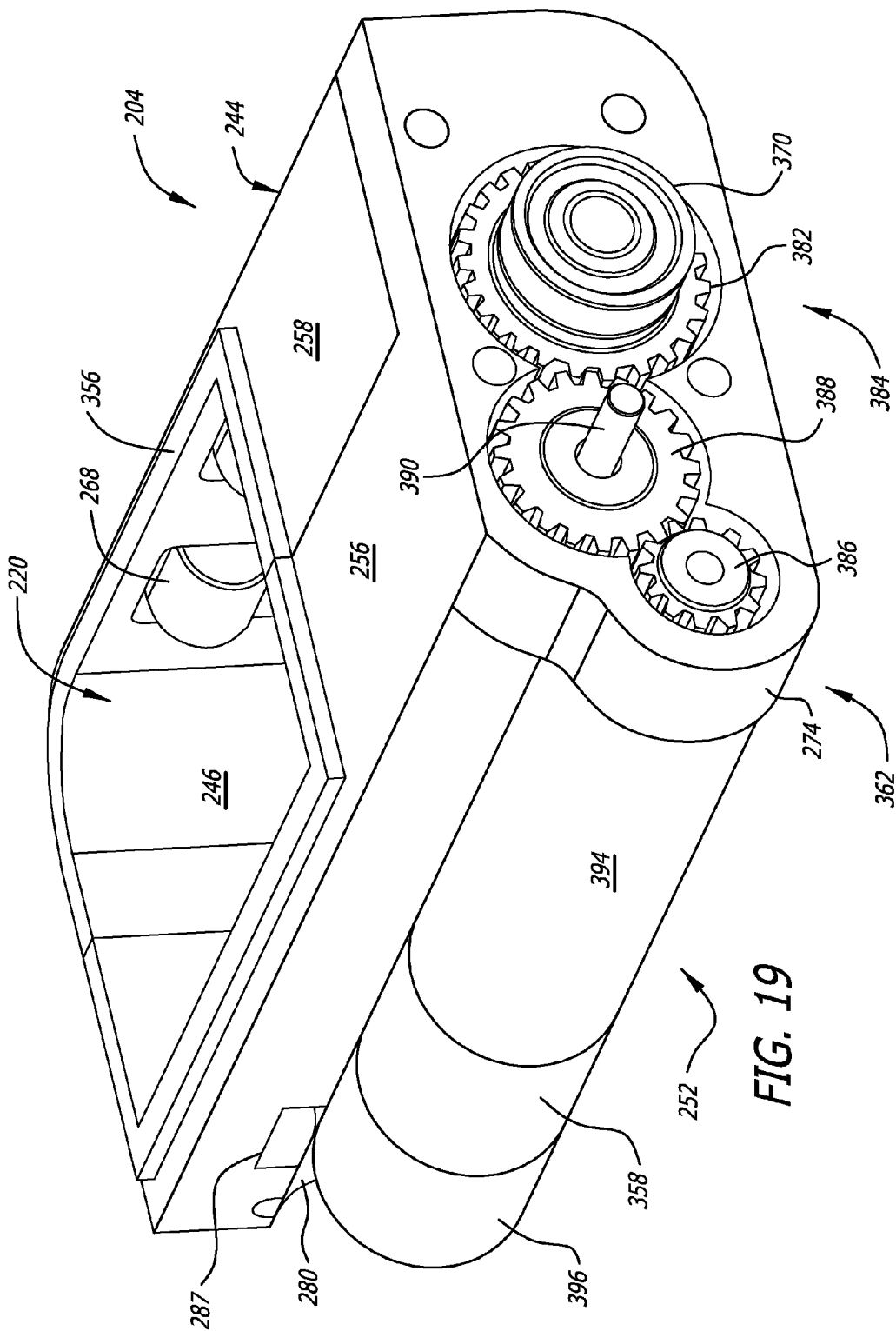
FIG. 19 is a perspective view of the pump module illustrated in FIG. 18 with the end gear cap omitted.

As part of the exemplary assembly method, bottom ends of the spring clips 268 are fitted into (or otherwise affixed in) bottom ends of the respective recessed areas 310. The clips 268 are compressed slightly and their upper ends are inserted into the upper ends of the respective recessed areas 310 and into the respective openings 312. The clips 268 are thereby compressed and bulging slightly into the cartridge compartment 246, as can be seen in FIGS. 18 and 19. Thus, when the medicament cartridge 100 is in the cartridge compartment 246, the spring clips 268 bias the cartridge 100 to and against the opposite wall of the cartridge compartment. This not only helps to insert and releasably hold the cartridge 100 in the cartridge compartment 246, but also pushes the cartridge 100 closer to the chassis window 287 to hold occlusion sensor components in fixed relation as is discussed in detail in Section IV-H.

The first and second side frame members 256, 258 are positioned together as part of the chassis assembly process. When positioned together, the connector bar 266 is inserted in through the through-hole 306 and into the opening 294 to thereby connect the first and second transverse portions 278, 304 together. Alternatively, the connector bar 266 may be inserted into the through-hole 306, the first and second side frame members 256, 258 positioned together and the connector bar 266 then pushed into the opening 294.

With the first and second side frame members 256, 258 positioned together and the end gear cap 260 positioned against the rearward face 290 of the dog leg 272 of the first side frame member 256, it can be understood from the drawings that many of the holes or openings will align for operative insertion therein of respective fasteners. Specifically, and referring to FIG. 22, holes 286, 330, 342 will align for receipt therein of fasteners 262 with the heads 263 disposed in the wells 340; and holes 288, 348 will align for receipt therein of fasteners 264 with the heads 265 disposed in the wells 346. The heads 263 and 265 are disposed in their respective wells, and do not extend out exposed beyond the outer surface envelope of the end gear cap 260, as can be seen in FIG. 20.

Referring to FIG. 22, the two longer fasteners 262 pass through respective holes 342 in the end gear cap 260 and the first and second side frame members 256, 258. In contrast, the two shorter fasteners 264 do not extend into the second side frame member 258, but only through holes in the end gear cap 260 and the first side frame member 256. This arrangement has the advantage that the fasteners 262, 264 not only attach the gear cap 260 to the first and second side frame members 256, 258, but also attach aft ends of the side frame members together and in a relatively compact construction.

When the chassis 244 is assembled, the first and second halves 284, 314 (FIG. 21) adjoin to form the circular longitudinal opening 350 (FIG. 18). The opening 350 extends between the cartridge compartment 246 and the chassis chamber 352 illustrated in FIG. 21. The top surface of chamber 352 is formed by the adjoining top plate portions 296, 324 and the bottom surface is formed by the adjoining bottom plate portions 298, 326. The opening 316 (FIG. 18), which is adjacent to the opening 350, also extends between the cartridge compartment 246 and the chamber 352.

As can be understood from the drawings, including FIGS. 18, 19 and 20, the bulging portions 274, 334 of the first side frame member 256 and the end gear cap 260, respectively, are similarly configured such that when the end gear cap 260 is attached to the first side frame member 256 the bulging portions 274, 334 mate and form a continuous smooth curving surface.

The cartridge compartment bottom opening 248 (FIG. 18), which is formed when the first and second side frame members 256, 258 are mated, may have a generally rectangular shape with three right angle corners and one rounded corner 354, which is shown in the bottom perspective views of FIGS. 18 and 20. The bottom opening 248 may be formed or defined by a rim 356, as shown for example in FIGS. 19 and 20 and described above. The opening 248 and the cartridge compartment 246 itself may be configured to receive therein with a relatively close fit the medicament cartridge 100. The opening 248, cartridge compartment 246 and medicament cartridge 100 may be configured so that there advantageously is only one orientation in which the cartridge 100 may be inserted into the cartridge compartment 312.

With respect to materials, the chassis 244 may be made, for example, of ceramic, plastic filled with a stiffening material, glass-reinforced plastic, carbon reinforced plastic, aluminum, steel, titanium or other metal. The chassis 244 may be formed of a material having a modulus of elasticity greater than 1 million psi, 3 million psi, 10 million psi or 10-30 million psi. This is considerably more rigid than the material of the housing 202 itself. Turning to dimensions, in some implementations, the chassis 244 may have a length of 40 mm+/−1.0, 40 mm+/−0.10 mm or 37.0-41.0 mm; a thickness of 9 mm+/−1.0, 9 mm+/−1-0.10 mm or 8.9-9.1 mm; and a width of 16 mm+/−1.0, 16 mm+/−0.10 mm, or 15.8-16.2 mm. The cartridge compartment 246, in turn, may have a length of 19 mm+/−1.0, 19 mm+/−0.10 mm or 18.8-19.2 mm and a width of 12 mm+/−1.0, 12 mm+/−0.10 mm or 11.8-12.2 mm. The cartridge compartment 246 also may help shield the medicament 101 (FIG. 23) in the medicament cartridge 100 from heat generated by the rechargeable battery 238 (FIG. 18) during dispensing and/or recharging procedures.

As an example, the configuration and construction of the present chassis 244 may contribute to a frame and drive line rigidity sufficient to withstand axial loads to ten pounds without extension greater than 0.0005 inch through 200,000 rotational (turns) cycles or 400 axial cycles. Axial cycles refer to the nut 364 traveling down the lead screw 360 (discussed below with reference to FIGS. 23 and 25).

D. Exemplary Plunger Pushers and Drive Mechanisms

The exemplary pump module 204 illustrated in FIG. 18 includes, as noted above, a plunger pusher 250, to push the cartridge plunger 106 in the dispensing direction, and a drive mechanism 252 that drives the plunger pusher. Generally speaking, the exemplary drive mechanism 252 may, in some instances, include a motor 358, a lead screw 360 (FIG. 23), a gear assembly 362 (FIG. 19) operatively between the motor and the lead screw, a drive nut 364 (FIG. 23) attaching the pusher to the lead screw, and a thrust bearing 370 (FIG. 23). Each of these components is discussed in greater detail below.

As illustrated for example in FIG. 23, the exemplary plunger pusher 250 may be a hollow, generally cylindrical structure that includes a plunger engagement surface 366. The pusher 250 may, in some instances, have a flange (not shown) that prevents rotation of the pusher with the lead screw 360. Additionally, as noted in Section III above in the context of exemplary medicament cartridge 100, the exemplary pusher 250 may be configured such that it is not connectable (or "is unconnectable") to the cartridge plunger 106. Put another way, and referring to FIG. 23, the exemplary plunger pusher 250 does not include any structural components that are (or could be) connected to the plunger pusher. For example, the plunger pusher does not include external threads, a fastener, a magnetic catch, a ratchet, or other such instrumentality. The plunger engagement surface 366 may, for example, simply be planar as shown. Given the lack of connectability, under no circumstances will reverse movement of the plunger pusher 250 pull the plunger 106 rearwardly and draw medicament back into the reservoir 104.

Suitable materials for the plunger pusher 250 include, but are not limited to, stainless steel, polystyrene and polycarbonate. The dimensions will correspond to the other aspects of the overall system. For example, the plunger pusher 250 may have an outer diameter (or other "thickness" dimension of 6 mm+/−1 mm and a length of travel of 8.5 mm+/−2.0 mm.

With respect to the drive mechanism 252, and referring first to the motor, and although the present inventions are not limited to any particular motor, the exemplary motor 358 may be a stepper motor such as, for example, the Faulhaber ADM 0620 motor. The Faulhaber ADM 0620 motor has a 6 mm diameter, a planetary gearhead of 256 reduction, and the specifications of the motor are set forth at www.faulhaber.com. A stepper motor may in some instances control angular displacement and speed more precisely than a DC motor. Motors other than stepper motors, including DC motors, may be employed in the present pump assemblies.

Turning to the lead screw, and referring to FIG. 23, the exemplary lead screw 360 is connected to the plunger pusher 350 by a drive nut (or "retaining nut") 364 such that the rotational motion of the lead screw 360 may be translated into axial movement of the pusher 250. In other words, the drive nut 364 is in contact with the lead screw 360 and propels the pusher 250. The exemplary drive nut 364 may be molded with the pusher 250 or may be pressed into a flange of the pusher. Alternatively, the pusher 250 and drive nut 364 may be integrally machined of the same material or the pusher may be molded with internal threads.

The lead screw 360 and the drive nut 364 may be made of material that allows axial movement within an exemplary 0.0005 inch overall chassis "stretch" budget under a ten pound load through 200,000 rotational cycles or 400 axial cycles. The lead screw 360 may have a gearform accuracy in rotation of better than 0.0005" to prevent apparent missed delivery increment, and may have a 70% mechanical efficiency. The diameter of the lead screw 360 may be relatively small (e.g., 3.0 mm) to help minimize the size of the pump module 204. The threads 368 of the exemplary lead screw 360 may be Acme threads to provide high efficiency and precision, and may have a 0.5 mm lead pitch (approximately 0.020 inch/revolution).

An exemplary drive line 344 may be defined, as is illustrated in FIG. 28, by the retaining nut 364, lead screw 360 and thrust bearing 370. The thrust bearing 370 may be on the non-threaded shaft end 372 of the lead screw 360. The thrust bearing 370 may also be selected, for example, to allow axial movement within an exemplary 0.0005 inch overall chassis "stretch" budget under a 10 pound axial load, and have an axial length of 2 mm, an inner diameter of 2 mm and an outer diameter of 6 mm.

The thrust bearing may be a conventional ball bearing, angular contact bearing, or, as illustrated in FIG. 28, it may be a combined radial/thrust bearing of the type represented by reference numeral 370. The thrust bearing 370 may include ball bearings 374, a retainer 376 that guides the ball bearings, a thrust washer 378, and radial ball bearings 380 that ride on the thrust washer and also ride on a thrust face of a drive gear 382. The radial ball bearings 380 may take up the thrust of the lead screw 360 in the retraction direction. The drive gear 382 may be integrally machined with, or welded or bonded to, a portion of the lead screw 360 such as the non-threaded shaft end 372. The radial bearings 384 may be pressed onto the shaft 372 and, to resist axial force, pressed or bonded into the rear wall of the chassis 244 or more specifically into the opening 338 (FIG. 21) in the gear cap 260. As an example, the combined radial/thrust bearing 370 may be configured to resist ten pounds of axial force during medicament 101 dispensing from the medicament cartridge 100 and four pounds of axial force during retraction of the pusher 250.

Turning to FIG. 19, which shows the exemplary pump module 204 with the gear cap 260 removed therefrom for explanatory purposes, the drive gear 382 on the lead screw 360 is one of three gears of a transverse gear train 384. The other two gears may be a planetary gearbox output gear 386 and a transverse gear 388 that is operatively positioned between the drive gear 382 and the output gear 386. As illustrated in FIG. 21, the shaft 390 of the transverse gear 388 is fixed in the gear cap opening 392 and the gear 388 freely rotates on the shaft 390. The gear cap and first side member bulging portions 336, 274 define part of a gear box for the transverse gear train 384. Lubricant may be provided in the gear box to reduce the friction between the gears therein.

The transverse gear train 384 may be selected to withstand gearform loads of 10 mNm output torque at the motor 358. The accuracy of the gearform in rotation may be better than 0.0005 inch to prevent apparent missed delivery increment (decremented by the gear ratio closer to the motor output). The transverse gear train 384 may have a 2:1 gear ratio.

The exemplary gear assembly 362 may also include a planetary gearbox 394. The planetary gearbox 394 may be selected to withstand gearform loads of 10 mNm output torque at the motor 358, and may have a 256:1 gear ratio.

As illustrated for example in FIGS. 18 and 19, the drive mechanism 252 may also include an encoder 396 positioned on the shaft of motor 358 opposite the planetary gearbox 394. The encoder 396 may be used to define/resolve the number of revolutions (or "angular displacement") and/or the rotational direction of the motor shaft. The displacement/direction information is sent to the controller 240 and used to control various operations of the pump assembly 200, as is discussed in greater detail in Section IV-L (among others) below. Briefly, during normal operation, the controller 240 sends paired drive signals to the motor 358 (stepping pulses) while monitoring the pulse train back from the encoder 396. For example, the number of encoder signals (or "ticks") for a particular dispensing operation may be calculated, encoder 396 is monitored in near real time to determine if it is moving as predicted. The encoder 396 may also be used to detect gear assembly issues as well as motor operation errors.

As is also illustrated in FIGS. 18 and 19, the motor 358, planetary gearbox 394, and encoder 396 together define a cylinder. The cylinder fits in a compact manner partially into and against the outer recessed surface 280 of the chassis first side frame member 256. Turning to FIGS. 23 and 25, when viewed in plan, the exemplary drive mechanism 252 defines a U-shape with one leg of the U being defined by the longitudinal axis of the motor 358, planetary gearbox 394, and encoder 396, while the other leg of the U is defined by the longitudinal axis of the lead screw 360. The two axes (or legs of the U) are only 9.5+/−1.0 mm apart in the illustrated embodiment. The base of the U is defined at least substantially by the transverse gear train 384.

Figure 29:
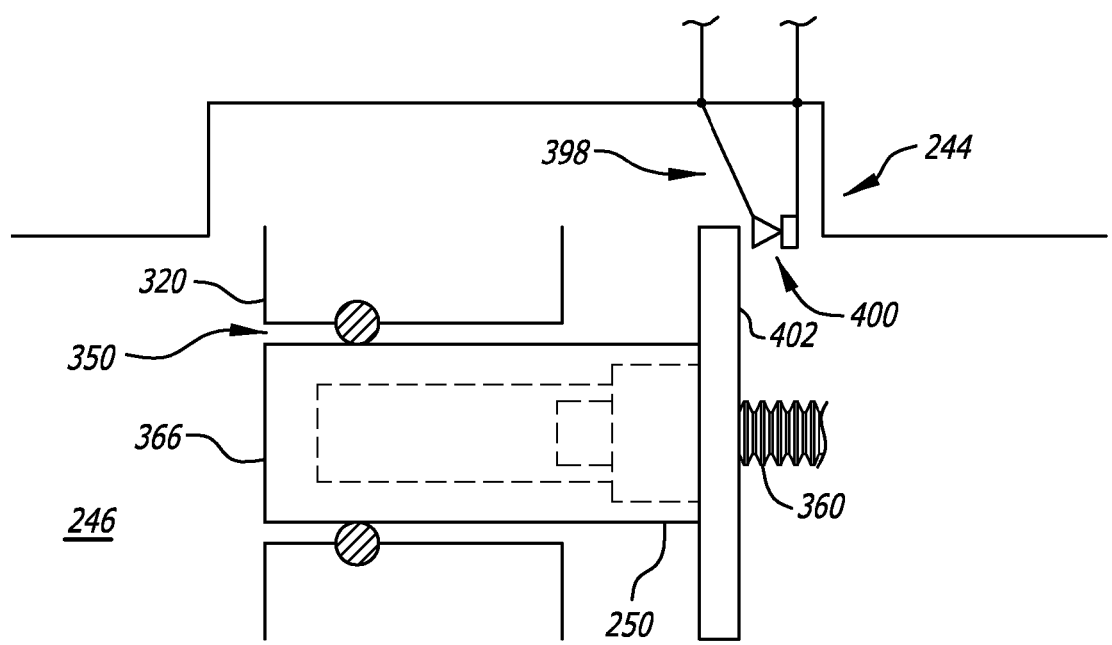
FIG. 29 is a simplified view showing a switch that detects when a plunger pusher is in a home position.

In at least some instances, it may be desirable to detect when the plunger pusher 250 is in the fully retracted (or "home") position illustrated in FIGS. 18 and 29. This may be accomplished in a variety of ways. One exemplary structure for performing the retracted position detection function is the position detector 398 illustrated in FIG. 29. The exemplary position detector 398 includes a switch 400, which may be mounted to the chassis 244 aft of the opening 350, and a flange 402 that may be carried by the pusher 250. When the pusher 250 is in the retracted position illustrated in FIG. 29, the switch 400 is closed by the flange 402 and sends a signal to the controller 240 indicating that the pusher 250 is in the home position. The switch is open when the pusher 250 is not in the home position and a portion thereof is within the cartridge compartment 246.

In other embodiments, different types of switches may be employed, or the flange may be omitted and the switch positioned such that it will be closed by the pusher 250 when the pusher 250 is in the retracted position. For example, switch contacts (e.g. a metalized pattern) may be carried on the chassis 244 and a conductive pad may be carried on the flange 402. Non-mechanical detectors, such as magnetic detectors and optical detectors, may be used in place of a switch. Additionally, regardless of the type of detector employed, the detector may be configured to provide a signal to the controller 240 when the pusher 250 is not in the retracted position.

Another alternative is to simply detect that the motor encoder 396 is not turning when running the motor 358 in reverse. To that end, a hard mechanical stop (not shown) may be provided at a location that stops the pusher 250 and stalls drive mechanism 252 when the pusher reaches the home position. Such a hard mechanical stop may be non-binding, i.e., configured such that the drive mechanism 252 can be stalled by the stop but can also easily reverse without mechanism binding. Homing may be accomplished by retracting the pusher 250 with controlled torque and speed until the pusher hits the hard mechanical stop, thereby stalling the motor 358. Motor stall may be identified in response to the encoder 396 indicating no rotation. The expected stall (home) location may be remembered by the device and compared to the actual stall position for additional control or, in at least some implementations, the motor 358 may be given a reverse displacement command that is larger than the total possible travel of the drive mechanism 252, and the actual stall (home) position determined based on the stall of the motor. The various techniques described herein for increasing motor torque in response to a motor stall to verify stall position may be employed to improve this technique of home position determination by stalling at the hard stop.

E. Exemplary Reservoir Clamping

Figure 30:
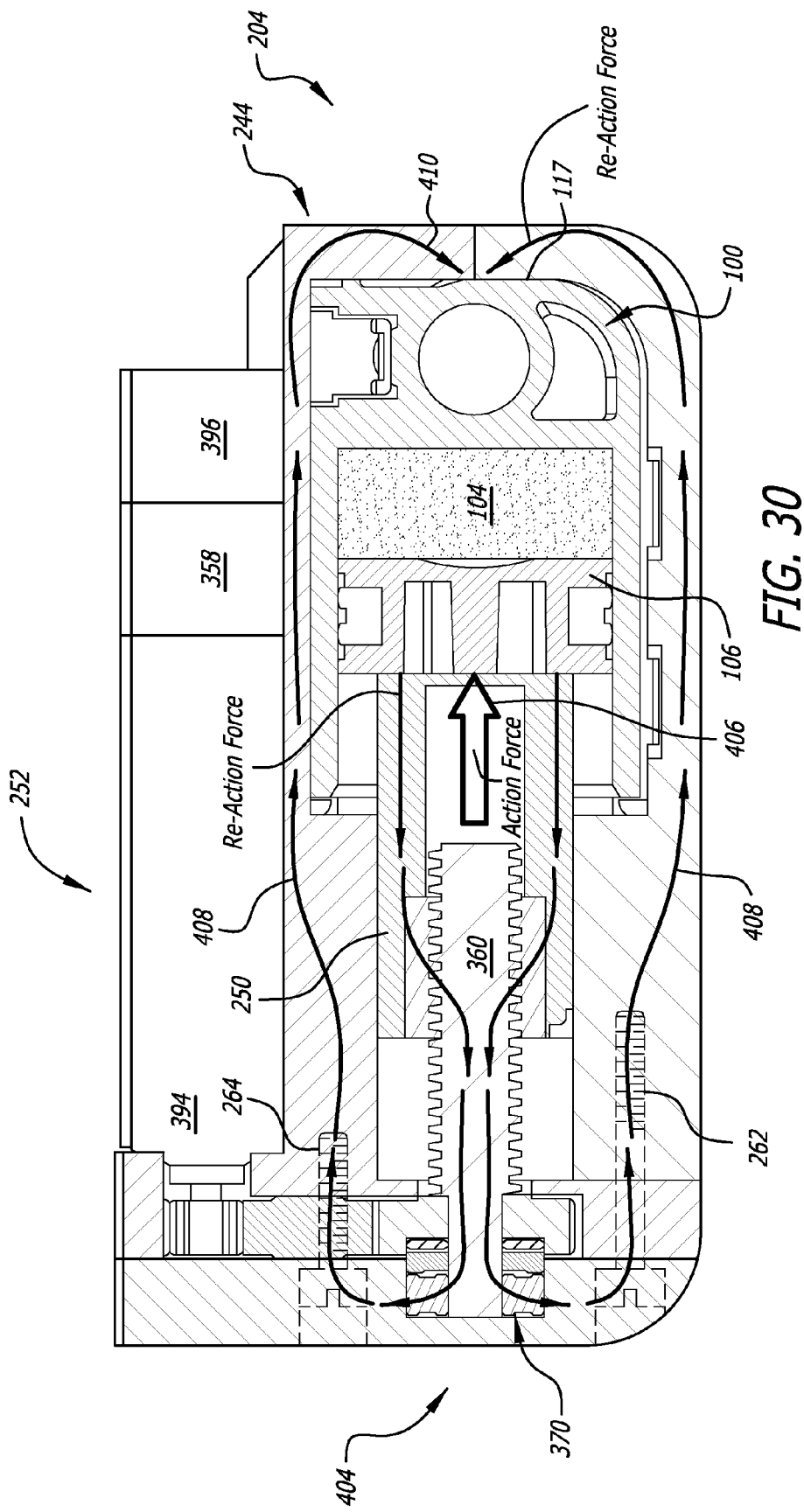
FIG. 30 is a section view of an exemplary pump module with various structures omitted and medicament cartridge reservoir clamping forces displayed.

The arrangement, configuration and materials of the chassis 244 and drive line 344 in the exemplary implementation together create a force "clamp" that is generally represented by reference numeral 404 in FIG. 30. The clamp 404 clamps the reservoir 104 between the dry side of the plunger 106 and the outer surface of the cartridge front wall 117. Put another way, both ends of the reservoir 104 are held in such a manner that movement of the reservoir relative plunger pusher 250 (e.g., due to cartridge movement) may be prevented, and the corresponding loss of delivery accuracy prevented.

The thick arrow 406 in FIG. 30 represents the action force associated with the pusher 250 pushing the plunger 106 as a result of rotation of the motor 358. The thin arrows 408 show the reaction forces originating in the plunger 106, traveling back in the opposite direction through the drive line 344 and then forward through the fasteners 262 and 264, and through the chassis 244 to the front wall 117 of cartridge 100. A reaction force 410 on the outer surface of the front wall 117 and opposite to the action force 406 is thereby created. The force "clamp" 404 may be generally configured as a pair of oppositely-facing C-shaped clamps, as can be understood from FIG. 30.

The clamping displacement of the reservoir 104 applied by the clamp 404 adjusts incrementally as the cartridge plunger 106 is advanced towards the front wall 117 by the pusher 250. For example, the clamping displacement may adjust incrementally by 0.001 inch. The exemplary clamp 404 may apply a clamping displacement with, for example, a precision of better than 2% over a force range of zero to ten pounds.

F. Exemplary Cartridge Lock and Bias Apparatus

In at least some implementations, structure is provided to block removal of a cartridge from the pump assembly when the plunger pusher 250 is in the cartridge 100, and to allow a cartridge to be inserted into and removed from a compartment within the pump assembly when the pusher is retracted.

One example of such as structure is the releasable, linear one-way clutch (or a "latching mechanism," or an "interlock") that is generally represented by reference numeral 412 in FIGS. 23-27. The clutch 412 blocks removal of a cartridge (e.g., cartridge 100) from the pump module 204 when the plunger pusher 250 is in the cartridge, but allows the cartridge to be inserted into and removed from the cartridge compartment 246 when the pusher is in a retracted "home" position.

Figure 24:
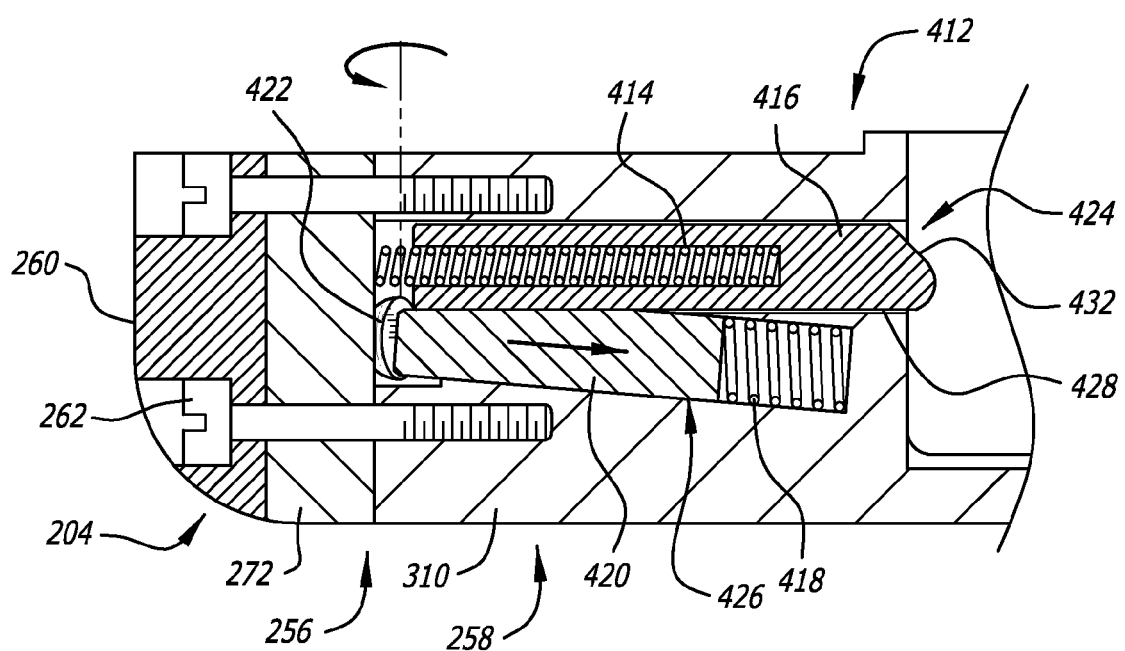
FIG. 24 is a section view taken on line 24-24 in FIG. 23.

Referring first to FIG. 24, the exemplary clutch 412 may include a first coil spring 414, a first pin or elongate member 416, a second coil spring 418, a second pin or elongate member 420, and a "teeter-totter" toggle ball 422. The second elongate member 420 may include friction-engaging surface 428 (FIG. 27). The first coil spring 414 is positioned inside of the first elongate member 416 to form a spring-biased first member 424. The second coil spring 418 is positioned in the second elongate member 420 to form a spring-biased second member 426.

In one exemplary implementation, the first and second springs 414, 418 may each have one to two pounds of spring force. The first spring 414 may have a one mm diameter, and the second spring 418 may also have a one mm diameter. The first and second elongate members 416, 420 may have respective lengths of 12.5 and 7.25 mm. The second elongate member 420 may be a two mm diameter steel rod, and the friction-engaging surface 428 may be a two to five degree beveled surface.

With respect to operation of the exemplary clutch 412, the mode of the spring-biased first member 424 determines whether the clutch 412 is in a locked condition (FIGS. 23 and 24) or an unlocked condition (FIGS. 25 and 26). The spring-biased second member 426, when the pusher 250 is in a non-retracted position, holds the spring-biased first member 424 in a friction-contact locked condition with the friction-engaging surface 428. The cartridge 100 is thereby latched in place in the cartridge compartment 246.

The toggle ball 422 toggles when the pusher 250 is moved to the retracted home position. The toggling action moves the spring-biased second member 426 to a position with the friction-engaging surface 426 out of friction contact with the spring-biased first member 424. In this unlocked or unlatched condition (FIGS. 25 and 26), the cartridge 100 may be removed from or inserted into the cartridge compartment 246. In this fully retracted mode, the spring-biased first member 424 retracts when the spring force of the first coil spring 414 therein is overcome by the force of a cartridge 100 being inserted into or removed from the cartridge compartment 246.

The spring-biased first member 424 may have a patterned end 430 with a sixty-degree beveled face 432 on the cartridge insertion side, as shown in FIG. 24 for example. This beveled face 432 facilitates easy cartridge insertion, with a radius where the spring-biased first member 424 engages the cartridge 100 in a small slot (not shown) for detent action. FIG. 18 shows the end 428 of the spring-biased first member 424 protruding or extending into the cartridge compartment 246 with the sixty-degree beveled face 432 disposed upwards. So positioned, the spring-biased first member 424 will engage the inner surface 112 (FIG. 23) of the cartridge medicament cartridge when the medicament cartridge is in the cartridge receiving area and, given the close fit between the exterior of the cartridge and the interior of the chassis, removal will be prevented.

More particularly, when the clutch 412 is in the locked condition illustrated in FIGS. 23 and 24, the second member 426 intersects the first member 424 at generally five degrees with a light spring force of 0.1 to 0.5 pound, biasing the spring-biased second member 426 towards the spring-biased first member 424. That is, the second member 426 is spring biased towards the first member 424, and thereby operates similar to a one-way roller clutch. Referring to FIG. 24, the first member 424 is on top with the second member 426 below and intersecting at generally five degrees with the light spring bias of 0.1 to 0.5 pound. With the pusher 250 in any position other than the fully retracted home position (FIG. 25), the second member 426 is self-energized by friction with the first member 424, thereby preventing rearward motion of the first member 424. Then, when the pusher 250 is in a fully retracted position, the second member 426 is moved slightly forward by the half ball toggle 422, releasing friction contact with the first member 424. The spring-biased first and second members 424, 426 are thereby in the positions shown in FIG. 26.

In other words, when the pusher 250 is fully retracted, the first member 424 is biased towards the cartridge 100 with a one to two pound spring force and acts like a spring plunger detent. In this fully retracted mode, the first member 424 is able to retract when the spring force is overcome by cartridge insertion or removal. Then when the pusher 250 is not fully retracted, the second member 426 locks the first member 424 from rearward motion and blocks cartridge insertion and removal.

The half ball toggle 422 may be formed from a two mm diameter steel ball, and may rest in a spherical recess 434, such as one machined into a surface of the chassis 244. The half ball toggle 422 thereby can toggle the second member 426 forward when the pusher 250 retracts fully and engages the half ball toggle 422, as can be understood from the arrows 436, 438, 440 in FIG. 23. Other toggling or "teeter-totter"

constructions may be used instead of the exemplary half-ball toggle 422. The clutch 412 also self-adjusts for cartridge 100 tolerance.

The pusher 250 and the spring-biased first member 424 may be provided with o-ring sealing surfaces (not shown) to help make the clutch 412 waterproof.

The pusher 250 may be retracted automatically when the reservoir 104 is empty (see FIG. 25) as discussed elsewhere in this disclosure, which thereby automatically causes the clutch 412 to be unlocked when the reservoir is empty. Alternatively, by operating the remote control 1000 (see, e.g., FIG. 81), the patient may cause the pusher 250 to be retracted before the reservoir 104 is empty, as when he wants to remove the medicament cartridge 100 before it is empty and replace it with a new cartridge 100. This retraction of the pusher 250 by the patient's instructions also causes the clutch 412 to unlock.

Another way of describing the mechanism of the clutch 412 is that the mechanism functions as an interlock that prevents removal of the medicament cartridge 100 from the receiving area 220 when the cartridge 100 is in the inserted position and the pusher 250 is in a non-retracted position, and that allows removal of the medicament cartridge 100 from the receiving area 220 when the cartridge 100 is in the inserted position and the pusher 250 is in a retracted position. The interlock/clutch 412 automatically unlocks the cartridge 100 when the pusher 250 is in the retracted position, and automatically locks the cartridge 100 when the pusher 250 is advanced out from the retracted position.

Figure 31:
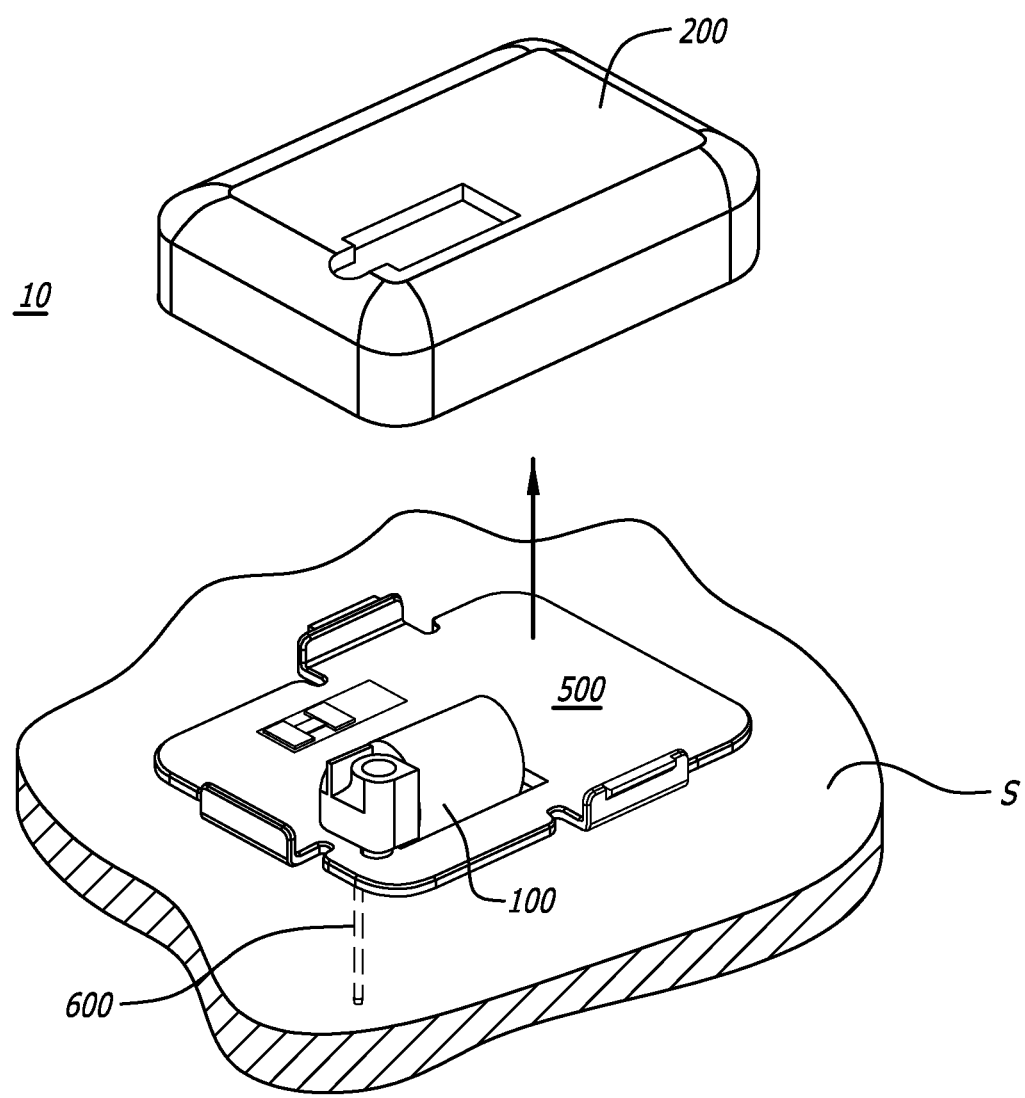
FIG. 31 is a perspective view of an exemplary infusion pump system with the pump assembly removed from the medicament cartridge, cannula and baseplate.

Additionally, one exemplary advantage of the aforementioned light spring bias is illustrated in FIG. 31 in the context of system 10. When a user of the exemplary patch pump system 10 desires to replace the cartridge 100, baseplate 500 and cannula 600, the pump assembly 200 may simply be pulled off the baseplate. The baseplate adhesive (discussed below) will hold the baseplate 500 to the skin, the cannula latch (discussed below) will hold the cannula to the baseplate, and frictional engagement between the cannula and the cartridge through-bore will hold the cartridge to the cannula. In other words, the reusable portion of the system readily and conveniently separates from the disposable portions.

A further way to view the operation of the clutch 412 is that by operating the remote control 1000, a cartridge-biasing member (the spring-biased first member 424) may be changed from a blocking condition, where the cartridge-biasing member (the spring-biased first member 424) blocks removal of a medicament cartridge 100 from the pump module 204, to a release condition, where the cartridge-biasing member (the spring-biased first member 424) does not prevent the medicament cartridge 100 from being removed from the pump module 204. The clutch 412 biases the cartridge 100 forwards, acts as a spring plunger detent during insertion of the cartridge 100 into the compartment 246, and prevents backwards motion during use.

When in a locked condition, the spring-biased first member 424 may engage and bias the medicament cartridge 100 forward in the cartridge compartment 246. The cartridge 100 is thereby biased to a "held" position to secure the cartridge 100 firmly in place, such as against a rigid wall of the chassis, for accurate and precise medicament dispensing. The first member 424 may bias the cartridge 100 forward and thereby closer to the chassis window 287 (see FIG. 20) to fix the relative positions of various occlusion sensor components, as discussed elsewhere in detail in this disclosure.

Another exemplary structure that blocks removal of a cartridge from the pump assembly when the plunger pusher is in the cartridge, and allows a cartridge to be inserted into and removed from a compartment within the pump assembly when the pusher is retracted, is the sliding latch mechanism (or "sliding latch") generally represented by reference numeral 412a in FIGS. 32-35A. The exemplary latch 412a is described below in the context of the pump assembly 200' and baseplate 500', which are identical to pump assembly 200 and baseplate 500 but for minor accommodations for the latch 412a, and similar elements are represented by similar reference numerals. With respect to the minor accommodations, which are discussed below in context, the pump assembly housing 202' includes a bottom portion 208' with a latch slot 209, the chassis 244' includes minor adjustments, the plunger pusher 250' includes a recess 468, and the baseplate 500' includes a latch indentation 509.

The sliding latch 412a is configured to secure the cartridge 100 in place when the pusher 250' is at least partially in the cartridge 100, such as during the dispensing process. In addition to securing the medicament cartridge 100 within the pump module 204', the sliding latch 412a biases the cartridge forward to a "held position" against the rigid chassis front wall 245 when the pusher 250' is at least partially in the cartridge 100. Such biasing facilitates accurate and precise medicament dispensing, and ensures that the cartridge will be accurately located relative to the chassis window 287 (FIG. 20).

Figure 32:
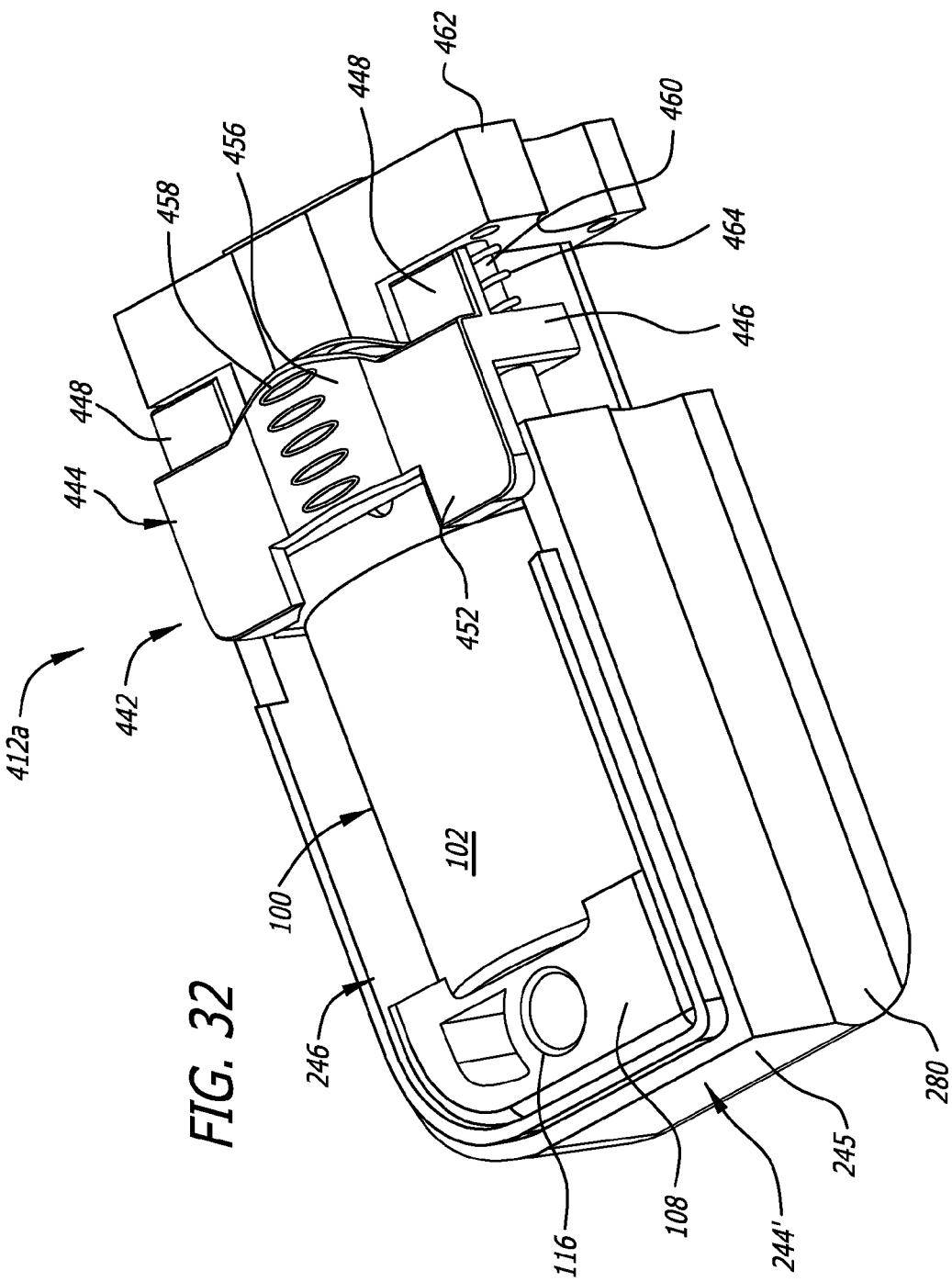
FIG. 32 is a perspective view of an alternative exemplary chassis and latch.

Turning to the components of the exemplary sliding latch 412a, and referring to the bottom perspective view presented in FIG. 32, the sliding latch includes a slidable latch member 442 with a bottom lateral body member 444 as well as a pair of legs 446 (one shown) extending up from opposite ends of the body member. A pair of abutment tabs 448 respectively extend rearwardly from the legs 446. The bottom lateral body member 444 includes a pair of flange portions 452 and an arched (convex) finger tab 456, with friction ridges 458, that is operatively accessible to the user when no baseplate attached (FIGS. 33 and 34).

A pair of rods 460 (one not shown) extend longitudinally through holes in the legs 446 and the front ends of the rods are secured in a wall of the chassis 244, such as the aft wall 320 (FIG. 18). The rear ends of the rods 460 are secured in a chassis flange 462. A pair of bias springs 464 (one not shown) respectively encircle the rods 460 between the legs 446 and the flange 462, and bias the slidable latch member 442 forward, towards the chassis cartridge compartment 246 and to a normal forward biased position.

When the latch member 442 is in the normal forward biased position, the ends of the flange portions 452 will extend over the opening of the cartridge compartment 246, thereby blocking insertion of a medicament cartridge (e.g., cartridge 100) into the pump assembly 200' as well as the removal of cartridge from the pump assembly. When the pusher 250a is in a retracted home position, the slidable latch member 442 is unlocked (as discussed below) and the user can slide the latch member rearward against the bias force of springs 464 (FIGS. 32 and 33) within the housing slot 209. The latch member 442 reaches the rearward position when the tabs 448 abut the rear flange 462 (FIG. 32). Here, the flange portions 452 no longer overlap the opening of the cartridge compartment 246 and block insertion (or removal) of a cartridge.

Turning to FIG. 33, the exemplary sliding latch 412a may also include a locking apparatus 466. The exemplary locking apparatus 466 may include a recess 468 in the plunger pusher 250', a recess 470 in the lateral body member 444, a hole 472 in the chassis 244', and a movable ball 474 carried within the hole. When the latch 412a is in the state illustrated in FIG. 33, which is the result of the user sliding the lateral body member 444 to the rearward position, the movable ball 474 will be located within the pusher recess 468. After a cartridge 100 is inserted into the cartridge compartment 246 and the user releases the lateral body member 444, the springs 464 will push the lateral body member to the position illustrated in FIG. 34. Here, movable ball 474 will be aligned with both the pusher recess 468 and the lateral body member recess 470. Depending on the rotational orientation of the pump assembly 200', the movable ball 474 will either be in the pusher recess 468 or the lateral body member recess 470. When the baseplate 500' is attached as shown in FIG. 35, the user will no longer have access to the latch 412a and the finger tab 456 will be located in the baseplate recess 509 (FIG. 35A). After the plunger pusher 250' is moved forwardly by operation of the lead screw 360, the movable ball 474 will be held in the lateral body member recess 470 and, given that a portion of the ball is also in the chassis hole 472, the lateral body member 444 will held in place and the latch 412a will be in the locked state. The user will not be able to unlock the latch 412a until the pusher 250' is returned to the home position.

It should be noted that the relationship between the finger tab 456 and the baseplate slot 509 also helps to facilitate proper alignment of the baseplate 500' relative to the pump assembly 200' and, for example, proper alignment of the structures that are associated with the baseplate identification process (described in Section VI below with reference to FIGS. 66-78) on the pump assembly (e.g., electrical contacts 228, 230 and 232 in FIG. 16) and the baseplate (e.g., identification devices 582-0, 582-1 and 582-2 in FIG. 1).

Figure 36:
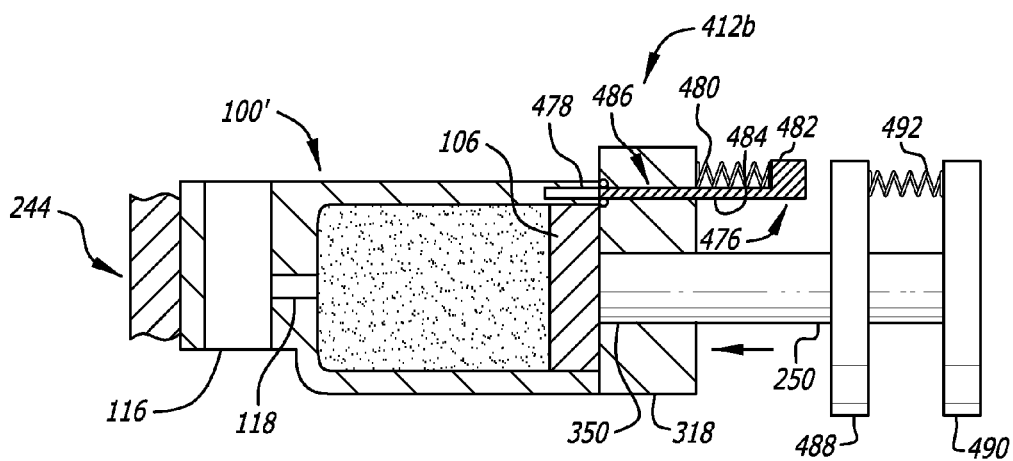
FIG. 36 is a simplified section view of another alternative latch in an unlatched position.
Figure 37:
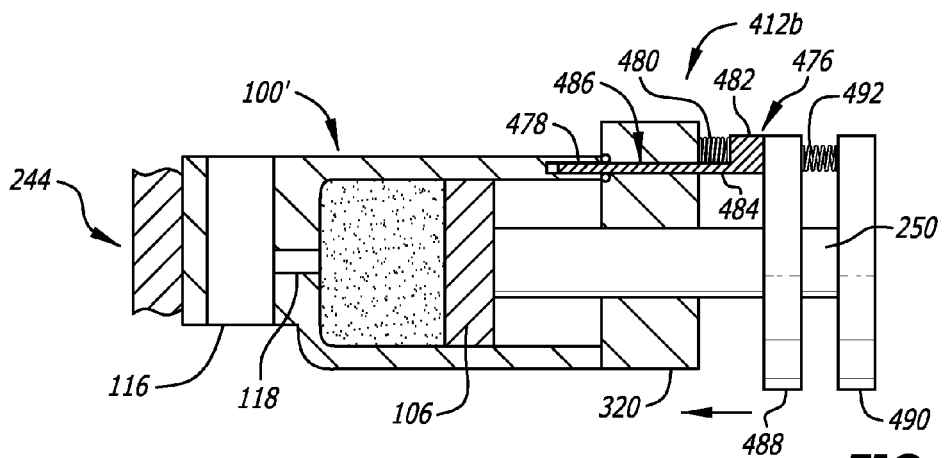
FIG. 37 is a simplified section view of the latch illustrated in FIG. 36 in a latched position.
Figure 38:
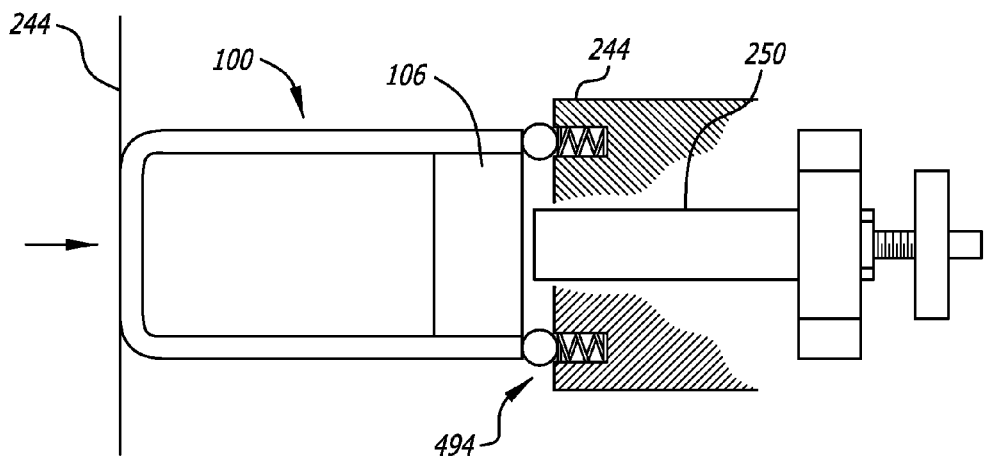
FIG. 38 is a simplified view showing an alternative mechanism that biases a medicament cartridge against the front wall of a chassis.

Another exemplary structure that blocks removal of a cartridge from the pump assembly when the plunger pusher is in the cartridge, and allows a cartridge to be inserted into and removed from a compartment within the pump assembly when the pusher is retracted, is the sliding latch mechanism (or "sliding latch") generally represented by reference numeral 412b in FIGS. 36 and 37. The latch 412b may be used in conjunction with, for example, the cartridges, pump assemblies and baseplates described herein with the minor accommodations described below. The exemplary latch 412b is described below in the context of the cartridge 100', which is identical to cartridge 100 but for minor accommodations for the latch 412b, and the pump assembly chassis 244. Similar elements are represented by similar reference numerals. With respect to the minor accommodations, which are discussed below in context, the cartridge body 102 includes a slot 478 and the chassis wall 318 includes a longitudinal aperture 486.

The exemplary latch 412b may include a latch element 476, which is carried by the chassis 244, and is biased to a retracted, unblocking position by a spring 480. In the illustrated embodiment, the latch element 476 includes a flange portion 482 and a thinner extension portion 484. The spring 480 may be positioned between the chassis wall 318 (or some other fixed structure) and the flange portion 482. The thinner extension portion 484 extends through the longitudinal aperture 486.

The latch assembly 412b may also include a sliding latch tensioner 488 that slides relative to the pusher 250 along a longitudinal axis of the pusher. A flange or other structure 490 may be secured to, or be an integrally formed part of, the pusher 250 and may be positioned aft of the sliding latch tensioner 488. A tensioner spring 492 may be disposed between the sliding latch tensioner 488 and the flange 490. The tensioner spring 492 may be stronger than the latch spring 480. As the pusher 250 is driven into and against the plunger 106, the latch spring 480 compresses quickly, propelling the extension portion 484 into the cartridge slot 478 (FIG. 37), thereby preventing the cartridge from moving in a direction orthogonal to the longitudinal axis of the plunger 250. The tensioner spring 492 absorbs additional propelling energy. The biasing force of the spring 480 pulls the extension portion 484 out of the cartridge slot 478, thereby unlocking the latch, when the plunger 250 returns to the home position (FIG. 36).

The clutch 412 (FIGS. 16-20) and the sliding latch mechanism 412a (FIGS. 27-27C), in addition to performing latching/locking functions, also perform a pushing function. The latch assembly 412b (FIGS. 36-37) may be adapted to perform a pushing function. They all are examples of structures that perform the function of pushing (or "biasing") a medicament cartridge (e.g., cartridge 100) against a wall and, more specifically, engaging an aft end of a cartridge and pushing the medicament cartridge that is in the inserted position within the pump assembly against a rigid wall to a held position. The rigid wall may, for example, be the front wall of the chassis 244. Other examples structures that performing these function are schematically represented by reference numeral 494 in FIG. 38. Such structures include, but are not limited to, coil springs, leaf springs, interfering bumps, interference fits, and deformable resilient members. Such structures may be attached to the aft wall 320 of the cartridge compartment 246 or some other structure.

G. Exemplary Encoders

One aspect of present system control instrumentalities, which is applicable to variety of individual control methodologies discussed herein, is monitoring the actual movement of the shaft of motor 358. Specifically, the number of revolutions (or "angular displacement") and/or the rotational direction of the motor shaft is resolved. For purposes of simplicity, rotation of the shaft of the motor is simply referred to as rotation of the motor. The number of revolutions in the forward direction may be used to determine the amount of medicament that has been dispensed. For example, in some implementations, 14.4 revolutions may equal one μL and, accordingly, may equal 0.50 IU of U-500 insulin dispensed.

A wide variety of apparatus may be used to monitor angular displacement and rotational direction of the motor 358 so that the controller 240 can, for example, determine if the motor is moving as predicted. Although the present inventions employ an encoder to perform this function, other apparatus that may be employed include, but are not limited to, monitoring coil current of the motor. It should also be noted that the present inventions are not limited to any particular type of encoder.

In the exemplary embodiments, an encoder 396 may be positioned on the shaft of motor 358 in the manner illustrated, for example, in FIG. 18. The motor/encoder relationship is schematically represented in FIG. 39 and various exemplary encoders are described below with reference to FIGS. 40A-40I. Briefly, during normal operation of at least one embodiment, the controller 240 sends paired pulse/phase drive signals (stepping pulses) to the motor 358 while monitoring the pulse train back from the encoder 396. The pulse trains associated with exemplary encoders are also presented in FIGS. 40A-40I. The encoder 396 is monitored in near real time to determine if its movable portion associated with the motor shaft 357 (and, therefore, the motor 358) is moving as predicted.

Figure 40E:
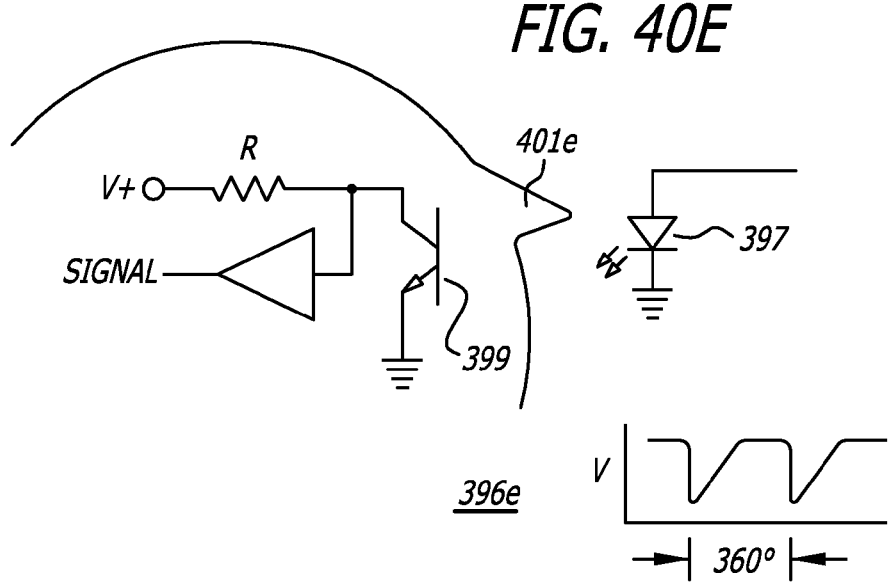
FIG. 40E is a schematic view of another optical encoder system.
Figure 40F:
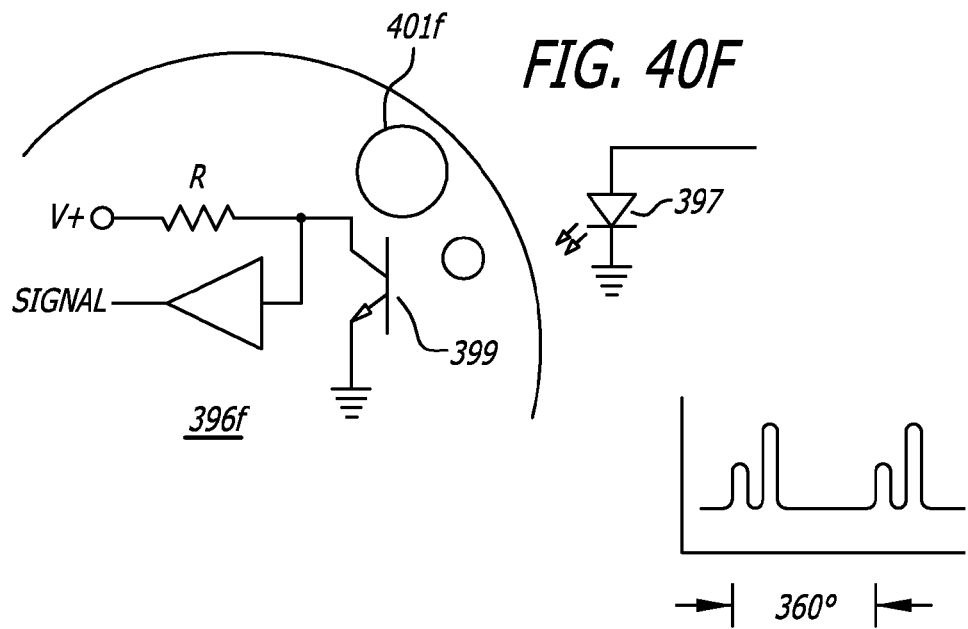
FIG. 40F is a schematic view of yet another optical encoder system.

Referring to FIG. 40A, an exemplary encoder 396a may be an optical encoder. Such encoders may have a light emitter 397, a photodetector 399, and one or more optical interrupters 401. The interrupters 401 are positioned and/or configured so that a different waveform is produced when the portion of the encoder 396a with the interrupters is rotated in a forward direction as opposed to a rearward direction, as shown. The optic interrupters 401 in the exemplary encoder 396a are in the form of two occluding tabs spaced apart at an angle other than 180 degrees. Turning to FIG. 40B, exemplary encoder 396*b* has two encoder openings 401*b* spaced apart at an angle other than 180 degrees. An exemplary encoder 396*c* with two reflective surfaces 401*c*, also spaced apart at an angle other than 180 degrees, is shown in FIG. 40C. The exemplary encoder 396*d* in FIG. 40D has a single encoder opening 401*d* with an asymmetrical shape that forms different forward and reverse waveforms. The occluding tab 401*e* in exemplary encoder 396*e* (FIG. 40E) is also asymmetrical and the waveform produced thereby is different in the forward and reverse directions. The exemplary encoder 396*f* in FIG. 40F has openings 401*f* of different size that result in a waveform that is different in the forward and reverse directions.

Figure 40G:
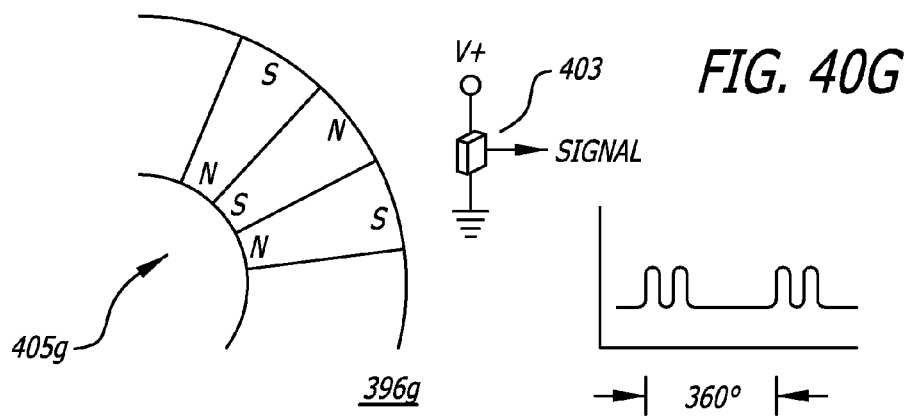
FIG. 40G is a schematic view of a magnetic encoder system.
Figure 40H:
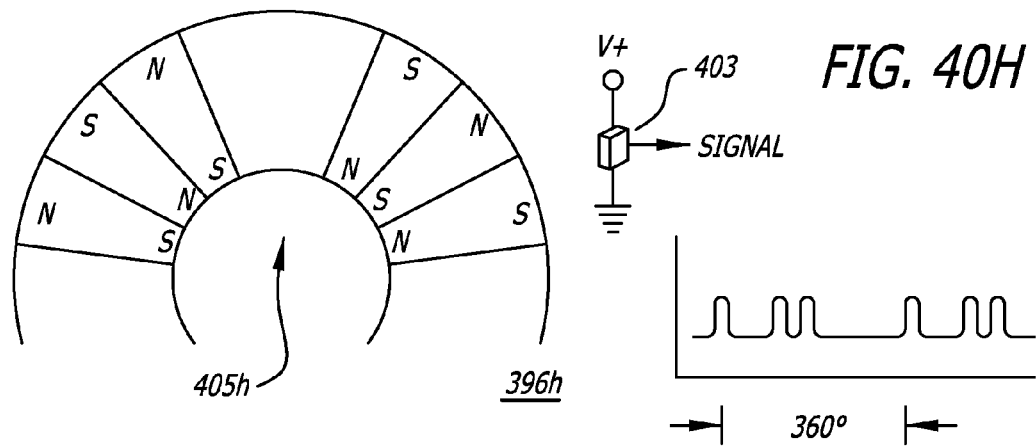
FIG. 40H is a schematic view of another magnetic encoder system.
Figure 40I:
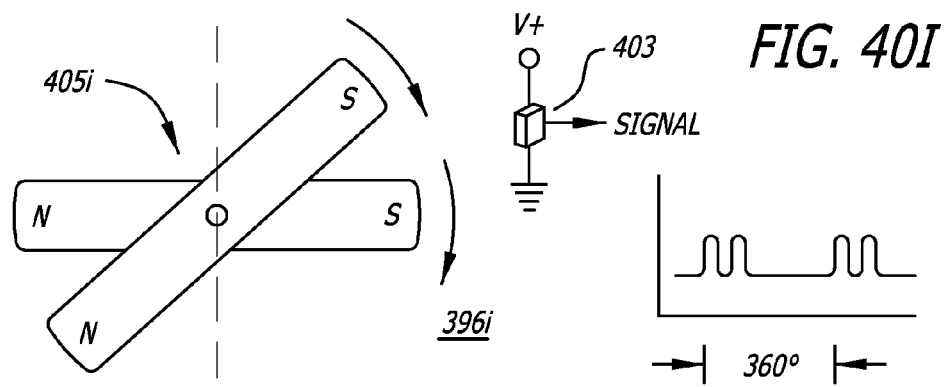
FIG. 40I is a schematic view of yet another magnetic encoder system.
Figure 51:
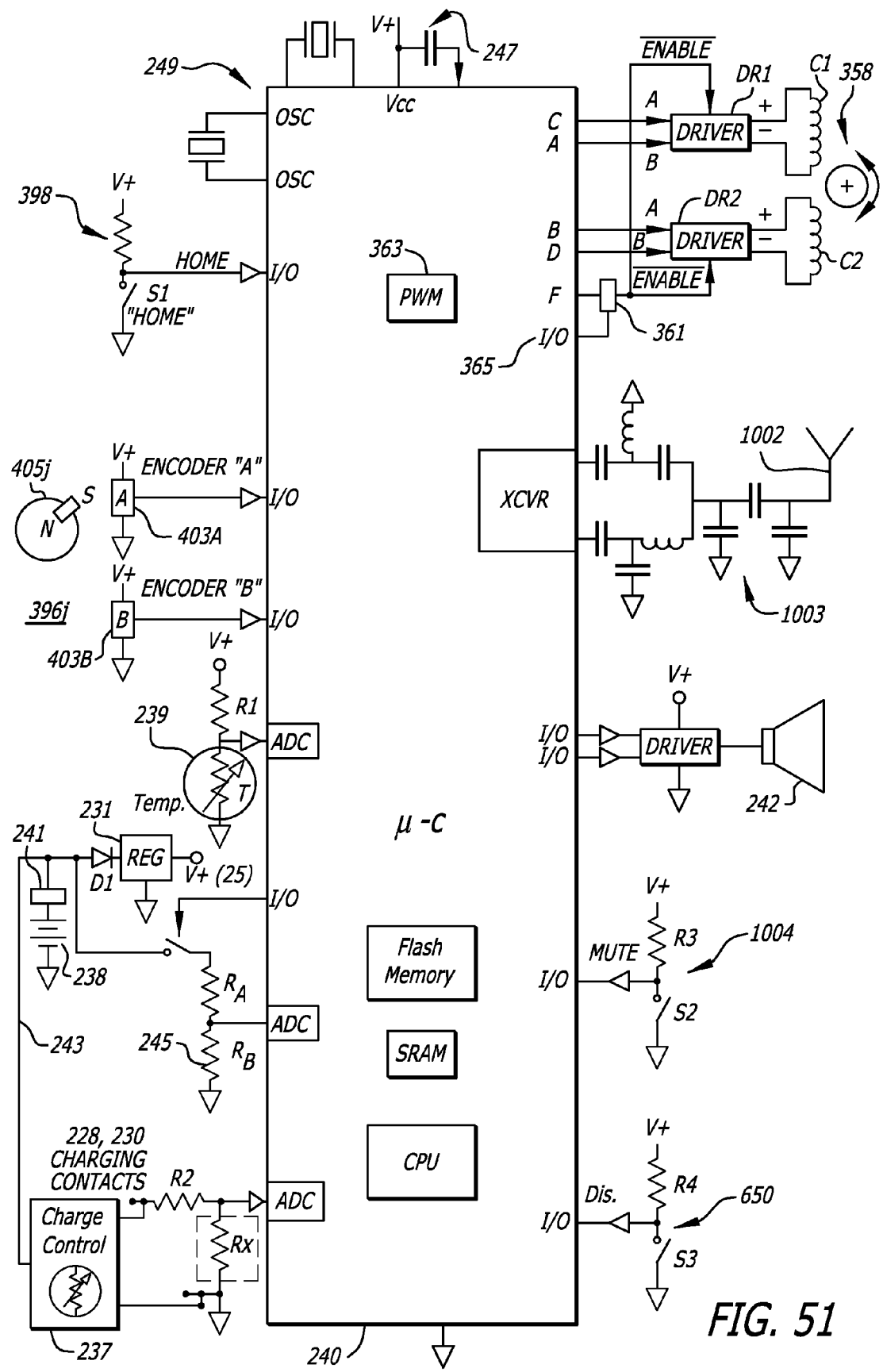
FIG. 51 is a schematic view of an exemplary infusion pump assembly controller.

Turning to FIGS. 40G-40I, other exemplary encoders employ magnetic detectors. Such encoders may include a sensor that senses changes in magnetic fields, such as a Hall-effect sensor or a magnetoresistive sensor, and a magnet arrangement on or rotating with the motor shaft to produce magnetic fields that are different in the forward and reverse directions of rotation. To that end, the exemplary encoder 396*g* illustrated in FIG. 40G includes a sensor 403 and a magnet arrangement 405*g*, with S-N-S magnetized domains, that produces the illustrated signal waveform. The exemplary encoder 396*h* (FIG. 40H) includes a magnet arrangement 405*h* with S-N-S magnetized domains and N-S-N magnetized domains. Another exemplary encoder, which is generally represented by reference numeral 396*i* in FIG. 40I, has a rotation axis that passes through a two-bar magnet arrangement 405*i*. Another exemplary encoder 396*j* is illustrated in FIG. 51. Here, the rotating portion 405*j* includes a single magnet and there is a pair of sensors 403*a* and 403*b*. Another exemplary encoder may be in the form of an optical encoder with a pair of sensors.

H. Exemplary Pressure/Occlusion Sensors

As discussed in Section III above, pressure sensors may be provided to, among other things, detect occlusions in a cannula or infusion set tube. Occlusions may occur for any number of reasons including, but not limited to, cannula kinks caused by movement of the pump assembly relative to a deployed cannula, kinks in the infusion set tube, or granuloma formation at the outlet end of a cannula. The structures that are used to sense pressure may also be used to, for example, sense medicament cartridge presence and alignment within a pump assembly. In at least some implementations, one portion of the pressure sensor may be part of the medicament cartridge and another portion of the pressure sensor may be part of the pump assembly. With respect to the medicament cartridge pressure sensor portions, a variety of different embodiments are described in Section III above with reference to FIGS. 3-8. Also, although the term "pressure sensor" is employed because pressure tends to increase when fluid is pumped into a lumen that is completely or partially occluded, the sensor may simply be a device that responds to a predetermined threshold pressure or a predetermined increase in volume within a particular region, as opposed to a sensor that is capable of measuring various pressures within a range of pressures. Also, actual pressure need not be determined. For example, for a sensor that is calibrated to produce a predetermined range of outputs over a predetermined range of pressures, the rate of pressure change (which may be indicative of an occlusion) may be determined without actual pressure determinations.

Figure 41:
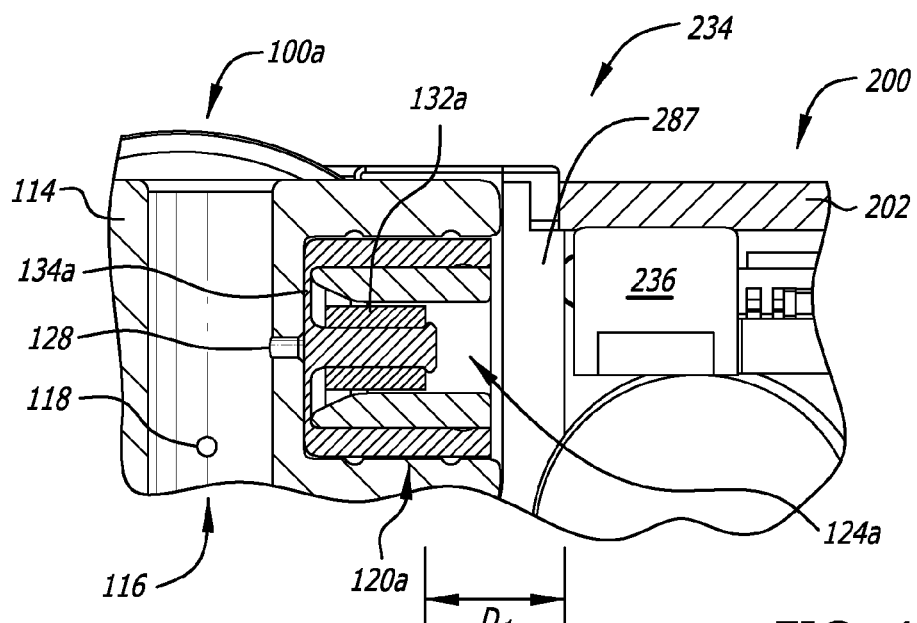
FIG. 41 is a section view of an exemplary pressure sensor arrangement.
Figure 42:
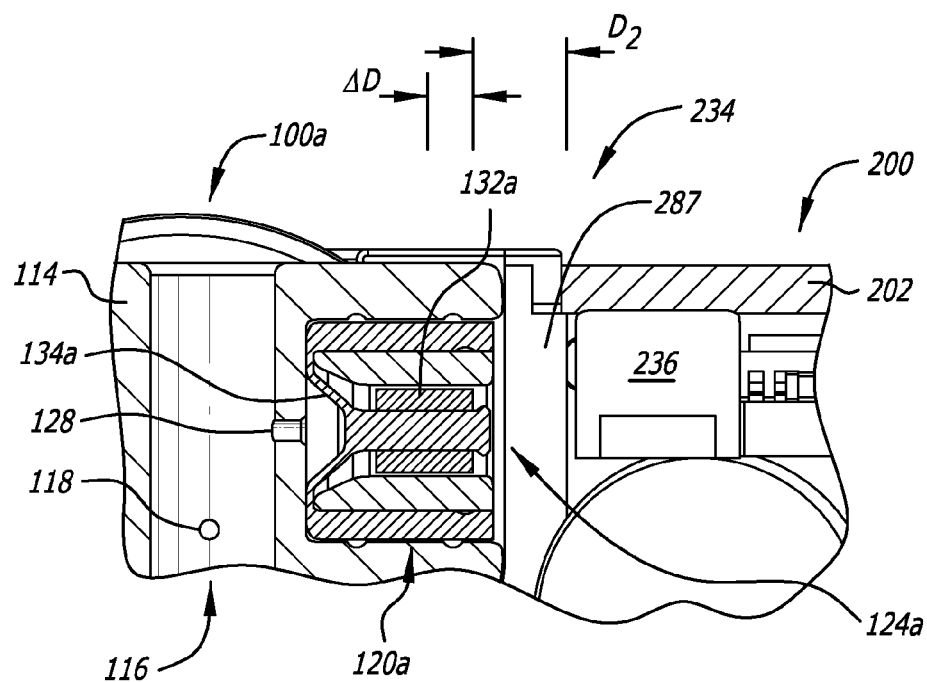
FIG. 42 is another section view of the pressure sensor arrangement illustrated in FIG. 43.

Referring now to FIGS. 41 and 42, the exemplary pressure sensor 234 includes the cartridge portion 120*a*, which is associated with medicament cartridge 100*a* described in Section III above, and the pump assembly portion 236. The cartridge portion 120*a* may include, among other things, a detectable structure 124*a* with a magnet 132*a* that is carried by a resilient diaphragm 134*a*. The diaphragm 134*a*, which is exposed to reservoir pressure by way of the aperture 128, flexes in response to pressure increases, thereby resulting in movement of the magnet 132*a*. The pump assembly portion 236, whose location is fixed relative to the medicament cartridge 100*a*, may be a sensor that responds to changes in the adjacent magnetic field (e.g., a Hall-effect sensor or a magnetoresistive sensor). As the magnet 132*a* moves relative to the pump assembly portion 236, the sensor responds to the associated changes in the adjacent magnetic field (e.g., with a change in output voltage or a change in resistivity). The pump assembly portion 236 is operably connected to the controller 240, and the controller may be configured to equate sensor responses to changes in pressure within the through-bore 116. To that end, the pump assembly portion 236 can be mounted on the circuit board associated with the controller and/or may be thought of as the powered part of the sensor.

With respect to operation of the pressure sensor 234, it should initially be noted that a fluid delivery procedure would be performed with, for example, a cannula connector plug (e.g., plug 602 in FIG. 57) or a connector plug 550 for an infusion set (FIG. 63) located within the cartridge through-bore 116. Such structures have been omitted from FIGS. 41 and 42 to simplify the illustrations. The detectable structure 124*a* is shown in the "at rest" position in FIG. 41, which may correspond to little or no pressure within the cartridge through-bore 116. The distance between the magnet 132*a* and the pump assembly portion 236 is D1. As pressure within the cartridge through-bore 116 increases, deflection of the diaphragm 134*a* results in the distance between the magnet 132*a* and the pump assembly portion 236 decreasing, and the associated sensor will respond accordingly. A pressure change associated with the missed delivery of six µl of medicament (e.g., 5 psi), which may be considered to be the result of an occlusion, will decrease the distance between the magnet 132*a* and the pump assembly portion 236 by an amount ΔD to D2 in the illustrated embodiment.

The discussion here is, of course, equally applicable to the exemplary medicament cartridge 100 (with cartridge portion 120*a*) described in Section III. Also, as discussed above in the context of FIGS. 3-8, other exemplary detectable structure arrangements include, but are not limited to, a magnetically permeable structure carried on a diaphragm and movable relative to a coil; and an optical element carried on a diaphragm and movable relative to an optical sensor; and an electrical conductor carried on a diaphragm and movable relative to a pair of switch contacts. It should also be noted that, with respect to the implementations that include a pressure sensor, the present inventions are not limited to pressure sensor arrangements that include a diaphragm, or to pressure sensor arrangements that include a cartridge portion and a pump assembly portion. For example, a medicament cartridge may include a pressure sensor that communicates with the pump assembly by way of electrical contacts.

Given the very short distance that the magnet or other detectable structure travels (e.g., ΔD=about 0.1 to 1 mm), changes in the location of the medicament cartridge (e.g., cartridge 100 or 100*a*) relative to the pump assembly portion 236 of the sensor 234 may adversely effect the accuracy of the measurements. Accordingly, in at least some implementations, various structures are provided to position and hold the medicament cartridge at a predetermined location within the cartridge receiving area 220, e.g., the spring bias clips 268 and the latches 412 and 412*a* described above with reference to FIGS. 18, 23-26 and 32-35A. It should also be noted here that the above-described "low system compliance" aspect of the present pump assemblies contributes to the accuracy of the sensor measurements by maintaining the intended spatial relationships between the sensor components, such as pressure sensor cartridge portion 120*a*, pump assembly portion 236, and the window 287 therebetween (FIG. 41).

I. Exemplary Fall-Off Detectors

The present inventors have determined that one issue associated with any patch pump is that it may be fully or partially dislodged from the patient's skin (i.e., "falls off") without the patient's knowledge. Such full or partial dislodgement could bend the cannula or otherwise interfere with medicament delivery.

A variety of mechanisms that detect when a patch pump has been dislodged, and provide an appropriate signal to the system controller (e.g., controller 240), are discussed below with reference to FIGS. 43-47. The system controller may take various steps, e.g., activation of an alarm and/or stopping of the motor, in response to a fall-off signal. Although not limited to use with any particular type of patch pump, the detection mechanisms are described below in the context of patch pump systems that are otherwise identical to the above-described system 10 (FIGS. 1 and 54) to simplify the explanation. Similar elements are represented by similar reference numerals. Other exemplary implementations include, but are not limited to, patch pumps that do not include a baseplate.

Figure 43:
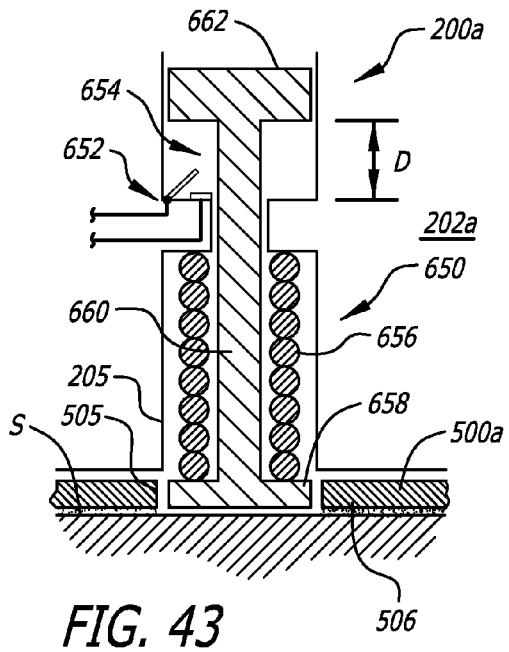
FIG. 43 is a section view of an exemplary fall-off detector.
Figure 44:
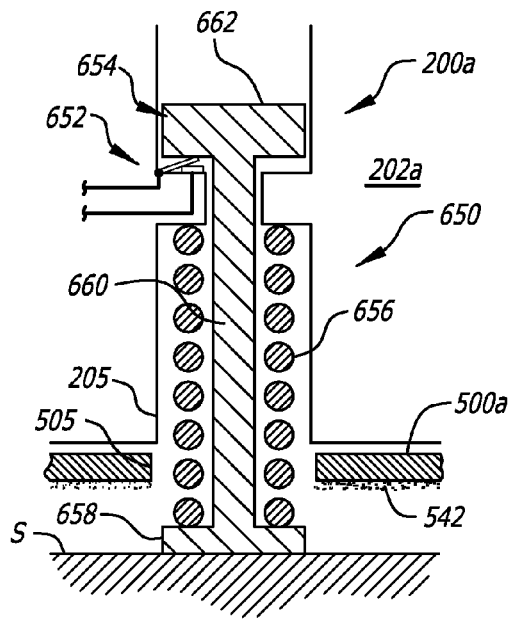
FIG. 44 is another section view of the fall-off detector illustrated in FIG. 43.

As illustrated for example in FIGS. 43 and 44, an exemplary pump assembly 200*a* is provided with a switch-type detector 650 within the housing 202*a*, and the exemplary baseplate 500*a* is provided with a detector aperture 505 that extends through the plate member 506. The exemplary detector 650 may include a switch 652 and a movable switch actuator 654. The switch 652 may be a self-contained structure that is biased to the open state (FIG. 43) and that closes in response to contact with the switch actuator (FIG. 44). In other implementations, some or all of the switch may be carried by the associated switch actuator. The switch actuator 654, which is biased to an extended position (FIG. 44) by a spring 656 or other bias device, may include an abutment 658 that rests on the skin surface S when the baseplate 500*a* is secured to the skin and the pump assembly 200*a* is secured to the baseplate (FIG. 43). A detector aperture 205 is provided on the housing 202*a* to permit movement of the switch actuator 654. The abutment 658 is carried on one end of a post 660, and a stop 662 is carried on the other end. The stop 662 both limits travel of the switch actuator 654 and engages the switch 652 during a "fall-off."

So configured, the actuator 654 will be out of contact with the switch 652 when the baseplate 500*a* is secured to the skin and the pump assembly 200*a* is secured to the baseplate (FIG. 43). As the baseplate 500*a* separates from the skin surface S due to failure of the adhesive 542 (FIG. 44) or a pulling force on the baseplate or pump assembly, or the pump assembly 200*a* separates from the baseplate due to failure of the connection therebetween, the biasing force of the spring 656 will move the stop 662 toward the switch 652 until contact is made, the switch is closed, and a signal is sent to the controller.

The exemplary switch-type detector 650 may be calibrated, by adjusting the distance D that the switch actuator 654 must travel prior to closing the switch 656, to define the magnitude of the separation that will trigger a signal to the controller 240 and, in at least some instances, a subsequent patient alert. In the illustrated implementation, the distance D may about 0.5 to 2.0 mm.

Figure 45:
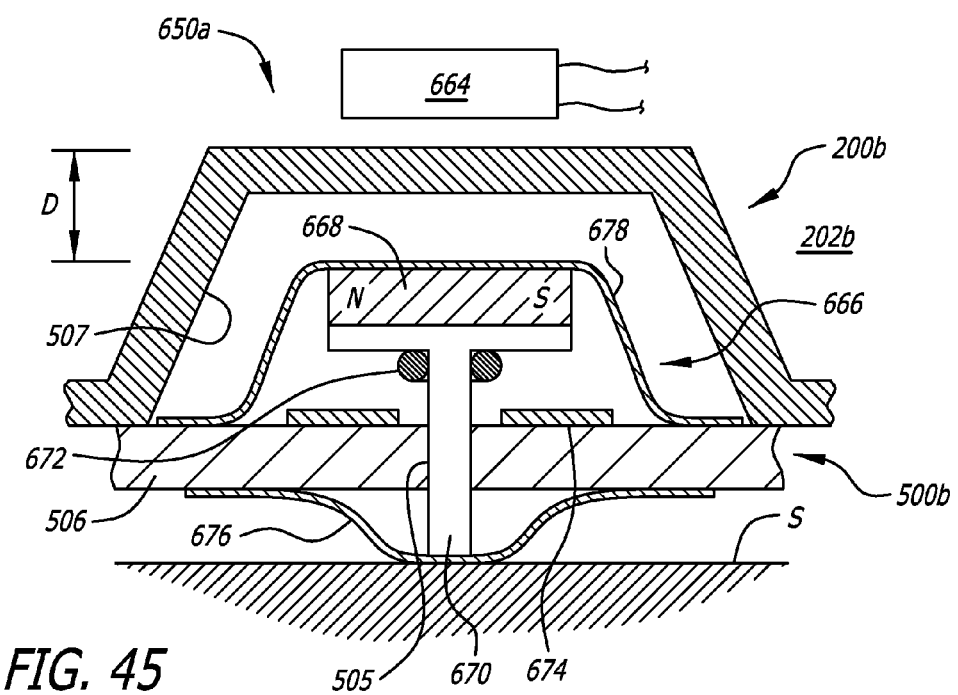
FIG. 45 is a section view of another exemplary fall-off detector.

Another exemplary fall-off detector arrangement is generally represented by reference numeral 650*a* in FIG. 45. The exemplary detector 650*a* includes a sensor 664, which is carried within or by the housing 202*b* of a pump assembly 200*b*, and a movable sensed structure 666 that is carried by the baseplate 500*b*. The type of sensor will depend upon the type of structure being sensed. In the exemplary implementation, the sensed structure includes a magnet 668 and, accordingly, the sensor 664 is a sensor that is configured to sense changes in magnetic fields such as, for example, a Hall-effect sensor or magnetoresistive sensor. The housing 202*b* also includes an indentation 207 to accommodate the sensed structure 666.

The manner in which the magnet 668 (or other sensed structure) is carried on the baseplate may vary. As illustrated for example in FIG. 45, the magnet 668 is carried on a post 670 that extends through a detector aperture 505 in the plate member 506. A seal 672 may be carried on the post 670. A steel disk 674 is carried by the plate member 506. Elastomeric sheets 676 and 678 may be secured to the plate member 506 to enclose the magnet 668, post 670 and steel disk 674.

So configured, the sensed structure 666 will be relatively close to the sensor 664 when the baseplate 500*b* is secured to the skin and the pump assembly 200*b* is secured to the baseplate (not shown). As the baseplate 500*b* and attached pump assembly 200*b* separate from the skin surface S due to failure of the baseplate adhesive (not shown), the magnetic attraction between the magnet 668 and steel disk 674 will pull the magnet away from the sensor 664. When the distance therebetween increases to distance D, the magnitude of the change in the magnetic field experienced by the sensor 664 will be such that a signal is sent to the controller. The sensor 664 will experience a similar change in the adjacent magnetic field should the pump assembly 200*b* separate from the baseplate 500*b* due to failure of the connection therebetween.

The exemplary sensor-type detector 650*a* may be calibrated by adjusting the distance D that the appropriate portion of the sensed structure 666 (e.g., magnet 668) must travel prior to a signal to the controller being triggered and, in at least some instances, a patient alert being provided. In the illustrated implementation, the distance D may be about 0.5 to 2.0 mm.

Figure 46:
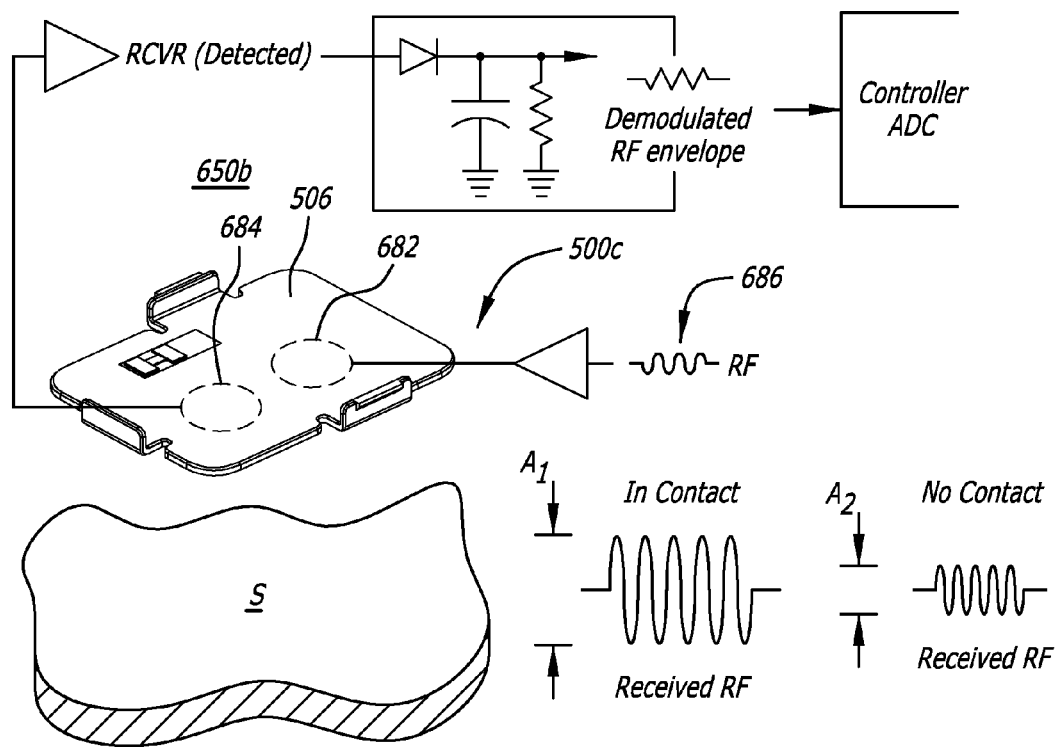
FIG. 46 is a schematic representation of yet another exemplary fall-off detector.
Figure 66:
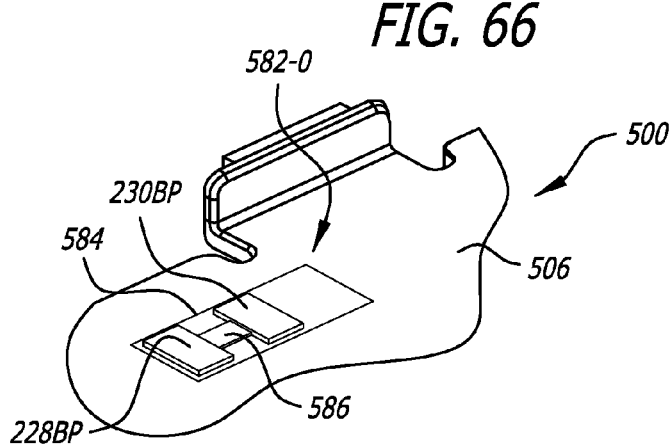
FIG. 66 is a perspective view of a portion of an exemplary baseplate.
Figure 67:
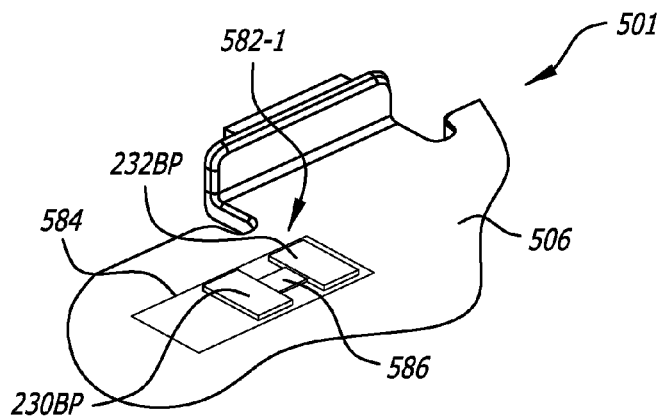
FIG. 67 is a perspective view of a portion of an exemplary baseplate.
Figure 68:
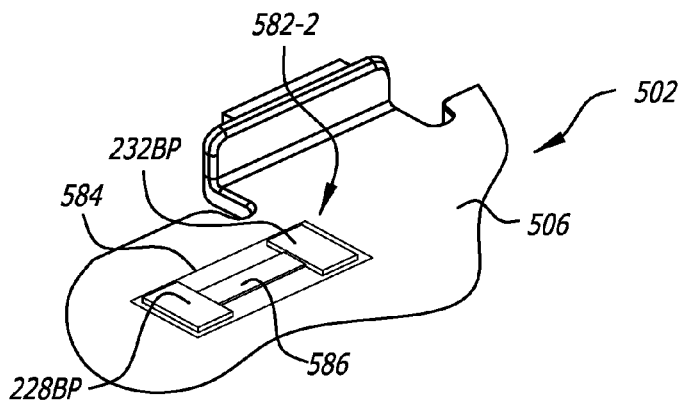
FIG. 68 is a perspective view of a portion of an exemplary baseplate.

Another exemplary detector, which is generally represented by reference numeral 650*b* in FIG. 46, is in the form of an RF circuit with a transmitting antenna 680, a receiving antenna 682, and an RF energy source 684. The RF energy source may be powered by the system battery 238. The receiving antenna 682 is positioned relative to the transmitting antenna 680 such that the amplitude of the RF field received changes as the baseplate becomes separated from the user's skin surface S, as shown by waveforms A1 and A2. For example, A1 may be about twice A2. The received RF field has a greater amplitude against skin than in air. In response to a decrease in amplitude, the RF circuit sends a signal to the controller. The transmitting antenna 680 can be mounted in either one of the baseplate and the pump assembly (not shown), the receiving antenna 682 can mounted in either one of the baseplate and the pump assembly, and transmitting antenna and the receiving antenna can both be embedded in the baseplate 500*c* (as shown). In those instances where the RF energy source is carried by the baseplate, power may be provided by way of the pump assembly electrical contacts 228 and 230 (FIG. 16) and the baseplate contacts 228BP and 230 BP (FIG. 66)

Figure 47:
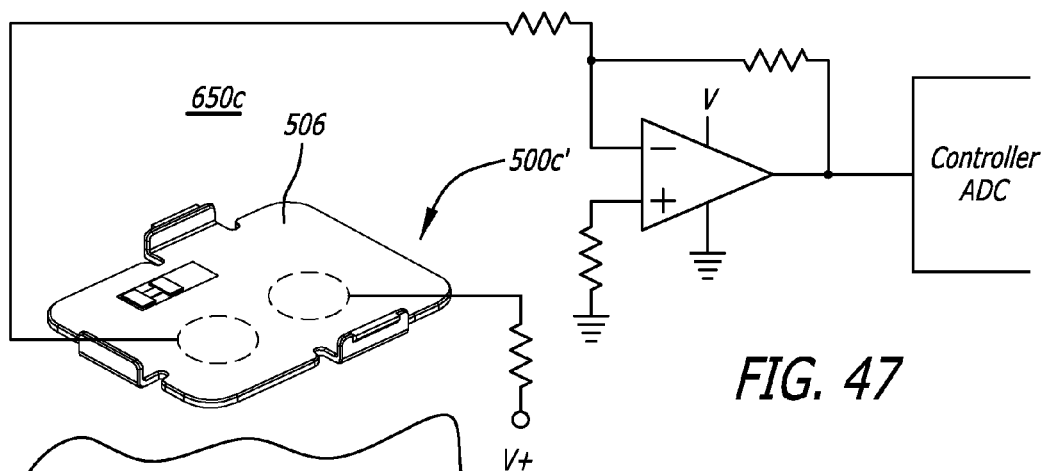
FIG. 47 is a schematic representation of still another exemplary fall-off detector.
Figure 48:
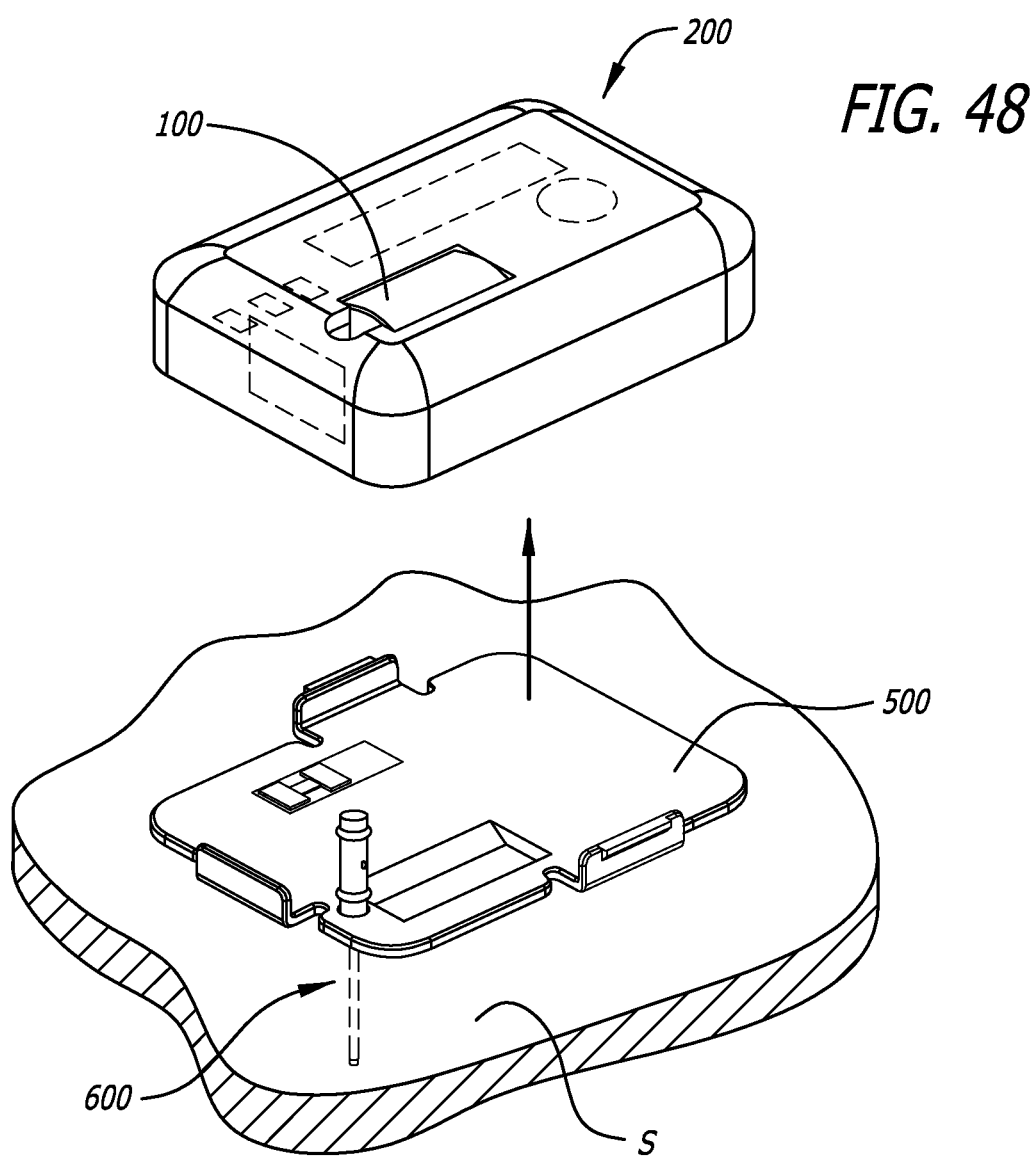
FIG. 48 is a perspective view of an exemplary infusion pump system with the pump assembly and medicament cartridge removed from the cannula and baseplate.

Another exemplary detector, which is generally represented by reference numeral 650*c* in FIG. 47, is in the form of an electrical circuit having a first electrical terminal 686 and a second electrical terminal 688, spaced from the first terminal, and carried on baseplate 500*c*'. The electrical circuit is completed between the first and second terminals 686 and 688 by the user's skin when the associated baseplate 500c' is adhered to the skin surface S by the baseplate adhesive, and is broken when the baseplate becomes separated from the skin. A signal is sent to the controller when the circuit is broken. In the illustrated embodiment, the first and second terminals 686, 688 may be in the form of electrically conductive pads carried on the bottom surface of the baseplate 500c'. The "fall-off" signal may be a voltage signal and the exemplary circuit is configured to convert current of the electrical circuit to the voltage signal.

J. Exemplary Batteries and Battery Rechargers

Figure 49:
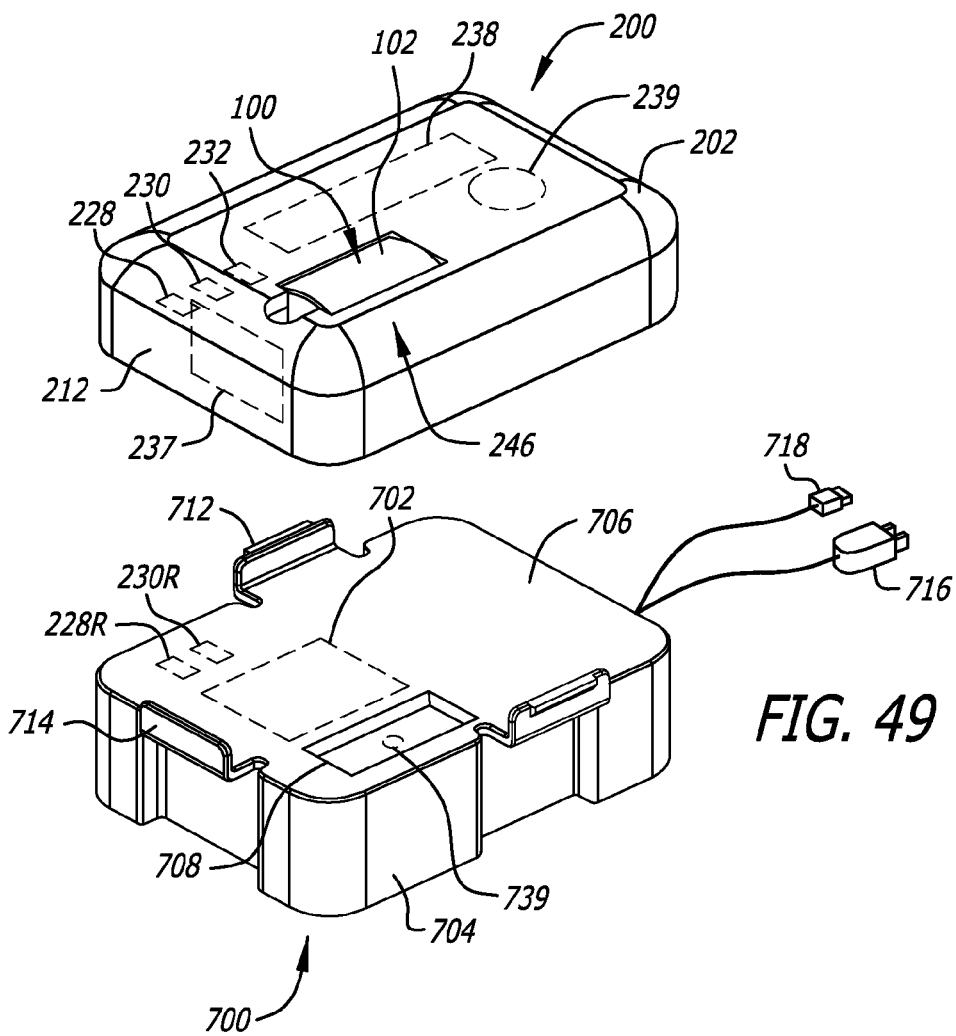
FIG. 49 is a perspective view of an infusion pump assembly, with a medicament cartridge therein, being attached to a battery recharging device.

The battery that drives the motor may be a rechargeable battery, such as a rechargeable lithium polymer battery or a rechargeable lithium ion battery. At least some implementations will employ a rechargeable battery having a fully charged, open circuit voltage of generally 4.2 Volts, or 4.18-4.24 Volts. One advantage of lithium polymer and lithium ion batteries is that they can be recharged quickly by the patient, have high energy density, and have desirable linear decay that facilitates accurate charge state indication. Turning to FIG. 49, the exemplary battery 238 may be carried within the pump assembly housing 202 in a compartment that is separate from the cartridge compartment 246. Additionally, because the battery 238 is rechargeable and the housing includes external recharging contacts 228 and 230, the exemplary housing 202 does not include a door or a cover to provided access to the battery, and the exemplary housing may be sealed (i.e., it cannot be opened without damage thereto).

In at least some instances, the user may seek to recharge the battery 238 when there is medicament in the cartridge 100. Note that the cartridge 100 will be locked into the pump assembly 200 so long as the plunger pusher 250 is not in the fully retracted position, as is discussed above with reference to, for example, FIGS. 23-26. So locked, the cartridge 100 and pump assembly 200 will separate from the "patch pump" baseplate 500 and cannula 600 in the manner illustrated in FIG. 48, while the baseplate and cannula remain on the skin surface S of the user, when the user pulls the pump assembly off of the baseplate. Similar separation will occur in the context of an "infusion set" baseplate 501 and a "non-delivery" baseplate 502 (FIG. 1).

Given the relatively close proximity of the battery 238 to the medicament cartridge 100, heat from the battery 238 could possibly increase the temperature of the medicament during recharging, especially during rapid recharging. The medicament temperature may be relevant to certain medicaments such as insulin, for example, which can be damaged and have its viability become undefined at about 37° C. Accordingly, a temperature sensor 239 (e.g., a thermistor or thermocouple) may also be carried within the pump assembly housing 202 in such a manner that the temperature sensor can sense the temperature of the medicament in the cartridge 100 (or a temperature that is at least representative thereof). For example, the temperature sensor 239 may be carried on the circuit board associated with the exemplary controller 240 (FIG. 18) or on the chassis 244 (FIG. 18). Temperature sensing apparatus, such as a heat pipe that extends to the reservoir (not shown), may also be included on some cartridge implementations. The temperature information may be provided to the controller 240, or to another controller, to modulate the battery recharging process as a function of temperature as is described below.

One example of a battery recharger, which is generally represented by reference numeral 700 in FIG. 49, includes recharging circuitry 702 (e.g., a controller and power circuitry) within a housing 704. The top portion of the recharger housing 704 may be configured in a manner similar to the baseplate 500. To that end, the top portion of the housing 704 may include a plate 706, a cartridge recess 708, a pair of opposing connectors 712, a hook 714, and electrical contacts 228R and 230R. In some implementations, a temperature sensor 739 may be provided at or near the recess 708 to sense the temperature of medicament in the cartridge 100 during recharging. Power and data connectors 716 and 718 may also be provided.

The respective configurations of the pump assembly 200 and battery recharger 700 are such that, when the pump assembly is placed on the plate 706 with an end wall 212 abutting the hook 714, the pump assembly recharge contacts 228 and 230 will be electrically connected to the recharger contacts 228R and 230R. Also, when the cartridge 100 is within the pump assembly 200 during the recharging procedure, the cartridge barrel 102 will nest in the recess 708 to insure proper alignment of the electrical contacts 228/230 and 228R/230R. The recess 708 may also be configured to accommodate the finger tab 456 associated with the latch 412a (FIG. 32).

The recharging process may be controlled by circuitry 237 associated with the pump assembly controller 240, the recharger controller 702, separate circuitry, or some combination thereof, which are collectively referred to as the "recharge controller." The recharge controller 702 may modulate the recharging of the battery 238 as a function of the temperature sensed by temperature sensor 239 and/or temperature sensor 739. For example, and weighing the desire to rapidly recharge the battery 238 against the desire to avoid medicament damage, the recharge controller may be configured to maintain the sensed temperature within a temperature range that is above a predetermined threshold and below a predetermined maximum for the particular medicament. In the exemplary context of insulin and a lithium polymer battery, the threshold temperature can be 37° C. (or range from, for example, 36.6-37.4° C.) and the predetermined maximum temperature can range from, for example, 45-50° C.

It should also be noted that it may be difficult for the battery 238 to provide enough current if the temperature within the pump housing 202 is low. The temperature sensor 239 may, therefore, be used to monitor temperature during operation of the pump assembly 200. An alarm may be actuated by the controller 240 if the temperature is too low.

Modulation of the recharging process may be accomplished by, for example, selectively increasing or decreasing the rate at which the battery 238 is recharged (e.g., by controlling current) as a function of sensed temperature. For example, and referring to FIG. 50, the modulation process may be designed to perform temperature control in a manner that prevents the sensed temperature from overshooting the predetermined maximum temperature ($T_{MAX}$) as shown by the dashed lines. To that end, as temperature reaches a modulation temperature ($T_{MOD}$) below the maximum temperature $T_{MAX}$, the recharging rate is reduced to keep the temperature at or below the maximum temperature $T_{MAX}$.

In at least some implementations, the charge controller may be configured to identify and/or prevent charging faults, such as battery overcharge that can cause the battery to swell, vent and otherwise stress other components within the pump assembly.

It should be noted here that the present pump assemblies and battery rechargers are not limited to those which make a direct electrical connection through the use of electrical contacts. By way of example, but not limitation, inductive coupling may be employed. It should also be noted here that at least some implementations of the present pump assemblies may be configured to accept a replaceable battery. Such implementations would, however, require a waterproof battery compartment cover.

K. Exemplary Alarms

As noted above with reference to FIG. 18, the exemplary pump assembly 200 may include an alarm 242 that is carried within the housing 202. The alarm may be audible (e.g., a buzzer), palpable (e.g., a vibrator), visible (e.g., an LED with a portion that extends through the housing 202) and/or any combination thereof. A number of conditions may result in alarm activation in the exemplary embodiments. For example, as discussed in Section IX below, alarm conditions include, but are not limited to, low or dead battery, occlusion, low or empty reservoir, hardware self-test, firmware error, absence of a baseplate, device fall-off, battery charge overtemperature, unable to find plunger, and/or charging faults.

L. Exemplary System Controllers

The exemplary pump assemblies described herein may include a controller that is configured to perform the various control functions described herein. The controller may also operate/execute algorithms for periodic safety checks such as memory checksums, hardware verification self tests, and the like. The present inventions are not limited to any particular type of controller and include those currently available or yet to be developed. By way of example, but not limitation, such a controller may be in the form of a microcontroller and stored firmware programs. The microcontroller may include, among other things, some or all of a microprocessor or other central processing unit (CPU), other digital and/or analog control circuitry, digital and/or analog communication circuitry, and memory such as static random access memory (SRAM), flash memory, and synchronous dynamic random access memory (SDRAM). The controller may employ any suitable control principles including, but not limited to, proportional, adaptive, neural network, fuzzy logic, and/or proportional integral derivative (PID). The microcontroller may also support firmware updates through an RF interface.

One exemplary controller is generally represented by reference numeral 240 in FIG. 18 and is described here, in the context of various system components that are connected thereto, with reference to FIG. 51. The exemplary controller 240 may include a microcontroller (labeled p-C in FIG. 51) with a CPU, flash memory, SRAM, and a built-in RF transceiver. Building the RF circuitry into the controller decreases the size of the controller by positioning everything on a single chip. One example of a suitable microcontroller is the Texas Instruments CC2530 microcontroller.

A pair of oscillator crystals 249 respectively provide clock sources for the RF transceiver and the microcontroller. A filter capacitor for the microcontroller power supply is shown at 247.

As discussed above and below, a variety of devices may be operably connected to the controller 240. Referring to FIG. 51, such devices may include the position detector 398 (FIG. 29) that detects when the plunger pusher 250 is in the fully retracted (or "home") position, the sensor(s) from an encoder that monitor motor shaft rotation (e.g., sensors 403a and 403b of encoder 396j), and the temperature sensor 239, which may be a thermistor, creates a variable analog voltage which connects to an analog ADC input.

With respect to power, the recharging contacts 228, 230 connect the battery 238 to the battery recharger 700 (FIG. 49). The charging voltage is distributed by a distribution circuit 243 to the battery 238 and to a voltage regulator 231. A protection circuit 241 is provided for the battery 238, and a regulator 231 regulates the power delivered to the microcontroller. The recharger controller 237, if present, may be used to control recharging of the battery 238 in those instances where the battery recharger 700 does not perform this function. A voltage divider 245 reduces the voltage to be compatible with the analog input of the microcontroller and allows the microcontroller to read the full range of the output of the battery 238. To conserve battery power, the divider 245 is only enabled when battery voltage is being sensed. When the divider 245 is enabled, the voltage at the associated pin is BatteryVoltage*Rb/(Ra+Rb). Thus, the voltage is a fractional representation of the actual battery voltage so that the input range of the pin is not exceeded. The analog-to-digital converter input senses this voltage. The microcontroller's built-in analog-to-digital converter converts the voltage to a digital value (e.g., a 10 bit digital value).

In those implementations where a switch-type fall-off detector is employed (e.g., detector 650 in FIGS. 43 and 44), the input to R4 is a digital input that senses the actuation of associated switch S3. This input allows the microcontroller to sense the position of the portion of the detector that protrudes through the housing 202 (e.g. abutment 658) and can be programmed to wake the microcontroller up from an extremely low power state.

The alarm 242, which may be audible, palpable and/or visible, has a driver circuit to increase the current drive to it. A mute switch 1004 may also be provided, e.g., on the pump assembly housing 202, to mute an audible alarm.

A sending and receiving antenna 1002 is provided to communicate with, for example, the remote control 1000. An impedance matching circuit 1003 for the antenna 1002 receives its power from the transceiver.

M. Exemplary Motor Control

Turning to motor control, and referring to FIG. 51, the motor 358 (e.g., a stepper motor) actuated by the phases of the motor coils C1, C2. The phases are energized in the proper sequence to drive the motor 358 at the desired speed and in the desired direction. The interlock circuit 361 is a simple missing pulse detector which can be implemented with a re-triggerable monostable multivibrator integrated circuit such as a 74HC123 CMOS device from NXP Semiconductors. The interlock circuit 361 is enabled by a pin 365 that continuously toggles from high to low, and software of the microcontroller causes the pin to toggle. Thus, if the software stops functioning, the pin will not toggle and the motor 358 will be automatically disabled for safety reasons by the interlock circuit 361. More particularly, output 365 enables the motor interlock circuit 361, protecting against over-delivery of medicament due to a software lockup.

Pulse width modulating (PWM) circuit 363 is the motor enable output that enables the drivers DR1, DR2 to the motor 358. Put another way, the PWM circuit 363 modulates energy from the battery 238 applied to motor coils C1, C2. This pulse width modulated output enables control of the motor current depending on the programmed torque and the voltage of the battery 238. Circuit 363 operates at a frequency ten to one hundred times higher than the motor phases, and avoids having to use a regulator for the motor voltage.

Drivers DR1, DR2 energize the coils C1, C2 of the motor 358 and change their polarities. Assuming the interlock circuit 361 has been enabled and output F is at a logic 1, driver DR1 is enabled with positive drive to coil C1 when output C is a logic 1 and A is a logic 0. Likewise driver DR2 is enabled with positive drive to coil C2 when output B is a logic 1 and D is a logic 0. Under the same conditions, driver DR1 is enabled with negative drive to coil C1 when output C is a logic 0 and A is a logic 1. Likewise driver DR2 is enabled with negative drive to coil C2 when output B is a logic 0 and D is a logic 1. If A=C, driver DR1 is disabled. Similarly if B=D, driver DR2 is disabled. If output F is a logic 0 or if the interlock circuit 361 is disabled, both drivers are disabled regardless of the state of outputs A-D. The pulse width modulation occurs when output F of PWM circuit 363 pulses at a given duty cycle. If F pulses at a 75% duty cycle, then the coils will be turned on with the polarity as selected by A-D, with an effective voltage of 75% of the battery voltage.

Figure 51A:
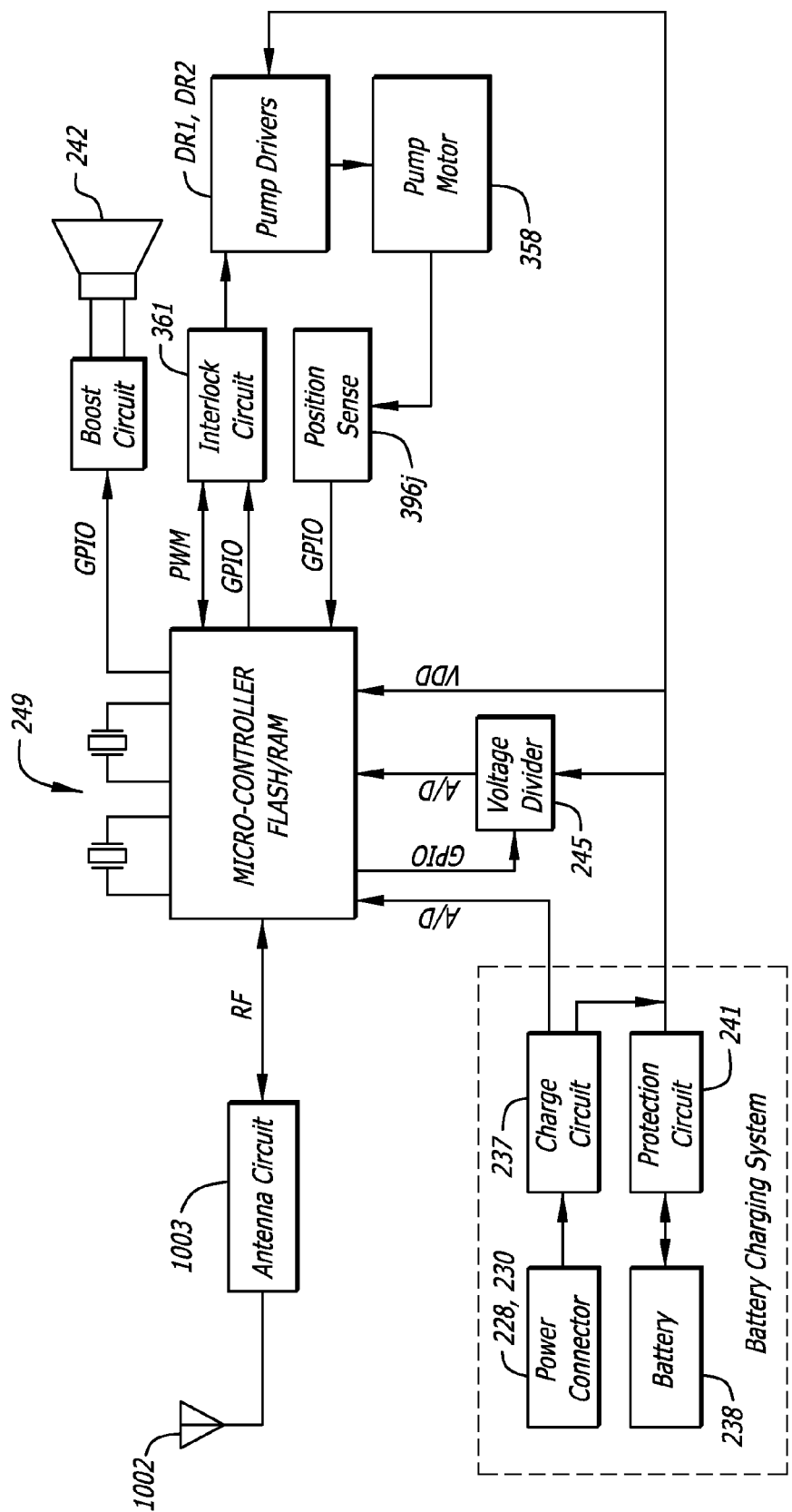
FIG. 51A is a block diagram showing certain functional relationships of the battery charging system illustrated in FIG. 49 and the controller illustrated in FIG. 51.

FIG. 51A is a block diagram that illustrates the functional relationships of certain elements/components shown in FIG. 51 and, in particular, the relationship of the battery charging system to the other components of the system. The battery charging system, as shown in the lower left in a dotted line block, includes the battery 238, the battery protection circuit 241, the power connectors 228, 230 and the charge circuit 237. As can be seen in FIG. 51A, one way the battery charging system connects to the microcontroller is through the voltage divider 245. The motor drivers DR1, DR2 receive power from the battery and drive the motor 358 whose position is sensed by the position sense encoder 396j. The interlock circuit 361 provides a safety shutoff of the motor drivers DR1, DR2 when there is a software problem in the microcontroller. Oscillator crystals 249 provide clocking functions for the microcontroller and RF transceiver. The microcontroller controls the operation of the alarm 242. The antenna 1002 is connected to the microcontroller by way of the antenna circuit 1003.

Figure 52:
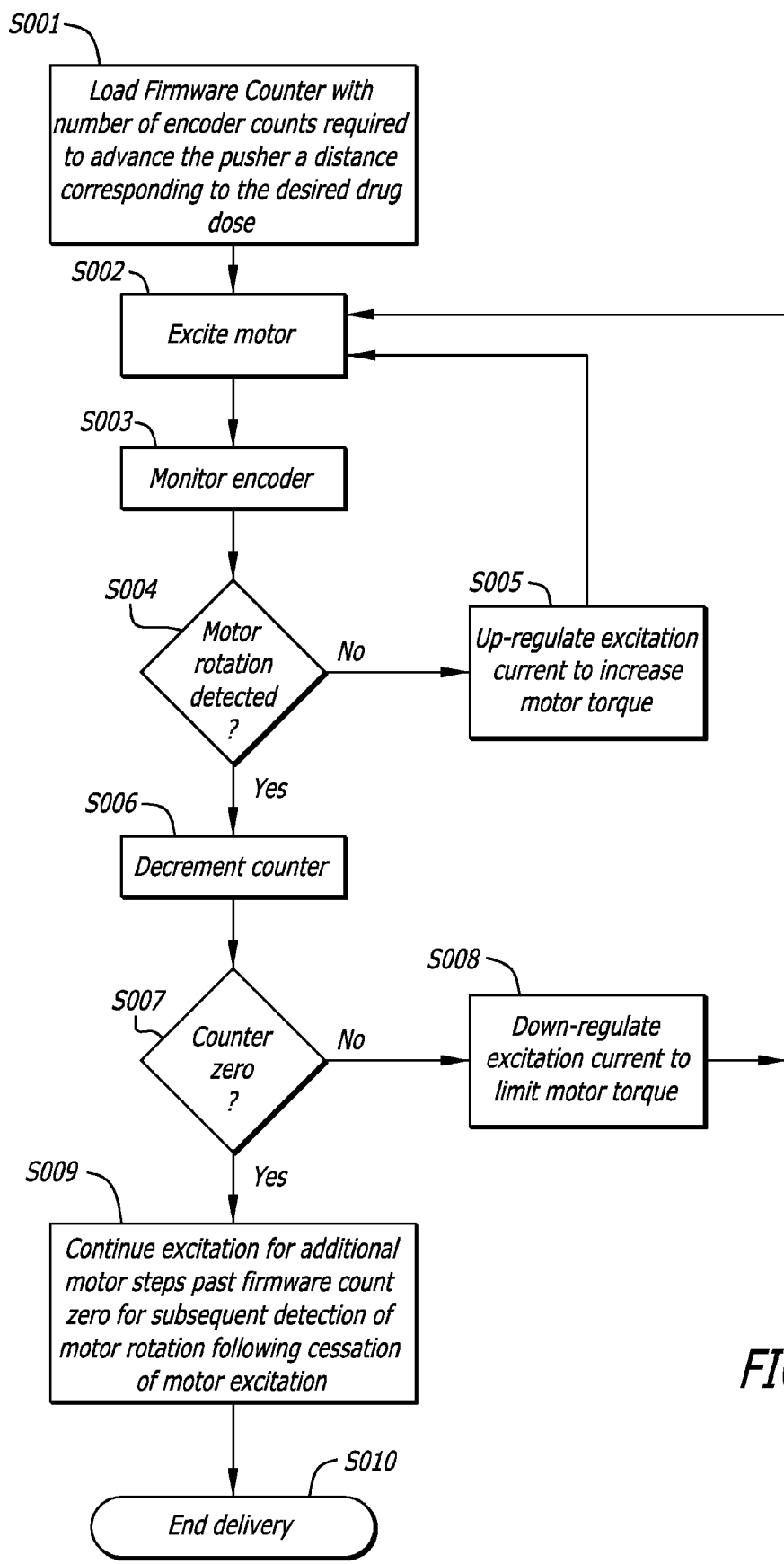
FIG. 52 is a flow chart showing an exemplary motor torque control method.

Energy to the motor 358 may be controlled so as to be within a range having a lower limit that provides sufficient torque to overcome drive line inefficiencies and axial cartridge friction and move the plunger 106, and an upper limit that is low enough so as to not cause leakage past plunger seals 152. FIG. 52 is a flow chart showing an exemplary low torque motor control procedure. Referring thereto, a firmware counter with the number of encoder counts required to advance the pusher a distance corresponding to the desired drug dose is loaded in the controller 240 (Step S001). The motor 358 is excited (Step S002) and the encoder 396 is monitored (Step S003). If no motor rotation is detected (Step S004), then the excitation current is up-regulated to increase the motor torque (Step S005) and the process is returned to the previously-mentioned motor excitation step (Step S002). On the other hand, if motor rotation is detected, the counter is decremented (Step S006).

If the counter is not zero (Step S007), then the excitation current is down-regulated to limit the motor torque and to conserve energy (Step S008), and the process is returned to the previously-mentioned motor excitation step (Step S002). If the counter is zero (Step S007), then motor excitation is continued for additional motor steps past the firmware count zero for subsequent detection of motor rotation following cessation of motor excitation (Step S009). Following completion of the additional motor steps, delivery is thereby at an end (Step S010).

The excitation current regulation method mentioned in the up-regulate and down-regulate steps above varies with the method used. Examples of methods are (a) pulse width modulation and (b) a programmable linear or switching type voltage regulator. Up and down regulation using a voltage regulator increases or reduces the voltage output to the coil drivers. For a pulse width modulation method, down regulation reduces the duty cycle and up regulation increases the duty cycle.

In other words, pulse width modulation is one way to control energy consumption and provide a prescribed (e.g., 10 pound) stall limit. A stall limit that is too low will not provide sufficient performance against drive line and cartridge inefficiencies, while a stall limit that is too high can overdrive the cartridge and, potentially, create excessive reservoir pressure that will cause leakage past the cartridge seals 152 during a pusher "zeroing" procedure (described in Section VIII-B with reference to FIG. 91) or during an occlusive event (described in Section VIII-C with reference to FIGS. 92 and 93).

Pursuant to an exemplary embodiment the motor 358 always runs under pulse width modulation or other torque control method, as the motor is designed with excess torque that needs to be controlled. Pulse width modulation is one effective method to control the torque. The electronic drive provided for the motor is important to minimize battery drain as well as to control the torque the motor is providing to the system and what forces the lead screw 360 is putting on the cartridge 100 in all cases, e.g., retracting, homing, zeroing, running, and occlusion detecting.

Figure 52A:
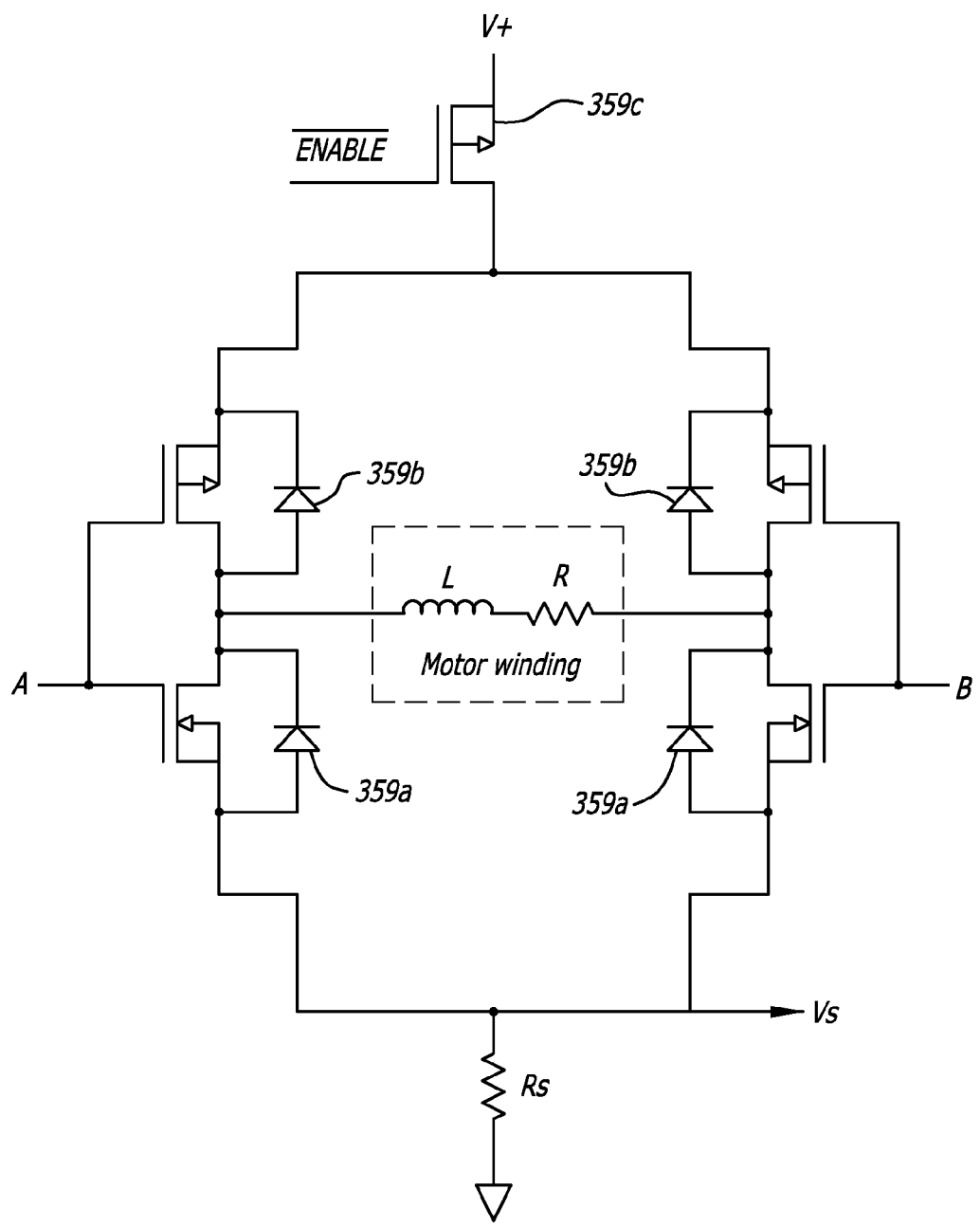
FIG. 52A is a diagram of an exemplary motor driving bridge circuit.

Referring to FIG. 52A, one of the drivers DR1, DR2 in FIG. 51 is shown connected to the associated motor winding. Rs is a current sensing resistor (about 1Ω) for implementations that directly sense the coil current, and Vs is the current sensing voltage. The inductor (L) is the inductance of the motor winding and the load (R) is the winding resistance. The switch 359c is a FET driver, and diodes 359a and 359b are intrinsic back-diodes within the FET drivers. These components essentially form the elements of a basic buck-type switching regulator, with R being the load. When the ENABLE bar shown in that figure (and in FIG. 51) is a logic 0 (the true condition), the switch 359c turns on and power is thereby provided to the rest of the circuit, thereby enabling the coil drivers. If the switch 359c is turned on and off at a rate faster than R/L, then the voltage to the load R will be effectively reduced in the manner of a buck-type switching regulator. During the on time of switch 359c, inductor L charges by ramping up its current, thereby limiting the voltage applied to load R. During the off time of switch 359c, the inductor L discharges by ramping down its current, thereby continuing to supply voltage to load R. Inductor L discharges through the load R and the intrinsic back-diodes 359a and 359b. This circuit could be further enhanced by adding Schottky diodes across the intrinsic back-diodes 359a and 359b to reduce the voltage drop when the inductor L discharges through them during the off time of switch 359c. This is much in the same manner that Schottky diodes are found in buck-type switching regulators.

The equation to be relied on is: $Veff=D*Vbatt$, where Veff is the effective voltage to the coil resistance R, D is the pulse-width modulation duty cycle, and Vbatt is the battery voltage. If the battery 238 is fully charged to 4.0 volts and the motor 358 is to be run as though the battery voltage were only 3.0 volts, pulse-width modulation is done at a 75% duty cycle. The effective voltage to the coil resistance R is 0.75*4.0=3.0 volts. As the battery voltage drops to 3.0 volts the duty cycle will be increased to 100% and no switching will take place. The frequency of the switching will be determined by the L/R time constant. For an exemplary motor L=3.5 mH and R=30 Ohm, so L/R=117 μSec. The frequency has a period less than the time constant to insure a relatively linear ramp-up and down of the inductor current. This ensures that the equation Veff=D*Vbatt holds true. This method can be used to further reduce the effective voltage to the coil resistance if desired. This can be done to limit the pressure within the reservoir. A filter capacitor across the load R used in a traditional buck type switching regulator is not necessary due to conservation of energy. It simply holds charge to reduce voltage ripple, while the motor actually operates on electrical current, not voltage. In the description above, the coil current is directly proportional to the effective voltage Veff, since this voltage is considered to be across the purely resistive portion R of the coil load. Thus, for example, if the effective voltage to R is reduced by 25%, the current will also be reduced by 25%.

The pulse width modulation system may include an analog-to-digital (A/D) converter which converts voltage of the battery to a digital representation. The controller (a) operates through a driver circuit to control the operation of the motor and to pulse-width modulate energy from the battery applied to coils of the motor, (b) reads the digital output of the encoder and (c) reads the digital output of the A/D converter.

The controller 240 may include a first software algorithm adapted to use the digital representation of the motor position to program a first digital timer/counter circuit in the controller to provide low level signal outputs that enable the drivers DR1, DR2 of the motor 358 to facilitate a sequencing of voltage at the coils C1, C2 of the motor to produce a desired motor rotation. The controller 240 may also include a second software algorithm that uses the output of the A/D converter to program a second digital timer/counter circuit in the controller to provide a low level signal output that further enables the drivers DR1, DR2 of the motor 358 to facilitate the pulse-width modulation of the voltage to the coils C1, C2 of the motor 358.

The steps of the first software algorithm may be as follows: (1) determine the position of the motor shaft by reading the encoder 396; (2) determine the direction of rotation (either forward/delivery or reverse/retraction); (3) determine the number of rotations required (how much drug delivery or how far to retract); (4) step the motor 358 according to the sequence defined by the motor manufacturer's specification by driving coil phase A and B either + or −; and (5) repeat step (4) at a rate, which is determined by analysis and characterization during development, that guarantees movement with normal loads until the desired number of rotations is read from the encoder 396. Steps (4) and (5) may be performed by the first digital timer/counter circuit where the outputs are connected to the drivers DR1, DR2 for the motor coils C1, C2 while the microcontroller is reading the outputs of the encoder 396.

The steps of the second software algorithm may be as follows: (1) determine the effective motor coil voltage (Veff) required (for example, 2.7 volts to run the motor 358 in the forward direction, 1.1 volts to run the motor in the reverse direction; the actual voltages will be determined after analysis and characterization during development); (2) read the A/D converter output containing the digital representation of the battery voltage (Vbatt); (3) calculate Veff/Vbatt; and (4) program the second digital counter/timer circuit to output a digital pulse waveform with a duty cycle of Veff/Vbatt at a frequency of 10 to 100 times the rate of step (5) of the first software algorithm. The output of the second digital timer circuit will be a global enabling signal for both motor coil drivers DR1, DR2.

Thus, even though the circuit determines, for example, that at a particular time, coil phase A should be driven at +Vbatt and coil phase B should be driven at −Vbatt, the output of the second timer is the gating signal that determines when the drivers are actually enabled to drive the selected levels to the coils. The result will be that coil phase A will be driven at +Vbatt, but on and off at a duty cycle of Veff/Vbatt and likewise for coil phase B. This on and off rate will be much higher than the rate that the drivers DR1, DR2 will switch the polarity of the coil phases to perform the specified sequencing that causes the motor 358 to rotate. The effect is to limit the current to Veff/Vbatt times the amount of current that would be used if the full battery voltage were applied to the coils 100% of the rotation time.

Thus, torque can be limited by limiting the current to the motor coils C1, C2. Other ways to limit the current are to use a constant current source. However, this can be somewhat complex and wasteful of battery energy. A constant voltage source can be used. Since the coil resistance limits the current, limiting the voltage will effectively limit the current. This can be done in either of two ways. A linear voltage regulator may be employed, although this may be an unnecessary drain on the battery. Alternatively, a switching voltage regulator may be employed, which is more efficient in that it uses a coil to store energy, but includes more parts.

V. EXEMPLARY BASEPLATES AND CANNULAS

As noted above, and as illustrated for example in FIG. 1, the present infusion systems may include any one of a variety of different baseplates in combination with a cartridge (e.g., cartridge 100) and a pump assembly (e.g., pump assembly 200). Each baseplate may be configured for a different mode of system operation. Baseplate 500 is a body adherable baseplate that may be used in conjunction with a cannula such as cannula 600 (FIGS. 56-57) which is directly connected to the cartridge 100 so that the system may be deployed as a "patch pump." Baseplate 501 is configured to connect the cartridge 100 to an infusion set 503 so that the system may be deployed as a "pocket pump," a "belt-worn pump" or some other wearable pump. Baseplate 502 is a medicament non-delivery baseplate that includes a plug 504 which may be used to seal the cartridge 100 during periods of non-use. Additionally, and as discussed in Section VI below, pump assemblies (e.g., pump assembly 200) and baseplates (e.g., baseplates 500-502) may be respectively configured such that a pump assembly can determine which one of a variety of baseplates is attached to the pump assembly and then prepare to proceed in accordance with the operational mode associated with that baseplate. Also, although the exemplary baseplates are described herein in the context of the exemplary cartridge 100 and the exemplary pump assembly 200, the present baseplates may be used in conjunction with other cartridges, cartridge-based pumps, and pumps that are not cartridge-based.

Turning to FIGS. 53-55, the exemplary body adherable baseplate 500 may include a plate member 506 that is configured to cover the insertion opening 218 (FIG. 16) in the housing bottom portion 208. A cartridge aperture 508 (or simply a recess) may be provided to accommodate a medicament cartridge such as cartridge 100, or may be omitted, and a cannula aperture 510 may be provided to permit passage of a cannula in those instances where the plate member 506 would otherwise block the cannula. It should also be noted that the cartridge 100, pump assembly 200 and baseplate 500 are respectively configured such that a portion of the cartridge manifold 108 will rest on the plate member 506.

The exemplary baseplate 500 also includes structure that perform the function of securing the baseplate to the associated pump assembly. For example, in the embodiment illustrated in FIGS. 53-55, the baseplate 500 includes a pair of opposing connectors 512 and a hook 514. The connectors 512 frictionally engage the side walls 210 of the pump assembly housing 202, and may have an engagement portion 516, a support portion 518 that connects the engagement portion to the plate member 506, and a protrusion 520 to engage the user's finger. Gaps 522, which are located on either side of the support portion 518, allow the support portion to pivot in the direction shown by arrow P. The distance between the engagement portions 516 is less than the distance between the outer surfaces of housing side walls 210 when the connectors are in an unstressed state. As such, when the housing 202 and baseplate 500 are pressed together (FIGS. 54-55), thereby pivoting the connectors 512 out of their unstressed states, the engagement portions will apply forces F to the housing side walls 210 that are sufficient to provide enough frictional engagement to prevent separation during normal usage. The hook 514 may include an engagement portion 526 and a support portion 524, and gaps 528 may be located on either side of the support portion 524 if hook flexibility is desired.

During attachment of the baseplate 500 to the pump assembly 200, a bottom corner of the housing end wall 212 may be aligned with the space 528 defined by the hook 514. The baseplate 500 and pump assembly 200 are then moved relative to one another (e.g., pivoted about the hook 214) to the position illustrated in FIGS. 54-55, where the connectors 512 frictionally engage the housing side walls 210 and secure the baseplate to the pump assembly.

In at least some embodiments, the baseplate and associated cannula may be configured to secure themselves to one another. As a result, the pump assembly (e.g., pump assembly 100) and medicament cartridge (e.g., cartridge 200) may be removed together as unit from the baseplate with the cannula remaining secured to the baseplate as noted above with reference to FIG. 31. This allows, for example, the pump assembly battery to be recharged without removing the cartridge. The user may also use this capability to remove the baseplate and cannula from his/her body and then redeploy the system with a new baseplate and cannula at a different location.

One exemplary baseplate and cannula configuration is illustrated in FIGS. 55A-57. The exemplary baseplate 500" is essentially identical to baseplate 500 and similar elements are represented by similar reference numerals. In addition, a recess 511 with a mating surface 513 is positioned around the cannula aperture 510 on the bottom side (i.e., adhesive side) of the plate member 506. The recess 511 is used to secure a cannula to the baseplate 500" in the manner described below.

The exemplary cannula 600 is configured to establish a fluidic connection between a medicament cartridge (e.g., cartridge 100) and the patient. The exemplary cannula 600 is also configured to cooperate with the recess 511 such that axial movement of the cannula relative to the baseplate 501 is prevented, at least in the removal direction, after the cannula has been deployed into the patient.

With respect to the fluidic connection, the cannula 600 may include a connector plug 602 (or "head") that is configured to be inserted into the cartridge through-bore 116. The exemplary connector plug 602 may include a cylindrical member 604 with an internal lumen 606, at least one inlet port 608 connected to the internal lumen, o-ring or other seals 610 on opposite sides of the inlet port(s) 608. A cannula tube 612 may be connected to the connector plug 602. The exemplary seals 610 may be integral with the cylindrical member 604, or may be separate structures formed from rubber or other appropriate seal materials that are carried thereon.

Turning to cooperation with the baseplate recess 511, the exemplary cannula 600 includes a latch (or "hook") 614. Although the latch may be any suitable configuration, the exemplary latch 614 is a resilient structure that includes a latch surface 616 and a frustoconical support 618 below the latch surface. The latch 614 will deflect as the cannula 600 is deployed through the medicament cartridge through-bore 116 in the manner described above with reference to FIGS. 45-49. Here, the inserter trocar (e.g., trocar 812 in FIG. 85) will push through the top of the cylindrical member 604, through the internal lumen 606, and through the cannula tube 612, while the inserter drive structure (e.g., movable member 802 in FIG. 85) pushes the top of the cylindrical member.

Figure 57A:
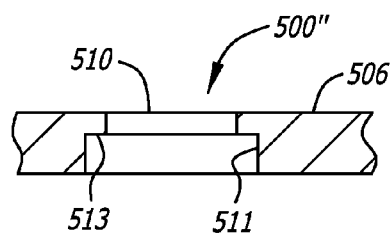
FIG. 57A is a section view of the baseplate illustrated in FIG. 57.
Figure 57:
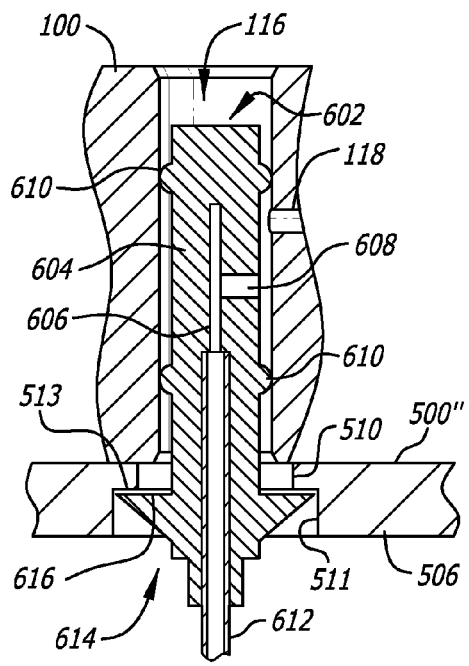
FIG. 57 is a section view of the cannula illustrated in FIG. 56 inserted through a cartridge and secured to a baseplate.

Once the resilient latch 614 passes through the cannula aperture 510, it will return to its relaxed state and the latch surface 616 will abut the mating surface 513 in the baseplate recess 511 (FIG. 57). The frustoconical support 618 will then prevent the cannula 600 from being pulled back through the cannula aperture 510.

It should also be noted that the respective sizes (e.g., diameters) of the recess 511 and the latch surface 616 are essentially the same. This relationship produces a tight fit that helps prevent lateral movement of the baseplate 500" relative to the cannula 600.

It should also be noted that the configuration of the associated inserter, e.g., inserter 800 in FIG. 85, prevents downward movement of the cannula 600 beyond that illustrated in FIG. 57. In other implementations, a cannula and/or baseplate may be provided with structure that performs this function.

Figure 58:
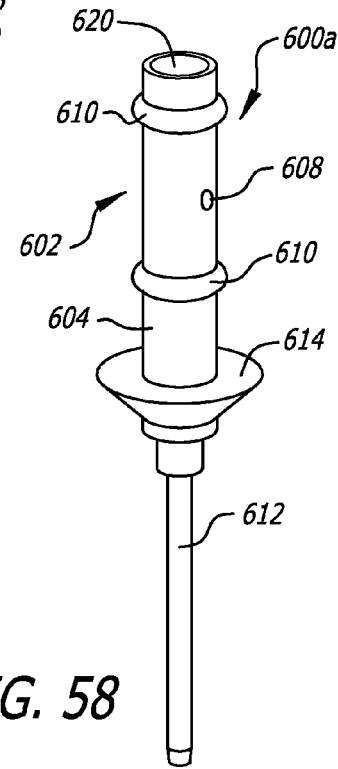
FIG. 58 is a perspective view of another exemplary cannula.
Figure 59:
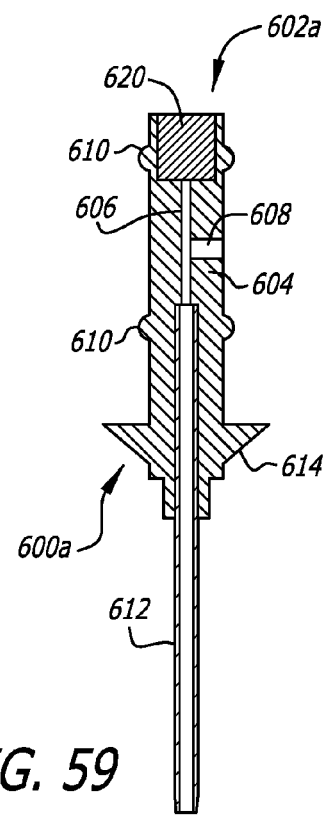
FIG. 59 is a section view of the cannula illustrated in FIG. 58.

The exemplary cannula 600a illustrated in FIGS. 58 and 59 is essentially identical to cannula 600 and similar elements are represented by similar reference numerals. In addition, cannula 600a includes a septum 620. The septum 620, which is formed from softer material than the cylindrical member 604, facilitates smooth passage of an inserter trocar to the internal lumen 606.

The dimensions of the exemplary cannulas 600 and 600a will depend on the intended patient as well as the configuration of the medicament cartridge. For example, the cylindrical member 604 may have a diameter of 4 mm+/−1 mm and a length of 7 mm+/−1 mm, while the cannula tube 612 may have an outer diameter of 0.5 mm, an inner diameter of 0.2 mm and a length of 6-10 mm. With respect to construction and materials, the plug 602 and cannula tube 612 may be formed as two separate pieces (as shown), and from two different materials, or integrally formed. Suitable materials for an integrally formed single cannula include, but are not limited to, FEP, PTFE, COP, medical grade plastics, and polypropylene. In a two piece arrangement, suitable materials for the cylindrical member 604 and integral resilient latch 614 include, but are not limited to PTFE, COP, medical grade plastics, and polypropylene, while the cannula tube 612 may be formed from materials such as PTFE, FEP and other fluoropolymers, and metals such as stainless steel.

Other exemplary instrumentalities for securing a cannula to a baseplate include, but are not limited to, other types of latches, including latches where a deflectable structure is included on the baseplate or both the baseplate and the cannula, as well as devices such as friction devices, adhesive, pivoting structures and sliding structures. A latching arrangement may also be associated with the cannula tube instead or, or in addition to, the cannula plug. The cannula latch may also be omitted and the cartridge through-bore and cannula plug respectively configured such that friction will maintain the relative positioning. One example of such a latch-less arrangement is discussed below with reference to FIG. 85.

Figure 60:
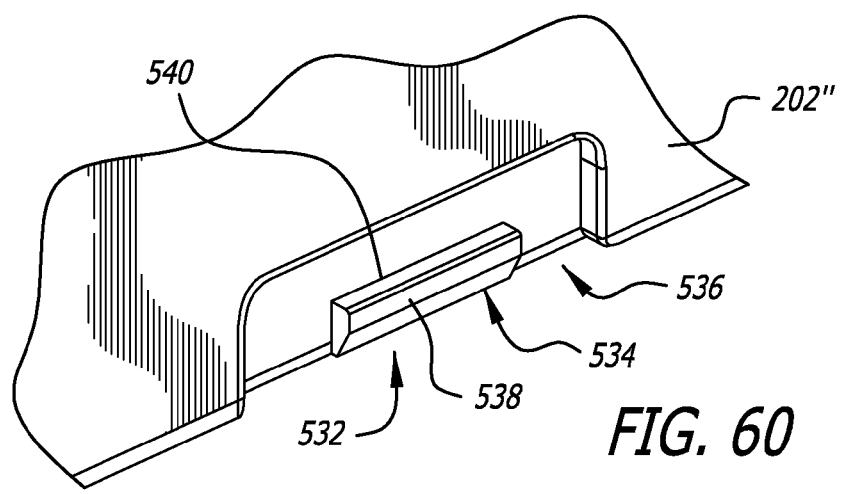
FIG. 60 is a perspective view of a portion of an exemplary pump assembly housing.
Figure 61:
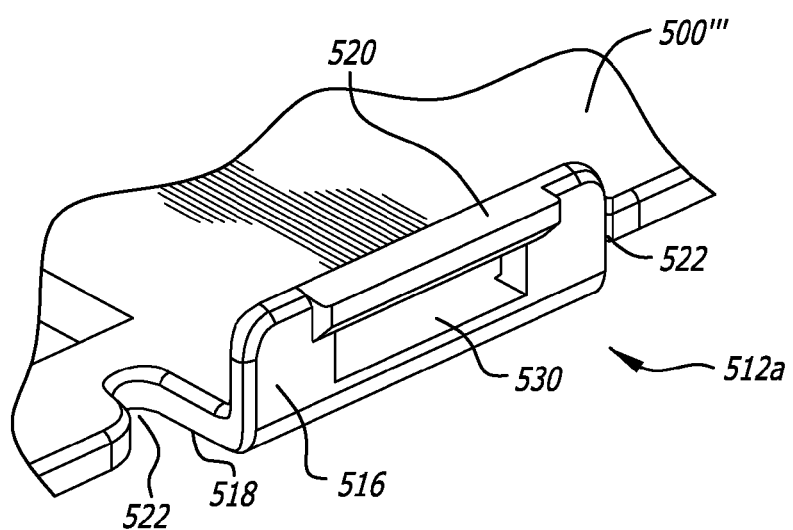
FIG. 61 is a perspective view of a portion of an exemplary baseplate.

The present baseplates and pump assemblies are not limited to any particular connector arrangement. One alternative is the interlocking latch arrangement illustrated in FIGS. 60 and 61, which may be employed in any of the pump assemblies and baseplates described herein. The interlocking arrangement is somewhat similar to the friction arrangement illustrated in FIGS. 53-55 and similar elements are represented by similar reference numbers. Here, however, the connection involves a mechanical interlock instead of mere friction. More specifically, the body adherable baseplate 500''' includes a pair of opposing connectors 512a (one shown) and a hook 514 (not shown). The exemplary connectors 512a have the aforementioned protrusions 520 as well as apertures 530. The side walls (one shown) of the associated pump assembly housing 202' have corresponding mating structures 532, each having a protrusion 534 that is sized and shaped to fit into an aperture 530. In the illustrated implementation, the mating structures 532 are carried within recesses 536 and have cam surfaces 538 and flat surfaces 540. As the baseplate 500''' is connected to the pump assembly 200', which is otherwise identical to pump assembly 200, the protrusions 520 will engage the cam surfaces 538, thereby pivoting the connectors 512a, until the apertures 530 are aligned with the mating structures 532. The resilience of the opposing connectors 512a will then cause them to move into the recess 536 and produce the mechanical interlock (or latched state) with protrusions 534. It should also be noted that the arrangements illustrated in FIGS. 53-55, 60 and 61 can be reversed, i.e., the connector structures on the housing moved to the baseplate and connector structures on the baseplate moved to the housing, and/or the connector structures can be associated with different housing walls. The number of connectors may also be increased and decreased, and other latching arrangements may be employed.

The present baseplates and pump assemblies are not limited to the exemplary structures for securing the baseplate to the associated pump assembly described above. Other suitable structures for securing a baseplate to a pump assembly include, but are not limited to, guided slide attachments, mechanical fasteners, magnet arrangements, hook-and-loop attachments, screw-on configurations, and low tack pressure sensitive adhesives. Also, the pump assembly or the baseplate may be provided with a pocket into which the other may be inserted.

The body adherable baseplate 500 will be, before, during and/or after the cartridge 100 and pump assembly 200 are combined therewith, adhered to the patient's skin. To that end, the bottom surface of the plate member 506 carries an adhesive layer 542 (FIG. 55) that releasably attaches the baseplate 500 to the patient's skin. The adhesive layer 542 may cover all, or less than all, of the bottom surface. A removable liner 544 (FIG. 54) may be used to cover the adhesive layer 542 until the time of use.

The present inventors have determined that it can be difficult to keep the cannula fixed and erect in the wound, given that the skin may be rough and non-planar and the wound area may be soft, wet and flexible, and that the failure to keep the cannula fixed and erect in the wound may cause the cannula to bend and occlude. Strong adhesive close to the cannula keeps the cannula fixed and tight. However, strong adhesive is more likely to irritate and even damage the skin. Thus, although the adhesive layer 542 may consist of a single type of adhesive, the exemplary baseplate 500 may include more than one type of adhesive in the adhesive layer 542, each serving a different purpose. In the illustrated embodiment, the adhesive layer has a first adhesive 546 and a second adhesive 548 that is stronger (or "more aggressive") than the first adhesive. The first adhesive 546 occupies the majority of the adhesive layer 542 and holds the majority of the baseplate to the skin with enough strength to prevent separation during normal usage. The second, more aggressive adhesive 548 surrounds the cannula opening 510 and keeps the cannula fixed and tight.

In the illustrated example, the second adhesive 546 may cover 0.75-1.25 mm around the cannula opening 510, bulging out and intersecting the adjacent corner of the plate member 506. The second adhesive may also cover 1-10% of the bottom surface. With respect to the relative strengths, in one example, the peel strength of the first adhesive 544 may be 60 oz/inch width+/−20 oz/inch width, and the peel strength of the second adhesive may be 50-100% more than that of the first. In another example, the first adhesive can have 80% of the strength of the stronger second adhesive.

The dimensions of the baseplate 500 may correspond to those of the associated pump assembly. In the context of the exemplary pump assembly 200 described above, the plate member may be 1 mm thick, with length/width relationships such as 42 mm×34 mm, 40 mm×32 mm, and/or 39.0-43.0 mm×31.0-35.0 mm.

Figure 62:
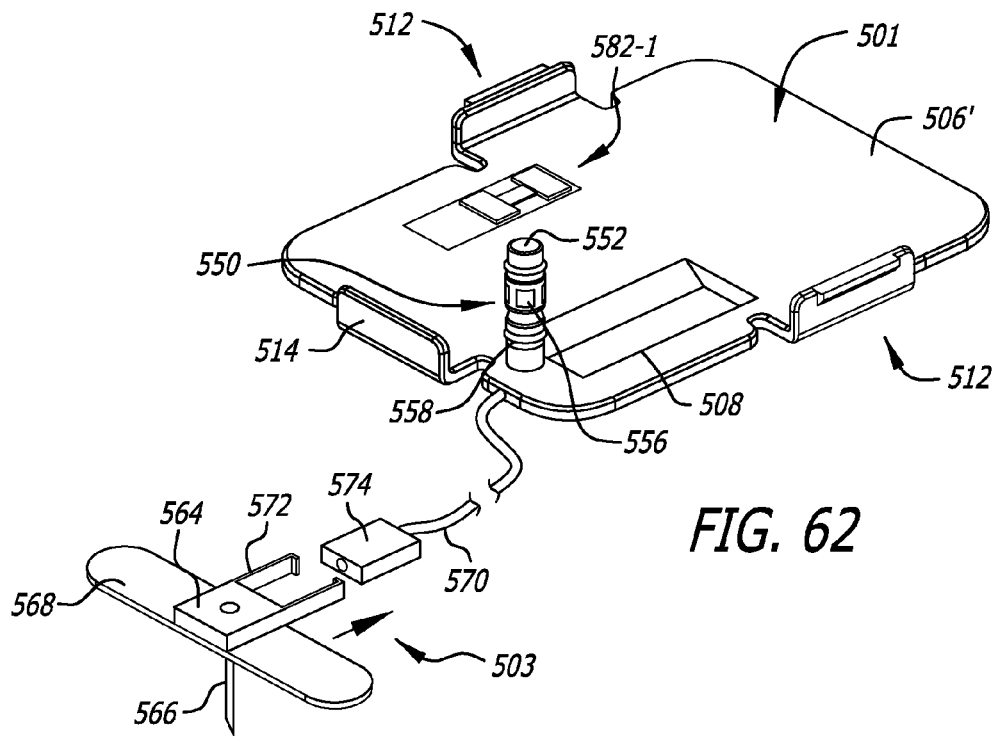
FIG. 62 is a perspective view of an exemplary baseplate and infusion set.
Figure 63:
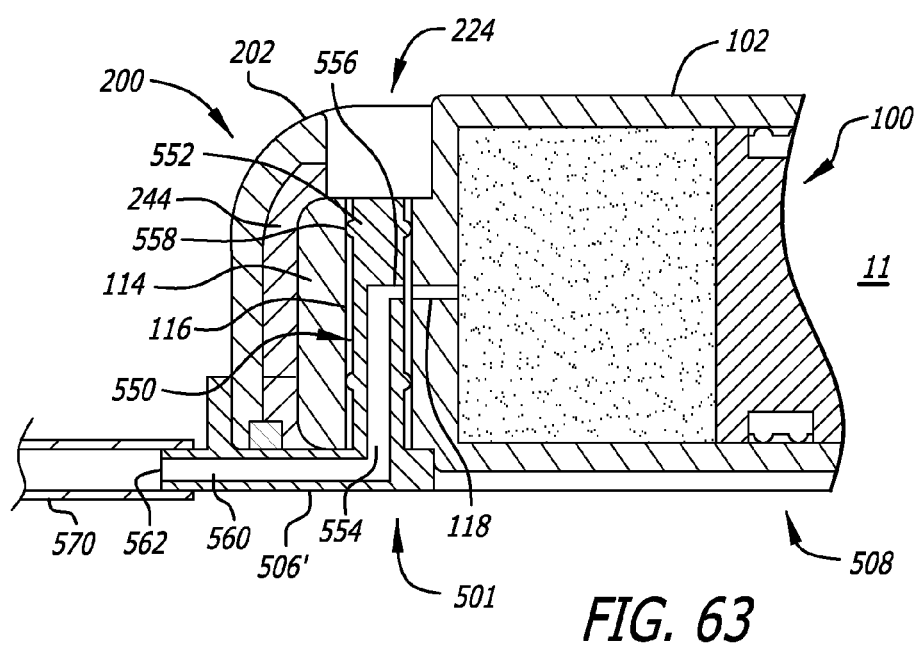
FIG. 63 is a section view of a portion of a system including the baseplate illustrated in FIG. 62.

The exemplary infusion set baseplate 501 illustrated in FIGS. 62 and 63 is substantially similar to the body adherable baseplate 500 and similar elements are represented by similar reference numerals. For example, the baseplate 501 may include a plate member 506', a cartridge aperture 508 (or recess), and connectors 512 (or any of the other connector structures described above). Here, however, the baseplate 501 may include an infusion set such as infusion set 503 (as shown) or may simply be configured to be connected to an infusion set. The baseplate 501 may also lack the adhesive layer.

The baseplate 501 in the illustrated example includes structures that establish a fluidic connection which extends from the medicament cartridge, such as cartridge 100, to the infusion set 503. To that end, and referring to FIGS. 62 and 63 the baseplate 501 may have a connector plug 550 that is configured to be inserted into the cartridge through-bore 116. The exemplary connector plug 550 includes a cylindrical member 552 with an internal lumen 554, a plurality of inlet ports 556 located around the perimeter of the cylindrical member and connected to the internal lumen, and o-ring or other seals 558 on opposite sides of the inlet ports 556. The exemplary connector plug 550 may be integral with the plate member 506' or may be a separate structure that is secured thereto. The exemplary seals 558 may be integral with the cylindrical member 552 or may be separate structures, formed from rubber or other appropriate seal materials, that are carried thereon. A lumen 560 within the plate member 506' extends to an outlet port 562.

The baseplate 501, pump assembly (e.g., pump assembly 200) and cartridge (e.g., cartridge 100) may be respectively configured such that, when the system 11 is assembled, the connector plug 550 will be located within the cartridge through-bore 116 with the connector plug seals 558 on opposite sides of the reservoir outlet port 118. Fluid flowing into the through-bore 116 from the outlet port 118 will enter the inlet ports 556, flow through the internal lumen 554, the baseplate lumen 560, and the outlet port 562 to the infusion set 503.

The exemplary infusion set 503 (FIG. 62), which may be any conventional infusion set, may have a hub 564, a cannula 566 extending from the hub, a flexible adhesive-backed wing-type base 568, and a fluid tube 570. Infusion sets with disk-type bases may also be employed. The adhesive may be a single type of adhesive, or may be two or more different adhesives as described above. The tube 570 may be removably or permanently connected to the outlet port 562. The tube 570 may also be any suitable length (e.g., 42 inches). Connectors 572 and 574 may be provided on the hub 564 and fluid tube 570 in those instances where the hub and fluid tube are separable.

Figure 64:
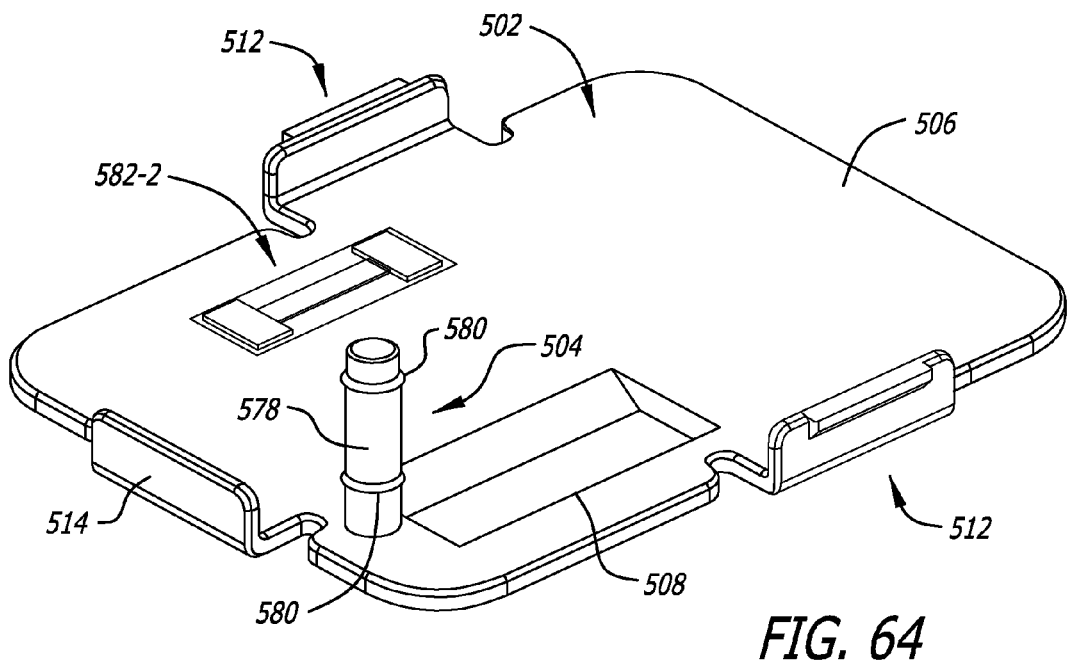
FIG. 64 is a perspective view of an exemplary baseplate.
Figure 65:
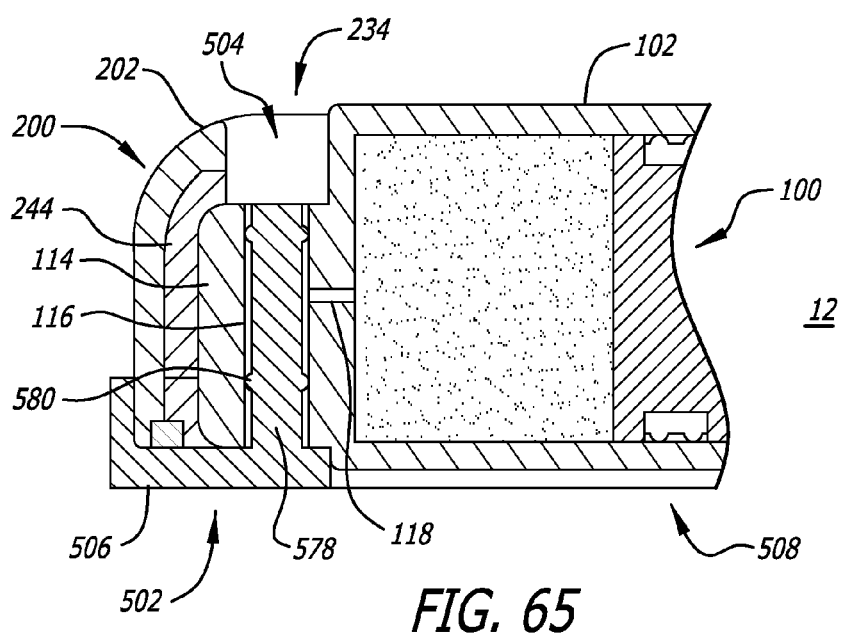
FIG. 65 is a section view of a portion of a system including the baseplate illustrated in FIG. 64.

Turning to the exemplary medicament non-delivery baseplate 502 illustrated in FIGS. 64 and 65, there may be instances where the user chooses not to use the pump assembly to deliver medicament and desires to re-plug the medicament cartridge to prevent leakage. Such periods of non-delivery may be associated with, for example, the use of an alternate pump or syringes to deliver medicament, or the shipment of the pump assembly to a service center.

The medicament non-delivery baseplate 502 illustrated in FIGS. 64 and 65 is substantially similar to the body adherable baseplate 500 and similar elements are represented by similar reference numerals. Given the small sizes of the cartridge 100 and pump assembly 200, users may find it easier to reseal the cartridge with the medicament non-delivery baseplate 502 than with the plug 110.

The exemplary baseplate 502 may include a plate member 506, a cartridge aperture 508 (or recess), and connectors 512 (or any of the other connector structures described above). Here, however, the baseplate 502 may also include a plug 504 that is configured to prevent flow from a medicament cartridge (e.g., cartridge 100) carried in a pump assembly (e.g., assembly 100). The baseplate 502 may also lack the adhesive layer.

The exemplary plug 504 includes a cylindrical member 578 and two or more o-ring or other seals 580. The exemplary plug 504 may be integral with the plate member 506 or may be a separate structure that is secured thereto. The exemplary seals 580 may be integral with the cylindrical member 578 or may be separate structures, formed from rubber or other appropriate seal materials, that are carried thereon. The baseplate 502, a pump assembly (e.g., pump assembly 200) and a cartridge (e.g., cartridge 100) may be respectively configured such that, when the system 12 is assembled, the plug 504 will be located within the cartridge through-bore 116 with the seals 580 on opposite sides of the reservoir outlet port 118, thereby preventing flow.

It should also be noted that the present inventions include kits which contain various combinations of baseplates, at least two of the baseplates being different. Kits may also include such combinations and, in addition, a pump assembly, and/or a medicament cartridge and/or a cannula. For example, a kit may include one or more of each of baseplates 500 and 502, a kit may include one or more of each of baseplates 501 and 502, a kit may include one or more of each of baseplates 500, 501 and 502. Kits may also include any of the combinations recited in the preceding sentence and, in addition, a pump assembly, and/or one or more medicament cartridges and/or one or more cannulas. The baseplates in such kits may also include the detection instrumentalities discussed in Section VI below. The components the present kits (e.g., combination of various baseplates) may be stored in a common package, with individual packages for each component if necessary, and provided to the user in the common package. Other instrumentalities that may be provided in such kits includes, but is not limited to, inserters that are preloaded with a cannula and cleaning swabs. A recharger may also be provided in a kit that includes a pump assembly.

VI. EXEMPLARY BASEPLATE IDENTIFICATION

Figure 50:
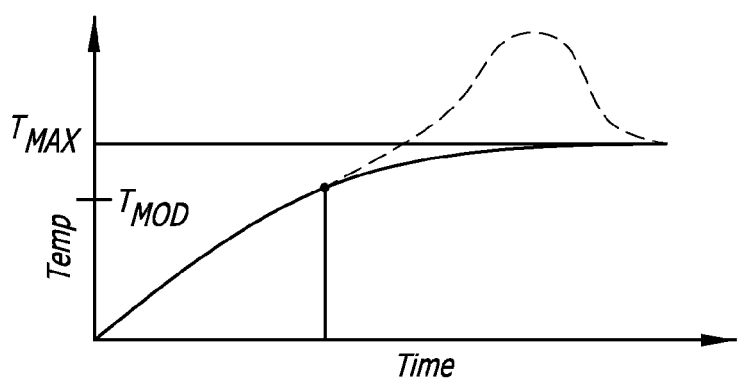
FIG. 50 is a graph showing recharging temperature during an exemplary battery recharging method.

It should be noted here that, but for the issue of priming, the dispensing procedures associated with an infusion system "patch pump" configuration, which may include a pump assembly 200 and a baseplate 500 (FIG. 53), are substantially the same as the dispensing procedures associated with a "pocket pump" configuration, which may include a pump assembly 200 and a baseplate 501 (FIGS. 62-63). With a "patch pump" configuration, priming is not necessary because the volume of the associated cannula will be very small and there is a direct connection between the cannula and the medicament cartridge (FIG. 50). Priming is, however, required to fill the infusion set tube (e.g., tube 570 in FIGS. 62-63) in a "pocket pump" configuration prior to the onset of medicament delivery. 20-30 μl may be required to fill the entire infusion set tube and, accordingly, the priming procedure may involve the rapid delivery of 10-15 IUs of U-500 insulin to the tube. The present inventors have determined that it would be advantageous to prevent users from initiating a priming procedure when the system is in the "patch pump" configuration, with a cannula positioned to deliver medicament essentially directly from the medicament cartridge to the patient, because rapidly delivering 10-15 IUs of insulin to the patient could adversely effect patient health.

To prevent such undesirable outcomes, at least some of the present baseplates may be provided with a baseplate identification device and at least some of the present pump assemblies may be provided with structure that cooperate with a baseplate identification device in such a manner that the pump assembly controller can make a "baseplate type" determination. For example, the baseplate identification devices may be carried by the baseplates and may be detectable by the pump assembly as well as distinguishable from one another. Once the "baseplate type" determination is made (e.g., baseplate 500 or baseplate 501), the pump assembly will proceed in a manner, or mode of operation, that is appropriate for the attached baseplate. For example, if the baseplate 500 is detected, the controller will not including priming as part of the delivery process and, in some implementations, will prevent the user from manually implementing a priming procedure. If, on the other hand, baseplate 501 is detected, then the delivery process may include appropriate priming of the infusion set tube.

A wide variety of baseplate identification instrumentalities and identification methodologies may be employed, and the present inventions are not limited to any particular instrumentalities and methodologies. Various illustrative examples of such instrumentalities and identification methodologies are presented below.

In the exemplary implementation illustrated in FIGS. 1 and 66-68, the baseplates 500, 501 and 502 respectively have identification devices 582-0, 582-1 and 582-2, each of which includes a pair of electrical contacts. The electrical contacts are located such that each pair will be aligned with (as well as contact or be otherwise electrically coupled to) a respective two of the three electrical contacts 228, 230 and 232 associated with the pump assembly (FIG. 16) when a baseplate is secured to the pump assembly. The electrical contacts 228 and 230 may also be used to recharge the pump assembly battery 238, as is noted above. For example, baseplate identification device 582-0 may include electrical contact pair 228BP/230BP (FIG. 66) that will align with pump assembly electrical contact pair 228/230, baseplate identification device 582-1 may include electrical contact pair 230BP/232BP (FIG. 67) that will align with pump assembly electrical contact pair 230/232, and baseplate identification device 582-2 may include electrical contact pair 228BP/232BP (FIG. 68) that will align with pump assembly electrical contact pair 228/232. The electrical contacts in each pair, which may be located in recesses 584, are electrically coupled to one another by conductors 586. The conductors 586 may be formed from a low resistance material and may be covered with an appropriate electrical insulator.

During use, and after a baseplate has been secured to the pump assembly (e.g., pump assembly 200), the pump assembly controller (e.g., controller 240) will cause voltage to be applied across the pump assembly electrical contacts 228, 230 and 232 and may measure resistance (or another suitable variable) between contact pairs 228/230, 230/232 and 228/232. The pair that is in contact with two of the baseplate electrical contacts will have low resistance therebetween, while the other two pairs will have extremely high (e.g., infinite) resistance therebetween. The pump assembly controller may store information which indicates that low resistance at contact pair 228/230 is indicative of baseplate 500, low resistance at contact pair 230/232 is indicative of baseplate 501, and low resistance at contact pair 228/232 is indicative of baseplate 502. The "baseplate type" determination may, therefore, be made by simply determining which two of the three pump assembly electrical contacts have a low resistance path therebetween.

Turning to FIGS. 69-72, the exemplary pump assembly 200*d* is essentially identical to pump assembly 200 and the baseplates 500*d*, 501*d* and 502*d* are essentially identical to baseplates 500, 501 and 502, respectively. Similar elements are represented by similar reference numerals. Here, however, the pump assembly 200*d* only includes the two recharging-related electrical contacts 228 and 230, and the baseplates 500*d*, 501*d* and 502*d* respectively include baseplate identification devices 588-0, 588-1 and 588-2 that each have two electrical contacts, i.e., electrical contacts 228BP and 230BP. The electrical contacts 228BP and 230BP, which will contact or otherwise electrically couple with the contacts 228 and 230 when a baseplate is attached to pump assembly, may be connected by resistors R1, R2 and R3 with different resistor values. The resistor values may be significantly different to reduce the likelihood of error. For example R1 may be 10 kΩ, R2 may be 22 kΩ, and R3 may be 68 kΩ. Also, in the illustrated implementation, the electrical contacts 228BP and 230BP are carried in recesses 590. Resistor value to baseplate type correspondence information may be stored by the pump assembly controller. During use, and after a baseplate has been secured to the pump assembly (e.g., pump assembly 200*d*), the pump assembly controller will cause voltage to be applied across the electrical contacts 228 and 230 and the resistance between the electrical contacts 228BP and 230BP will be measured. The "baseplate type" determination may be made based on this resistance measurement and a comparison of the measured value to the stored information.

The exemplary electrical contacts described above may be formed from materials such as copper or nickel. Also, although the surfaces of the electrical contacts are generally planar in the illustrated embodiments, the electrical contacts are not limited to any particular configuration. For example, opposing metallic half balls may be employed with proper accommodation on the pump assembly and baseplate.

Figure 73:
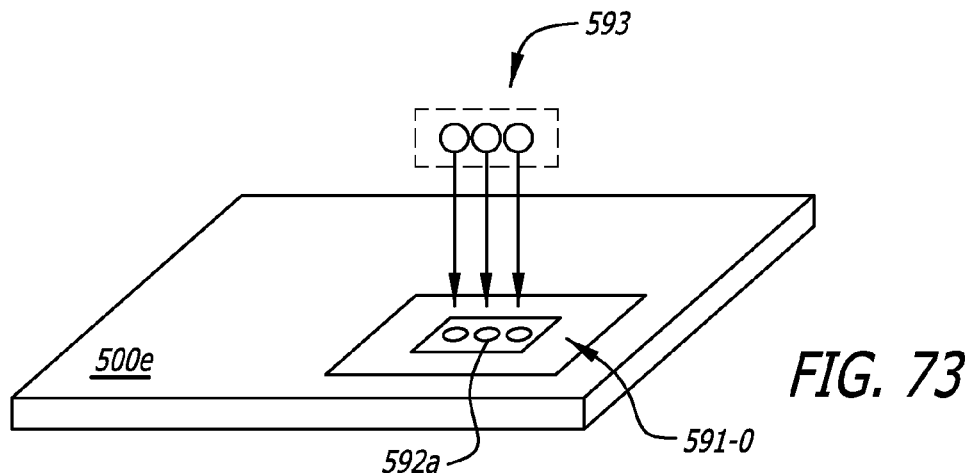
FIG. 73 is a diagrammatic representation of exemplary baseplate identification instrumentalities.
Figure 74:
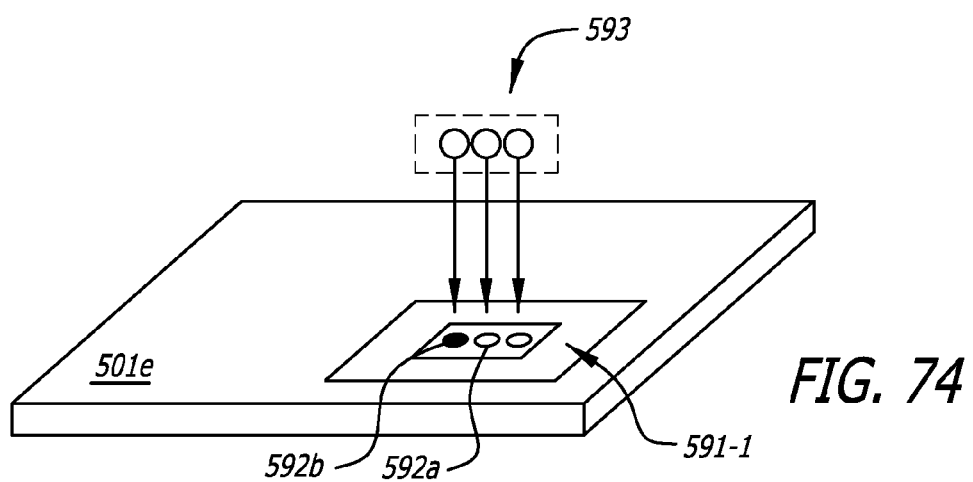
FIG. 74 is a diagrammatic representation of exemplary baseplate identification instrumentalities.
Figure 75:
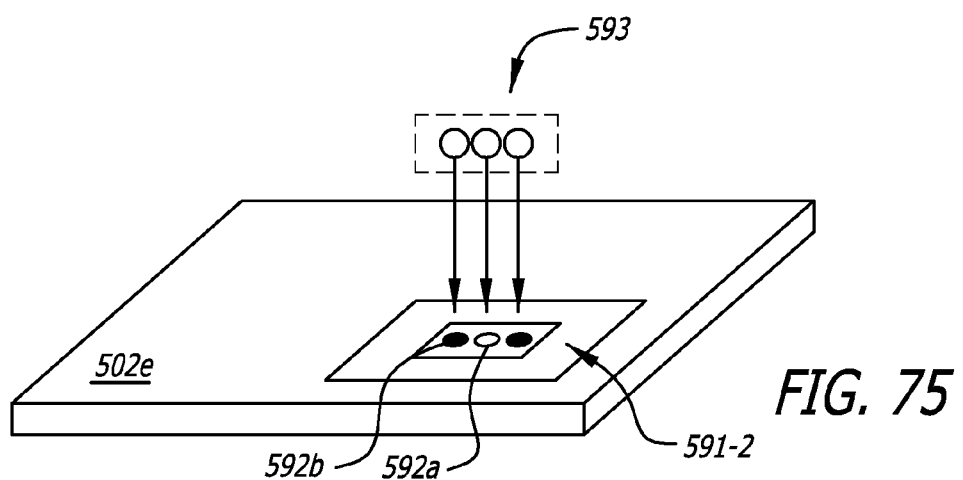
FIG. 75 is a diagrammatic representation of exemplary baseplate identification instrumentalities.

Other exemplary baseplate identification instrumentalities are illustrated in FIGS. 73-75. Here, the baseplates 500*e*, 501*e* and 502*e*, which are otherwise identical to baseplates 500, 501 and 502, respectively, carry baseplate identification devices 591-0, 591-1 and 591-2 with different patterns of optically identifiable targets. For example, the optically identifiable targets may be reflective targets 592*a* and occluded targets 592*b*. The associated pump assembly (e.g., pump assembly 200*d*) may be provided with an emitter/detector 593 that "reads" the patterns of optically identifiable targets and transmits a pattern signal to the pump assembly controller (e.g., controller 240) indicative of the pattern that has been read (e.g., 0,1,1 for the pattern illustrated in FIG. 74). Pattern to "baseplate type" correspondence information may be stored by the pump assembly controller, and the controller may identify the baseplate based on the pattern signal. Additionally, the baseplate identification devices 591-0, 591-1 and 591-2 may be carried or formed directly on the baseplate, or may be carried on structures (e.g. decals) that are secured to the baseplate.

Figure 76:
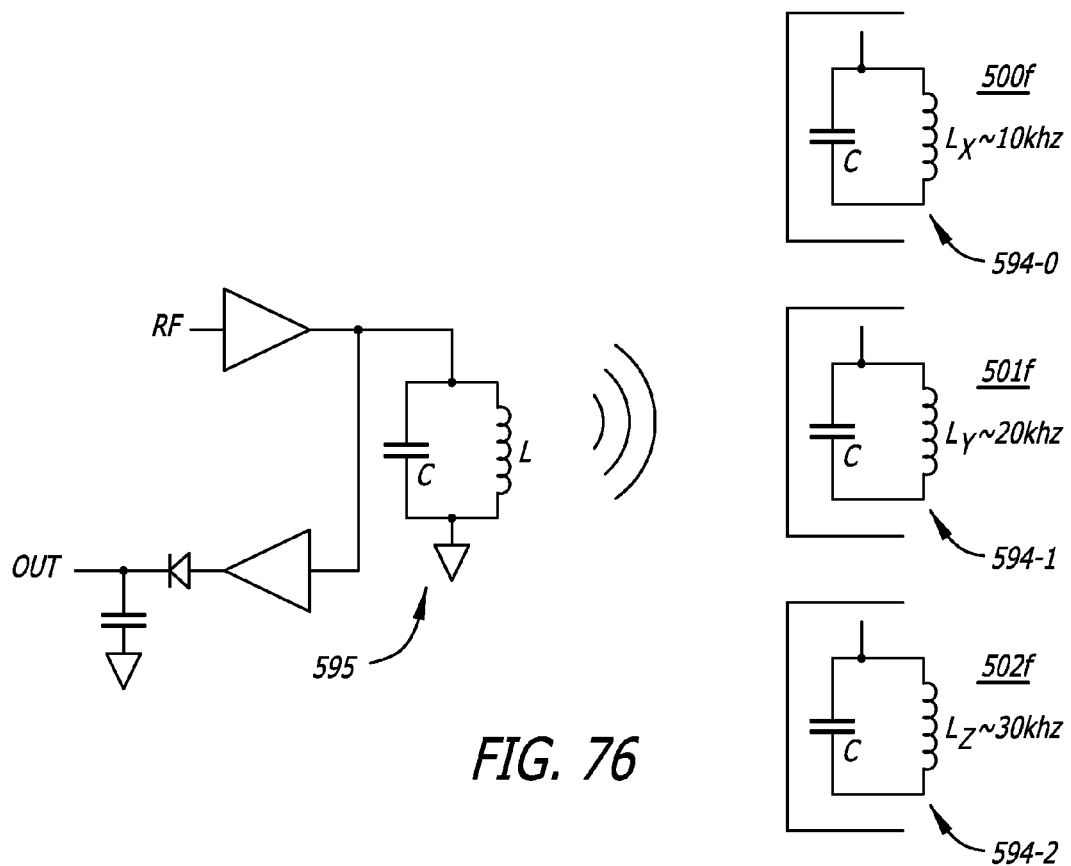
FIG. 76 is a diagrammatic representation of exemplary baseplate identification instrumentalities.

Other exemplary baseplate identification instrumentalities are illustrated in FIG. 76. Here, the baseplates 500*f*, 501*f* and 502*f*, which are otherwise identical to baseplates 500, 501 and 502, respectively, carry baseplate identification devices 594-0, 594-1 and 594-2 in the form of resonant circuits with different resonant frequencies. The associated pump assembly (e.g., pump assembly 200*d*) may be provided with an RF transmitter 595, including an RF transmitter antenna, a detector-demodulator, and RF electronics. The RF transmitter 595 may be used to detect the frequency of a resonant circuit in proximity thereto and to provide such frequency information to the controller. Exemplary resonant frequencies for the baseplate identification devices 594-0, 594-1 and 594-2 include, but are not limited to, 10 kHz, 20 kHz and 30 kHz, and frequency to "baseplate type" correspondence information may be stored by the controller.

Figures 77, 78:
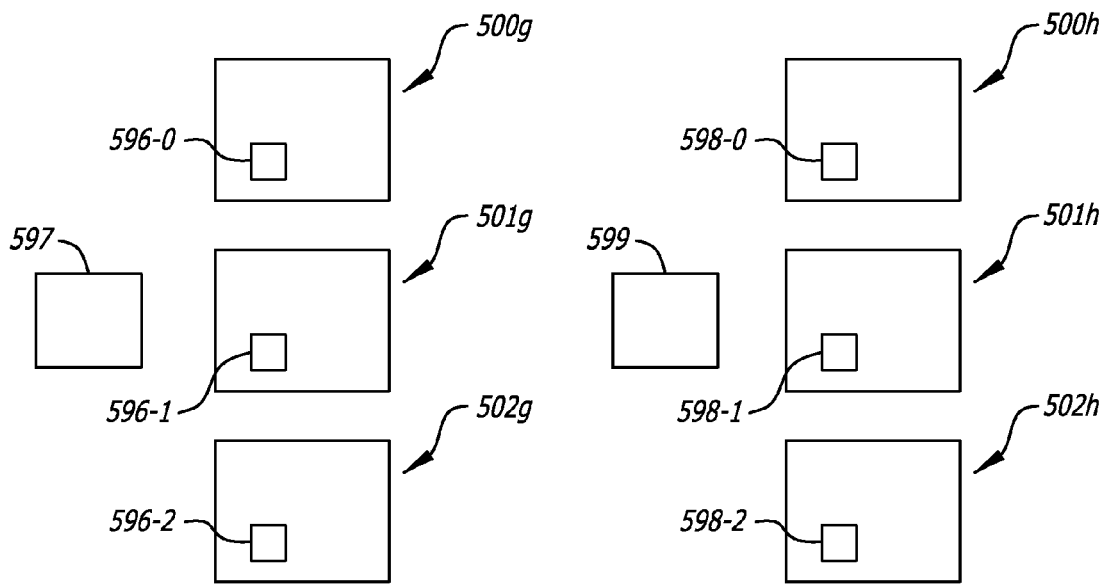
FIG. 77 is a diagrammatic representation of exemplary baseplate identification instrumentalities.
FIG. 78 is a diagrammatic representation of exemplary baseplate identification instrumentalities.

Still other exemplary baseplate identification instrumentalities are illustrated in FIG. 77. Here, the baseplates 500*g*, 501*g* and 502*g*, which are otherwise identical to baseplates 500, 501 and 502, respectively, carry baseplate identification devices 596-0, 596-1 and 596-2 in the form of magnets that create different magnetic fields. The associated pump assembly (e.g., pump assembly 200*d*) may be provided with a sensor 597, such as a Hall-effect sensor or a magnetoresistive sensor, that reads the magnetic field of the associated baseplate identification device, and sends a signal corresponding to the sensed magnetic field to the controller. Magnetic field to "baseplate type" correspondence information may be stored by the controller.

Turning to FIG. 78, the exemplary baseplate identification instrumentalities illustrated therein include baseplate identification devices 598-0, 598-1 and 598-2 in the form of RFID tags, each of which emits different identification data in response to being interrogated. The baseplate identification devices 598-0, 598-1 and 598-2 are respectively carried by baseplates 500*h*, 501*h* and 502*h*, which are otherwise identical to baseplates 500, 501 and 502. The associated pump assembly (e.g., pump assembly 200*d*) may be provided with an RFID reader 599 that interrogates the associated identification device, and sends a signal corresponding to the identification data to the controller.

The present baseplates and pump assemblies are not limited to the exemplary identification instrumentalities described above. By way of example, but not limitation, other identification instrumentalities include protrusions on the plate that depress buttons, or combinations of buttons, on the bottom surface of the pump assembly housing. Another example includes depressible pins that extend from the bottom surface of the pump assembly housing, such that they will be pressed by an attached baseplate. Here, different baseplates may be provided with different combinations of indentations that will be aligned with the pins, to prevent depression thereof, when the baseplate is attached. It should also be noted that the present baseplates and pump assemblies are not limited to identification instrumentalities that require the baseplate to be completely or partially attached to the pump assembly prior to the identification procedure. Instrumentalities that merely require suitable proximity (including those that involve RFID technology) may be employed.

VII. EXEMPLARY BASIC OPERATION AND USE

At the most basic level, use of the exemplary infusion pump system 10 (or 11) illustrated in FIG. 1 involves inserting a new medicament cartridge 100 into the pump assembly, connecting the baseplate 500 (or 501) to the pump assembly, gaining subcutaneous access, and initiating a medicament delivery operation. In some instances, use may involve additional steps such as removal of a previously inserted cartridge (whether empty or not) and battery recharging. Various aspects of the basic operation of the present systems are described below. Operation of a system does not require all of the steps each time the system is deployed, and the order of some of the steps may be changed. Operation is also discussed below, in the exemplary context of the above-described cartridge 100, pump assembly 200' and patch pump baseplate 500', through the use of a flow chart (FIG. 79) as well as through illustrations of the exemplary system itself in various states (FIGS. 80-90). The discussion is, however, equally applicable to other patch pump implementations, as well as to pocket pump implementations with minor variations. Also, unless otherwise indicated, the actions and determinations performed by the pump assembly 200' are controlled by controller 240 (FIGS. 18 and 84) and references to the controller are omitted in the interest of brevity.

Figure 79:
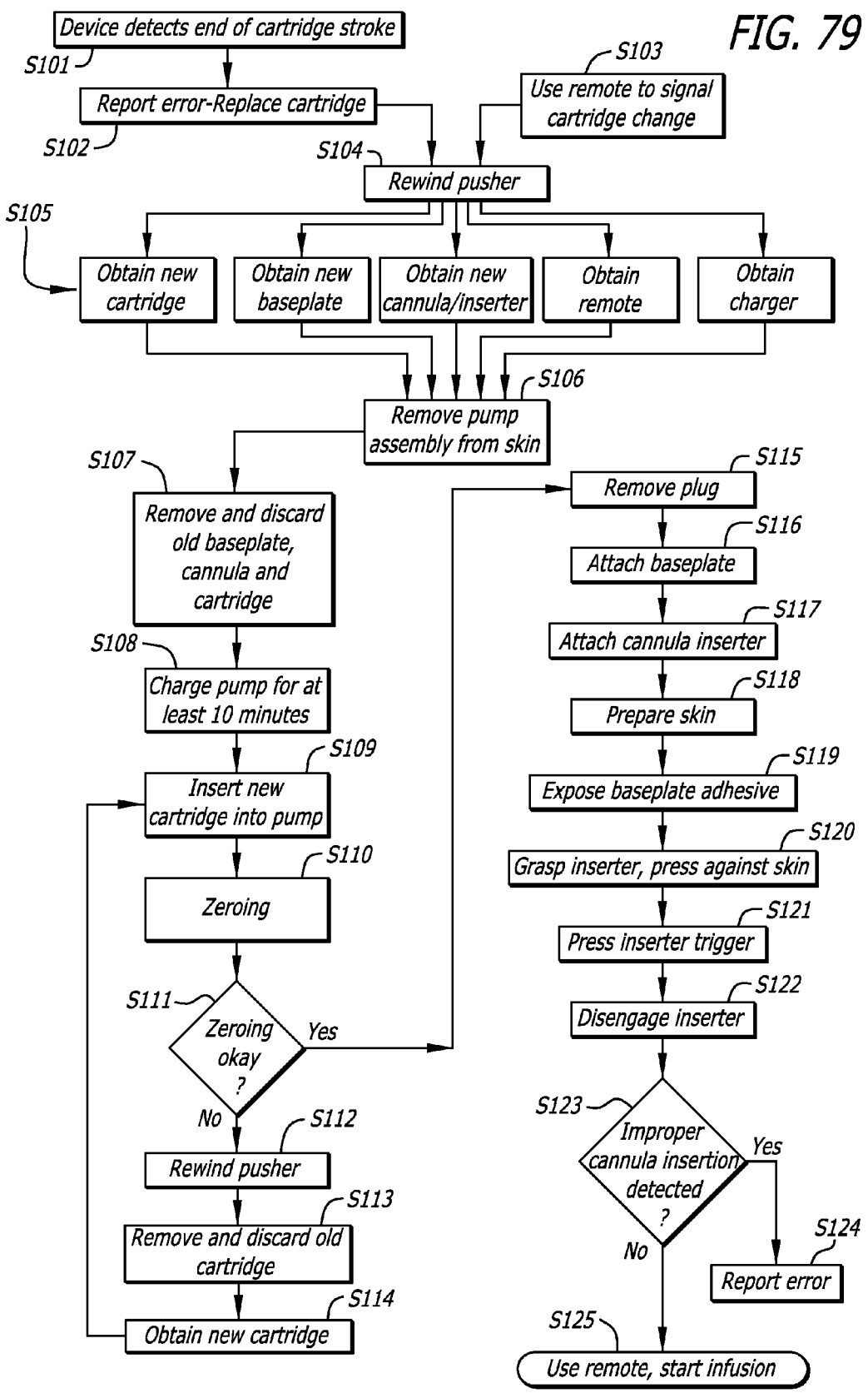
FIG. 79 is a flow chart showing an exemplary medicament cartridge removal and replacement method.

Referring first to FIG. 79, use of the present systems may involve removal of a cartridge from a pump assembly. This may occur (in some instances automatically) when the plunger pusher 250' is at the end of the pusher stroke (Step S101) and a "replace cartridge" report is presented (Step S102), or when the controller receives a user-initiated "replace cartridge" signal from the remote control 1000 (Step S103). The user may desire to replace a cartridge before it is empty for a variety of reasons such as, for example, to accommodate the user's sleep or travel schedule, when the medicament appears cloudy or otherwise exhibits a loss of effectiveness, when a dispensing problem arises, or due to a prescribed change in medicament. Whether automatic or user-initiated, the plunger will be returned to the fully retracted home position (Step S104). The user may then obtain a new cartridge 100, a new baseplate 500', a new cannula and inserter, the remote control 1000 (if not already at hand), and the battery recharger 700 (Step S105). The cartridge 100, pump assembly 200', baseplate 500' and cannula may then be removed from the skin, and the baseplate, cartridge and cannula discarded (Steps S106 and S107). The battery 238 may be recharged with the recharger 700 (Step S108) in the manner described in Section IV-J above with reference to FIGS. 49-50.

A new cartridge 100 may then be inserted in the pump assembly 200' (Step S109). In particular, as illustrated in FIG. 80, because the pusher 250' is in a retracted home position, the slidable latch 412a is unlocked and the latch member 442 can be pushed to the rearward position, thereby facilitating cartridge insertion, as described in Section IV-F above with reference to FIGS. 32-35A. The latch member 442 will return to the locked position (FIG. 81) when released, thereby pushing the cartridge 100 against the chassis 244.

The plug 110 may remain in the cartridge through-bore 116 should the user desire to perform the pusher zeroing procedure (or "zeroing procedure") described in Section VIII-B below with reference to FIG. 91 (Step S110). The zeroing procedure may also be an automatic aspect of pump operation. The user may use, for example, the remote control 1000 to initiate the zeroing procedure (FIG. 81) which involves briefly advancing the pusher 250' (FIG. 82), thereby locking the latch 412a and rigidly fixing the position of the cartridge 100 against the chassis 244 in a held position within the cartridge receiving area 220. If the results of the zeroing procedure are negative, the pusher 250' is withdrawn (FIG. 83), thereby unlocking the latch 412a. The medicament cartridge 100 is removed and discarded, a new cartridge is inserted, and the zeroing procedure is repeated (Steps S111, S112, S113 and S114). Alternatively, if the results of the zeroing procedure are positive, the pusher 250' is withdrawn, the plug 110 is removed and the baseplate 500' may be secured to the pump assembly 200', as shown in FIG. 84 (Steps S115 and S116). As discussed above in Section IV-F above with reference to FIG. 35A, the slidable latch member 442 will seat in the baseplate latch indentation 509 to properly align the pump assembly 200' and baseplate 500'.

A cannula inserter (or "inserter") may then be secured to the pump assembly 200' (Step S117). One exemplary inserter, which is generally represented by reference numeral 800 in FIG. 85, may include a movable member 802 within a housing 804, and a trigger-type actuator 806 that acts on the movable member. The exemplary actuator 806 may have a rotatable trigger 808 and a compressed spring or other biasing device 810. A trocar 812 is carried on the movable member 802. A cannula 600' is pre-mounted on the trocar 812 such that the sharp end of the trocar extends beyond the cannula tube 612. The inserter 800 may also be configured to withdraw the trocar back into the housing 804 after the cannula is deployed.

Figure 56:
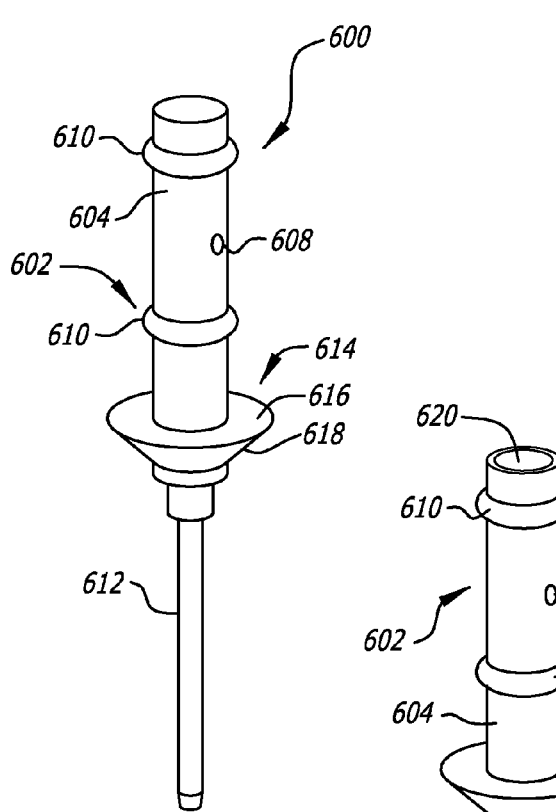
FIG. 56 is a perspective view of an exemplary cannula.

It should be noted here that the exemplary cannula 600' is substantially similar to the cannula 600 described in Section V above with reference to FIGS. 56-57 and similar elements are represented by similar reference numerals. Here, however, the cannula 600' does not include a latch. Instead, the respective configurations (e.g., shape, size and materials) of the cartridge through-bore 116 and the cannula plug 602' are such that friction therebetween will maintain the relative positioning after cannula deployment. The cannula plug 602' may also be formed from two different materials, e.g., a more rigid inner material to provide structural support and a softer outer material for sealing. The discussion concerning deployment of the cannula 600' is, of course, equally applicable to cannula 600, cannula 600a and/or any other cannula that may be used in conjunction with the present pump assemblies and baseplates.

Figure 87:
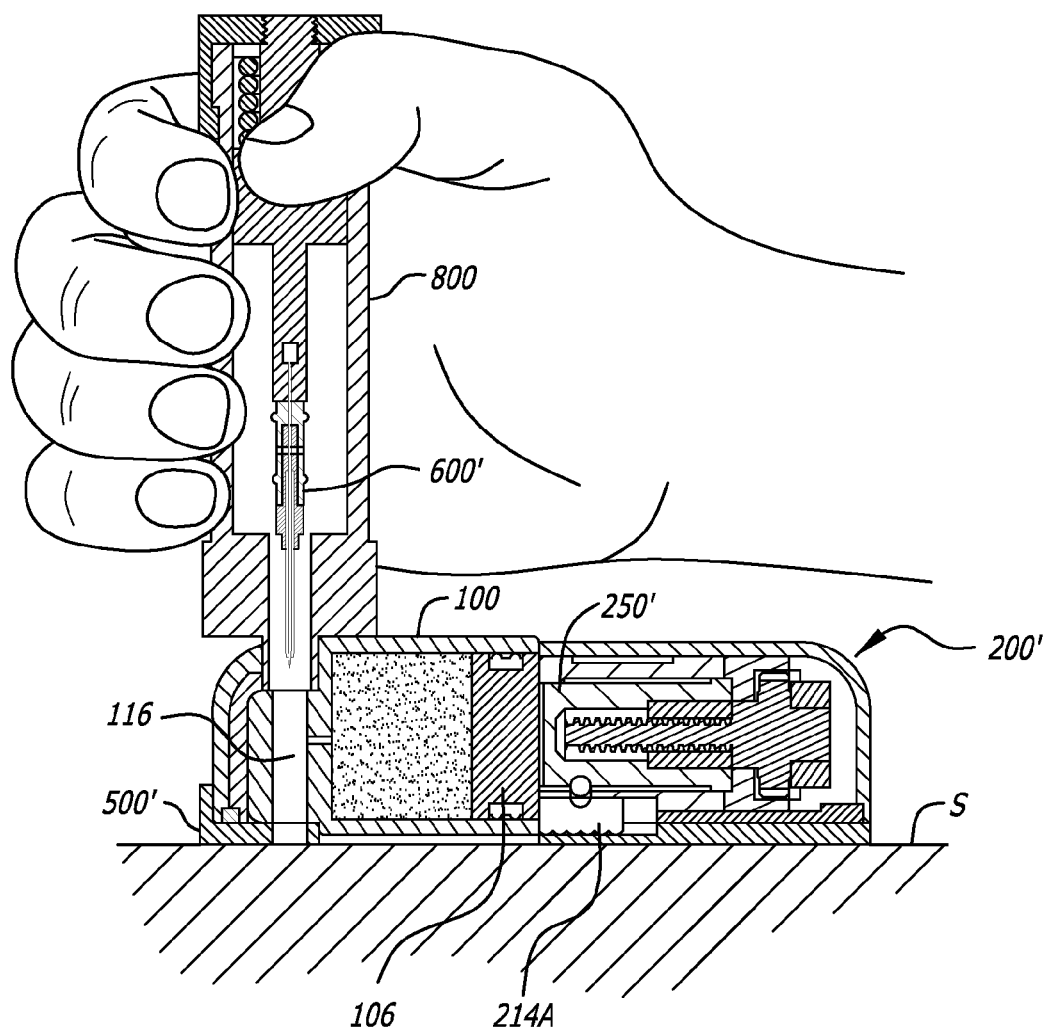
FIG. 87 is a section view showing the system illustrated in FIG. 85 on the cleaned skin prior to cannula insertion.
Figure 88:
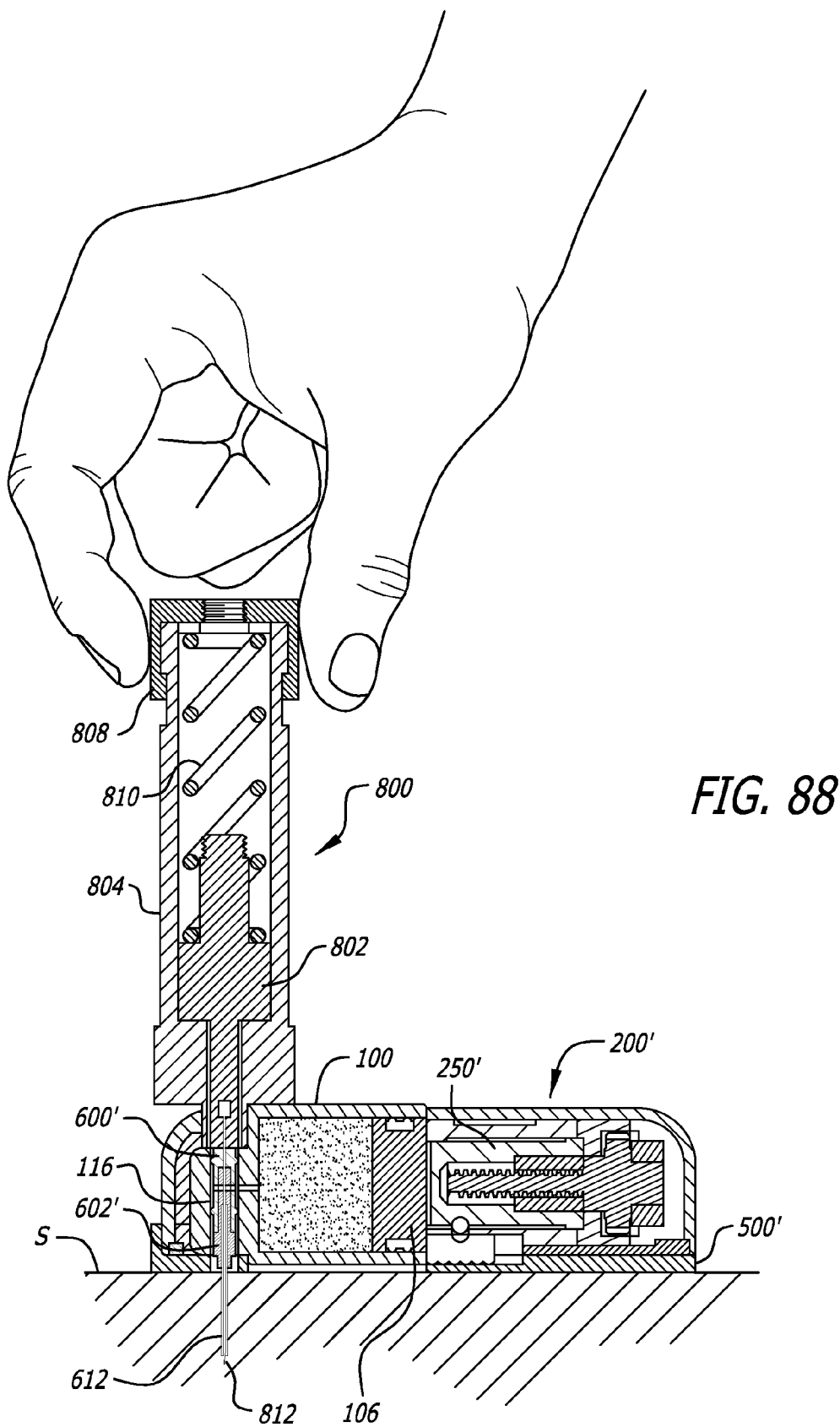
FIG. 88 is a section view showing the system illustrated in FIG. 87 after cannula insertion.
Figure 89:
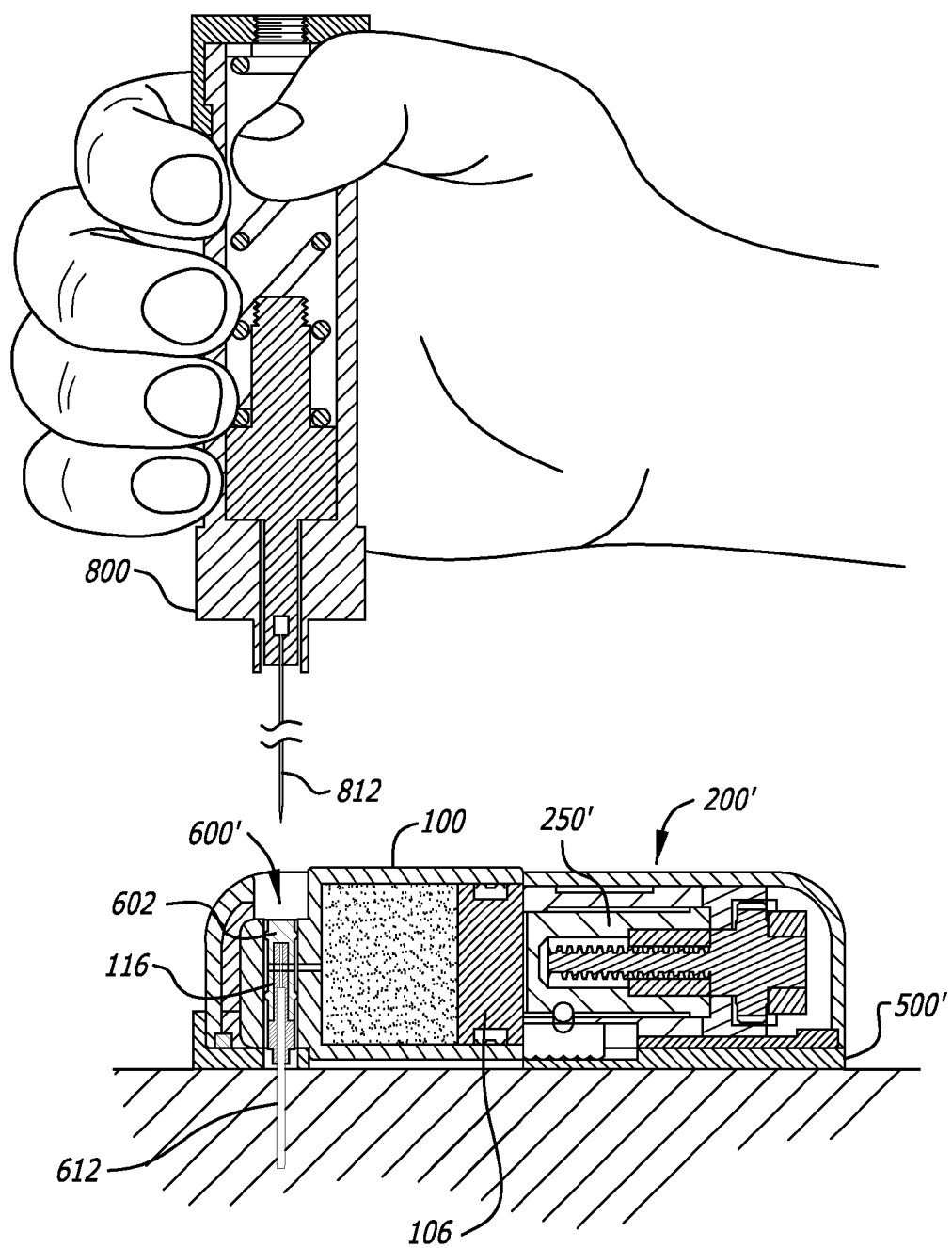
FIG. 89 is a section view showing the system illustrated in FIG. 88 on the skin with the cannula inserted and the inserter being removed.

The user may clean the skin surface S onto which the baseplate 500' will be adhered, and the liner 544 may be removed to expose the adhesive layer 542, as illustrated in FIGS. 85 and 86 (Steps S118 and S119). Turning to FIG. 87, the unit consisting of the cartridge 100, pump assembly 200', baseplate 500', cannula 600' and inserter 800 may be adhered to the skin surface S (Step S120). The inserter actuator 806 may then be actuated (FIG. 88) by rotating the trigger 808, thereby allowing the spring 810 to drive the movable member 802 towards the patient (Step S121). The cannula plug 602' will be properly seated in the cartridge through-bore 116, and the cannula tube 612 will be subcutaneously deployed, at the end of the movable member stroke. The inserter 800 may then be removed (FIG. 89, Step S122).

In some implementations, the pump assembly may be provided with structure (not shown) that performs the function of determining whether or not the cannula is properly inserted (Step S123). If not, an error message will be provided to the user (Step S124).

Figure 90:
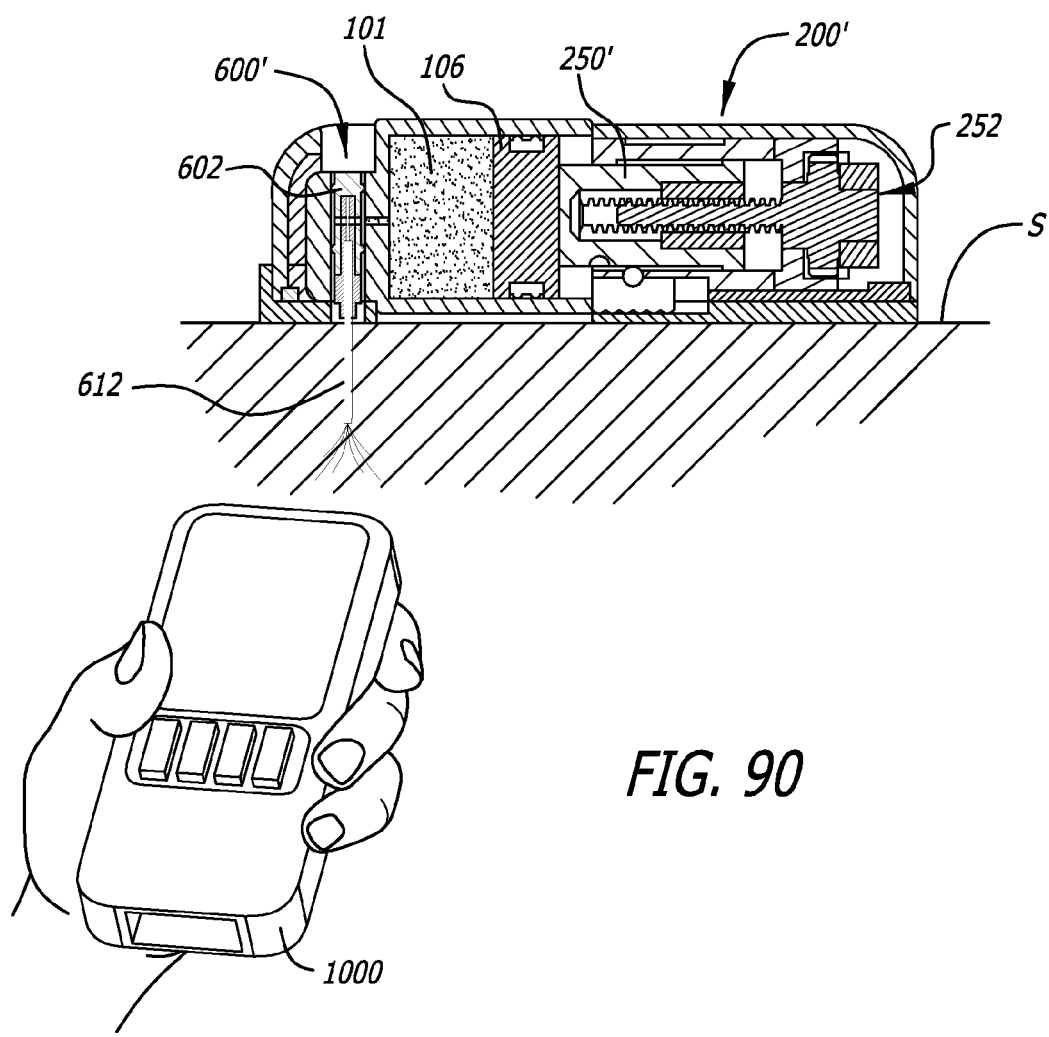
FIG. 90 is a section view showing the system illustrated in FIG. 89 dispensing medicament by way of the cannula.

Finally, as shown in FIG. 90, the remote control 1000 may be used to initiate a particular medicament delivery operation (Step S125). The delivery operation may follow a predetermined delivery profile (e.g. a particular basal rate, a series of time-spaced bolus deliveries, or some combination thereof) that is equated to motor rotations, at particular rates and times, required to deliver medicament in accordance with the profile. The profile may be input by the user with the remote control 1000 and stored by the controller 240. For example, as described below, the remote control may store a number of different delivery profiles and bolus deliveries from which the patient can choose. Such profiles may correspond to, for example and depending on the medicament, days where vigorous exercise is expected, days where it is not, incidences of increased pain, etc. Alternatively, or in addition, the profile stored in the controller may be set by a clinician's programming unit.

The discussion above is also applicable to use of the "pocket pump" system 11. Minor variations in the above-described procedure include, for example, use of the baseplate 501, deploying the infusion set 503 instead of a cannula, and priming of the infusion set tube.

VIII. EXEMPLARY OPERATIONAL METHODOLOGIES

Various methodologies are presented here in the context of the exemplary structures described in the preceding sections, and illustrated in FIGS. 1-90, for the purpose of explanation only. Although the present methodologies may employ the structures described above, they are not limited thereto. Additionally, the alarms, reports and other notifications associated with the methodologies described below may be provided in audible, visible and/or tactile form. A pump assembly may provide audible, visible and/or tactile notifications. A remote control may also provide audible, visible and/or tactile notifications as an alternative to, or in addition to, any notifications provided by a pump assembly. Additionally, embodiments of the present inventions may incorporate any one of the methodologies described below, or all of the methodologies described below, or any and all combinations of less than all of the methodologies described below.

A. Exemplary Cartridge Position Check

Given the relatively small size of the systems described above, the present inventors have determined that it would be desirable to determine whether or not a cartridge (e.g., cartridge 100) has been properly inserted into (or "positioned in" or "seated in") a pump assembly (e.g., pump assembly 200) cartridge receiving area. For example, it may be desirable to make such a determination when the cartridge is initially inserted into a pump assembly, and prior to the pusher zeroing procedure discussed in Section VIII-B below. Other procedures, such as pusher zeroing procedure, may also start automatically after the position check.

A variety of structures may be employed in such a position check. For example, as discussed in Section IV-H above with reference to FIGS. 41 and 42, an exemplary cartridge and pump assembly may be provided with a pressure sensor 234 that includes a detectable structure on the cartridge portion 120 (e.g., a magnet) and a detector on the pump assembly portion 236 that responds to the detectable structure (e.g., a sensor that responds to changes in magnetic fields). The prepressurization "at rest" position of the cartridge portion 120 within the cartridge receiving area 228 (and relative to the chassis window 287) is also closely controlled by, for example, the spring bias clips 268, the latches 412 and 412a and structures 494 described in Section IV-F above with reference to FIGS. 18, 23-26, 32-35A and 38. As a result, the controller 240 may use the signals from the pump assembly portion 236 to determine whether or not the cartridge has been properly positioned. In the exemplary context of magnet-based sensors, the controller would compare the measured magnetic field signals to expected magnetic field signals to determine whether or not the cartridge is properly positioned.

Figure 91:
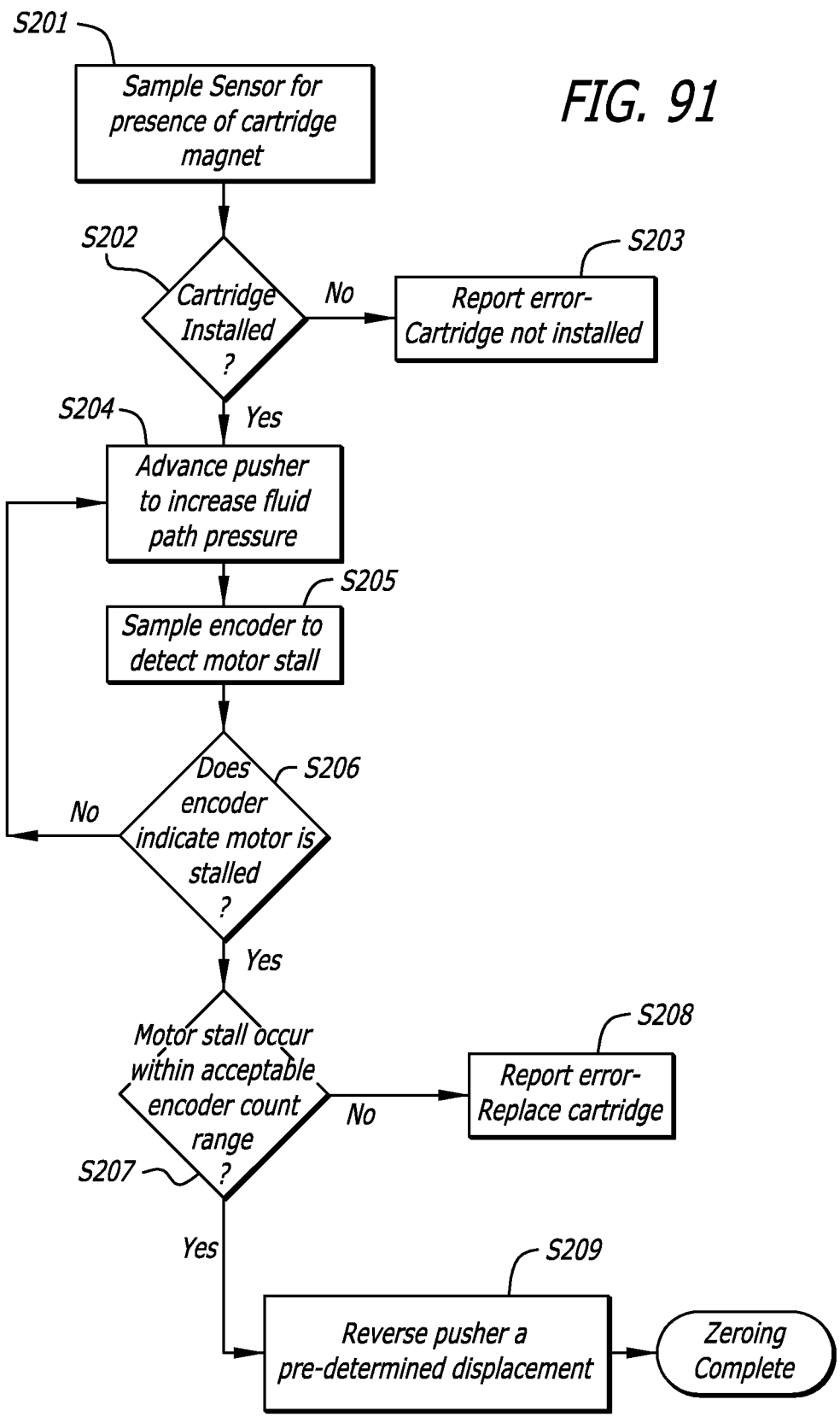
FIG. 91 is a flow chart showing exemplary cartridge position check and pusher zeroing methods.

Accordingly, and referring to FIG. 91, a method of checking cartridge position may include sampling the output of the pump assembly portion 236 of a pressure sensor 234 (Step S201) and determining whether or not the output is above a predetermined threshold and stable (Step S202). If not, then a "cartridge not installed" alert may be provided (Step S203) so that the user can take appropriate action, such as inserting a new cartridge or returning the pump to the manufacturer. If the cartridge is properly positioned, then the system will proceed with subsequent processes such as the pusher zeroing procedure described below.

It should also be noted here that in other implementations, structures other than the pressure sensor 234 may be used to determine whether or not the cartridge 100 is properly positioned in the pump assembly 200. For example, the cartridge barrel 102 may be provided with a pressure responsive structure that will not be isolated from the reservoir, as will the sensor cartridge portion 120 by the plug 110, during the pusher zeroing procedure described below. Here, a pressure-based cartridge position check may be performed at the onset of a pusher zeroing procedure. Switches, electrical contacts or other devices may also be employed.

B. Exemplary Pusher "Zeroing" Procedure

As discussed at great length above, precision is very important to dispensing procedures that involve highly concentrated medicaments such as U-500 insulin. The present inventors have determined that one aspect of dispensing precision is associated with the distance that the plunger pusher must travel, from the initial home position, before it will engage the cartridge plunger and begin to drive medicament out of the reservoir. Given that there may be some tolerances associated with cartridge manufacture and initial seating of the cartridge within the pump assembly, this distance may vary. Thus, a dispensing process based on an estimate/measurement of this distance at the time of manufacture may result in under delivery or over delivery in some circumstances.

The pusher zeroing procedure described below obviates this issue by precisely determining and/or setting, prior to actual dosing, exactly how far the plunger pusher 250 must travel before it will engage the cartridge plunger 106. This procedure may be performed each time a cartridge 100 is inserted into a pump assembly 200 and, in at least some instances, is performed after the position of the cartridge is checked in the manner described in the preceding section. Generally speaking, the zeroing procedure is performed when flow from the cartridge 100 is blocked by the plug 110. A test load (e.g., ten pounds) is applied to the cartridge 100 with the plunger pusher 250 to fully seat the cartridge and to generate a motor stall. Misalignment or misplacement of the cartridge 100 within the pump assembly 200, such as from a raised chip or other debris on mating surfaces, is either removed or accommodated by local deformation of the cartridge under the test load, thereby precluding subsequent cartridge movement during medicament delivery. The motor stall is presumed to be due to hydraulic lock and, therefore, indicative of the plunger pusher 250 engaging the plunger 106 of a plugged cartridge 100.

Referring again to FIGS. 81-83 and 91, one exemplary implementation of the zeroing procedure may be practiced in conjunction with pump assembly 200'. The zeroing procedure, which is equally applicable to pump assembly 200, commences by advancing a plunger pusher 250' into engagement with the cartridge plunger 106 (FIG. 81) to increase the fluid path pressure (Step S204). The encoder 396 or other monitoring device is sampled to determine whether a motor stall occurs as the pusher 250' continues to be advanced (Steps S205 and S206). One example of such a stall is illustrated in FIG. 82. The pusher 250' may be advanced up to a predetermined allotted distance (e.g., 0.5 mm) from the home position (FIG. 18), which corresponds to a predetermined number of encoder signals. The allotted distance is a distance that is sufficient to make contact with cartridge plunger 106 under normal conditions.

The pusher may be initially advanced at a relatively fast speed, and then advanced at a relatively slow speed (e.g., ½ of the faster speed) until the lack of encoder signals evidences that the motor is not turning. The faster speed can occur over a distance of 0.3 mm and the slower speed can occur over a distance of 0.2 mm. The slower speed is a "searching" speed employed over the portion of the allotted distance where it is anticipated that the pusher 250' will contact the plunger 106. The lower speed reduces the force of the impact. The faster speed is used to speed up the process over the portion of the allotted distance where it is less likely that the pusher 250' will contact the plunger 106. Also, the pusher 250' may be advanced at a controlled torque, or limited force, so that the motor will stall with the least amount of force possible for reliable results, in order to reduce the load on the system (e.g., the bearings and the battery).

If a motor stall does not occur within the allotted distance, the system controller 240 may determine that the associated cartridge 100 is either not new, not full, was improperly made or filled, or is otherwise defective and may preclude its use (Step S208). In those instances where the cartridge is not full, the preclusion is useful because, for example, the associated dispensing program may be based on a full cartridge with a known volume of medicament.

If the motor 358 does stall within an acceptable encoder count range, i.e., at or before the allotted distance, then the pusher 250' is retracted a predetermined distance by running the motor in reverse, which ends the process (Step S209). One example of pusher retraction is illustrated in FIG. 83. The retraction distance may be, for example, 0.001 to 0.005 inch (0.025 mm to 0.125 mm). The retraction distance may also be equated to dispensed medicament, e.g., 1 to 20 µl worth, or 5.5 to 6.5 µl worth. In any event, at the onset of dosing, the distance between the plunger pusher and the plunger is precisely set and can be taken into account as movement of the plunger pusher is controlled.

The advancing-retracting process can be repeated a few times to account, for example, for variability of the interface between the lead screw 360 and nut 364 (FIG. 23). The advancing-retracting process can be also repeated using a light force (e.g., two pounds) followed by a stronger force (e.g., four to five pounds) to confirm that the first motor stall was due to torque and not some other cause. Repeating the process increases the likelihood that the "zero" distance between the plunger pusher 250' and the dry side of the plunger 106 will be precisely established.

C. Exemplary Occlusion Detection

Various structures in the exemplary cartridges and pump assemblies may be used to detect occlusions in a cartridge, cannula or infusion set tube. Although precise occlusion detection may be desirable in any infusion pump, it is especially desirable in those instances where very high concentration medicament is dispensed. For example, some conventional insulin pumps alert the patient after approximately 30 µl of missed delivery without an undue number of false alarms. While this level of fidelity may be adequate in the context of U-100 insulin, where 30 µl equates to 3 IUs of insulin, it would result in a much more problematic 15 IUs of missed delivery in the U-500 context. Occlusions may also lead to other undesirable outcomes. For example, continuing to drive the motor in the presence of an occlusion may lead to cartridge leakage and/or damage to various aspects of the drive mechanism. The structures described above and methodologies described below address these issues.

Figure 92:
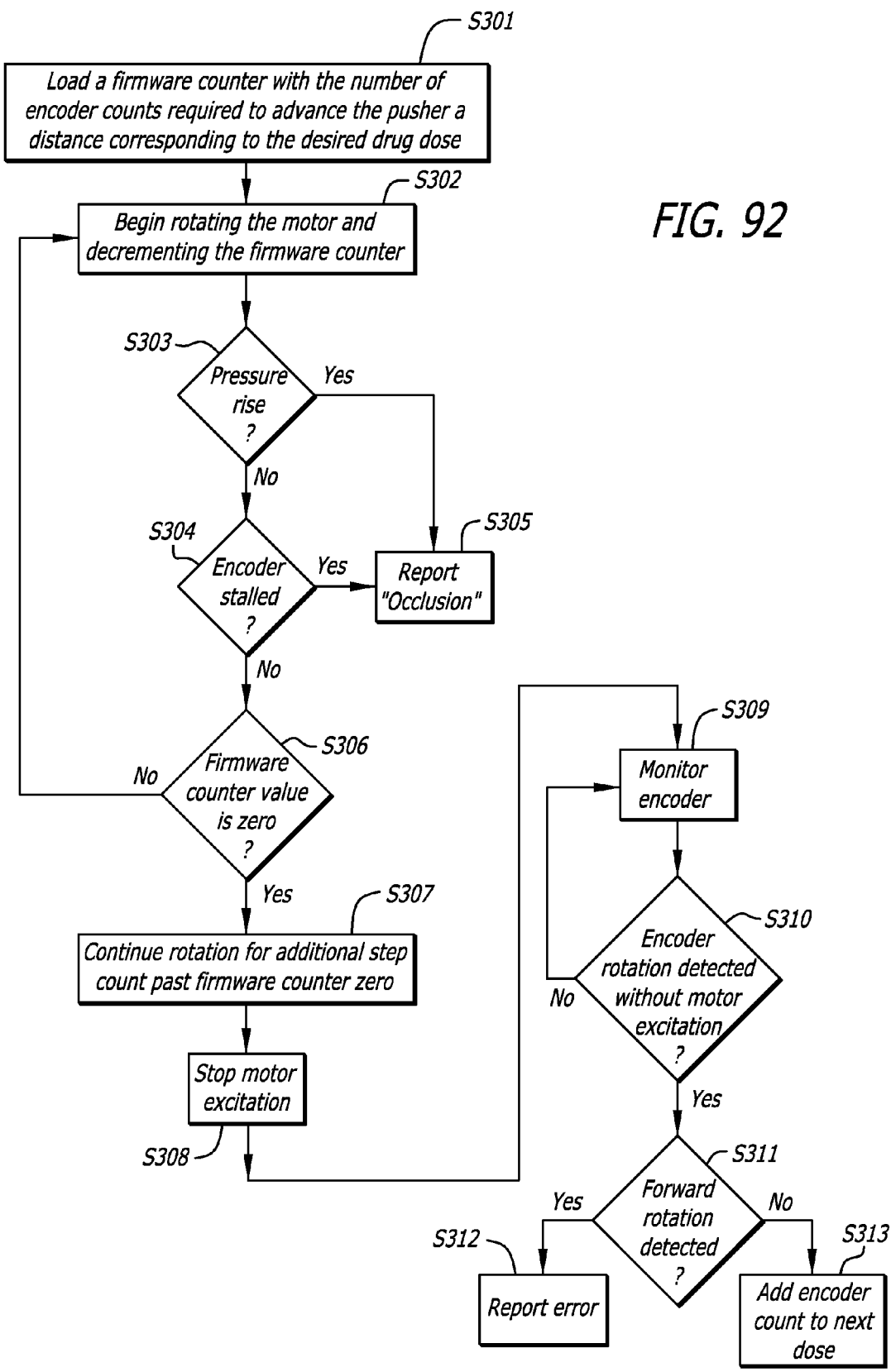
FIG. 92 is a flow chart showing an exemplary dispensing method with occlusion detection.
Figure 93:
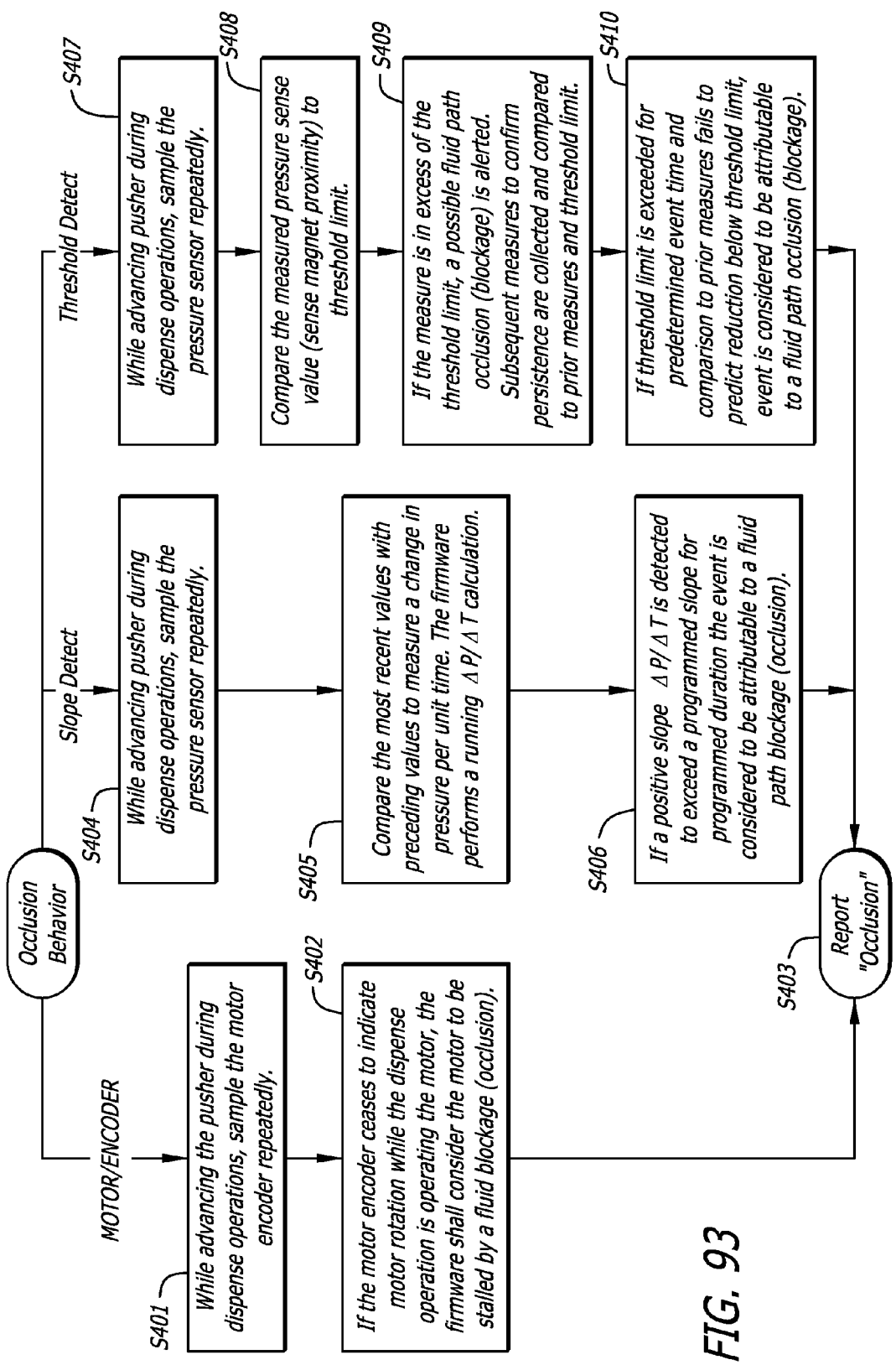
FIG. 93 is a flow chart showing a number of exemplary occlusion detection methods that may form part of the dispensing method illustrated in FIG. 92.

One exemplary dispensing method, which includes occlusion detection, is illustrated in FIGS. 92 and 93. The occlusion detection aspect of the exemplary method includes monitoring of the motor encoder 396 as well as monitoring of the pressure sensor 234. It should be noted, however, that only one of the two may be monitored in the occlusion detection context in other implementations.

Referring first to FIG. 92, at the initiation of a dosing operation, the firmware counter of the controller 240 is loaded with the number of encoder counts required to advance the pusher 250 a distance corresponding to the desired drug dose (Step S301). For example, in some implementations, a single dose of 1 µl (or 0.50 IU) of U-500 insulin would equate to 14.4 motor revolutions. In other words, in the context of the exemplary embodiment illustrated in FIG. 23, 14.4 motor revolutions will cause the drive screw 360 to drive the plunger pusher 250 (and cartridge plunger 106) a distance sufficient to force 1 µl from the reservoir 104.

Motor rotation begins, which causes the pusher 250 to advance, and the counter is decremented in response to signals from the encoder 396 (Step S302). Detected increases in pressure from the pressure sensor 234 and/or signals from the encoder 396 indicative of a stalled motor 358 result in the generation of an "occlusion" report (Steps S303, S304 and S305). In at least some implementations, the motor 358 will also be disabled (i.e., motor excitation ceases). Various exemplary occlusion detectors are discussed in greater detail in Section IV-H above with reference to FIGS. 41 and 42. In response to the detection of an occlusion, the user may be instructed to remove and replace the cartridge 100 as well as the baseplate 500 (and associated cannula) or baseplate 501. Also, in at least some implementations, the plunger pusher 250 will be automatically withdrawn from the cartridge and returned to the home position, as described in Section VIII-F below, in response to a detected occlusion. This readies the system for cartridge removal and replacement.

Absent an occlusion, the dispense operation will continue until the counter reaches zero (Step S306), which indicates that the desired dose has been delivered. At that point, the controller 240 will control the motor 358 to rotate until the next step count from the encoder 396, and will thereafter disable the motor (Steps S307 and S308). The controller 240 may, however, continue to monitor the encoder 396 (Step S309) to determine whether or not there is encoder (and motor 358) rotation in the absence of motor excitation (Step S310). If forward rotation of the motor 358 is detected in the absence of motor excitation (Step S311), which indicates that the motor 358 is at least attempting to drive the plunger pusher 250 in the dispensing direction, an error is reported (Step S312). If reverse rotation is detected in the absence of motor excitation, which is indicative of the plunger pusher moving away from the cartridge plunger due to, for example, system load or compliance, the appropriate number of encoder counts will be added to the next dispense dose (Step S313).

As alluded to above, occlusions may be detected by monitoring rotation of the motor 358 (e.g., by way of the encoder 396) and/or by monitoring pressure (e.g., with the sensor 234). With respect to pressure, a predetermined rate of pressure change (or $\Delta P/\Delta T$) or pressure above a predetermined threshold may be indicative of an occlusion. The present methods may employ one of, any two of, or all three of rotation, $\Delta P/\Delta T$ and threshold, as shown in FIG. 93. Motor rotation may be monitored during a dispense operation by continuously sampling the encoder 396 with the controller 240 (Step S401). If the encoder 396 does not sense rotation of the motor 358 during a dispense operation, the controller 240 will consider the motor 358 to be stalled due to, among other things, an occlusion (Step S402) and report accordingly (Step S403). Alternatively, or in addition, the controller 240 may repeatedly sample the output of the pressure sensor 234 (Step S404) and use a most recent value, the immediately preceding value, and the time period therebetween to create ΔP/ΔT values (Step S405). If the ΔP/ΔT values remain over a predetermined magnitude (e.g., 2 psi/sec.) for a predetermined period of time (e.g., 2 sec.), the controller 240 will consider the pressure increase to be due to an occlusion (Step S406) and report accordingly (Step S403). Alternatively, or in addition, the controller 240 may repeatedly sample the output of the pressure sensor 234 (Step S407) and compare the output to a predetermined threshold value (Step S408). In some instances, the controller 240 will provide a "possible occlusion" alert in response to any sample that is over the threshold value (e.g., the expected "occluded" value) and, regardless of whether the "possible occlusion" alert is provided, subsequent samples will be used to determine whether or not the condition persists (Step S409). If the "over the threshold" condition persists for a predetermined period (e.g., 1 sec.), and if a comparison of subsequent samples to the prior sample is not indicative of a future reduction below the threshold value, then the controller 240 will consider the pressure increase to be due to an occlusion (Step S410) and report accordingly (Step S403).

D. Exemplary Accounting for Unpowered Motor Reverse

The present inventors have determined that there may be some instances where an unpowered motor unintentionally rotates in reverse due to, for example, system load or compliance. Such load and compliance may be associated with a build-up in force in the gears which releases itself by the gears turning in the reverse direction when the motor is not energized. When this occurs, the motor is rotated in reverse. At the other end of the gear assembly, the plunger pusher, which has previously been brought into engagement with the cartridge plunger, may (or may not) pull away from the plunger. The initial motor turns in the next delivery procedure (or "dose" or "delivery cycle") will, in essence, simply rebuild the force in the gears and, if not already the case, bring the pusher back into contact with the plunger. As a result, the volume of medicament actually delivered to the patient in that dose will be less than expected.

In order to account for, or correct for, the delivery error that would otherwise be associated with this condition, the pump assembly may include an encoder 396 which senses rotations of the motor in both the forward and reverse directions. The controller 240 may be configured to determine from the encoder signals the amount of reverse rotation and to adjust the dispensing program accordingly so that the net result is the overall intended result.

Figure 94:
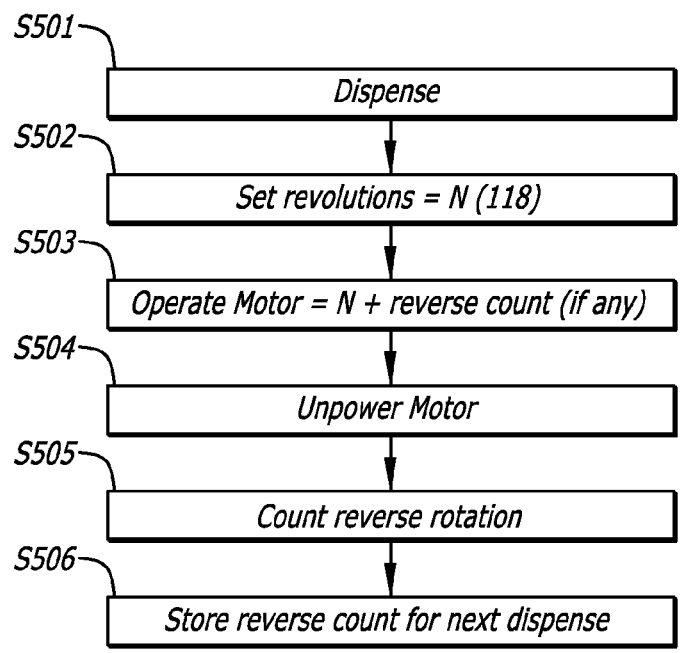
FIG. 94 is a flow chart showing an exemplary reverse rotation of an unpowered motor correction method.

One example of such a correction process is illustrated in FIG. 94. At the onset of a dispensing procedure (Step S501), the number of motor revolutions corresponding to the intended delivery is calculated and set (Step S502). Using the example above, a single dose of 1 μl (or 0.50 IU) of U-500 insulin may equate to 14.4 motor revolutions. The controller 240 will control the motor 358 to operate for the set number of revolutions (Step S503), unless one of the other alarm conditions described below with reference to FIG. 100 occurs. The controller 240 will then unpower the motor 358, and the motor will remain unpowered, until the next dosing (Step S504). Should the motor 358 rotate in reverse, as evidenced by signals from the associated encoder 396, the number of reverse rotations (or "reverse count") will be counted and stored until the next dosing (Steps S505 and S506). When the next dosing commences, the reverse count will be added to calculated and set number of rotations for that next dosing (Step S503). For example, if there were 2 reverse rotations prior to a dosing that equates to 14.4 motor revolutions, the controller would control the motor to perform 16.4 revolutions for that dosing.

E. Exemplary Motor Stopping

The present inventors have determined that another aspect of motor control which can effect the precision of medicament delivery is motor stopping. Briefly, when a controller cuts off power to a motor, the motor will continue to rotate, in a now uncontrolled state, due to its own momentum and the momentum of other rotating aspects of the drive mechanism. The plunger pusher will continue to travel in the forward dispensing direction, thereby driving the cartridge plunger, as the motor continues to rotate. Although one could simply cut off power a few revolutions prior to the end of a delivery cycle, the precise number of "extra," post cut-off revolutions is difficult to accurately and consistently estimate. As such, the simple act of turning the motor on and off, from dose to dose, can lead to under delivery and/or over delivery error due to the uncontrolled movement of the plunger pusher.

Figure 95:
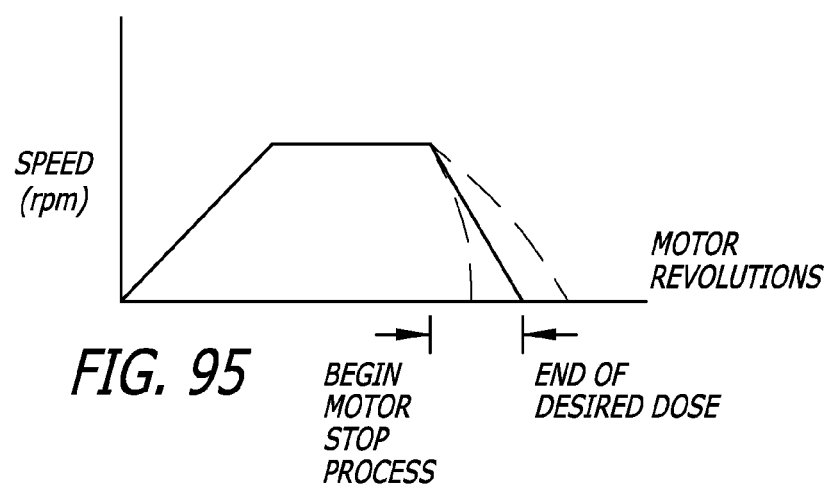
FIG. 95 is a graph showing motor rotational speed during an exemplary motor stopping method.

One exemplary method of controlling a motor such as a stepper motor 358 with a controller such as controller 240 is graphically illustrated in FIG. 95. In particular, the speed of motor is increased from zero at the beginning of the dispensing procedure (e.g., a single dose) and is then maintained at a constant rate. At a predetermined point prior to the end of the dispensing procedure (e.g., three revolutions prior), which is labeled "begin motor stop process" in FIG. 95, the frequency of the power waveform delivered to the motor 358 will be slowly decreased. Positive control over the motor 358 is maintained as the velocity of the plunger pusher 250 decreases from its propelling velocity to a complete stop, where the speed equals zero and the dosing ends. Maintaining positive control of the motor 358 in this manner allows the number of turns associated with a motor stoppage to be precisely controlled as is shown with a solid downwardly sloping line in FIG. 95. As a result, the intended number of rotations associated with stoppage will be the actual number of rotations, the distance of pusher travel will be the intended distance, and dispensing precision will be maintained. For purposes of comparison, stopping the motor by simply cutting off power at the same predetermined point may result in too much or too little rotation, as is shown with dashed lines. As a result, the distance of plunger travel (and dispensed volume) may be more or less than intended.

Accordingly, by employing the above-described stopping method, the controller can cause the motor 358 to propel the pusher 250 against the medicament reservoir plunger 106 according to a medicament dispensing program, having a plurality of individual dispensing operations, without stoppage related losses in precision. Also, the predetermined point prior to the end of the dispensing procedure at which frequency of the power waveform begins to decrease may vary from system to system. Although a three revolution slow down period is employed in the illustrated example, that number may be increased or decreased, and need not be a whole number.

F. Exemplary Automatic Plunger Pusher Retraction Procedures

For purposes of convenience and safety, the present pump assembly may be configured such that the plunger pusher is automatically retracted out of the associated medicament cartridge to the home position when the cartridge reaches the empty state, as evidenced by an encoder count or a motor stall, and/or when there is a motor stall due to an occlusion or other mechanical issue.

Figure 96:
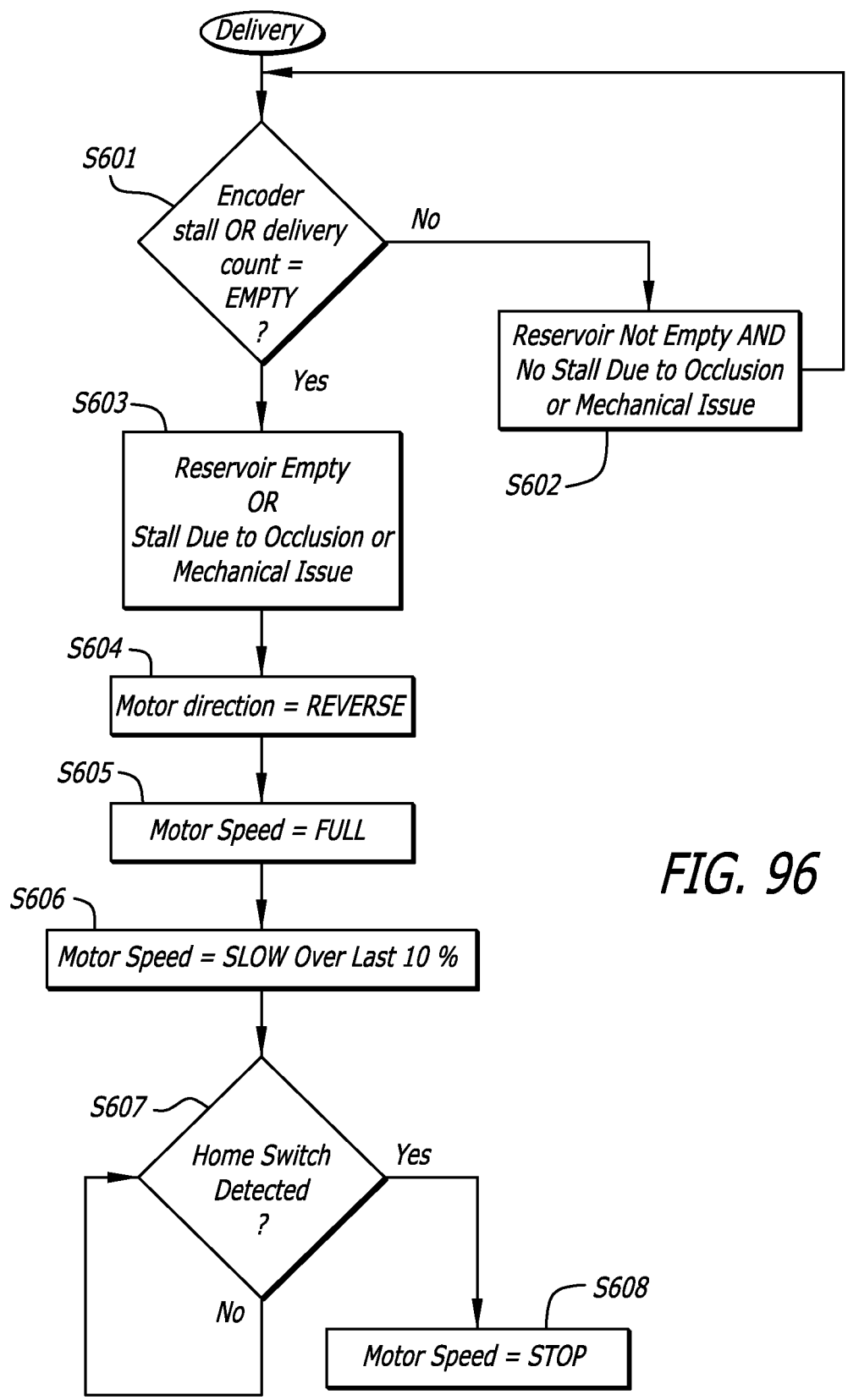
FIG. 96 is a flow chart showing an exemplary automatic plunger pusher retraction method.

Referring to FIG. 96, the controller 240 will monitor the encoder 396 to determine whether the motor 358 has stalled or the encoder count has reached the number that is indicative of an empty cartridge (Step S601). Such a stall would be evidenced by the cessation of encoder counts and could, for example, be the result of the plunger pusher 250 driving the cartridge plunger 106 into the cartridge end wall 119 (FIG. 25), or an occlusion, or a mechanical issue. The "empty" number could reflect the exact number of motor rotations that would result in, for example, the cartridge plunger 106 reaching the end wall 119 (FIG. 3A). However, in order to prevent damage to the drive mechanism that could result from the plunger pusher 250 repeatedly driving cartridge plungers into a fixed wall, the "empty" number could instead reflect slightly less than the exact number of motor rotations. It should also be noted that the encoder count may be adjusted to account for unpowered reverse motor rotations, during the life of the associated cartridge, in the manner described above with reference to FIG. 94.

Other issues notwithstanding, so long as the motor 358 has not stalled and the encoder count is not indicative of an empty cartridge, dispensing will be allowed to continue (Step S602). If, on the other hand, the motor 358 has stalled or the encoder count is indicative of an empty cartridge, then the controller 240 will control the motor to run in the reverse, pusher retraction direction (Steps S603 and S604). The retraction speed may be relatively slow, as compared to a user-initiated retraction, so as to conserve battery power. For example, a relatively slow retraction may take 1 minute, or between 1.5 and 2.5 minutes, while a faster user-initiated retraction may take 30 seconds, or between 20 and 40 seconds. The user is not inconvenienced by the slower automatic retraction because it is occurring automatically at a time when the user is most likely not waiting for it to end, as would be the case in a user-initiated retraction.

At least initially, the retraction will take place at the full retraction speed (Step S605). The speed may be reduced to a slower speed when the pusher 250 approaches the fully retracted home position (Step S606). For example, the speed may be reduced at a distance from the fully retracted position that corresponds to 10% of the total pusher travel distance (i.e., the distance between fully retracted and fully extended). Withdrawal will continue until the controller 240 determines that the pusher has reached the fully retracted position (e.g., by way of position detector 398 in FIG. 29), at which time the motor 358 will be stopped (Steps S607 and S608). To that end, it should be noted that the lower speed over the last 10% of pusher travel reduces the likelihood that the pusher 250 will damage the switch 398 or other position detector during impact therewith.

G. Exemplary Gear Assembly Verification Procedure

Figure 97:
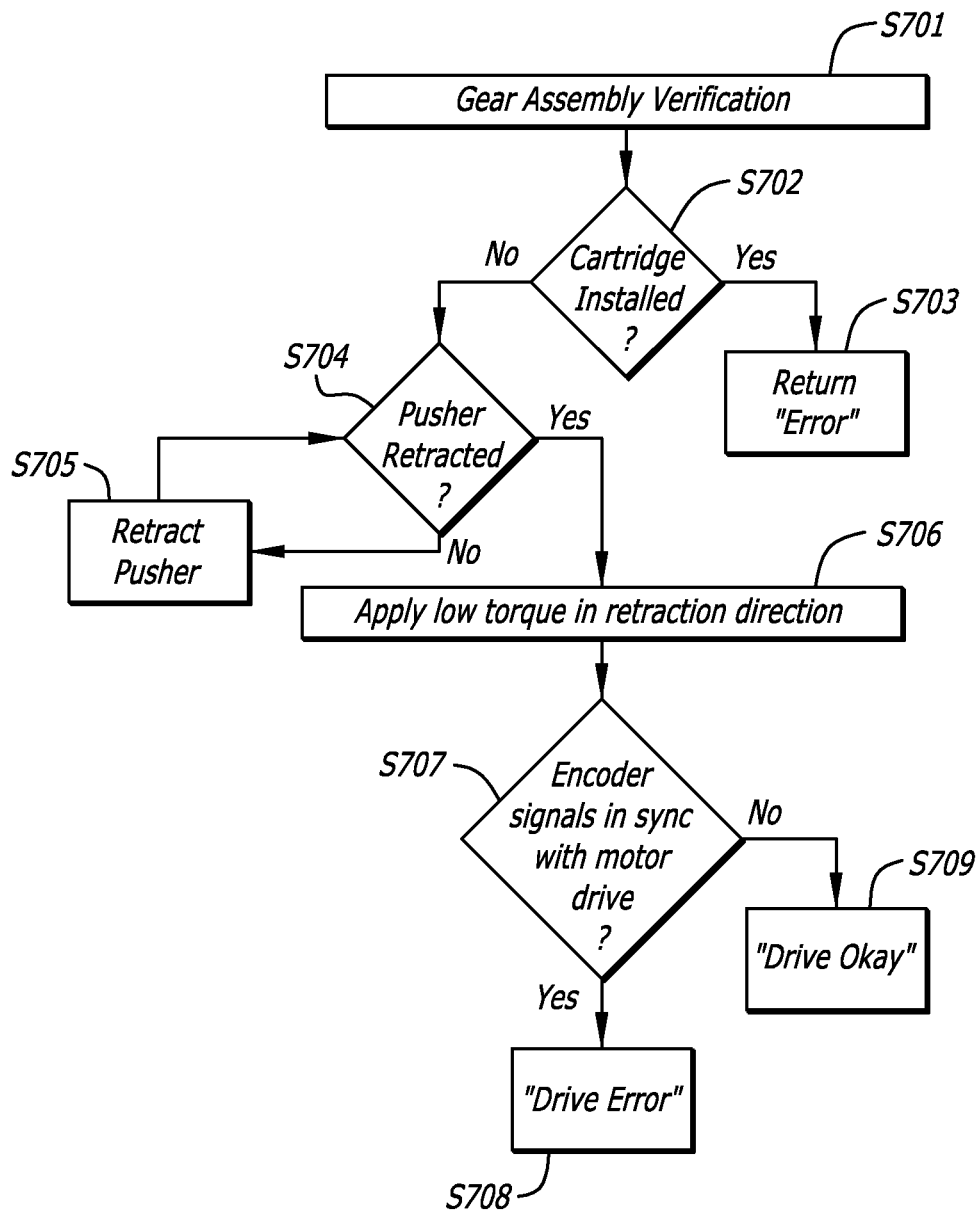
FIG. 97 is a flow chart showing an exemplary gear assembly verification method.

One aspect of the present pump assembly 200 that may require periodic operational verification is the gear assembly (e.g., gear assembly 362 in FIG. 19) and, for example, the interfaces thereof. One exemplary gear assembly verification procedure ("GAV procedure") is illustrated in FIG. 97. The exemplary GAV procedure will typically be performed by a controller when there is no medicament cartridge in a pump assembly in order to avoid the possibility of medicament being unintentionally dispensed. For example, controller may be configured to perform the GAV procedure each time the plunger pusher is returned to the fully retraced home position (e.g., against a hard stop), which is commonly associated with cartridge removal, or during a pusher zeroing procedure. Alternatively, or in addition, the GAV procedure may be a user implementable procedure initiated through operation of the remote control 1000.

Upon initiation of the GAV procedure (Step S701), the controller 240 may determine whether or not a cartridge 100 is within the pump assembly 200 by, for example, a method similar to those described in Section VIII-A above. Here, however, the controller need only determine whether a cartridge is in the pump assembly at all, as opposed to determining whether a cartridge is precisely located within the cartridge receiving area. If a cartridge is present, then the procedure is discontinued and an error message is provided to the user (Steps S702 and S703). If no cartridge is present, then the controller 240 determines whether or not the plunger pusher 250 is in the fully retracted home position and, if for some reason it is not, the controller automatically retracts the plunger pusher (Steps S704 and S705). Alternatively, the user could be instructed to retract the pusher 250 through operation of the remote control 1000.

Relatively low torque is then applied to the gear assembly 362 by the motor 358 in the reverse direction (Step S706). For example, approximately 20-70% (or 50%), or less than 20%, of the torque (e.g., 5-10 mNm) that is applied in the forward dispensing direction during normal delivery may be applied in the reverse direction. This may be accomplished by controlling power in the manner described in Section IV-M above. It should be noted here that there may be some built-up gear compression that will allow reverse motor rotation despite the fact that the plunger pusher has been fully retracted. Other situations are described below.

The power pulses will be sustained for a period corresponding to a predetermined number of motor revolutions (e.g., 50 revolutions). Signals from the encoder 396 and, therefore, motor rotation may be monitored. If the encoder signals indicate that the motor 358 has rotated at least a predetermined number of revolutions (e.g., 20 revolutions), precisely synchronized to motor driving sequence of pulses, the controller 240 determines that the motor is disconnected from the gear assembly 362 and creates a "drive error" signal (Steps S707 and S708). If, on the other had, the encoder signals indicate that less than the predetermined number of revolutions have occurred and that there is not a 1:1 correlation between the driving pulses and the encoder signals, then the controller determines that gear assembly 362 is intact and creates a "drive OK" signal (Step S709). In other words, and somewhat counter intuitively, the controller 240 determines that the gear assembly 362 is not operating properly if signals from the encoder 396 indicate that the motor 358 is synchronized with the motor driving pulse sequence, and determines that the gear assembly is operating properly if signals from the encoder indicate that the motor is not synchronized with the motor driving pulse sequence.

In those instances where the plunger pusher 250 has been fully retracted and there is no built-up gear compression that would allow reverse rotation of the motor 358 under normal circumstances, the process may be adjusted slightly. Here, the motor 358 may be driven first in the forward direction and then in the rearward direction several times to verify whether or not the motor stalls after the same number of pulses (as determined by, for example, the switch 398 in FIG. 29).

As alluded to above, a GAV procedure may be performed each time the motor 358 stalls. During zeroing and, in some embodiments, during homing, the motor 358 is stalled at controlled torque either against the plunger (zeroing) or against a hard stop (homing). During this procedure, the motor 358 is controlled to advance the mechanism at a known controlled torque while the motor encoder 396 is monitored for rotation. Correct operation requires the system to stall (encoder 396 ceases to turn while driving the motor 358) at a predetermined position. If the encoder 396 continues to indicate motor rotation while drive signals are being sent to the motor 358, past the region of expected motor stall, it indicates the possibility of gear assembly failure.

IX. EXEMPLARY REMOTE CONTROLS AND ASSOCIATED METHODOLOGIES

The present infusion pumps may be used in conjunction with a wide variety of remote controls. Such remote controls may be used to, for example, allow the user to transmit instructions to the pump assembly or facilitate communication between the pump assembly and the user (e.g., an alarm condition message or other message concerning the conditions of the pump assembly).

The particular type of remote control may depend on the desired level of functionality for a particular user. A key fob type remote control which has one to four buttons may be provided in those instances where the user's control options are to be limited to, for example, starting and stopping medicament delivery procedures and withdrawing the plunger pusher from the cartridge. On the other end of the spectrum, commercially available devices with full-function user interfaces (e.g., a keyboard and a display, or a touch screen display), such as mobile telephones and personal digital assistants, may be programmed to provide the desired level of remote control functionality.

Figure 98:
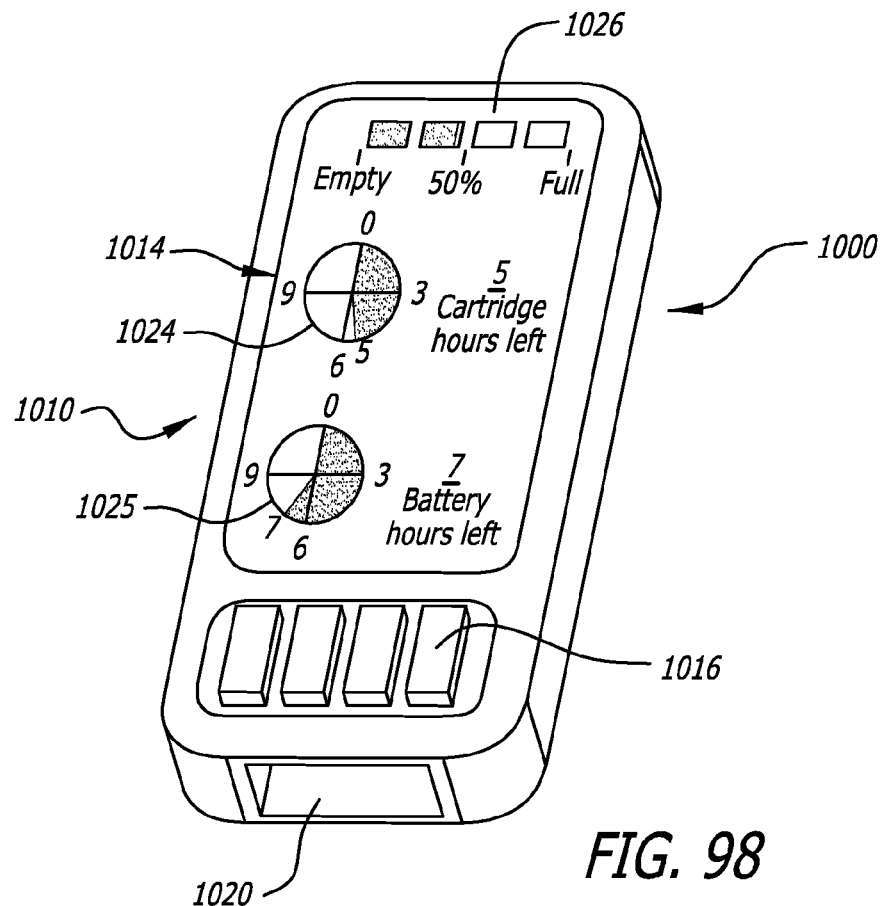
FIG. 98 is a perspective view of an exemplary remote control.
Figure 99:
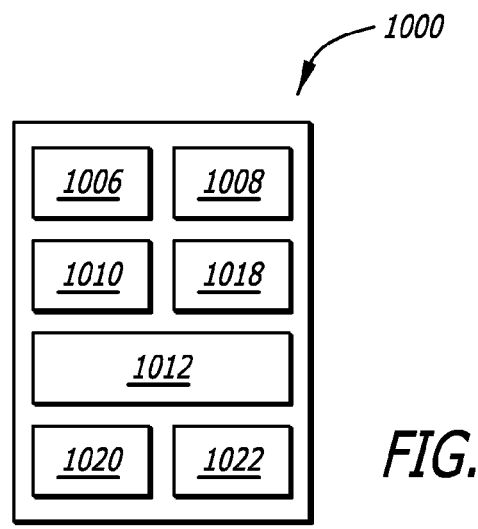
FIG. 99 is a block diagram of the exemplary remote control illustrated in FIG. 98.

One exemplary remote control, which is generally represented by reference numeral 1000 in FIGS. 98 and 99, is configured and dimensioned to be easily grasped and manipulated in the user's hand. The exemplary remote control 1000 may include a power supply 1006 (e.g., one or more replaceable or rechargeable batteries), a sending and receiving antenna 1008 that is adapted for use with a corresponding sending and receiving antenna in the pump assembly (e.g., antenna 1002 in FIG. 51), and a user interface 1010. Operations may be controlled by a controller 1012 (e.g. a microprocessor, memory, firmware and/or software). Communication between the pump assembly 200 and remote control 1000 may be in the form of RF based communication (as described above) or other communication mediums such as infrared and magnetic. The user interface 1010 may include a visual display 1014 (e.g., an LCD display) and a plurality of buttons 1016 (e.g., switches, membrane keys, etc.). An alarm device 1018, which may be audible (e.g., a buzzer), palpable (e.g., a vibrator), visible (e.g., an LED), or any combination thereof, may also be provided.

The exemplary remote control 1000 may also include a port or connector 1020 (e.g., a USB connector) that allows communication with, for example, a personal computer, a printer, or a clinician's programmer.

The exemplary remote control 1000 may also be provided with a proximity sensor 1022 that, when active, senses the distance between the remote control and the pump assembly 200. The controller 1012 may actuate the alarm device 1018 if the distance is too great, in order to remind the user to keep the remote control 1000 close at hand.

The exemplary remote control 1000 may be configured to facilitate one, some or all of the following operations: (1) turning the remote control 1000 on or off, (2) associating (or "assigning") the remote control 1000 to the pump assembly 200, (3) obtaining status information such as battery charge level, medicament level, and/or alarm conditions, (4) silencing the pump assembly alarm, (5) selecting options that may be associated with the pump assembly alarm such as type of alarm (audible, palpable, and/or visible) and strength/volume of alarm, (6) connecting the remote control to a computer to, for example, update remote control or pump assembly firmware, load and delete delivery profiles stored in the pump assembly or remote control, and otherwise re-program the pump assembly or remote control, and (7) selecting medicament options such as medicament concentrations.

Other operations that may be performed through operation of the remote control 1000 include (1) selecting and initiating a stored medicament delivery profile, (2) increasing and decreasing medicament dose rate, (3) retracting the plunger pusher from the cartridge to the home position, and/or (4) pausing a dispensing operation. A user may pause delivery in order to remove or replace a patient applied structure (e.g. a cartridge, cannula or baseplate), adjust for a current or anticipated change body condition (e.g., low glucose, vigorous exercise), follow a physician's suggestion, or disconnect the pump assembly from the body for any other reason.

The exemplary remote control 1000 may be configured to generate an indicator, based on information from the pump assembly controller (e.g., controller 240), that is indicative of the amount of time remaining in the current dispensing program and/or the amount of time until the next cartridge replacement and/or the amount of time until the pump assembly battery requires recharging. The indicator may be audible, visible, palpable or combinations thereof. A time remaining indicator, such as the exemplary time indicator 1024 on the remote control visual display 1014 (FIG. 98), may be useful for a variety of reasons. For example, knowledge of the time remaining prior to next cartridge replacement and/or battery recharging allows the patient to determine, based at least in part on the current time of day and upcoming events (e.g., travel or sleep), whether or not it would be more convenient to replace the medicament cartridge at a time prior to the end of the dispensing program and/or recharge the battery prior to the point at which it is necessary.

One exemplary type of visible time remaining indicator is the pie chart style "hours left" gauges 1024 and 1025 illustrated in FIG. 98. Any other suitable visible indicator may be employed. The visible indicators 1024 and/or 1025 may be displayed whenever the display 1014 is active, displayed in response to a user inquiry, displayed intermittently, and/or displayed in response to predetermined event (e.g., when 8 hours are remaining).

The exemplary remote control 1000 may be configured to generate an indicator, based on information from the pump assembly controller, that is indicative of the amount of medicament remaining in the cartridge. The indicator may be audible, visible, palpable, or combinations thereof. The exemplary visible "volume remaining" indicator 1026 may be displayed whenever the display 1014 is active, displayed in response to a user inquiry, displayed intermittently, and/or displayed in response to predetermined event (e.g. 25% remaining).

Remaining time calculations may be performed by the pump assembly controller 240 and be based, for example, on the total delivery duration for the associated cartridge (in view of the delivery program and cartridge volume) and the portion of that total delivery duration which has thus far passed based on actual delivery time (i.e., taking into account user stoppages, if any). Alternatively, or in addition, the calculations may be based on the initial volume of the associated cartridge, the total number of motor revolutions necessary to completely deliver the initial volume, the number of motor revolutions that have occurred prior to the calculation (as evidenced by, for example, encoder signals), and amount of time, based on the delivery program, before the total number of revolutions will be reached. Remaining volume (as opposed to remaining time) calculations performed by the controller 240 may be based on the initial volume of the associated cartridge, the number of motor revolutions necessary to completely deliver the initial volume, and the number of motor revolutions that have occurred prior to the calculation (as evidenced by, for example, encoder signals). Here, the information received by the remote control 1000 from the pump assembly controller 240 will be the actual time/volume information to be displayed.

It should also be noted that the calculations described above may be performed by the remote control controller 1012. Here, the information received by the remote control 1000 from the pump assembly controller 240 may simply be encoder information. All other information (e.g. start time, program being implemented, etc.) would be already available at the remote control itself.

Additionally, in lieu of actual calculations, the pump assembly controller 240 and/or the remote control controller 1012 may be pre-programmed to automatically generate a time and/or volume indicator based on encoder information and a pre-programmed look-up table associated with the dispensing program.

With respect to the amount of time until the battery 238 requires recharging, the pump assembly may be provided with a battery management chip (or other suitable battery management apparatus) that determines when recharging is necessary. For example, recharging may be necessary when the battery voltage is reduced from the fully charged voltage to a predetermined voltage that is less than the fully charged voltage. The amount of time remaining may be estimated by the battery management apparatus based on factors such as battery age, battery temperature, and the dispensing program. The battery management apparatus may be part of, or operably connected to, the pump assembly controller 240. The controller 240 is configured to generate a signal indicative of the amount of time remaining until the battery will require recharging.

One exemplary method that may stem from use of the information provided by a pump assembly and/or a remote control is as follows. The user learns from the remote control (e.g., remote control 1000) the amount of time (or medicament) remaining in the medicament dispensing program running on the associated infusion device (e.g., cartridge 100 and pump assembly 200). The information may be provided by the remote control 1000 in audible, visible and/or palpable form (e.g., with the time indicator 1024 and/or the volume remaining indicator 1026). The patient then determines, based on anticipated activity or activities, whether it would be preferable to remove a not yet empty medicament cartridge and replace it with a new medicament cartridge immediately, in the near future, or after the dispensing program has been completed and the cartridge is empty. It may be that, at the end of the remaining time, the user anticipates activity (e.g., sleeping, traveling, exercising, attending a social or business event) which would render cartridge replacement inconvenient or impossible. Thus, the user may decide that it is better to replace the cartridge before it is empty, and then do so.

Turning to FIG. 100, the exemplary remote control 1000 may be used to alert the user to, and specifically identify, a variety of alarm causes (or "conditions"). The exemplary remote control 1000 may be used to suggest actions to be taken in response to the alarms. The alarm causes and suggested actions may be provided in audible or visible form. Exemplary alarm causes are identified AC1-AC16 in FIG. 100, and are followed by a suggest action. "R and R" is used in FIG. 100 to represent "remove and replace," and references to "cannula/baseplate" are references to both "patch pump" style baseplates (e.g., baseplate 500), which are used in conjunction with a separate cannula, and "pocket pump" style baseplates (e.g., baseplate 501), which may have their own cannula as part of an attached infusion set.

The exemplary alarm cause (or "conditions") may include some or all of, but are not limited to, a pump assembly 100 (and/or a baseplate 500) falling off the user's skin (AC-1), a battery with a low charge level (AC-2), an error associated with an acoustic transducer or other alarm (AC-3), a fully depleted battery (AC-4), a battery fault (AC-5), an occlusion (AC-6), a telemetry fault (AC-7), a motor error, such motor current too low (AC-8), a baseplate/pump assembly disconnection (AC-9), a firmware checksum error (AC-10), a variables checksum error (AC-11), a low reservoir (AC-12), an empty reservoir (AC-13), a battery fault (AC-14), a zeroing procedure error (AC-15), and a temperature (e.g. within the housing 202) above a preset limit (AC-16). Other alarm conditions may include an error associated with pressure sensing hardware and delivery decision hardware.

Although the inventions disclosed herein have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims set forth below.

Finally, with respect to terminology that may be used herein, whether in the description or the claims, the following should be noted. The terms "comprising," "including," "carrying," "having," "containing," "involving," and the like are open-ended and mean "including but not limited to." Ordinal terms such as "first", "second", "third" in the claims do not, in and of themselves, connote any priority, precedence, or order of one claim element over another or temporal order in which steps of a method are performed. Instead, such terms are merely labels to distinguish one claim element having a certain name from another element having a same name (but for the ordinal term) to distinguish the claim elements. "And/or" means that the listed items are alternatives, but the alternatives also include any combination of the listed items. The terms "approximately," "about," "substantially" and "generally" allow for a certain amount of variation from any exact dimensions, measurements, and arrangements, and should be understood within the context of the description and operation of the invention as disclosed herein. Terms such as "top," "bottom," "above," and "below" are terms of convenience that denote the spatial relationships of parts relative to each other rather than to any specific spatial or gravitational orientation. Thus, the terms are intended to encompass an assembly of component parts regardless of whether the assembly is oriented in the particular orientation shown in the drawings and described in the specification, upside down from that orientation, or any other rotational variation therefrom.

We claim:

1. An infusion pump apparatus, comprising:
   a medicament cartridge including a medicament reservoir, a plunger, an outlet port and a seal that seals the outlet port; and
   an infusion pump assembly including
      a housing having a cartridge receiving area,
      a plunger pusher in the housing,
      a drive mechanism, that drives the plunger pusher and has a motor, a lead screw, a gear assembly operatively positioned between the motor and the lead screw, and an encoder, and
      a controller to control the operation of the motor;
   wherein the medicament cartridge is insertable through an opening in the housing and into the cartridge receiving area to an inserted position where the plunger is proximate to but spaced from the plunger pusher; and wherein the controller executes, with the medicament cartridge in the inserted position, a plunger pusher zeroing procedure including causing the motor to advance the plunger pusher to contact the plunger while the seal is sealing the outlet port and then to back the plunger pusher off a predetermined distance from the plunger.

2. An apparatus as claimed in claim 1, wherein the controller determines from a received signal when the plunger pusher is contacting the plunger during the plunger pusher zeroing procedure.

3. An apparatus as claimed in claim 2, wherein the received signal is from a pressure deformable part that is in fluid communication with the medicament reservoir.

4. An apparatus as claimed in claim 2, wherein the received signal is from an occlusion pressure sensor that is in fluid communication with the medicament reservoir.

5. An apparatus as claimed in claim 2, wherein the received signal is from the encoder.

6. An apparatus as claimed in claim 2, wherein the controller commences the plunger pusher zeroing procedure after receiving an instruction via a remote control to do so.

7. An apparatus as claimed in claim 1, wherein the controller automatically starts the plunger pusher zeroing procedure after receiving a signal that the medicament cartridge is in the cartridge receiving area.

8. An apparatus as claimed in claim 7, wherein the signal is received from a sensor in the housing which senses the nearby presence of a magnet carried by the medicament cartridge.

9. An apparatus as claimed in claim 1, wherein the motor operates at a controlled torque so that the motor can stall out when contacting the plunger when advancing the plunger pusher to contact the plunger during the plunger pusher zeroing procedure.

10. An apparatus as claimed in claim 1, wherein the plunger pusher is in a retracted home position out of interference with the medicament cartridge when the medicament cartridge is inserted in through the opening and into the cartridge receiving area.

11. An apparatus as claimed in claim 1, further comprising:
a slidable latch attached to the housing and movable between a first position that allows the medicament cartridge to be inserted through the opening and a second position that prevents removal of the medicament cartridge from the inserted position during the plunger pusher zeroing procedure.

12. An apparatus as claimed in claim 1, wherein the predetermined distance corresponds to between one and twenty microliters worth of dispensed medicament or between 5.5 and 6.5 microliters worth of dispensed medicament.

13. An apparatus as claimed in claim 1, wherein the predetermined distance is between 0.001 and 0.005 inch.

14. An apparatus as claimed in claim 1, wherein the controller causes the plunger pusher to be in a retracted home position before the medicament cartridge is inserted into the cartridge receiving area.

15. An apparatus as claimed in claim 1, wherein the seal is configured to be movable by grasping and pulling on a portion thereof accessible from outside of the housing, after the controller has caused the apparatus to be in a plunger pusher zeroed condition, so that the seal is in a non-sealing position relative to the outlet port.

16. An apparatus as claimed in claim 1, wherein the controller causes the motor to advance the plunger pusher at a first speed and then at a second slower speed until the plunger pusher contacts the plunger during the plunger pusher zeroing procedure.

17. An apparatus as claimed in claim 16, wherein the second speed is approximately one half of the first speed.

18. An apparatus as claimed in claim 17, wherein the first speed is for 0.35-0.45 mm and the second speed is for 0.15-0.25 mm.

19. An apparatus as claimed in claim 1, wherein the controller determines from input from the encoder when the motor has stalled during the plunger pusher zeroing procedure and to then cause the motor to back the plunger off.

20. An infusion pump apparatus, comprising:
a medicament cartridge including a medicament reservoir, a plunger, an outlet port and a removable seal that seals the outlet port;
an infusion pump assembly including
a housing having an opening and a cartridge receiving area,
a plunger pusher in the housing, and
a drive mechanism that drives the plunger pusher and has a motor, a lead screw, a gear assembly operatively positioned between the motor and the lead screw, and an encoder;
the medicament cartridge and cartridge receiving area being respectively sized and shaped such that the cartridge is insertable through the opening and into the cartridge receiving area, while the removable seal is sealing the outlet port, to an inserted position where the plunger is proximate to but spaced apart from the plunger pusher; and
means for executing a plunger pusher zeroing procedure, while the medicament cartridge is in the inserted position and the removable seal is sealing the outlet port, that causes the motor to advance the plunger pusher that is spaced apart from the plunger into contact with the plunger, that determines that the plunger pusher has contacted the plunger, and in response to a contact determination, that causes the motor to retract the plunger pusher a predetermined distance away from the plunger.

21. An apparatus as claimed in claim 20, wherein the predetermined distance corresponds to between one and twenty microliters worth of dispensed medicament or between 5.5 and 6.5 microliters worth of dispensed medicament.

22. An apparatus as claimed in claim 20, wherein the predetermined distance is between 0.001 and 0.005 inch.

* * * * *